US008017753B2

(12) United States Patent
James et al.

(10) Patent No.: US 8,017,753 B2
(45) Date of Patent: Sep. 13, 2011

(54) MYCOBACTERIAL ANTIGENS EXPRESSED UNDER LOW OXYGEN TENSION

(75) Inventors: Brian William James, Salisbury (GB); Joanna Bacon, Salisbury (GB); Philip Marsh, Salisbury (GB)

(73) Assignee: Health Protection Agency, Salisbury (GB)

( * ) Notice: Subject to any disclaimer, the term of this patent is extended or adjusted under 35 U.S.C. 154(b) by 226 days.

(21) Appl. No.: 12/140,939

(22) Filed: Jun. 17, 2008

(65) Prior Publication Data

US 2009/0054367 A1 Feb. 26, 2009

Related U.S. Application Data

(62) Division of application No. 10/481,265, filed as application No. PCT/GB02/02845 on Jun. 21, 2002, now Pat. No. 7,393,539.

(30) Foreign Application Priority Data

Jun. 22, 2001 (GB) .................................. 0115365.9
Sep. 7, 2001 (GB) .................................. 0121780.1

(51) Int. Cl.
*C07H 21/04* (2006.01)
*A61K 39/04* (2006.01)
*A61K 39/02* (2006.01)

(52) U.S. Cl. ........ 536/23.7; 536/23.1; 424/9.1; 424/9.2; 424/184.1; 424/185.1; 424/234.1; 424/248.1

(58) Field of Classification Search .................. 424/9.1, 424/9.2, 184.1, 185.1, 234.1, 248.1; 536/23.1, 536/23.7
See application file for complete search history.

(56) References Cited

U.S. PATENT DOCUMENTS

| | | | |
|---|---|---|---|
| 5,783,386 | A | 7/1998 | Jacobs, Jr. et al. |
| 5,876,991 | A | 3/1999 | DeHoff et al. |
| 5,998,194 | A | 12/1999 | Summers et al. |
| 6,183,957 | B1 | 2/2001 | Cole et al. |
| 6,572,865 | B1 | 6/2003 | Nano |
| 6,573,361 | B1 | 6/2003 | Bunkers et al. |
| 6,583,266 | B1 | 6/2003 | Smith et al. |
| 6,613,553 | B1 | 9/2003 | Rock et al. |
| 6,892,139 | B2 | 5/2005 | Eisenberg et al. |
| 7,393,539 | B2 | 7/2008 | James et al. |
| 7,393,540 | B2 | 7/2008 | James et al. |
| 7,811,588 | B2 | 10/2010 | James et al. |
| 2004/0241826 | A1 | 12/2004 | James et al. |
| 2004/0253711 | A1 | 12/2004 | James et al. |
| 2004/0254349 | A1 | 12/2004 | James et al. |
| 2009/0054367 | A1 | 2/2009 | James et al. |
| 2009/0082296 | A1 | 3/2009 | James et al. |
| 2011/0091881 | A1 | 4/2011 | James et al. |

FOREIGN PATENT DOCUMENTS

| | | |
|---|---|---|
| JP | 2000-508525 | 7/2000 |
| WO | WO 92/08484 | 5/1992 |
| WO | WO 94/01441 | 1/1994 |
| WO | WO 96/17951 | 6/1996 |
| WO | WO 97/35611 | 10/1997 |
| WO | WO 98/16645 | 4/1998 |
| WO | WO 98/53076 | 11/1998 |
| WO | WO 98/55624 | 12/1998 |
| WO | WO 99/04005 | 1/1999 |
| WO | WO 99/10536 | 3/1999 |
| WO | WO 99/24067 | 5/1999 |
| WO | WO 99/57130 | 11/1999 |
| WO | WO 00/52139 | 9/2000 |
| WO | WO 02/077183 | 10/2002 |
| WO | WO 03/000721 | 1/2003 |
| WO | WO 03/004520 | 1/2003 |
| WO | WO 03/035681 | 5/2003 |

OTHER PUBLICATIONS

Cunningham, A. F. and C. L. Spreadbury. 1998. Mycobacterial stationary phase induced by low oxygen tension: cell wall thickening and localization of the 16-kilodalton alpha-crystallin homolog. J. Bacteriol. 180:801-808.

Daniel, T.M., "Soluble Mycobacterial Antigens", in, The Mycobacteria, a sourcebook, Part A, eds. Kubica and Wayne, Marcel Dekker, Inc., New York, pp. 417-465, 1984.

Stedman's Medical Dictionary, $26^{th}$ edition, Williams & Wilkins, Baltimore, MD, 1995, p. 868.

Cole, S.T., et al., "Deciphering the biology of *Mycobacterium tuberculosis* from the complete genome sequence," Nature 393:537-544, Nature Pub. Group (1998).

Murugasu-Oei, B., et al., "Upregulation of stress response genes and ABC transporters in anaerobic stationary-phase *Mycobacterium smegmatis*,"Mol. Gen. Genet. 262:677-682, Springer-Verlag (1999).

Sherman, D.R., et al., "Regulation of the *Mycobacterium tuberculosis* hypoxic response gene encoding a-crystallin," Proc. Natl. Acad. Sci. 98:7534-7539, National Academy of Sciences (Jun. 19, 2001).

Yuan, Y., et al., "The 16-kDa a-crystallin (Acr) protein of *Mycobacterium tuberculosis* is required for growth in macrophages," Proc. Natl. Acad. Sci. 95:9578-9583, National Academy of Sciences (1998).

Boon, C. et al., "Proteins of *Mycobacterium bovis* BCG induced in the wayne dormancy model", Journal of Bacteriology, vol. 183, No. 8, pp. 2672-2676, (2001).

James, B.W. et al., "The physiology and pathogenicity of *Mycobacterium tuberculosis* grown under controlled conditions in a defined medium", Journal of Applied Microbiology, vol. 88, pp. 669-677, The Society for Applied Microbiology, (2000).

(Continued)

*Primary Examiner* — Rodney P. Swartz
(74) *Attorney, Agent, or Firm* — Evan Law Group LLC

(57) ABSTRACT

A method is provided for identifying mycobacterial genes that are induced or up-regulated under continuous culture conditions defined by a dissolved oxygen tension of up to 10% air saturation measured at 37° C. when compared with a dissolved oxygen tension of at least 40% air saturation measured at 37° C. Said induced or up-regulated genes form the basis of nucleic acid vaccines, or provide targets to allow preparation of attenuated mycobacteria for vaccines against mycobacterial infections. Similarly, peptides encoded by said induced or up-regulated genes are employed in vaccines. In a further embodiment, the identified genes/peptides provide the means for identifying the presence of a mycobacterial infection in a clinical sample by nucleic acid probe or antibody detection.

24 Claims, No Drawings

OTHER PUBLICATIONS

EMBL Database Accession No. Z75555, Cole, S.T. et al., "*Mycobacterium tuberculosis* H37Rv complete genome; segment 60/162", Jun. 30, 1996.

Bacon, J. et al., "The influence of reduced oxygen abailability on pathogenicity and gene expression in *Mycobacterium tuberculosis*", Tuberculosis, vol. 4, pp. 205-217, (2004).

Chaitra, et al., "Modulation of immune responses in mice to recomnbinant antigens from PE and PPE families of proteins of *Mycobacterium tuberculosis* by the ribi adjuvant", Vaccine, vol. 25, pp. 7168-7176, (2007).

Ramakrishnan, L. et al., "Granuloma-specific expression of *Mycobacterium virulence* proteins from the glycine-rich PE-PGRS family", Science, vol. 288, pp. 1436-1439, (2000).

Vipond, et al., "Selection of novel TB vaccine candidates and their evaluation as DNA vaccines against aerosol challenge", Vaccine, vol. 24, pp. 6340-6350, (2006).

Dialog file 351, accession No. 8374384, WPI English language abstract for JP 2000-508525.

European Search Report for European application No. 02747549, Mailed Jan. 10, 2008, European Patent Office, Munich, DE.

Database Uniprot, Accession No. O53247, "Possible conserved transmembrane protein", 4 pages, (first available 1998).

Database EMBL Accession No. Z97188, "*Mycobacterium tuberculosis* H37Rv complete genome; segment 158/162", 20 pages, (1998).

Database EMBL, Accession No. AL021287, "*Mycobacterium tuberculosis* H37Rv complete genome; segment 132/162", 50 pages, (1999).

McKinney, J.D., et al., Persistence of *Mycobacterium tuberculosis* in macrophages and mice requires the glyoxylate shunt enzyme isocitrate lyase [see comments]. Nature, 2000. 406(6797): p. 735-8.

Pelicic, V., et al., Efficient allelic exchange and transposon mutagenesis in *Mycobacterium tuberculosis*. Proc Natl Acad Sci U S A, 1997. 94(20): p. 10955-60.

Lee, M.H., et al., Site-specific integration of mycobacteriophage L5: integration- proficient vectors for *Mycobacterium smegmatis, Mycobacterium tuberculosis*, and bacille Calmette-Guerin. Proc Natl Acad Sci U S A, 1991. 88(8): p. 3111-5.

McShane, H., et al., Enhanced immunogenicity of CD4(+) t-cell responses and protective efficacy of a DNA-modified vaccinia virus Ankara prime-boost vaccination regimen for murine tuberculosis. Infect Immun, 2001.69(2): p. 681-6.

Movahedzadeh, F., M.J. Colston, and E.O. Davis, Characterization of *Mycobacterium tuberculosis* LexA: recognition of a Cheo (*Bacillus*-type SOS) box. Microbiology, 1997. 143(Pt 3): p. 929-36.

Sambrook, J., E. F. Fritsch, and T. Maniatis. 1989. Molecular cloning: a laboratory manual, 2nd ed. Cold Spring Harbour Laboratory Press, Cold Spring Harbour, N. Y.

Lefever, P., O. Denis, L. De Wit, A. Tanghe, P. Vandenbussche, J. Content, and K. Huygen. 2000. Cloning of the gene encoding a 22-kilodalton cell surface antigen of *Mycobacterium bovis* BCG and analysis of its potential for DNA vaccination against tuberculosis. Infection and Immunity. 68:1040-1047.

Vordermeire, H. M., P. J. Cockle, A. O. Whelan, S. Rhodes, M. A. Chambers, D. Clifford, K. Huygen, R. Tascon, D. Lowrie, M. J. Colston, and R. G. Hewinson. 2000. Effective DNA vaccination of cattle with the *Mycobacterial antigens* MPB83 and MPB70 does not compromise the specificity of the comparative intradermal tuberculin skin test. Vaccine. 19:1246-1255.

Cheng, W., C. Hung, C. Chai, K. Hsu, L. He, C. Rice, M. Ling, and T. Wu. 2001. Enhancement of Sindbis virus self-replicating RNA vaccine potency by linkage of *Mycobacterium tuberculosis* heat shock protein 70 gene to an antigen. J. Immunol. 166:6218-6226.

Lalvani, A. et al., 2001. Enhanced contact tracing and spatial tracking of *Mycobacterium tuberculosis* infection by enumeration of antigen-specific T cells. The Lancet 357:2017-2021.

Rook, G. A. W. and B. R. Bloom. 1994. Mechanisms of pathogenesis in tuberculosis, pp. 460-485. In B. R. Bloom (ed), Tuberculosis-pathogenesis, protection and control. ASM Press, Washington DC.

Wayne, L. G. 1994. Dormancy of *Mycobacterium tuberculosis* and latency of disease. Eur. J. Clin. Microbiol. Infect. Dis. 13:908-914.

Wayne, L. G. and L. G. Hayes. 1996. An in vitro model for sequential study of shift-down of *Mycobacterium tuberculosis* through two stages of non-replicating persistence. Infect. Immun. 64:2062-2069.

Wayne, L. G. and K. Lin. 1982. Glyoxylate metabolism and adaptation of *Mycobacterium tuberculosis* to survival under anaerobic conditions. Infect. Immun. 37:1042-1049.

Lefevre, P., O. Denis, L. De Wit, A. Tanghe, P. Vandenbussche, J. Content, and K. Huygen. 2000. Cloning of the gene encoding a 22-kilodalton cell surface antigen of *Mycobacterium bovis* BCG and analysis of its potential for DNA vaccination against tuberculosis. Infection and Immunity. 68:1040-1047.

Vordermeier, H. M., P. J. Cockle, A. O. Whelan, S. Rhodes, M. A. Chambers, D. Clifford, K. Huygen, R. Tascon, D. Lowrie, M. J. Colston, and R. G. Hewinson. 2001. Effective DNA vaccination of cattle with the *Mycobacterial antigens* MPB83 and MPB70 does not compromise the specificity of the comparative intradermal tuberculin skin test. Vaccine. 19:1246-1255.

Primm et al., "The Stringent Response of *Mycobacterium tuberculosis* is Required for Long-Term Survival," Journal of Bacteriology, vol. 182, No. 17, pp. 4889-4898, (2000).

Betts, J.C., et al., "Evaluation of a nutrient starvation model of *Mycobacterium tuberculosis* persistence by gene and protein expression profiling" Mol. Microbiology, vol. 43, pp. 717-731, Blackwell Scientific Ltd (Feb. 2002).

Blanton, R., et al., "A 60K Protein is Induced by *Mycobacterium avium* Intracellulare by Nutritional Deprivation and Heat Shock," Clin. Res. 38:553A, Charles B. Slack (1990).

Cole, S.T., et al., "Deciphering the biology of *Mycobacterium tuberculosis* from the complete genome sequence (Erratum)," Nature 396:190-198, Nature Pub. Group (1998).

DeMaio, J., et al., "A stationary-phase stress-response sigma factor from *Mycobacterium tuberculosis*,"Proc. Natl. Acad. Sci. 93:2790-2794, National Academy of Sciences (1996).

Gupta, S., et al., "Proteomics analysis of carbon-starved *Mycobacterium smegmatis*: Induction of Dps-like protein," Protein Eng. 15:503-511, Oxford University Press (Jun. 2002).

Hutter, B., and Dick, T., "Analysis of the dormancy-inducible narK2 promoter in *Mycobacterium bovis* BCG," FEMS Microbiol. Letts 188:141-146, Elsevier Science B.V. (Jul. 15, 2000).

Mahenthiralingam, E., et al., Cloning and sequencing of the gene which encodes the highly inducible acetamidase of *Mycobacterium smegmatis*,'J Gen. Microbiol. 139:575-583. SGM (1993).

Michele, T.M., et al., "Exposure to Antibiotics Induces Expression of the *Mycobacterium tuberculosis* sigF Gene: Implications for Chemotherapy against Mycobacterial Persistors," Antimicrobial Agents and Chemotherapy 43:218-225, American Society for Microbiology (1999).

Rivera-Marrero, C.A., et al., "Identification of genes differentially expressed in *Mycobacterium tuberculosis* by differential display PCR," Microb. Pathog 25:307-316, Academic Press (1998).

Sambrook, J., et al., eds., Molecular Cloning: A Laboratory Manual, 2nd Edition, Cold Spring Harbor Laboratory Press, Cold Spring Harbor, NY, pp. 8.48-8.49 (1989).

Smeulders, M.J., et al., "Adaptation of *Mycobacterium smegmatis* to Stationary Phase" J. Bacteriol. 181:270-283, American Society for Microbiology (1999).

Derwent WPI English language abstract for WO 94/01441 (1994).

NCBI Entrez, GenBank Report, Accession No. P71591, from Cole, S.T., et al. (1998).

Search Report under Section 17(6) for Application No. GB 0116385.6, The Patent Office, United Kingdom, mailed May 29, 2002.

EBI Accession No. AAW73663, Alderson, M.R., et al., "*M. tuberculosis* antigen clone Tb436 protein sequence" (First entered Mar. 24, 1999).

EBI Entry, Accession No. ABU34862, Wang, L., et al., "Protein encoded by *Prokaryotic* essential gene #20389" (First entered Jun. 19, 2003).

EBI Entry, Accession No. ABU36420, Wang, L., et al., "Protein encoded by *Prokaryotic* essential gene #21947" (First entered Jun. 19, 2003).

UniProt Accession No. 053247, Q7D6A6, Cole, S.T., et al., "UniProtKB/TrEMBL entry 053633" (First entered Jun. 1, 1998).

Barker, L.P. et al., "The identification of *Mycobacterium marinum* genes differentially expressed in macrophage phagosomes using promoter fusions to green fluorescent protein", Molecular Microbiology, vol. 29, No. 5, pp. 1167-1177, (1998).
Smith, T.F. et al., "Comparison of biosequences", Advances in Applied Mathematics, vol. 2, issue 4, pp. 482-489, (1981).
Needleman, S.B. et al., "A general method applicable to the search for similarities in the amino acid sequence of two proteins", Journal of Molecular Biology, vol. 48, issue 3, pp. 443-453, (1970).
Pearson, W.R. et al., "Improved tools for biological sequence comparison", Proceedings of the National Academy of Science, vol. 85, pp. 2444-2448, (1988).
Altschul, S.F. et al., "Basic local alignment search tool", Journal of Molecular Biology, vol. 215, issue 3, pp. 403-410, (1990).
Kanehisa, M. "Use of statistical criteria for screening potential homologies in nucleic acid sequences", Nucleic Acids Research, vol. 12, No. 1, part 1, pp. 203-213, (1984).
Wetmur, J.G. et al., "Kinetics of renaturation of DNA", Journal of Molecular Biology, vol. 31, issue 3, pp. 349-370, (1968).
Mujumdar, R.B. et al., "Cyanine dye labeling reagents: Sulfoindocyanine succinimidyl esters", Bioconjugate Chemistry, vol. 4. No. 2, pp. 105-111, (1993).
Yu, H. et al., "Cyanine dye dUTP analogs for enzymatic labeling of DNA probes" Nucleic Acids Research, vol. 22, No. 15, pp. 3226-3232, (1994).
Zhu, Z. et al., "Directly labeled DNA probes using fluorescent nucleotides with different length linkers", Nucleic Acids Research, vol. 22, No. 16, pp. 3418-3422, (1994).
Jungblut, P.R. et al., "Proteomics reveals open reading frames in *Mycobacterium tuberculosis* H37Rv not predicted by genomics", Infection and Immunity, vol. 69, No. 9, pp. 5905-5907, (2001).
Flynn, J.L. et al., "Tuberculosis: Latency and reactivation", Infect. Immun., vol. 69, pp. 4195-4201, (2001).
Ohno, H. et al., "Trends in research concerning pulmonary myocobacteriosis genome and pathogenicity of tuberculosis", Resp. Moled. Med., vol. 6, pp. 202-209, (2002).
Unverified English language translation of Ohno, H. et al., "Trends in research concerning pulmonary myocobacteriosis genome and pathogenicity of tuberculosis", Resp. Moled. Med., vol. 6, pp. 202-209, (2002).
Wilson, M. et al., "Exploring drug-induced alterations in gene expression in *Mycobacteriums tuberculosis* by microarray hybridization", Proceedings of the National Academy of Science, vol. 96, pp. 12833-12838, (1999).
Ojha, A.K. et al., "High intracellular level of guanosine tetraphosphate in *Mcobacterium smegmatis* changes the morphology of the bacterium", Infection and Immunity, vol. 68, pp. 4084-4091, (2000).
Honore, N. et al., "Nucleotide sequence of the first cosmid from the *Mycobacterium leprae* genome project: structure and function of the Rif-Str regions", Molecular Micro, 7, No. 2, pp. 207-214, (1993).
Ohara, N. et al., "Isolation and amino acid sequence of the 30S ribosomal protein S19 from *Myucobacterium bovis* BCG", FEBS Letters, vol. 331, No. 1,2, pp. 9-14, (1993).
Hutter, B. et al., "Up-regulation of narX, encoding a putative "fused nitrate reductase" in anaerobic dormant *Muycobacterium bovis* BCG", FEMS Microbiology Letters, vol. 178, pp. 63-69, (1999).
Talaat, A.M. et al., "Genome-directed primers for selective labeling of bacterial transcripts for DNA microarray analysis", Nat. Biotechnology, vol. 18, pp. 679-682, (2000).
EMBL Online Database Sequence, Accession No. 053607, "Putative cellulose of *Mycobacterium tuberculosis*", created Jun. 1, 1998.
McMurray, D., "Recent progress in the development and testing of vaccines against human tuberculosis", International Journal for Parasitology, vol. 33, pp. 547-554, (2003).
von Reyn, C.F. et al., "New vaccines for the prevention of tuberculosis", Clinical Infectious Diseases, vol. 35, pp. 465-474, (2002).
Orme, I.M. et al., "Tuberculosis vaccine development: recent progress", Trends in Microbiology, vol. 9, No. 3, pp. 115-118, (2001).
Hampshire, T. et al., "Stationary phase gene expression of *Mycobacterium tuberculosis* following a progressive nutrient depletion: a model for persistent organisms?" Tuberculosis, vol. 84, pp. 228-238, (2004).
European Search Report for European Application No. 0123993.8, 3 pages, dated May 31, 2002.
European Search Report for European Application No. 0116385.6, 4 pages, dated Feb. 28, 2002.
European Search Report for European Application No. 0116385.6, 2 pages, dated May 29, 2002.
International Search Report dated Apr. 22, 2003 for PCT application No. PCT/GB02/03052.
International Search Report dated Mar. 25, 2003 for PCT application No. PCT/GB02/04718.
European Search Report for European Application No. 02747549.0, 7 pages, dated Jan. 10, 2008.

MYCOBACTERIAL ANTIGENS EXPRESSED UNDER LOW OXYGEN TENSION

CROSS REFERENCE TO RELATED APPLICATION

This application is a divisional application of U.S. application Ser. No. 10/481,265, Jul. 19, 2004 now U.S. Pat. No. 7,393,539, having international filing date Jun. 21, 2002, entitled "MYCOBACTERIAL ANTIGENS EXPRESSED UNDER LOW OXYGEN TENSION ", international application no. PCT/GB02/002845, now allowed.

The present invention relates to a method of identifying a gene in mycobacteria the expression of which gene is induced or up-regulated during continuous culture of mycobacteria under growth conditions defined by a low dissolved oxygen tension, to the isolated peptide products, variants, derivatives or fragments thereof, to antibodies that bind to said peptides, variants, derivatives or fragments, to DNA and RNA vectors that express said peptides, variants, derivatives or fragment, to attenuated mycobacteria in which the activity of at least one of said induced or up-regulated genes has been modified, to vaccines against mycobacterial infections, and to methods of detecting a mycobacterial infection.

Many microorganisms are capable of forming intracellular infections. These include: infections caused by species of *Salmonella, Yersinia, Shigella, Campylobacter, Chlamydia* and *Mycobacteria*. Some of these infections are exclusively intracellular, others contain both intracellular and extracellular components. However, it is the intracellular survival cycle of bacterial infection which is suspected as a main supportive factor for disease progression.

Generally, these microorganisms do not circulate freely in the body, for example, in the bloodstream, and are often not amenable to drug treatment regimes. Where drugs are available, this problem has been exacerbated by the development of multiple drug resistant microorganisms.

A number of factors have contributed to the problem of microbial resistance. One is the accumulation of mutations over time and the subsequent horizontal and vertical transfer of the mutated genes to other organisms. Thus, for a given pathogen, entire classes of antibiotics have been rendered inactive. A further factor has been the absence of a new class of antibiotics in recent years. The emergence of multiple drug-resistant pathogenic bacteria represents a serious threat to public health and new forms of therapy are urgently required.

For similar reasons, vaccine therapies have not proved effective against such intracellular microorganisms. Also, increased systemic concentration of antibiotics to improve bioavailability within cells may result in severe side effects.

*Mycobacterium tuberculosis* and closely related species make up a small group of mycobacteria known as the *Mycobacterium tuberculosis* complex (MTC). This group comprises four species *M. tuberculosis, M. microti, M. bovis* and *M. africanum* which are the causative agent in the majority of tuberculosis (TB) cases throughout the world.

*M. tuberculosis* is responsible for more than three million deaths a year world-wide. Other mycobacteria are also pathogenic in man and animals, for example *M. avium* subsp. *paratuberculosis* which causes Johne's disease in ruminants, *M. bovis* which causes tuberculosis in cattle, *M. avium* and *M. intracellulare* which cause tuberculosis in immunocompromised patients (eg. AIDS patients, and bone marrow transplant patients) and *M. leprae* which causes leprosy in humans. Another important mycobacterial species is *M. vaccae*.

*M. tuberculosis* infects macrophage cells within the body. Soon after macrophage infection, most *M. tuberculosis* bacteria enter, persist and replicate within cellular phagosome vesicles, where the bacteria are sequestered from host defences and extracellular factors.

It is the intracellular survival and multiplication or replication of bacterial infection which is suspected as a main supportive factor for mycobacterial disease progression.

A number of drug therapy regimens have been proposed for combating *M. tuberculosis* infections, and currently combination therapy including the drug isoniazid has proved most effective. However, one problem with such treatment regimes is that they are long-term, and failure to complete such treatment can promote the development of multiple drug resistant microorganisms.

A further problem is that of providing an adequate bioavailability of the drug within the cells to be treated. Whilst it is possible to increase the systemic concentration of a drug (eg. by administering a higher dosage) this may result in severe side effects caused by the increased drug concentration.

The effectiveness of vaccine prevention against *M. tuberculosis* has varied widely. The current *M. tuberculosis* vaccine, BCG, is an attenuated strain of *M. bovis*. It is effective against severe complications of TB in children, but it varies greatly in its effectiveness in adults particularly across ethnic groups. BCG vaccination has been used to prevent tuberculous meningitis and helps prevent the spread of *M. tuberculosis* to extra-pulmonary sites, but does not prevent infection.

The limited efficacy of BCG and the global prevalence of TB has led to an international effort to generate new, more effective vaccines. The current paradigm is that protection will be mediated by the stimulation of a Th1 immune response.

BCG vaccination in man was given orally when originally introduced, but that route was discontinued because of loss of viable BCG during gastric passage and of frequent cervical adenopathy. In experimental animal species, aerosol or intratracheal delivery of BCG has been achieved without adverse effects, but has varied in efficacy from superior protection than parenteral inoculation in primates, mice and guinea pigs to no apparent advantage over the subcutaneous route in other studies.

Conventional mycobacterial culture systems for analysing gene and protein expression profiles have been based on simple batch-type systems, such as those described in:—Sherman, D. R. et al (2001) PNAS, vol. 98, no. 13, pp. 7534-7539; Boon, C. et al (2001) J. Bacteriol, vol. 183, no. 8, pp. 2672-2676; Cunningham, A. F. et al (1998) J. Bacteriol, vol. 180, no. 4, pp. 801-808; and Murugasu-Oei, B. et al (1999) Mol. Gen. Genet, vol. 262, pp. 677-682. In these batch-type systems, mycobacterial growth follows a typical sigmoid growth curve involving an exponential growth phase and a stationary phase. The transition from exponential phase to stationary phase involves rapid and transient switches in terms of gene and protein expression, which switches are initiated by a complex set of undefined or poorly defined interactive stimuli as the mycobacteria become starved of essential nutrients.

There is therefore a need for an improved and/or alternative vaccine or therapeutic agent for combating mycobacterial infections.

According to a first aspect of the invention there is provided an isolated mycobacterial peptide or a fragment, derivative or variant thereof, wherein the peptide is encoded by a gene the expression of which is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C.

The continuous culture methods employed by the present invention are particularly advantageous when compared with batch culture methods. This is because continuous culture permits strict control of growth culture parameters such as pH, available nutrients, constant growth rate, and dissolved oxygen tension.

Thus, in use of the present invention it is possible to ensure that the principal, preferably the only mycobacterial virulence induction parameter is that of a low dissolved oxygen tension. This means that the accidental induction or up-regulation of genes that are solely responsive to environmental switches other than to a low dissolved oxygen tension may be substantially prevented. Accordingly, false-positive identification of genes whose induction or up-regulation is unrelated to a low dissolved oxygen tension may be substantially avoided.

Mycobacterial batch culture systems involve a variety of interactive stimuli as the mycobacteria become starved of essential nutrients. As a result, the mycobacteria are exposed to a complex range of starvation stimuli, which stimuli may obscure or modify the cellular effects associated with a single rapid or transient stimulus in isolation. In contrast, the present invention concerns the principal stimulus of oxygen limitation.

A further distinction between the continuous culture conditions of the present invention and batch-type systems is that the present invention employs oxygen limitation as the principal stimulus and does not involve oxygen starvation. During oxygen limitation, the mycobacteria are capable of growth and reproduction, and the present invention therefore maintains mycobacterial growth under carefully controlled environmental conditions. In contrast, mycobacteria do not substantially grow and reproduce when exposed to starvation stimuli such as those experienced with batch-type culture systems. Such starvation stimuli are typically associated with stress-type environmental conditions, and invoke mycobacterial cellular responses that are different from those associated with nutrient limitation. The dissolved oxygen tension parameter is calculated by means of an oxygen electrode and conventional laboratory techniques. Thus, 100% air saturation corresponds to a solution that is saturated with air, whereas 0% corresponds to a solution that has been thoroughly purged with an inert gas such as nitrogen. Calibration is performed under standard atmospheric pressure conditions, and with conventional air comprising approximately 21% oxygen.

The low oxygen tension induction conditions of the present invention are culture conditions which are conducive for a mycobacterium to express at least one gene which would be normally expressed in vivo during infection of the mycobacterium's natural target cell, which the present inventors believe to involve a low oxygen environment.

The terms "isolated," "substantially pure," and "substantially homogenous" are used interchangeably to describe a peptide which has been separated from components which naturally accompany it. A peptide is substantially pure when at least about 60 to 75% of a sample exhibits a single peptide sequence. A substantially pure peptide will typically comprise about 60 to 90% w/w of a protein sample, more usually about 95%, and preferably will be over about 99% pure. Peptide purity or homogeneity may be indicated by, for example, polyacrylamide gel electrophoresis of a protein sample, followed by visualizing a single polypeptide band upon staining the gel. Alternatively, higher resolution may be provided by using, for example, HPLC. A peptide is considered to be isolated when it is separated from the contaminants which accompany it in its natural state. Thus, a peptide which is chemically synthesized or synthesized in a cellular system different from the cell from which it naturally originates will be substantially free from its naturally associated components. The present invention provides peptides which may be purified from mycobacteria as well as from other types of cells transformed with recombinant nucleic acids encoding these peptides. If desirable, the amino acid sequence of the proteins of the present invention may be determined by protein sequencing methods.

The terms "peptide", "oligopeptide", "polypeptide", and "protein" are used interchangeably and do not refer to a specific length of the product. These terms embrace post-translational modifications such as glycosylation, acetylation, and phosphorylation.

The term "fragment" means a peptide having at least five, preferably at least ten, more preferably at least twenty, and most preferably at least thirty-five amino acid residues of the peptide which is the gene product of the induced or up-regulated gene in question. The fragment preferably includes an epitope of the gene product in question.

The term "variant" means a peptide or peptide "fragment" having at least seventy, preferably at least eighty, more preferably at least ninety percent amino acid sequence homology with the peptide which is the gene product of the induced or up-regulated gene in question. An example of a "variant" is a peptide or peptide fragment of an induced/up-regulated gene which contains one or more analogs of an amino acid (eg. an unnatural amino acid), or a substituted linkage. The terms "homology" and "identity" are considered synonymous in this specification. In a further embodiment, a "variant" may be a mimic of the peptide or peptide fragment, which mimic reproduces at least one epitope of the peptide or peptide fragment. The mimic may be, for example, a nucleic acid mimic, preferably a DNA mimic.

For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat'l. Acad. Sci. USA 85: 2444 (1988)], by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Wis. 53705), or by visual inspection [see Current Protocols in Molecular Biology, F. M. Ausbel et al, eds, Current Protocols, a joint venture between Greene Publishing Associates, In. And John Wiley & Sons, Inc. (1995 Supplement) Ausbubel].

Examples of algorithms suitable for determining percent sequence similarity are the BLAST and BLAST 2.0 algorithms [see Altschul (1990) J. Mol. Biol. 215: pp. 403-410; and the National Center for Biotechnology Information website].

In a preferred homology comparison, the identity exists over a region of the sequences that is at least 50 nucleotides in length.

The term "derivative" means a peptide comprising the peptide (or fragment, or variant thereof which is the gene product of the induced or up-regulated gene in question. Thus, a derivative may include the peptide in question, and a further peptide sequence which may introduce one or more additional epitopes. The further peptide sequence should preferably not interfere with the basic folding and thus conformational structure of the peptide in question. Examples of a "derivative" are a fusion protein, a conjugate, and a graft. Thus, two or more peptides (or fragments, or variants) may be joined together to form a derivative. Alternatively, a peptide (or fragment, or variant) may be joined to an unrelated molecule (eg. a peptide). Derivatives may be chemically synthesized, but will be typically prepared by recombinant nucleic acid methods. Additional components such as lipid, and/or polysaccharide, and/or polyketide components may be included.

All of the molecules "fragment", "variant" and "derivative" have a common antigenic cross-reactivity and/or substantially the same in vivo biological activity as the gene product of the induced or up-regulated gene in question from which they are derived. For example, an antibody capable of binding to a fragment, variant or derivative would be also capable of binding to the gene product of the induced or up-regulated gene in question. It is a preferred feature that the fragment, variant and derivative each possess the active site of the peptide which is the induced or up-regulated peptide in question. Alternatively, all of the above embodiments of a peptide of the present invention share a common ability to induce a "recall response" of a T-lymphocyte which has been previously exposed to an antigenic component of a mycobacterial infection.

In a preferred embodiment, the peptide is selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, and 137.

According to a second aspect of the present invention there is provided a method of identifying a mycobacterial gene the expression of which is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C., said method comprising:— culturing a first mycobacterium under continuous culture conditions defined by a dissolved oxygen tension of up to 10% air saturation measured at 37° C.;

culturing a second mycobacterium under continuous culture conditions defined by a dissolved oxygen tension of at least 40% air saturation measured at 37° C.;

obtaining first and second mRNA populations from said first and second mycobacteria, respectively;

preparing first and second cDNA populations from said first and second mRNA populations, respectively, during which cDNA preparation a detectable label is introduced into the cDNA molecules of the first and second cDNA populations;

isolating corresponding first and second cDNA molecules from the first and second cDNA populations, respectively;

comparing relative amounts of label or corresponding signal emitted from the label present in the isolated first and second cDNA molecules;

identifying a greater amount of label or signal provided by the isolated first cDNA molecule than that provided by the isolated second cDNA molecule; and identifying the first cDNA and the corresponding mycobacterial gene which is induced or up-regulated during culture of a mycobacterium under continuous culture conditions defined by a dissolved oxygen tension of up to 10% air saturation measured at 37° C.

Reference to gene throughout this specification embraces open reading frames (ORFs).

The various embodiments described for the first aspect of the present invention apply equally for the second and subsequent aspects of the present invention. "Corresponding first and second cDNA molecules from the first and second cDNA populations" refers to cDNAs having substantially the same nucleotide sequence. Thus, by isolating the cDNA copies relating to a given gene under each culture condition (ie. high oxygen, and low oxygen), it is possible to quantify the relative copy number of cDNA for that gene for each culture condition. Since each cDNA copy has been produced from an mRNA molecule, the cDNA copy number reflects the corresponding mRNA copy number for each culture condition, and thus it is possible to identify induced or up-regulated genes.

The mycobacterium is selected from the species *M. phlei, M. smegmatis, M. africanum, M. caneti, M. fortuitum, M. marinum, M. ulcerans, M. tuberculosis, M. bovis, M. microti, M. avium, M. paratuberculosis, M. leprae, M. lepraemurium, M. intracellulare, M. scrofulaceum, M. xenopi, M. genavense, M. kansasii, M. simiae, M. szulgai, M. haemophilum, M. asiaticum, M. malmoense, M. vaccae* and *M. shimoidei*. Of particular interest are members of the MTC, preferably *M. tuberculosis*. Similarly, all embodiments of the present invention may be based on the above-identified mycobacterial sources.

Suitable media for culturing mycobacteria are described in Wayne, L. G. (1994) [in Tuberculosis: Pathogenesis, Protection, and Control published by the American Society for Microbiology, pp. 73-83]. These include Middlebrook 7H9 Medium [see Barker, L. P., et al. (1998) Molec. Microbiol., vol. 29(5), pp. 1167-1177], and WO00/52139 in the name of the present Applicant.

In one embodiment, the first and second cDNA molecules are isolated from the corresponding cDNA populations by hybridisation to an array containing immobilised DNA sequences that are representative of each known gene (or ORF) within a particular mycobacterial species' genome. Thus, a first cDNA may be considered "corresponding" to a second cDNA if both cDNAs hybridise to the same immobilised DNA sequence. Alternatively, representative DNA sequences from a particular mycobacterial strain, or from a number of different species and/or strains may be employed in the array.

In another embodiment, the first and second cDNAs are prepared by incorporation of a fluorescent label. The first and second cDNAs may incorporate labels which fluoresce at different wavelengths, thereby permitting dual fluorescence and simultaneous detection of two cDNA samples.

The type of label employed naturally determines how the output of the detection method is read. When using fluorescent labels, a confocal laser scanner is preferably employed.

In use, it is preferred that those genes (ie. as represented by cDNAs in the detection assay) which are up-regulated by at least 1.5-fold under low oxygen culture conditions vis-a-vis high oxygen culture conditions are selected. In more preferred embodiments, the corresponding up-regulation selection criterium is at least 2-fold, more preferably 3-fold, most preferably 4-fold. In further embodiments up-regulation levels of at least 10-fold, preferably 50-fold may be employed.

The preferred nucleic acid and peptide sequences of the present invention are those that are up-regulated by the above-identified levels.

According to one embodiment, fluorescently labelled cDNA sequences from low and high oxygen cultured systems were allowed to hybridise with a whole mycobacterial genome array. The first cDNA population was labelled with fluorescent label A, and the second cDNA population was labelled with fluorescent label B. The array was scanned at two different wavelengths corresponding to the excitable maxima of each dye and the intensity of the emitted light was recorded. Multiple arrays were prepared for each cDNA and a mean intensity value was calculated across the two cDNA populations for each spot with each dye, against which relative induction or up-regulation was quantified.

In addition to the above mRNA isolation and cDNA preparation and labelling, genomic DNA may be isolated from the first and second mycobacteria. Thus, in a preferred embodiment, labelled DNA is also prepared from the isolated DNA. The labelled DNA may be then included on each array as a control.

As an alternative to the above-described transcriptomics based method for identifying up-regulated or induced genes, identification may be performed at the protein level rather than at the mRNA level. In more detail, protein samples may be removed from the first and second mycobacteria, and then exposed to conventional separation techniques such as SDS-PAGE or non-denaturation electrophoresis prior to conventional analysis such as by densitometer analysis. By comparing the relative amounts of a particular protein from each of the first and second mycobacteria, those proteins the production of which is up-regulated or induced under oxygen limitation may be identified.

The preferred maximum dissolved oxygen tension threshold defining the low oxygen culture condition is up to 5% air saturation measured at 37° C., more preferably up to 2% air saturation measured at 37° C., and most preferably up to 1% air saturation measured at 37° C. The corresponding minimum DOT is typically at least 0.5% air saturation measured at 37° C., preferably at least 1% air saturation measured at 37° C.

Similarly, the preferred minimum dissolved oxygen tension threshold defining the high oxygen culture condition is 45% air saturation measured at 37° C., and more preferably 50% air saturation measured at 37° C.

The pH of the culture medium is preferably maintained between pH 6 and 8, more preferably between pH 6.5 and 7.5, most preferably at about pH 6.9.

Preferred nucleic acid and peptide sequences of the present invention are those that are up-regulated under the above-identified DOT and pH conditions.

According to a third aspect of the present invention, there is provided an inhibitor of a mycobacterial peptide, wherein the peptide is encoded by a gene the expression of which is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C., and wherein the inhibitor is capable of preventing or inhibiting the mycobacterial peptide from exerting its native biological effect.

Inhibition of the mycobacterial peptide may be effected at the nucleic acid level (ie. DNA, or RNA), or at the peptide level.

In one embodiment, the inhibitor is capable of inhibiting one or more of acyl carrier protein, monooxygenase, mycobactin synthesis protein, transcription regulator, oxidoreductase, acyl CoA dehydrogenase, esterase/acetyl hydrolase, cytochrome D, methyl transferase, transaminase, PPE protein, valyl-tRNA synthetase, guanylate kinase, ketol acid reductoisomerase, ABC transporter, ATP-binding protein, protoporphyrinogen oxidase, sigma factor, pyruvate kinase, heat shock protein, and aminotransferase.

In a further embodiment, the inhibitor may be an antibiotic capable of targeting the induced or up-regulated mycobacterial gene identifiable by the present invention, or the gene product thereof. The antibiotic is preferably specific for the gene and/or gene product.

Inhibitors of the present invention may be prepared utilizing the sequence information of provided herein. For example, this may be performed by overexpressing the peptide, purifying the peptide, and then performing X-ray crystallography on the purified peptide to obtain its molecular structure. Next, compounds are created which have similar molecular structures to all or portions of the polypeptide or its substrate. The compounds may be then combined with the peptide and attached thereto so as to block one or more of its biological activities.

Also included within the invention are isolated or recombinant polynucleotides that bind to the regions of the mycobacterial chromosome containing sequences that are associated with induction/up-regulation under low oxygen tension (ie. virulence), including antisense and triplex-forming polynucleotides. As used herein, the term "binding" refers to an interaction or complexation between an oligonucleotide and a target nucleotide sequence, mediated through hydrogen bonding or other molecular forces. The term "binding" more specifically refers to two types of internucleotide binding mediated through base-base hydrogen bonding. The first type of binding is "Watson-Crick-type" binding interactions in which adenine-thymine (or adenine-uracil) and guanine-cytosine base-pairs are formed through hydrogen bonding between the bases. An example of this type of binding is the binding traditionally associated with the DNA double helix and in RNA-DNA hybrids; this type of binding is normally detected by hybridization procedures. The second type of binding is "triplex binding". In general, triplex binding refers to any type of base-base hydrogen bonding of a third polynucleotide strand with a duplex DNA (or DNA-RNA hybrid) that is already paired in a Watson-Crick manner.

In a preferred embodiment, the inhibitor may be an antisense nucleic acid sequence which is complementary to at least part of the inducible or up-regulatable gene.

The inhibitor, when in the form of a nucleic acid sequence, in use, comprises at least 15 nucleotides, preferably at least 20 nucleotides, more preferably at least 30 nucleotides, and most preferably at least 50 nucleotides.

According to a fourth aspect of the invention, there is provided an antibody which binds to a peptide encoded by a gene, or to a fragment or variant or derivative of said peptide, the expression of which gene is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C.

The antibody preferably has specificity for the peptide in question, and following binding thereto may initiate coating of the mycobacterium. Coating of the bacterium preferably leads to opsonization thereof. This, in turn, leads to the bacterium being destroyed. It is preferred that the antibody is specific for the mycobacterium (eg. species and/or strain) which is to be targeted.

Opsonization by antibodies may influence cellular entry and spread of mycobacteria in phagocytic and non-phagocytic cells by preventing or modulating receptor-mediated entry and replication in macrophages.

The peptides, fragments, variants or derivatives of the present invention may be used to produce antibodies, including polyclonal and monoclonal. If polyclonal antibodies are desired, a selected mammal (eg. mouse, rabbit, goat, horse, etc.) is immunized with an immunogenic polypeptide. Serum from the immunized animal is collected and treated according to known procedures. If serum containing polyclonal antibodies to a desired mycobacterial epitope contains antibodies to other antigens, the polyclonal antibodies may be purified by immunoaffinity chromatography. Alternatively, general methodology for making monoclonal antibodies by hybridomas involving, for example, preparation of immortal antibody-producing cell lines by cell fusion, or other techniques such as direct transformation of B lymphocytes with oncogenic DNA, or transfection with Epstein-Barr virus may be employed.

The antibody employed in this aspect of the invention may belong to any antibody isotype family, or may be a derivative or mimic thereof. Reference to antibody throughout this specification embraces recombinantly produced antibody, and any part of an antibody which is capable of binding to a mycobacterial antigen.

In one embodiment the antibody belongs to the IgG, IgM or IgA isotype families.

In a preferred embodiment, the antibody belongs to the IgA isotype family. Reference to the IgA isotype throughout this specification includes the secretory form of this antibody (ie. sIgA). The secretory component (SC) of sIgA may be added in vitro or in vivo. In the latter case, the use of a patient's natural SC labelling machinery may be employed.

In one embodiment, the antibody may be raised against a peptide from a member of the MTC, preferably against *M. tuberculosis*.

In a preferred embodiment, the antibody is capable of binding to a peptide selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, and 137 (or fragment, variant, of derivative thereof).

In a further embodiment, the antigen is an exposed component of a mycobacterial *bacillus*. In another embodiment, the antigen is a cell surface component of a mycobacterial *bacillus*.

The antibody of the present invention may be polyclonal, but is preferably monoclonal.

Without being bound by any theory, it is possible that following mycobacterial infection of a macrophage, the macrophage is killed and the bacilli are released. It is at this stage that the mycobacteria are considered to be most vulnerable to antibody attack. Thus, it is possible that the antibodies of the present invention act on released bacilli following macrophage death, and thereby exert a post-infection effect.

It is possible that the passive protection aspect (ie. delivery of antibodies) of the present invention is facilitated by enhanced accessibility of the antibodies of the present invention to antigens on mycobacterial bacilli harboured by the infected macrophages. Indeed, acr expression is low during logarithmic growth, but increases at the stationary or oxygen limiting stage, and particularly in organisms which replicate within macrophages. As acr expression appears to be necessary for mycobacterial infectivity, it is possible that antibody binding may block macrophage infection by steric hindrance or disruption of its oligomeric structure. Thus, antibodies acting on mycobacterial bacilli released from killed, infected macrophages may interfere with the spread of re-infection to fresh macrophages. This hypothesis involves a synergistic action between antibodies and cytotoxic T cells, acting early after infection, eg. γδ and NK T cells, but could later involve also CD8 and CD4 cytotoxic T cells.

According to a fifth aspect of the invention, there is provided an attenuated mycobacterium in which a gene has been modified thereby rendering the mycobacterium substantially non-pathogenic, wherein said gene is a gene the expression of which is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C.

The term "modified" refers to any genetic manipulation such as a nucleic acid or nucleic acid sequence replacement, a deletion, or an insertion which renders the mycobacterium substantially non-pathogenic. In one embodiment the entire inducible or up-regulatable gene may be deleted.

In a preferred embodiment, the gene to be modified has a wild-type coding sequence corresponding to one of the group consisting of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, and 138.

It will be appreciated that the wild-type sequences may include minor variations depending on the Database employed.

According to a sixth aspect of the invention there is provided an attenuated microbial carrier, comprising a peptide encoded by a gene, or a fragment or variant or derivative of said peptide, the expression of which gene is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C.

In use, the peptide (or fragment, variant or derivative) is either at least partially exposed at the surface of the carrier, or the carrier becomes degraded in vivo so that at least part of the peptide (or fragment, variant or derivative) is otherwise exposed to a host's immune system.

In one embodiment, the attenuated microbial carrier is selected from the group consisting of attenuated *salmonella*, attenuated vaccinia virus, attenuated fowlpox virus, or attenuated *M. bovis* (eg. BCG strain).

In a preferred embodiment, the peptide is selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135 and 137 (or fragment, variant, of derivative thereof).

According to a seventh aspect of the invention, there is provided a DNA plasmid comprising a promoter, a polyadenylation signal, and a DNA sequence that encodes a gene or a fragment or variant or derivative of said gene, the expression of which gene is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C., wherein the promoter and polyadenylation signal are operably linked to the DNA sequence. The term DNA "fragment" used in this invention will usually comprise at least about 5 codons (15 nucleotides), more usually at least about 7 to 15 codons, and most preferably at least about 35 codons. This number of nucleotides is usually about the minimal length required for a successful probe that would hybridize specifically with such a sequence.

In preferred embodiments, the DNA "fragment" has a nucleotide length which is at least 50%, preferably at least 70%, and more preferably at least 80% that of the coding sequence of the corresponding induced/up-regulated gene.

The term DNA "variant" means a DNA sequence which has substantial homology or substantial similarity to the coding sequence (or a fragment thereof) of an induced/up-regulated gene. A nucleic acid or fragment thereof is "substantially homologous" (or "substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95 to 98% of the nucleotide bases. Homology determination is performed as described supra for peptides.

Alternatively, a DNA "variant" is substantially homologous (or substantially similar) with the coding sequence (or a fragment thereof of an induced/up-regulated gene when they are capable of hybridizing under selective hybridization conditions. Selectivity of hybridization exists when hybridization occurs which is substantially more selective than total lack of specificity. Typically, selective hybridization will occur when there is at least about 65% homology over a stretch of at least about 14 nucleotides, preferably at least about 70%, more preferably at least about 75%, and most preferably at least about 90%. See, Kanehisa (1984) Nuc. Acids Res. 12:203-213. The length of homology comparison, as described, may be over longer stretches, and in certain embodiments will often be over a stretch of at least about 17 nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration (eg. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. However, the combination of parameters is much more important than the measure of any single parameter. See, eg., Wetmur and Davidson (1968) J. Mol. Biol. 31:349-370.

The term DNA "derivative" means a DNA polynucleotide which comprises a DNA sequence (or a fragment, or variant thereof) corresponding to the coding sequence of the induced/up-regulated gene and an additional DNA sequence which is not naturally associated with the DNA sequence corresponding to the coding sequence. The comments on peptide derivative supra also apply to DNA "derivative". A "derivative" may, for example, include two or more coding sequences of a mycobacterial operon that is induced during oxygen limitation. Thus, depending on the presence or absence of a non-coding region between the coding sequences, the expression product/s of such a "derivative" may be a fusion protein, or separate peptide products encoded by the individual coding regions.

The above terms DNA "fragment", "variant", and "derivative" have in common with each other that the resulting peptide products have cross-reactive antigenic properties which are substantially the same as those of the corresponding wild-type peptide. Preferably all of the peptide products of the above DNA molecule embodiments of the present invention bind to an antibody which also binds to the wild-type peptide. Alternatively, all of the above peptide products are capable of inducing a "recall response" of a T lymphocyte which has been previously exposed to an antigenic component of a mycobacterial infection.

The promoter and polyadenylation signal are preferably selected so as to ensure that the gene is expressed in a eukaryotic cell. Strong promoters and polyadenylation signals are preferred.

In a related aspect, the present invention provides an isolated RNA molecule which is encoded by a DNA sequence of the present invention, or a fragment or variant or derivative of said DNA sequence.

An "isolated" RNA is an RNA which is substantially separated from other mycobacterial components that naturally accompany the sequences of interest, eg., ribosomes, polymerases, and other mycobacterial polynucleotides such as DNA and other chromosomal sequences.

The above RNA molecule may be introduced directly into a host cell as, for example, a component of a vaccine.

Alternatively the RNA molecule may be incorporated into an RNA vector prior to administration.

The polynucleotide sequences (DNA and RNA) of the present invention include a nucleic acid sequence which has been removed from its naturally occurring environment, and recombinant or cloned DNA isolates and chemically synthesized analogues or analogues biologically synthesized by heterologous systems. The term "recombinant" as used herein intends a polynucleotide of genomic, cDNA, semisynthetic, or synthetic origin which, by virtue of its origin or manipulation: (1) is not associated with all or a portion of a polynucleotide with which it is associated in nature; or (2) is linked to a polynucleotide other than that to which it is linked in nature; and (3) does not occur in nature. This artificial combination is often accomplished by either chemical synthesis means, or by the artificial manipulation of isolated segments of nucleic acids, eg., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

In embodiments of the invention the polynucleotides may encode a peptide which is induced or up-regulated under low oxygen tension. A nucleic acid is said to "encode" a peptide if, in its native state or when manipulated, it can be transcribed and/or translated to produce the peptide or a fragment or variant or derivative thereof. The anti-sense strand of such a nucleic acid is also said to encode the sequence.

Also contemplated within the invention are expression vectors comprising the polynucleotide of interest. Expression vectors generally are replicable polynucleotide constructs that encode a peptide operably linked to suitable transcriptional and translational regulatory elements. Examples of regulatory elements usually included in expression vectors are promoters, enhancers, ribosomal binding sites, and transcription and translation initiation and termination sequences. These regulatory elements are operably linked to the sequence to be translated. A nucleic acid sequence is operably linked when it is placed into a functional relationship with another nucleic acid sequence. For instance, a promoter is operably linked to a coding sequence if the promoter affects its transcription or expression. Generally, operably linked means that the DNA sequences being linked are contiguous and, where necessary to join two protein coding regions, contiguous and in reading frame. The regulatory elements employed in the expression vectors containing a polynucleotide encoding a virulence factor are functional in the host cell used for expression.

The polynucleotides of the present invention may be prepared by any means known in the art. For example, large amounts of the polynucleotides may be produced by replication in a suitable host cell. The natural or synthetic DNA fragments coding for a desired fragment will be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines. The polynucleotides of the present invention may also be produced by chemical synthesis, e.g., by the phosphoramidite method or the triester method, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence. DNA constructs prepared for introduction into a prokaryotic or eukaryotic host will typically comprise a replication system recognized by the host, including the intended DNA fragment encoding the desired peptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals from polypeptides secreted from the host cell of choice may also be included where appropriate, thus allowing the protein to cross and/or lodge in cell membranes, and thus attain its functional topology or be secreted from the cell. Appropriate promoter and other necessary vector sequences are selected so as to be functional in the host, and may, when appropriate, include those naturally associated with mycobacterial genes. Promoters such as the trp, lac and phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and others.

Appropriate non-native mammalian promoters may include the early and late promoters from SV40 or promoters derived from murine moloney leukemia virus, mouse mammary tumour virus, avian sarcoma viruses, adenovirus II, bovine papilloma virus or polyoma. In addition, the construct may be joined to an amplifiable gene (e.g., DHFR) so that multiple copies of the gene may be made. While such expression vectors may replicate autonomously, they may less preferably replicate by being inserted into the genome of the host cell. Expression and cloning vectors will likely contain a selectable marker, a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, e.g. ampicillin, neomycin, methotrexate, etc.; (b) complement auxotrophic deficiencies; or (c) supply critical nutrients not available from complex media, e.g. the gene encoding D-alanine racemase for Bacilli. The choice of appropriate selectable marker will depend on the host cell. The vectors containing the nucleic acids of interest can be transcribed in vitro and the resulting RNA introduced into the host cell (e.g., by injection), or the vectors can be introduced directly into host cells by methods which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome). The cells into which have been introduced nucleic acids described above are meant to also include the progeny of such cells. Large quantities of the nucleic acids and peptides of the present invention may be prepared by expressing the nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or *Pseudomonas* may also be used. Mammalian or other eukaryotic host cells, such as those of yeast, filamentous fungi, plant, insect, amphibian or avian species, may also be useful for production of the proteins of the present invention. Propagation of mammalian cells in culture is per se well known. Examples of commonly used mammalian host cell lines are VERO and HeLa cells, Chinese hamster ovary (CHO) cells, and WI38, BHK, and COS cell lines, although other cell lines may be appropriate, e.g., to provide higher expression, desirable glycosylation patterns. Clones are selected by using markers depending on the mode of the vector construction. The marker may be on the same or a different DNA molecule, preferably the same DNA molecule. The transformant may be screened or, preferably, selected by any of the means well known in the art, e.g., by resistance to such antibiotics as ampicillin, tetracycline.

The polynucleotides of the invention may be inserted into the host cell by any means known in the art, including for example, transformation, transduction, and electroporation. As used herein, "recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. "Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

In one embodiment, a DNA plasmid or RNA vector may encode a component of the immune system which is specific to an immune response following challenge with a peptide, wherein said peptide is encoded by a mycobacterial gene which is induced or up-regulated during oxygen limitation of mycobacterial growth.

An example of such a component is an antibody to the peptide product of an induced or up-regulated gene. Thus, in one embodiment, the nucleic acid sequence (eg. DNA plasmid or RNA vector) encodes the antibody in question.

An eighth aspect provides use of a peptide, an inhibitor, an antibody, an attenuated mycobacterium, an attenuated microbial carrier, a DNA sequence corresponding to the coding sequence of an induced or up-regulated gene or a fragment or variant or derivative of said DNA sequence, a DNA plasmid comprising said DNA sequence or said fragment or variant or derivative, an RNA sequence encoded by said DNA sequence or said fragment or variant or derivative, and/or an RNA vector comprising said RNA sequence according to the present invention, in the manufacture of a medicament for treating or preventing a mycobacterial infection.

The term "preventing" includes reducing the severity/intensity of, or initiation of, a mycobacterial infection.

The term "treating" includes post-infection therapy and amelioration of a mycobacterial infection.

In a related aspect, there is provided a method of treating or preventing a mycobacterial infection, comprising administration of a medicament selected from the group consisting of a peptide, an inhibitor, an antibody, an attenuated mycobacterium, an attenuated microbial carrier, a DNA sequence corresponding to the coding sequence of an induced or up-regulated gene or a fragment or variant or derivative of said DNA sequence, a DNA plasmid comprising said DNA sequence or said fragment or variant or derivative, an RNA sequence encoded by said DNA sequence or said fragment or variant or derivative, and/or an RNA vector comprising said RNA sequence according to the present invention, to a patient.

The medicament may be administered by conventional routes, eg. intravenous, intraperitoneal, intranasal routes.

The immunogenicity of the epitopes of the peptides of the invention may be enhanced by preparing them in mammalian or yeast systems fused with or assembled with particle-forming proteins such as, for example, that associated with hepatitis B surface antigen. Vaccines may be prepared from one or more immunogenic peptides of the present invention. Typically, such vaccines are prepared as injectables, either as liquid solutions or suspensions; solid forms suitable for solution in, or suspension in, liquid prior to injection may also be prepared. The preparation may also be emulsified, or the peptide encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-s n-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The vaccines are conventionally administered parenterally, by injection, for example, either subcutaneously or intramuscularly. Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%. The peptides may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each subject. The vaccine may be given in a single dose schedule, or preferably in a multiple dose schedule. A multiple dose schedule is one in which a primary course of vaccination may be with 1-10 separate doses, followed by other doses given at subsequent time intervals required to maintain and or re-enforce the immune response, for example, at 1-4 months for a second dose, and if needed, a subsequent dose(s) after several months. The dosage regimen will also, at least in part, be determined by the need of the individual and be dependent upon the judgment of the practitioner. In addition, the vaccine containing the immunogenic mycobacterial antigen(s) may be administered in conjunction with other immunoregulatory agents, for example, immunoglobulins, as well as antibiotics.

The outcome of administering antibody-containing compositions may depend on the efficiency of transmission of antibodies to the site of infection. In the case of a mycobacterial respiratory infection (eg. a *M. tuberculosis* infection), this may be facilitated by efficient transmission of antibodies to the lungs.

In one embodiment the medicament may be administered intranasally (i.n.). This mode of delivery corresponds to the route of delivery of a *M. tuberculosis* infection and, in the case of antibody delivery, ensures that antibodies are present at the site of infection to combat the bacterium before it becomes intracellular and also during the period when it spreads between cells.

An intranasal composition may be administered in droplet form having approximate diameters in the range of 100-5000 μm, preferably 500-4000 μm, more preferably 1000-3000 μm. Alternatively, in terms of volume, the droplets would be in the approximate range of 0.001-100 μl, preferably 0.1-50 μl, more preferably 1.0-25 μl.

Intranasal administration may be achieved by way of applying nasal droplets or via a nasal spray.

In the case of nasal droplets, the droplets may typically have a diameter of approximately 1000-3000 μm and/or a volume of 1-25 μl.

In the case of a nasal spray, the droplets may typically have a diameter of approximately 100-1000 μm and/or a volume of 0.001-1 μl.

It is possible that, following i.n. delivery of antibodies, their passage to the lungs is facilitated by a reverse flow of mucosal secretions, although mucociliary action in the respiratory tract is thought to take particles within the mucus out of the lungs. The relatively long persistence in the lungs' lavage, fast clearance from the bile and lack of transport to the saliva of some antibodies suggest the role of mucosal site specific mechanisms.

In a different embodiment, the medicament may be delivered in an aerosol formulation. The aerosol formulation may take the form of a powder, suspension or solution.

The size of aerosol particles is one factor relevant to the delivery capability of an aerosol. Thus, smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli.

The aerosol particles may be delivered by way of a nebulizer or nasal spray.

In the case of aerosol delivery of the medicament, the particles may have diameters in the approximate range of 0.1-50 μm, preferably 1-25 μm, more preferably 1-5 μm.

The aerosol formulation of the medicament of the present invention may optionally contain a propellant and/or surfactant.

By controlling the size of the droplets which are to be administered to a patient to within the defined range of the present invention, it is possible to avoid/minimise inadvertent antigen delivery to the alveoli and thus avoid alveoli-associated pathological problems such as inflammation and fibrotic scarring of the lungs.

I.n. vaccination engages both T and B cell mediated effector mechanisms in nasal and bronchus associated mucosal tissues, which differ from other mucosae-associated lymphoid tissues.

The protective mechanisms invoked by the intranasal route of administration may include: the activation of T lymphocytes with preferential lung homing; upregulation of co-stimulatory molecules, eg. B7.2; and/or activation of macrophages or secretory IgA antibodies.

Intranasal delivery of antigens may facilitate a mucosal antibody response is invoked which is favoured by a shift in the T cell response toward the Th2 phenotype which helps antibody production. A mucosal response is characterised by enhanced IgA production, and a Th2 response is characterised by enhanced IL-4 production.

Intranasal delivery of mycobacterial antigens allows targeting of the antigens to submucosal B cells of the respiratory system. These B cells are the major local IgA-producing cells in mammals and intranasal delivery facilitates a rapid increase in IgA production by these cells against the mycobacterial antigens.

In one embodiment administration of the medicament comprising a mycobacterial antigen stimulates IgA antibody production, and the IgA antibody binds to the mycobacterial antigen. In another embodiment, a mucosal and/or Th2 immune response is stimulated.

In another embodiment monoclonal antibodies, in particular, may be used to raise anti-idiotype antibodies. Anti-idiotype antibodies are immunoglobulins which carry an "internal image" of the antigen of the infectious agent against which protection is desired. These anti-idiotype antibodies may also be useful for treatment, vaccination and/or diagnosis of mycobacterial infections.

According to a ninth embodiment, the peptides of the present invention and antibodies to them are useful in immunoassays to detect the presence of antibodies to mycobacteria, or the presence of the virulence associated antigens in biological samples. Design of the immunoassays is subject to a great deal of variation, and many formats are known in the art. The immunoassay may utilize at least one epitope derived from a peptide of the present invention. In one embodiment, the immunoassay uses a combination of such epitopes. These epitopes may be derived from the same or from different bacterial peptides, and may be in separate recombinant or natural peptides, or together in the same recombinant peptides.

An immunoassay may use, for example, a monoclonal antibody directed towards a virulence associated peptide epitope(s), a combination of monoclonal antibodies directed towards epitopes of one mycobacterial antigen, monoclonal antibodies directed towards epitopes of different mycobacterial antigens, polyclonal antibodies directed towards the same antigen, or polyclonal antibodies directed towards different antigens. Protocols may be based, for example, upon competition, or direct reaction, or sandwich type assays. Protocols may also, for example, use solid supports, or may be by immunoprecipitation. Most assays involve the use of labelled antibody or polypeptide; the labels may be, for example, enzymatic, fluorescent, chemiluminescent, radioactive, or dye molecules. Assays which amplify the signals from the probe are also known; examples of which are assays which utilize biotin and avidin, and enzyme-labelled and mediated immunoassays, such as ELISA assays. Typically, an immunoassay for an antibody(s) to a peptide, will involve selecting and preparing the test sample suspected of containing the antibodies, such as a biological sample, then incubating it with an antigenic (i.e., epitope-containing) peptide(s) under conditions that allow antigen-antibody complexes to form, and then detecting the formation of such complexes. The immunoassay may be of a standard or competitive type. The peptide is typically bound to a solid support to facilitate separation of the sample from the peptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immulon), diazotized paper, nylon membranes, activated beads, and Protein A beads. For example, Dynatech Immulon microtiter plates or 60 mm diameter polystyrene beads (Precision Plastic Ball) may be used. The solid support containing the antigenic peptide is typically washed after separating it from the test sample, and prior to detection of bound antibodies. Complexes formed comprising antibody (or, in the case of competitive assays, the amount of competing antibody) are detected by any of a number of known techniques, depending on the format. For example, unlabelled antibodies in the complex may be detected using a conjugate of antixenogeneic Ig complexed with a label, (e.g., an enzyme label). In immunoassays where the peptides are the analyte, the test sample, typically a biological sample, is incubated with antibodies directed against the peptide under conditions that allow the formation of antigen-antibody complexes. It may be desirable to treat the biological sample to release putative bacterial components prior to testing. Various formats can be employed. For example, a "sandwich assay" may be employed, where antibody bound to a solid support is incubated with the test sample; washed; incubated with a second, labelled antibody to the analyte, and the support is washed again. Analyte is detected by determining if the second antibody is bound to the support. In a competitive format, a test sample is usually incubated with antibody and a labelled, competing antigen is also incubated, either sequentially or simultaneously. Also included as an embodiment of the invention is an immunoassay kit comprised of one or more peptides of the invention, or one or more antibodies to said peptides, and a buffer, packaged in suitable containers.

As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumours, organs, and also samples of in vitro cell culture constituents (including but not limited to conditioned medium resulting from the growth of cells in cell culture medium, putatively virally infected cells, recombinant cells, and cell components).

In a related diagnostic assay, the present invention provides nucleic acid probes for detecting a mycobacterial infection.

Using the polynucleotides of the present invention as a basis, oligomers of approximately 8 nucleotides or more can be prepared, either by excision from recombinant polynucleotides or synthetically, which hybridize with the mycobacterial sequences, and are useful in identification of mycobacteria. The probes are a length which allows the detection of the induced or up-regulated sequences by hybridization. While 6-8 nucleotides may be a workable length, sequences of 10-12 nucleotides are preferred, and at least about 20 nucleotides appears optimal. These probes can be prepared using routine methods, including automated oligonucleotide synthetic methods. For use as probes, complete complementarity is desirable, though it may be unnecessary as the length of the fragment is increased. For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are usually labeled. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies. The probes may be made completely complementary to the virulence encoding polynucleotide. Therefore, usually high stringency conditions are desirable in order to prevent false positives. The stringency of hybridization is determined by a number of factors during hybridization and during the washing procedure, including temperature, ionic strength, length of time, and concentration of formamide. It may be desirable to use amplification techniques in hybridization assays. Such techniques are known in the art and include, for example, the polymerase chain reaction (PCR) technique. The probes may be packaged into diagnostic kits. Diagnostic kits include the probe DNA, which may be labeled; alternatively, the probe DNA may be unlabeled and the ingredients for labeling may be included in the kit in separate containers. The kit may also contain other suitably packaged reagents and materials needed for the particular hybridization protocol, for example, standards, as well as instructions for conducting the test.

In a preferred embodiment, a peptide (or fragment or variant or derivative) of the present invention is used in a diagnostic assay to detect the presence of a T-lymphocyte which T lymphocyte has been previously exposed to an antigenic component of a mycobacterial infection in a patient.

In more detail, a T-lymphocyte which has been previously exposed to a particular antigen will be activated on subsequent challenge by the same antigen. This activation provides a means for identifying a positive diagnosis of mycobacterial infection. In contrast, the same activation is not achieved by a T-lymphocyte which has not been previously exposed to the particular antigen.

The above "activation" of a T-lymphocyte is sometimes referred to as a "recall response" and may be measured, for example, by determining the release of interferon (eg. IFN-Y) from the activated T-lymphocyte. Thus, the presence of a mycobacterial infection in a patient may be determined by the release of a minimum concentration of interferon from a T-lymphocyte after a defined time period following in vitro challenge of the T-lymphocyte with a peptide (or fragment or variant or derivative) of the present invention.

In use, a biological sample containing T-lymphocytes is taken from a patient, and then challenged with a peptide (or fragment, variant, or derivative thereof of the present invention.

The above T-lymphocyte diagnostic assay may include an antigen presenting cell (APC) expressing at least one major histocompatibility complex (MHC) class II molecule expressed by the patient in question. The APC may be inherently provided in the biological sample, or may be added exogenously. In one embodiment, the T-lymphocyte is a CD4 T-lymphocyte.

EXAMPLE 1

Continuous Culture of Mycobacteria

Materials and Methods

Strain

Studies were performed with *M. tuberculosis* strain H37Rv (NCTC cat. no. 7416)—a representative strain of *M. tuberculosis*. Stock cultures were grown on Middlebrook 7H10+OADC for 3 weeks at 37±2° C. harvested and stored at −70° C. as a dense suspension in deionised water.

Culture Medium

A chemically defined culture medium was developed, and was designated CAMR Mycobacterial Medium (see WO00/52139). The medium was prepared with high quality water from a Millepore water purification system and filter sterilised by passage through a 0.07 μm pore size cellulose acetate membrane filter capsule (Sartorius Ltd). Middlebrook 7H10+OADC agar was used to prepare inoculum cultures, enumerate the number of culturable bacteria in chemostat samples, and to assess culture purity.

Culture Apparatus

Culture experiments were performed in a one litre glass vessel operated at a working volume of 500 ml. The culture was agitated by a magnetic bar placed in the culture vessel coupled to a magnetic stirrer positioned beneath the vessel. Culture conditions were continuously monitored and controlled by an Anglicon Microlab Fermentation System (Brighton Systems, Newhaven), linked to sensor probes inserted into the culture through sealed ports in the top plate. The oxygen concentration was monitored with a galvanic oxygen electrode (Uniprobe, Cardiff) and was controlled through feedback control of the agitation rate. Temperature was monitored by an Anglicon temperature probe, and maintained by a heating pad positioned beneath the culture vessel. Culture pH was measured using an Ingold pH electrode (Mettler-Toledo, Leicester) and controlled by automatic addition of either sodium hydroxide (0.5 M) or sulphuric acid (0.5 M). For continuous culture, the culture system was operated by controlling nutrient addition from the medium reservoir and a constant culture volume was maintained by an overflow tube fitted to the side of the vessel.

Inoculation and Culture

The vessel was filled with 350 ml of sterile culture medium and parameters were allowed to stabilise at 37° C.±2° C., pH 6.9±0.2 and a dissolved oxygen tension of approximately 70% air saturation. A dense inoculum suspension was prepared by resuspending Middlebrook agar cultures, grown at 37±2° C. for 3 weeks, in sterile deionised water. The inoculum was aseptically transferred to the culture vessel, to provide an initial culture turbidity of approximately 0.25 at 540 nm. After inoculation the culture was allowed to establish for approximately 50 h. As the culture entered exponential growth, a further 100 ml medium was added and batch growth was monitored by optical density and viable count determination.

For continuous culture, the culture was inoculated and allowed to establish for approximately 50 h as detailed. The culture was then operated in fed batch mode for 48 h with medium addition (approx. 100 ml) as the culture entered exponential growth and 24 h later. Continuous culture was then initiated at a dilution rate of 0.03 $h^{-1}$ [equivalent to a mean generation time (MGT) of 24 h]. Culture parameters were maintained at a dissolved oxygen tension (DOT) of 50% (v/v) air saturation at 37±2° C. and pH 6.9±0.2 for "high" dissolved oxygen culture conditions, and a DOT of 1% (v/v) air saturation at 37±2° C. and pH 6.9±0.2 for "low" dissolved oxygen culture conditions. Growth was monitored by optical density, dry weight and viable count determination.

Continuous Culture

Steady-state growth, at a MGT of 24 h, was normally reached 10 days after initiation of continuous culture. Cultures were dense suspensions containing approximately $5\times10^8$ cfu $ml^{-1}$ and a biomass yield of approximately 1.2 $gl^{-1}$ cell dry weight. Cells were short rods 2 to 3 μm long with occasional clumps of up to 20 cells. Glycerol, the principal carbon source was not depleted during steady state growth, with a residual concentration of 1.25 $gl^{-1}$. Tween® 80 was present in an amount of 0.1% and enabled the growth of *M. tuberculosis* in a homogeneous suspension made up substantially of single cells at a growth rate conducive to chemostat culture. Cultures grown in the absence of Tween® 80 formed large clumps and surface pellicles and continuous culture was not possible.

EXAMPLE 2

Virulence Data

Cultures grown at a DOT of 50% were virulent in the guinea pig model of infection as determined by their ability to establish infection after aerosol delivery, proliferate in the lung, disseminate to the spleen and cause histopathology indicative of primary pulmonary tuberculosis.

A new virulence assay has developed to assess and compare the virulence of culture samples based on their ability to cause a disseminated infection. The assay determined the dose required in the lung at day 0 in order to produce a disseminated infection with 3.0 $\log_{10}$ cfu in the spleen at day 16. This value was termed the infectivity index.

Using this assay, the infectivity of cells grown in aerobic chemostat culture was comparable to that of cells grown on standard Middlebrook agar. This supports our previous finding that cells grown in our culture system are virulent and there is no loss in virulence associated with growth in our culture system (see Table 1).

The infectivity index for cells grown at low oxygen tension (1% DOT) was significantly lower than that for aerobic cells indicating that growth at low oxygen tension enhances the virulence of *M. tuberculosis* i.e. a significantly lower dose is required in order to produce a comparable infection.

TABLE 1

| Sample | Infectivity Index* |
|---|---|
| Plate | 2.0 |
| Aerobic chemostat (50% DOT) | 2.1, 2.2 |
| Low oxygen chemostat (1% DOT) | 1.4, 1.5 |

*Values are the dose $\log_{10}$ required in the lung at day 0 in order to produce a disseminated infection with 3.0 $\log_{10}$ in the spleen at day 16.

EXAMPLE 3

RNA Extraction from *M. tuberculosis* for Microarray Analysis

Materials and Methods

Trizol (Life Technologies)—formulation of phenol and guanidine thiocyanate.

GTC lysis solution containing: 5M guanidine thiocyanate, 0.5% N-lauryl sarcosine, 25 mM tri-sodium citrate, 0.1M 2-mercaptoethanol, and 0.5% Tween 80.

Chloroform

Isopropanol 3M sodium acetate

70% Ethanol microfuge ribolyser

Sterile plasticware-Falcon tubes, screw capped eppendorfs, gilson tips—all RNase free Glassware—baked at 160° C. for at least 16 hours Method Steps performed at Containment level 3; within a Class III microbiological safety cabinet.

Remove 10 or 20 ml of culture ($10^9$/ml) and immediately add this to 4 volumes of GTC lysis buffer in a plastic specimen pot. Seal the pot tightly.

Incubate the cells in GTC lysis buffer for 1 hour at room temperature. Surface decontaminate the plastic pot with 5% Hycolin for 5 minutes. Transfer the sample to the pass box and place it into a plastic carry tin with a sealable lid. Close the container securely and transport it to a non-toxic cabinet CL3 cabinet.

Equally distribute the lysis mixture between Falcon tubes. Place these tubes into centrifuge buckets and seal the buckets tightly. Surface-decontaminate the buckets for 5 minutes with 5% Hycolin. Then transfer them to the centrifuge (Baird and Tatlock Mark IV refrigerated bench-top centrifuge). Spin the tubes at 3,000 rpm for 30 minutes.

Return the unopened buckets to the cabinet. Remove the centrifuge tubes and pour the supernatant into a waste bottle for GTC lysis buffer.

Resuspend each pellet in 1 ml of Trizol (formulation of phenol and GTC cat no. 15596-026). The manufacturers guidelines recommend lysing cells by repetitive pipetting. Although this action alone will not lyse *M. tuberculosis*, it is important to completely resuspend the pellet in Trizol.

Transfer 1 ml of cells into a FastRNA tube and ribolyse it at power setting 6.5 for 45 seconds.

Leave the tube to incubate at room temperature for 5 minutes.

Remove the aqueous layer from the tube and add this to 200 µl of chloroform in a screw-capped eppendorf tube. Shake each tube vigorously for about 15 seconds. Incubate for 2-3 minutes at room temperature.

Spin the tube at 13,000 rpm for 15 minutes. Following centrifugation, the liquid separates into red phenol/chloroform phase, an interface, and a clear aqueous phase.

Carefully remove the aqueous phase and transfer it to a fresh eppendorf tube containing 500 µl of chloroform/isoamyl alcohol (24:1). Spin the tubes at 13,000 rpm for 15 minutes.

Transfer the aqueous phase to an eppendorf tube containing 50 µl of sodium acetate and 500 µl of isopropanol.

Surface decontaminate the eppendorf tube with 5% Hycolin for 5 minutes. Remove the tube from the CL3 laboratory and continue with the procedure in laboratory 157.

Steps performed at Containment level 2:

Precipitate the RNA at −70° C. for at least 30 minutes—can do this step overnight.

Spin the precipitated RNA down at 13,000 rpm for 10 minutes. Remove the supernatant and wash the pellet in 70% ethanol. Repeat centrifugation.

Remove the 70% ethanol and air-dry the pellet. Dissolve the pellet in RNAse free water.

Freeze the RNA at −70° C. to store it.

EXAMPLE 4 cDNA Labelling, Hybridisation, and Analysis

Preparation of the Arrays

PCR-amplified products are generated from *M. tuberculosis* genomic DNA using ORF-specific primers. Each gene of the genome is represented. These are spotted in a grid onto a standard glass microscope slide using a BioRobotics microgrid robot (MWG Biotech) at a resolution of >4000 spots/$cm^2$.

Fluorescently-labelled cDNA is transcribed from RNA which has been isolated from bacteria grown under different environmental conditions. The cDNA is labelled by incorporation of either Cy3 or Cy5 labelled dCTP (Dyes are supplied by Amersham Pharmacia Biotech). Dual fluorescence is used, allowing simultaneous detection of two cDNA samples. The output of the arrays is read using a confocal laser scanner (Affymetrix 428 scanner from MWG Biotech). More detailed information can be found in Mujumdar, R.B. (1993) Bioconjugate Chemistry, 4(2), pp. 105-111; Yu, H. (1994) Nucl. Acids Res. 22, pp. 3226-3232; and Zhu, Z. (1994) Nucl. Acids Res. 22, pp. 3418-3422.

Labelling and Hybridisation of the cDNA

1. Cy3/Cy5 Label cDNA

Prepare one Cy3 and one Cy5 labelled cDNA sample per microarray slide.

| | | |
|---|---|---|
| Each sample: | RNA | 2-10 µg |
| | Random primers (3 µg/µl) | 2 µl |
| | $H_2O$ | to 11 µl |

Heat at 95° C. for 5 min, snap cool on ice and briefly centrifuge.

| | | |
|---|---|---|
| Add to each: | 5x First Strand Buffer | 5 µl |
| | DTT (100 mM) | 2.5 µl |
| | dNTPs (5 mM dA/G/TTP, 2 mM dCTP) | 2.3 µl |
| | Cy3 OR Cy5 dCTP | 1.7 µl |
| | SuperScript II (200 U/µl | 2.5 µl |

Incubate at 25° C. for 10 min followed by 42° C. for 90 min.

2. Prehybridise Slide

Mix the prehybridisation solution in a coplin jar and incubate at 60° during the labelling reaction to equilibriate.

| | | |
|---|---|---|
| Prehybridisation: | 20xSSC | 8.75 ml (3.5xSSC) |
| | 20% SDS | 250 µl (0.1% SDS) |
| | BSA (100 mg/ml) | 5 ml (10 mg/ml) |
| | $H_2O$ | to 50 ml |

Incubate the microarray slide in the pre-heated prehybridisation solution at 60° C. for 20 min. Rinse slide in $H_2O$ for 1 min followed by rinse in propan-2-ol for 1 min and centrifuge slide in 50 ml centrifuge tube at 1500 rpm for 5 min to dry. Store slide until hybridisation.

3. Purify Cy3/Cy5 Labelled cDNA

Combine the Cy3 and Cy5 labelled cDNA samples together in a single tube.

| | | |
|---|---|---|
| Add: | 3M sodium acetate pH 4.8 | 5 µl (0.1 volume) |
| | Propan-2-ol | 40 µl (0.8 volume) |

Wrap the tube in foil and incubate at room temperature for 30 min. Centrifuge at 13000 rpm for 20 min and remove supernatant. Rinse pellet with 100 µl 70% ethanol and centrifuge at 13000 rpm for 5 min. Remove the supernatant and air dry the pellet for 10 min. Resuspend the pellet in 10.5 µl $H_2O$.

4. Hybridise Slide with Cy3/Cy5 Labelled cDNA

Place the prehybridise microarray slide in the hybridisation cassette and add two 15 µl aliquots of $H_2O$ to the wells in the cassette. Mix resuspended Cy3/Cy5 labelled cDNA sample with hybridisation solution.

| | | |
|---|---|---|
| Hybridisation: | Cy3/Cy5 labelled cDNA sample | 10.5 µl |
| | 20xSSC | 3.2 µl (4xSSC) |
| | 2% SDS | 2.3 µl (0.3% SDS) |

Heat hybridisation solution at 95° C. for 2 min. Do NOT snap cool on ice but allow to cool slightly and briefly centrifuge. Pipette the hybridisation solution onto the slide at the edge of the arrayed area avoiding bubble formation. Using forceps carefully drag the edge of a cover slip along the surface of the slide towards the arrayed area and into the hybridisation solution at the edge of the array. Carefully lower the cover slip down over the array avoiding any additional movement once in place. Seal the hybridisation cassette and submerge in a water bath at 60° C. for 16-20 h.

5. Wash Slide

Remove microarray slide from hybridisation cassette and initially wash slide carefully in staining trough of Wash A to remove cover slip. Once cover slip is displaced place slide(s) in slide rack and continue agitating in Wash A for a further 2 min.

| | | |
|---|---|---|
| Wash A: | 20xSSC | 20 ml (1xSSC) |
| | 20% SDS | 1 ml (0.05% SDS) |
| | $H_2O$ | to 400 ml |

Transfer slide(s) to a clean slide rack and agitate in first trough of Wash B for 2 min. Wash in second trough of Wash B with agitation for 2 min.

| | | |
|---|---|---|
| Wash B (x2): | 20xSSC | 1.2 ml (0.06xSSC) |
| | $H_2O$ | to 400 ml |

Place slide into a 50 ml centrifuge tube and centrifuge at 1500 rpm for 5 mins to dry slide.

6. Scan Slide

Scan slide using a ScanArray 3000 dual-laser confocal scanner and analyse data.

Reagents

Random primers (3 μl μl) [Life Technol., Cat# 48190-011]

dNTPs (5 mM dATP, dGTP, dTTP, & 2 mM dCTP) [Life Technol., Cat# 10297-018]

Cy3 dCTP Fluorolink [Amersham Pharmacia Biotech, Cat# PA53021]

Cy5 dCTP Fluorolink [Amersham Pharmacia Biotech, Cat# PA55021]

SuperScript II Reverse Transcriptase (200 U/μl) [Life Technol., Cat# 18064-014]

5× First Strand Buffer [Life Technol., supplied with Cat# 18064-014]

Dithiothreitol (DTT) (100 mM) [Life Technol., supplied with Cat# 18064-014]

Bovine serum albumin (BSA) Fraction V 96-99% (100 mg/ml) [Sigma, Cat# A9418]

General: 20×SSC

20% SDS 3M sodium acetate pH4.8

Propan-2-ol

70% ethanol

2% SDS

Equipment

Microarray hybridisation cassette [Telechem International (Arraylt.com), Cat# AHC-1]

Coplin staining jar [Fisher Scientific, Cat# MNK-820-H]

3× slide staining troughs (Fisher Scientific, Cat# MNK-836-K]

2× slide staining racks [Fisher Scientific, Cat# MNK-841-K]

Glass cover slips 22×22 mm [BDH, Cat# 406/0187/33].

Scanning and Analysis

The slides were scanned using an Affymetrix 428 scanner. The raw data were initially analysed in software known as ImaGene, which was supplied with the scanner. The scanned images were then transferred to another software package known as GeneSpring. This is a very powerful tool, which draws information from many databases allowing the complete analysis of the expression of each gene.

Results

Total RNA was extracted from steady state chemostat culture according to the protocol described above. RNA microarray hybridisation was performed in duplicate to compare RNA extracted from *M. tuberculosis* grown in aerobic (50% DOT) and low oxygen environments (1% DOT).

The two expression profiles were analysed and compared. Genes that appeared to be up regulated at least 1.5-fold under low oxygen conditions were selected for identification.

Nucleic acid sequences are given from the transcription start site to the stop codon.

EXAMPLE 5

Delete One or More of the Genes from *M. tuberculosis* in Order to Attenuate its Virulence while Retaining Immunogenicity One or more genes that are identified may be disrupted using allelic exchange. In brief, the gene of interest is cloned with 1-2 kb of flanking DNA either side and is inactivated by deletion of part of the coding region and insertion of an antibiotic resistance marker, such as hygromycin.

The manipulated fragment is then transferred to a suitable suicide vector e.g. pPR23 and is transformed into the wild-type parent strain of *M. tuberculosis*. Mutants are recovered by selecting for antibiotic resistant strains. Genotypic analysis (Southern Blotting with a fragment specific to the gene of interest) is performed on the selected strains to confirm that the gene has been disrupted.

The mutant strain is then studied to determine the effect of the gene disruption on the phenotype. In order to use it as a vaccine candidate it would be necessary to demonstrate attenuated virulence. This can be done using either a guinea pig or mouse model of infection. Animals are infected with the mutant strain and the progression of disease is monitored by determining the bacterial load in different organs, in particular the lung and spleen, at specific time points post infection, typically up to 16 weeks.

Comparison is made to animals infected with the wild-type strain which should have a significantly higher bacterial load in the different organs. Long-term survival studies and histopathology can also be used to assess virulence and pathogenicity.

Once attenuated virulence has been established, protection and immunogenicity studies can be performed to assess the potential of the strain as a vaccine. Suitable references for allelic exchange and preparation of TB mutants are McKinney et al., 2000 and Pelicic et al., 1997, [1, 2].

EXAMPLE 6

Select One or More of Our Genes, which Encode Proteins that are Immunogenic, and Put them into BCG or an Attenuated Strain of *M. tuberculosis* to Enhance its Overall Immunogenicity The gene of interest is amplified from the *M. tuberculosis* genome by PCR. The amplified product is purified and cloned into a plasmid (pMV306) that integrates site specifically into the mycobacterial genome at the attachment site (attB) for mycobacteriophage L5 [3].

BCG is transformed with the plasmid by electroporation, which involves damaging the cell envelope with high voltage electrical pulses, resulting in uptake of the DNA. The plasmid integrates into the BCG chromosome at the attB site generating stable recombinants. Recombinants are selected and are checked by PCR or Southern blotting to ensure that the gene has been integrated. The recombinant strain is then used for protection studies.

EXAMPLE 7

Use Recombinant Carriers Such as Attenuated *Salmonella* and the Vaccinia Virus to Express and Present TB Genes One of the best examples of this type of approach is the use of Modified Vaccinia virus Ankara (MVA) [4]. The gene of interest is cloned into a vaccinia virus shuttle vector, e.g. pSC11. Baby Hamster Kidney (BHK) cells are then infected with wild-type MVA and are transfected with the recombinant shuttle vector. Recombinant virus is then selected using a suitable selection marker and viral plaques, selected and purified.

Recombinant virus is normally delivered as part of a prime-boost regime where animals are vaccinated initially with a DNA vaccine encoding the TB genes of interest under the control of a constitutive promoter. The immune response is boosted by administering recombinant MVA carrying the genes of interest to the animals at least 2 weeks later.

EXAMPLE 8

Sub-Unit Vaccines Containing a Single Peptide/Protein or a Combination of Proteins To prepare sub-unit vaccines with one or more peptides or proteins it is first of all necessary to obtain a supply of protein or peptide to prepare the vaccine. Up to now, this has mainly been achieved in mycobacterial studies by purifying proteins of interest from TB culture. However, it is becoming more common to clone the gene of interest and produce a recombinant protein.

The coding sequence for the gene of interest is amplified by PCR with restriction sites inserted at the N terminus and C terminus to permit cloning in-frame into a protein expression vector such as pET-15b. The gene is inserted behind an inducible promoter such as lacZ. The vector is then transformed into *E. coli* which is grown in culture. The recombinant protein is over-expressed and is purified.

One of the common purification methods is to produce a recombinant protein with an N-terminal His-tag. The protein can then be purified on the basis of the affinity of the His-tag for metal ions on a Ni-NTA column after which the His-tag is cleaved. The purified protein is then administered to animals in a suitable adjuvant [5].

EXAMPLE 9

Plasmid DNA Vaccines Carrying One or More of the Identified Genes

DNA encoding a specific gene is amplified by PCR, purified and inserted into specialised vectors developed for vaccine development, such as pVAX1. These vectors contain promoter sequences, which direct strong expression of the introduced DNA (encoding candidate antigens) in eukaryotic cells (e.g. CMV or SV40 promoters), and polyadenlyation signals (e.g. SV40 or bovine growth hormone) to stabilise the mRNA transcript.

The vector is transformed into *E. coli* and transformants are selected using a marker, such as kanamycin resistance, encoded by the plasmid. The plasmid is then recovered from transformed colonies and is sequenced to check that the gene of interest is present and encoded properly without PCR generated mutations.

Large quantities of the plasmid is then produced in *E. coli* and the plasmid is recovered and purified using commercially available kits (e.g. Qiagen Endofree-plasmid preparation). The vaccine is then administered to animals for example by intramuscular injection in the presence or absence of an adjuvant.

EXAMPLE 10

Preparation of DNA Expression Vectors

DNA vaccines consist of a nucleic acid sequence of the present invention cloned into a bacterial plasmid. The plasmid vector pVAX1 is commonly used in the preparation of DNA vaccines. The vector is designed to facilitate high copy number replication in *E. coli* and high level transient expression of the peptide of interest in most mammalian cells (for details see manufacturers protocol for pVAX1. catalog no. V260-20.

The vector contains the following elements

- Human cytomegalovirus immediate-early (CMV) promoter for high-level expression in a variety of mammalian cells
- T7 promoter/priming site to allow in vitro transcription in the sense orientation and sequencing through the insert
- Bovine growth hormone (BGH) polyadenylation signal for efficient transcription termination and polyadenylation of mRNA
- Kanamycin resistance gene for selection in *E. Coli*
- A multiple cloning site
- pUC origin for high-copy number replication and growth in *E. coli*
- BGH reverse priming site to permit sequencing through the insert Vectors may be prepared by means of standard recombinant techniques which are known in the art, for example Sambrook et al., (1989). Key stages in preparing the vaccine are as follows:

- The gene of interest is ligated into pVAX1 via one of the multiple cloning sites
- The ligation mixture is then transformed into a competent *E. coli* strain (e.g. TOP10) and LB plates containing 50 μg/ml kanamycin are used to select transform ants.
- Clones are selected and may be sequenced to confirm the presence and orientation of the gene of interest.
- Once the presence of the gene has been verified, the vector can be used to transfect a mammalian cell line to check for protein expression. Methods for transfection are known in the art and include, for example, electroporation, calcium phosphate, and lipofection.
- Once peptide expression has been confirmed, large quantities of the vector can be produced and purified from the appropriate cell host, e.g. *E. coli.* pVAX1 does not integrate into the host chromosome. All non-essential sequences have been removed to minimise the possibility of integration. When constructing a specific vector, a leader sequence may be included to direct secretion of the encoded protein when expressed inside the eukaryotic cell.

Other examples of vectors that have been used are VlJns.tPA and pCMV4 (Lefevre et al., 2000 and Vordermeier et al., 2000).

Expression vectors may be used that integrate into the genome of the host, however, it is more common and more preferable to use a vector that does not integrate. The example provided, pVAX1, does not integrate. Integration would lead to the generation of a genetically modified host which raises other issues.

EXAMPLE 11

RNA vaccine

As discussed on page 15 of U.S. Pat. No. 5,783,386, one approach is to introduce RNA directly into the host.

Thus, the vector construct (Example 10) may be used to generate RNA in vitro and the purified RNA then injected into the host. The RNA would then serve as a template for translation in the host cell. Integration would not occur.

Another option is to use an infectious agent such as the retroviral genome carrying RNA corresponding to the gene of interest. Here you will get integration into the host genome Another option is the use of RNA replicon vaccines which can be derived from virus vectors such as Sindbis virus or Semliki Forest virus. These vaccines are self-replicating and self-limiting and may be administered as either RNA or DNA which is then transcribed into RNA replicons in vivo. The vector eventually causes lysis of the transfected cells thereby reducing concerns about integration into the host genome. Protocols for RNA vaccine construction are detailed in Cheng et al., (2001).

EXAMPLE 12

Diagnostic Assays Based on Assessing T Cell Responses

For a diagnostic assay based on assessing T cell responses it would be sufficient to obtain a sample of blood from the patient. Mononuclear cells (monocytes, T and B lymphocytes) can be separated from the blood using density gradients such as Ficoll gradients.

Both monocytes and B-lymphocytes are both able to present antigen, although less efficiently than professional antigen presenting cells (APCs) such as dendritic cells. The latter are more localised in lymphoid tissue.

The simplest approach would be to add antigen to the separated mononuclear cells and incubate for a week and then assess the amount of proliferation. If the individual had been exposed to the antigen previously through infection, then T-cell closes specific to the antigen should be more prevalent in the sample and should respond.

It is also possible to separate the different cellular populations should it be desired to control the ratio of T cells to APC's.

Another variation of this type of assay is to measure cytokine production by the responding lymphocytes as a measure of response. The ELISPOT assay described below in Example 13 is a suitable example of this variation.

EXAMPLE 13

Detection of Latent Mycobacteria

A major problem for the control of tuberculosis is the presence of a large reservoir of asymptomatic individuals infected with tubercle bacilli. Dormant bacilli are more resistant to front-line drugs.

The presence of latent mycobacteria-associated antigen may be detected indirectly either by detecting antigen specific antibody or T-cells in blood samples.

The following method is based on the method described in Lalvani et al. (2001) in which a secreted antigen, ESAT-6, was identified as being expressed by members of the *M. tuberculosis* complex but is absent from *M. bovis* BCG vaccine strains and most environmental mycobacteria. 60-80% of patients also have a strong cellular immune response to ESAT-6. An ex-vivo ELISPOT assay was used to detect ESAT-6 specific T cells.

As applied to the present invention:

A 96 well plate is coated with cytokine (e.g. interferon-γ, IL-2)-specific antibody. Peripheral blood monocytes are then isolated from patient whole blood and are applied to the wells.

Antigen (ie. one of the peptides, fragments, derivatives or variants of the present invention) is added to stimulate specific T cells that may be present and the plates are incubated for 24 h. The antigen stimulates cytokine production which then binds to the specific antibody.

The plates are washed leaving a footprint where antigen-specific T cells were present.

A second antibody coupled with a suitable detection system, e.g. enzyme, is then added and the number of spots are enumerated after the appropriate substrate has been added.

The number of spots, each corresponding to a single antigen-specific T cell, is related to the total number of cells originally added.

The above Example also describes use of an antigen that may be used to distinguish TB infected individuals from BCG vaccinated individuals. This could be used in a more discriminative diagnostic assay.

EXAMPLE 14

Alternative Protocol for Transcriptomics Analysis a) Experimental Design

RNA was extracted from aerobic (50% DOT) and low-oxygen (1% DOT) cultures and fluorescently labelled cDNA was transcribed from each sample of RNA. Fluorescently labelled cDNA was also transcribed from genomic DNA which had been extracted from *M. tuberculosis*.

In each microarray experiment a whole genome array was hybridised with a sample of labelled cDNA generated from RNA from one culture sample (Test sample). Each array was also hybridised with control cDNA prepared from genomic DNA (Control sample). The test and control cDNAs were each labelled with a different cy dye.

Nine separate arrays were performed for aerobic samples and seven low-oxygen arrays were performed. Each array was scanned at two different wavelengths corresponding to the excitation maxima of each dye using an Affymetric 428 array scanner. The intensity of the emitted light was recorded and the data was analysed using GeneSpring software.

The test sample data on each chip was normalised against the control data followed by per chip normalisation about the median intensity value, using the 50th percentile, and finally per gene normalisation across all the arrays. In this instance those genes which were expressed at least 1.5-fold higher under low-oxygen conditions relative to aerobic culture were selected for identification.

b) RNA Extraction from *M. tuberculosis* for Microarray Analysis

Materials and Methods

Trizol (Life Technologies)—formulation of phenol and guanidine thiocyanate.

GTC lysis solution containing: 5M guanidine thiocyanate, 0.5% N-lauryl sarcosine, 25 mM tri-sodium citrate, 0.1M 2-mercaptoethanol, and 0.5% Tween 80.

Chloroform, Isopropanol 3M sodium acetate

70% Ethanol microfuge, ribolyser

Sterile plasticware-Falcon tubes, screw capped eppendorfs, gilson tips—all RNase free Glassware—baked at 160° C. for at least 16 hours Method Steps performed at Containment level 3; within a Class III microbiological safety cabinet.

Remove 10 or 20 ml of culture ($10^9$/ml) and immediately add this to 4 volumes of GTC lysis buffer in a plastic specimen pot. Seal the pot tightly.

Incubate the cells in GTC lysis buffer for 1 hour at room temperature. Surface decontaminate the plastic pot with 5% Hycolin for 5 minutes. Transfer the sample to the pass box and place it into a plastic carry tin with a sealable lid. Close the container securely and transport it to a non-toxic cabinet CL3 cabinet.

Equally distribute the lysis mixture between Falcon tubes. Place these tubes into centrifuge buckets and seal the buckets tightly. Surface-decontaminate the buckets for 5 minutes with 5% Hycolin. Then transfer them to the centrifuge (Baird and Tatlock Mark IV refrigerated bench-top centrifuge). Spin the tubes at 3,000 rpm for 30 minutes.

Return the unopened buckets to the cabinet. Remove the centrifuge tubes and pour the supernatant into a waste bottle for GTC lysis buffer.

Resuspend each pellet in 1 ml of Trizol (formulation of phenol and GTC cat no. 15596-026). The manufacturers guidelines recommend lysing cells by repetitive pipetting. Although this action alone will not lyse *M. tuberculosis*, it is important to completely resuspend the pellet in Trizol.

Transfer 1 ml of cells into each FastRNA tube and ribolyse them at power setting 6.5 for 45 seconds.

Leave the tubes to incubate at room temperature for 5 minutes.

Remove the aqueous layer from each tube and add this to 200 µl of chloroform in a screw-capped eppendorf tube. Shake each tube vigorously for about 15 seconds. Incubate for 2-3 minutes at room temperature.

Spin the tubes at 13,000 rpm for 15 minutes. Following centrifugation, the liquid separates into red phenol/chloroform phase, an interface, and a clear aqueous phase.

Carefully remove the aqueous phase and transfer it to fresh eppendorf tubes containing 500 µl of chloroform/isoamyl alcohol (24:1). Spin the tubes at 13,000 rpm for 15 minutes.

Transfer the aqueous phase to eppendorf tubes containing 50 µl of sodium acetate and 500 µl of isopropanol.

Surface decontaminate the eppendorf tubes with 5% Hycolin for 5 minutes. Remove the tubes from the CL3 laboratory and continue with the procedure in laboratory 157.

Steps performed at Containment level 2:

Precipitate the RNA at −70° C. for at least 30 minutes—can do this step overnight.

Spin the precipitated RNA down at 13,000 rpm for 10 minutes. Remove the supernatant and wash the pellet in 70% ethanol. Repeat centrifugation.

Remove the 70% ethanol and air-dry the pellet. Dissolve the pellet in RNAse free water.

Freeze the RNA at −70° C. to store it.

The RNA was treated with DNAse1 to remove genomic DNA and was then purified using RNeasy mini columns (Qiagen). Both methods were performed according to the manufacturers guidelines.

c) Isolation of Genomic DNA from *M. tuberculosis* Grown in Chemostat Culture

DNA is then used to generate Cy3 or Cy5 labelled DNA for use as a control in microarray experiments Materials and Methods Beads 0.5 mm in diameter Bead beater Bench top centrifuge Platform rocker Heat block Falcon 50 ml centrifuge tubes Sorvall RC-5C centrifuge 250 ml polypropylene centrifuge pots.

Screw capped eppendorf tubes

Pipettes 1 ml, 200 µl, 10 ml, 5 ml

Breaking buffer—

50 mM Tris HCL pH 8.0 mM EDTA 100 mM NaCl

Procedure

Mechanical Disruption of Mtb Cells 150 ml of chemostat cells (O.D of 2.5 at 540 nm) are spun down at 15,000 rpm for minutes in 250 ml polypropylene pots using centrifuge Sorvall RC-5C.

The supernatant is discarded.

Cells are re-suspended in 5 ml of breaking buffer in a 50 ml Falcon tube and centrifuged at 15,000 rpm for a further 15 minutes.

The supernatant is removed and additional breaking buffer is added at a volume of 5 ml. Beads are used to disrupt the cells. These are used at a quantity of 1 ml of beads for 1 ml of cells. Place the sample into the appropriate sized chamber. Place in the bead beater and secure the outer unit (containing ice) and process at the desired speed for 30 seconds.

Allow the beads to settle for 10 minutes and transfer cell lysate to a 50 ml Falcon centrifuge tube Wash beads with 2-5 ml of breaking buffer by pipetting washing buffer up and down over the beads.

Add this washing solution to the lysate in the falcon tube

Removal of Proteins and Cellular Components

Add 0.1 volumes of 10% SDS and 0.01 volumes of proteinase K.

Mix by inversion and heat at 55° C. in a heat block for 2-3 hours

The resulting mix should be homogenous and viscous. If it isn't then add more SDS to bring the concentration up to 0.2%

Add an equal volume of phenol/chloroform/Isoamyl alcohol in the ratio: 25/24/1.

Gently mix on a platform rocker until homogenous

Spin down at 3,000 rpm for 20 minutes

Remove the aqueous phase and place in a fresh tube

Extract the aqueous phase with an equal volume of chloroform to remove traces of cell debris and phenol. Chloroform extractions may need to be repeated to remove all the debris.

Precipitate the DNA with 0.3 M sodium acetate and an equal volume of isopropanol.

Spool as much DNA as you can with a glass rod

Wash the spooled DNA in 70% ethanol followed by 100% ethanol

Leave to air dry

Dissolve the DNA in sterile deionised water (500 μl)

Allow DNA to dissolve at 4° C. for approximately 16 hours.

Add RNase 1 (500 U) to the dissolved DNA

Incubate for 1 hour at 37° C.

Re-extract with an equal volume of phenol/chloroform followed by a chloroform extraction and precipitate as before Spin down the DNA at 13,000 rpm Remove the supernatant and wash the pellet in 70% ethanol Air dry Dissolve in 200-500 μl of sterile water.

d) Preparation of Cy3 or Cy5 labelled DNA from DNA

Prepare One Cy3 or One Cy5 Labelled DNA Sample Per Microarray Slide. For each sample:

| | |
|---|---|
| DNA | 2-5 μg |
| Random primers (3 μg/μl) | 1 μl |
| $H_2O$ | to 41.5 μl |

Heat at 95° C. for 5 min, snap cool on ice and briefly centrifuge.

| Add to each: | |
|---|---|
| 10xREact 2 buffer | 5 μl |
| dNTPs (5 mM dA/G/TTP, 2 mM dCTP) | 1 μl |
| Cy3 OR Cy5 dCTP | 1.5 μl |
| Klenow (5 U/μl) | 1 μl |

Incubate at 37° C. in dark for 90 min.

Prehybridise Slide

Mix the prehybridisation solution in a Coplin jar and incubate at 65° C. during the labelling reaction to equilibrate.

| | | |
|---|---|---|
| Prehybridisation: 20xSSC | 8.75 ml | (3.5xSSC) |
| 20% SDS | 250 μl | (0.1% SDS) |
| BSA (100 mg/ml) | 5 ml | (10 mg/ml) |
| $H_2O$ | to 50 ml | |

Incubate the microarray slide in the pre-heated prehybridisation solution at 65° C. for 20 min. Rinse slide thoroughly in 400 ml $H_2O$ for 1 min followed by rinse in 400 ml propan-2-ol for 1 min and centrifuge slide in 50 ml centrifuge tube at 1,500 rpm for 5 min to dry. Store slide in dark, dust-free box until hybridisation (<1 h).

Purify Cy3/Cy5 labelled DNA—Qiagen MinElute Purification

Combine Cy3 and Cy5 labelled DNA samples in single tube and add 500 μl Buffer PB.

Apply to MinElute column in collection tube and centrifuge at 13,000 rpm for 1 min.

Discard flow-through and place MinElute column back into same collection tube.

Add 500 μl Buffer PE to MinElute column and centrifuge at 13,000 rpm for 1 min.

Discard flow-through and place MinElute column back into same collection tube.

Add 250 μl Buffer PE to MinElute column and centrifuge at 13,000 rpm for 1 min.

Discard flow-through and place MinElute column back into same collection tube.

Centrifuge at 13,000 rpm for an additional 1 min to remove residual ethanol.

Place the MinElute column into a fresh 1.5 ml tube.

Add 10.5 μl $H_2O$ to the centre of the membrane and allow to stand for 1 min.

Centrifuge at 13,000 rpm for 1 min.

e) Preparation of Cy3 or Cy5 Label cDNA from RNA

| Prepare one Cy3 and one Cy5 labelled cDNA sample per microarray slide. | |
|---|---|
| For each sample: | |
| RNA | 2-10 μg |
| Random primers (3 μg/μl) | 1 μl |
| $H_2O$ | to 11 μl |

Heat at 95° C. for 5 min, snap cool on ice and briefly centrifuge.

| Add to each: | |
|---|---|
| 5xFirst Strand Buffer | 5 μl |
| DTT (100 mM) | 2.5 μl |
| dNTPs (5 mM dA/G/TTP, 2 mM dCTP) | 2.3 μl |
| Cy3 OR Cy5 dCTP | 1.7 μl |
| SuperScript II (200 U/μl) | 2.5 μl |

Incubate at 25° C. in dark for 10 min followed by 42° C. in dark for 90 min.

Prehybridise Slide

Mix the prehybridisation solution in a Coplin jar and incubate at 65° C. during the labelling reaction to equilibrate.

| | | |
|---|---|---|
| Prehybridisation: 20xSSC | 8.75 ml | (3.5xSSC) |
| 20% SDS | 250 μl | (0.1% SDS) |
| BSA (100 mg/ml) | 5 ml | (10 mg/ml) |
| $H_2O$ | to 50 ml | |

Incubate the microarray slide in the pre-heated prehybridisation solution at 65° C. for 20 min. Rinse slide thoroughly in 400 ml $H_2O$ for 1 min followed by rinse in 400 ml propan-2-ol for 1 min and centrifuge slide in 50 ml centrifuge tube at 1500 rpm for 5 min to dry. Store slide in dark, dust-free box until hybridisation (<1 h).

Purify Cy3/Cy5 Labelled cDNA—Qiagen MinElute Purification

Combine Cy3 and Cy5 labelled DNA samples in single tube and add 250 μl Buffer PB.

Apply to MinElute column in collection tube and centrifuge at 13,000 rpm for 1 min.

Discard flow-through and place MinElute column back into same collection tube.

Add 500 μl Buffer PE to MinElute column and centrifuge at 13,000 rpm for 1 min.

Discard flow-through and place MinElute column back into same collection tube.

Add 250 μl Buffer PE to MinElute column and centrifuge at 13,000 rpm for 1 min.

Discard flow-through and place MinElute column back into same collection tube.

Centrifuge at 13,000 rpm for an additional 1 min to remove residual ethanol.

Place the MinElute column into a fresh 1.5 ml tube.

Add 10.5 μl $H_2O$ to the centre of the membrane and allow to stand for 1 min.

Centrifuge at 13,000 rpm for 1 min.

f) Hybridise Slide with Cy3/Cy5 Labelled cDNA/DNA

Place the prehybridised microarray slide in the hybridisation cassette and add two 15 μl aliquots of $H_2O$ to the wells in the cassette. Mix resuspended Cy3/Cy5 labelled cDNA sample with hybridisation solution.

| Hybridisation: | |
|---|---|
| Cy3/Cy5 labelled cDNA sample | 10.5 μl |
| 20xSSC | 3.2 μl (4xSSC) |
| 2% SDS | 2.3 μl (0.3% SDS) |

Heat hybridisation solution at 95° C. for 2 min. Do NOT snap cool on ice but allow to cool slightly and briefly centrifuge. Pipette the hybridisation solution onto the slide at the edge of the arrayed area avoiding bubble formation. Using forceps carefully drag the edge of a cover slip along the surface of the slide towards the arrayed area and into the hybridisation solution at the edge of the array. Carefully lower the cover slip down over the array avoiding any additional movement once in place. Seal the hybridisation cassette and submerge in a water bath at 60° C. for 16-20 h.

Wash Slide

Remove microarray slide from hybridisation cassette and initially wash slide carefully in staining trough of Wash A, preheated to 65° C., to remove cover slip. Once cover slip is displaced place slide(s) in slide rack and continue agitating in Wash A for a further 2 min.

| Wash A: | |
|---|---|
| 20xSSC | 20 ml (1xSSC) |
| 20% SDS | 1 ml (0.05% SDS) |
| $H_2O$ | to 400 ml |

Transfer slide(s) to a clean slide rack and agitate in first trough of Wash B for 2 min. Wash in second trough of Wash B with agitation for 2 min.

| Wash B (x2): | |
|---|---|
| 20xSSC | 1.2 ml (0.06xSSC) |
| $H_2O$ | to 400 ml |

Place slide into a 50 ml centrifuge tube and centrifuge at 1500 rpm for 5 mins to dry the slide and then scan fluorescence using a microarray slide scanner. The slides were scanned using an Affymetrix 428 scanner. The raw data was analysed using a combination of ImaGene and GeneSpring software.

g) Preparation of the Arrays

Whole *M. tuberculosis* genome arrays were prepared from *M. tuberculosis* genomic DNA using ORF-specific primers. PCR products corresponding to each ORF were spotted in a grid onto a standard glass microscope slide using a BioRobotics microgrid robot (MWG Biotech) at a resolution of >4000 spots/$cm^2$.

Results

Transcriptomics analysis of *M. tuberculosis* DNA coding sequences that are up-regulated under low DOT continuous culture conditions has identified the following SEQ IDs (see Table 2). Referring to the SEQ. ID. NO. column, the first identified number is an amino acid sequence and the second identified number is the corresponding DNA sequence.

TABLE 2

| Gene | Assigned function | SEQ ID NO. |
|---|---|---|
| Rv1344 | Acyl carrier protein | 1, 2 |
| Rv0283 | | 3, 4 |
| Rv3402c | Aminotransferase in polysaccharide biosynthesis | 5, 6 |
| Rv3049c | Monooxygenase | 7, 8 |
| Rv2382c (mbtC) | Involved in mycobactin biosynthesis | 9, 10 |
| Rv2381c (mbtD) | Involved in mycobactin biosynthesis | 11, 12 |
| Rv2379c (mbtF) | Involved in mycobactin biosynthesis | 13, 14 |
| Rv1994c | Transcription regulator, similar to eg MERR probable mercury resistance operon | 15, 16 |
| Rv0251c (hsp) | Heat shock protein belonging to HSP20 family | 17, 18 |
| Rv3174 | Oxidoreductase | 19, 20 |
| fadE14 (Rv1346) | Acyl CoA dehyrogenase | 21, 22 |
| LipK (Rv2385) | Esterase/acetyl hydrolase | 23, 24 |
| appC (Rv1623c) | Cytochrome D | 25, 26 |
| Rv0725c | | 27, 28 |
| Rv3639c | | 29, 30 |
| Rv0560c | Methyltransferase | 31, 32 |
| Rv2053c | | 33, 34 |
| lpqS (Rv0847) | Lipoprotein containing a signal peptide | 35, 36 |
| Rv3767c | Protein with a probable N-terminal signal peptide | 37, 38 |
| Rv3812 | | 39, 40 |
| Rv2210c (ilvE) | Branched chain amino acid transaminase | 41, 42 |
| Rv2516c | Protein containing a helix-turn-helix motif | 43, 44 |
| Rv0870c | Hydrophobic protein | 45, 46 |
| Rv1168c | PPE protein | 47, 48 |
| Rv2448c (valS) | Valyl-tRNA synthetase | 49, 50 |
| Rv2378c (mbtG) | Involved in mycobactin biosynthesis. Lysine hydroxylase | 51, 52 |
| Rv2377c (mbtH) | Involved in mycobactin biosynthesis | 53, 54 |
| Rv0135c | Transcriptional regulator | 55, 56 |
| Rv2025c | | 57, 58 |
| Rv0985c (mscL) | | 59, 60 |
| Rv0938 | | 61, 62 |
| Rv2554c | | 63, 64 |
| Rv1342c | Membrane protein | 65, 66 |
| Rv0397 | | 67, 68 |
| Rv1389 (gmk) | Guanylate kinase | 69, 70 |
| Rv0123 | | 71, 72 |
| Rv3001c (ilvC) | Ketol acid reducto isomerase | 73, 74 |
| Rv3839 | | 75, 76 |
| Rv2164c | Proline rich protein | 77, 78 |
| Rv2017 | Transcriptional regulator | 79, 80 |
| Rv1982c | | 81, 82 |
| Rv3758c (proV) | ABC transporter. ATP binding protein | 83, 84 |
| Rv3697c | | 85, 86 |
| Rv1228 (lpqX) | Protein containing a signal peptide | 87, 88 |
| Rv3000 | | 89, 90 |
| Rv3037c | | 91, 92 |
| Rv1634 | Membrane protein of major facilitator super family, similar to many antibiotic resistance (efflux) proteins | 93, 94 |
| Rv1300 (hemK) | Protoporphyrinogen oxidase | 95, 96 |
| Rv2327 | unknown | 97, 98 |

TABLE 2-continued

| Gene | Assigned function | SEQ ID NO. |
|---|---|---|
| Rv1221 (sigE) | Sigma factor | 99, 100 |
| Rv1617 (pykA) | Pyruvate kinase | 101, 102 |
| Rv0792c | Transcriptional regulator, similar to many of GntR family e.g. *Bacillus subtilis* | 103, 104 |
| Rv1509 | | 105, 106 |
| Rv3081 | Contains PS0 0850 | 107, 108 |
| Rv0347 | Similar to Rv0831c | 109, 110 |
| Rv0573c | | 111, 112 |
| Rv2019 | | 113, 114 |

EXAMPLE 15

Protocol for Protein Extraction and Characterisation

*M. tuberculosis* H37Rv was grown in continuous culture under aerobic (50% DOT) and low oxygen (1% DOT) conditions and samples were collected during the steady-state (see Example 1).

Harvesting of Culture Cell Pellets 300-350 ml of culture is collected overnight on ice.

The culture is centrifuged for 10 minutes at 15,000 rpm in dry-spin tubes using a Sorvall RC5B centrifuge at 4° C.

The supernatant is decanted off and the cell pellets are collected in to tubes and stored frozen at −40° C.

Preparation of Protein Extracts from Cell Pellets

One sample of steady state cell pellets from each of 3 aerobic and 2 low oxygen chemostat cultures were removed from the freezer and allowed to thaw at room temperature for 1 hour.

Each pellet is resuspended in 40 mis Tris-HCL buffer [40 mM Tris, 1 mM EDTA (pH 6.9) and 200 µl protease inhibitor cocktail (Sigma, P8645) per 40 mls] and re-pelleted by centrifugation at 12,000 rpm at 4° C.

Each cell pellet is then resuspended with approximately 1 ml of buffer.

0.5 ml aliquots of the bacterial suspensions are dispensed into separate ribolyser tubes (Anachem).

Each tube is ribolysed for 3×90 seconds cycles (maximum power—setting 6.5) with 5 mins on ice between each cycle.

After ribolysing the protein preparations for each sample were pooled and the following chemicals added:

| | | |
|---|---|---|
| 3.2 | g | Urea |
| 64.8 | mg | DTT |
| 300 | µl | Ampholytes (servalyte 2-4 serva electrophoresis) |
| 0.24 | g | CHAPS |

Each chemical is allowed to dissolve before adding the next.

The samples are incubated for 30 minutes at room temperature.

The samples were dispensed in to eppendorf tubes and centrifuged at 12,000 rpm for 5 minutes.

The clear soluble protein preparations are then removed and double filtered through a 0.2 µm cellulose acetate filter membrane.

Protein determinations of the samples using a Biorad assay was performed with a Bovine serum albumin standard curve and the samples found to contain between 6-8.5 mg/ml of protein.

Proteomics Analysis Using 2D Electrophoresis

Representative protein samples of the low-oxygen and aerobic chemostat cultures were sent away for 2D Electrophoresis analysis to the Wittman Institute of Technology and Analysis of Biomolecules (WITA), Berlin.

Protein separation of each sample by 2D electrophoresis (Jungblut et al., Infect Immun 2001 September; 69(9): 5905-7) was carried out on both Coomassie brilliant blue and silver stained gels produced using 70 µl and 25 µl of protein samples respectively.

Protein Identification

The most abundant protein spots on the Coomassie low oxygen gel were excised and sent for Mass spectrometry determination by Robin Wait (Jungblut et al., Infect Immun 2001 September; 69(9):5905-7) for protein identification.

The following proteins were identified, and are listed (together with their corresponding DNA coding sequences) in Table 3.

TABLE 3

| Gene | Assigned function | SEQ ID NO. |
|---|---|---|
| Rv3040 | 31.5 kDa protein | 115, 116 |
| Rv1288 | Antigen 85B-precursor | 117, 118 |
| Rv0649 | Malonyl CoA-acyl carrier protein transacylase | 119, 120 |
| Rv1357c | 29.8 and 31.7 kDa proteins | 121, 122 |
| Rv2230c | 39.6 kDa protein | 123, 124 |
| Rv2468c | | 125, 126 |
| Rv3011c | Glutamyl-tRNA (Gln) amidotransferase subunit/ATPB MYCTU ATP synthase beta chain | 127, 128 |
| Rv2868c | GcpE protein homolog | 129, 130 |
| Rv0718 | 30S ribosomal protein S8 | 131, 132 |
| Rv1267c | Response regulator, similar to AFSR_STRCO P25941 | 133, 134 |
| Rv1294 | Homoserine dehydrogenase | 135, 136 |
| Rv0844c | Nitrate/nitrite response regulator (NARL) | 137, 138 |

REFERENCES

1. McKinney, J. D., et al., Persistence of *Mycobacterium tuberculosis* in macrophages and mice requires the glyoxylate shunt enzyme isocitrate lyase [see comments]. Nature, 2000. 406(6797): p. 735-8.
2. Pelicic, V., et al., Efficient allelic exchange and transposon mutagenesis in *Mycobacterium tuberculosis*. Proc Natl Acad Sci USA, 1997. 94(20): p. 10955-60.
3. Lee, M. H., et al., Site-specific integration of mycobacteriophage L5: integration-proficient vectors for *Mycobacterium smegmatis, Mycobacterium tuberculosis*, and *bacille* Calmette-Guerin. Proc Natl Acad Sci USA, 1991. 88(8): p. 3111-5.
4. McShane, H., et al., Enhanced immunogenicity of CD4(+) t-cell responses and protective efficacy of a DNA-modified vaccinia virus Ankara prime-boost vaccination regimen for murine tuberculosis. Infect Immun, 2001. 69(2): p. 681-6.
5. Movahedzadeh, F., M. J. Colston, and E. O. Davis, Characterization of *Mycobacterium tuberculosis* LexA: recognition of a Cheo (Bacillus-type SOS) box. Microbiology, 1997. 143(Pt 3): p. 929-36.

ADDITIONAL REFERENCES

Sambrook, J., E. F. Fritsch, and T. Maniatis. 1989. Molecular cloning: a laboratory manual, 2nd ed. Cold Spring Harbour Laboratory Press, Cold Spring Harbour, N.Y.

Lefever, P., O. Denis, L. De Wit, A. Tanghe, P. Vandenbussche, J. Content, and K. Huygen. 2000. Cloning of the gene encoding a 22-kilodalton cell surface antigen of *Mycobacterium bovis* BCG and analysis of its potential for DNA vaccination against tuberculosis. Infection and Immunity. 68:1040-1047.

Vordermeire, H. M., P. J. Cockle, A. O. Whelan, S. Rhodes, M. A. Chambers, D. Clifford, K. Huygen, R. Tascon, D. Lowrie, M. J. Colston, and R. G. Hewinson. 2000. Effective DNA vaccination of cattle with the mycobacterial antigens MPB83 and MPB70 does not compromise the specificity of the comparative intradermal tuberculin skin test. Vaccine. 19:1246-1255.

Cheng, W., C. Hung, C. Chai, K. Hsu, L. He, C. Rice, M. Ling, and T. Wu. 2001. Enhancement of Sindbis virus self-replicating RNA vaccine potency by linkage of *Mycobacterium tuberculosis* heat shock protein 70 gene to an antigen. J. Immunol. 166:6218-6226.

Lalvani, A. et al., 2001. Enhanced contact tracing and spatial tracking of *Mycobacterium tuberculosis* infection by enumeration of antigen-specific T cells. The Lancet 357:2017-2021.

The invention claimed is:

1. An isolated *M. tuberculosis* DNA sequence selected from the group consisting of SEQ ID NOs: 40 and 90, or a variant thereof having at least 70% nucleotide sequence identity therewith, or a derivative thereof, wherein the peptide encoded by said variant or derivative has a common antigenic cross-reactivity to the peptide encoded by said DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

2. A therapeutic agent for combating mycobacterial infections, comprising an *M. tuberculosis* DNA sequence selected from the group consisting of SEQ ID NOs: 40 and 90, or a derivative thereof, wherein the peptide encoded by said derivative has a common antigenic cross-reactivity to the peptide encoded by said DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

3. A medicament for treating a mycobacterial infection, or for reducing the severity or intensity of a mycobacterial infection, or for preventing mycobacterial disease progression, comprising an *M. tuberculosis* DNA sequence selected from the group consisting of SEQ ID NOs: 40 and 90, or a derivative thereof, wherein the peptide encoded by said derivative has a common antigenic cross-reactivity to the peptide encoded by said DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

4. A method of treating a mycobacterial infection, or for reducing the severity or intensity of a mycobacterial infection, or for preventing mycobacterial disease progression, comprising administering to a patient an M. tuberculosis DNA sequence selected from the group consisting of SEQ ID NOs: 40 and 90, or a derivative thereof, wherein the peptide encoded by said derivative has a common antigenic cross-reactivity to the peptide encoded by said DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

5. An isolated DNA sequence, wherein said DNA sequence is:

(i) a fragment of an *M. tuberculosis* DNA sequence selected from the group consisting of SEQ ID NOs:40 and 90; wherein said fragment has at least 15 nucleotides; or (ii) a variant of (i) having at least 70% nucleotide sequence identity therewith; or (iii) a derivative of (i) or (ii);

wherein the peptide encoded by said fragment, variant or derivative has a common antigenic cross-reactivity to the peptide encoded by said *M. tuberculosis* DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

6. A therapeutic agent for combating mycobacterial infections, comprising an isolated DNA sequence, wherein said isolated DNA sequence is:

(i) a variant having at least 90% nucleotide sequence identity to a DNA sequence selected from the group consisting of:

(a) an *M. tuberculosis* DNA sequence selected from the group consisting of SEQ ID NOs: 40 and 90; or (b) a fragment of (a) having at least 15 nucleotides; or (ii) a derivative of (i);

wherein the peptide encoded by said variant, fragment or derivative has a common antigenic cross-reactivity to the peptide encoded by said *M. tuberculosis* DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

7. A medicament for treating a mycobacterial infection, or for reducing the severity or intensity of a mycobacterial infection, or for preventing mycobacterial disease progression, comprising an isolated DNA sequence, wherein said isolated DNA sequence is:

(i) a variant having at least 90% nucleotide sequence identity to a DNA sequence selected from the group consisting of:

(a) an *M. tuberculosis* DNA sequence selected from the group consisting of SEQ ID NOs: 40 and 90; or (b) a fragment of (a) having at least 15 nucleotides; or (ii) a derivative of (i);

wherein the peptide encoded by said variant, fragment or derivative has a common antigenic cross-reactivity to the peptide encoded by said *M. tuberculosis* DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

8. A method of treating a mycobacterial infection, or for reducing the severity or intensity of a mycobacterial infection, or for preventing mycobacterial disease progression, comprising administering to a patient an isolated DNA sequence, wherein said isolated DNA sequence is:

(i) a variant having at least 90% nucleotide sequence identity to a DNA sequence selected from the group consisting of:

(a) an *M. tuberculosis* DNA sequence selected from the group consisting of SEQ ID NOs: 40 and 90; or (b) a fragment of (a) having at least 15 nucleotides; or (ii) a derivative of (i);

wherein the peptide encoded by said variant, fragment or derivative has a common antigenic cross-reactivity to the peptide encoded by said *M. tuberculosis* DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

9. A therapeutic agent for combating mycobacterial infection, comprising an isolated DNA sequence, wherein said isolated DNA sequence is:

(i) a fragment of an *M. tuberculosis* DNA sequence selected from the group consisting of SEQ ID NOs: 40 and 90; wherein said fragment has at least 15 nucleotides; or (ii) a derivative of (i);

wherein the peptide encoded by said fragment or derivative has a common antigenic cross-reactivity to the peptide encoded by said *M. tuberculosis* DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

10. A medicament for treating a mycobacterial infection, or for reducing the severity or intensity of a mycobacterial infection, or for preventing mycobacterial disease progression, comprising an isolated DNA sequence, wherein said isolated DNA sequence is:

(i) a fragment of an *M. tuberculosis* DNA sequence selected from the group consisting of SEQ ID NOs: 40 and 90; wherein said fragment has at least 15 nucleotides; or (ii) a derivative of (i);

wherein the peptide encoded by said fragment or derivative has a common antigenic cross-reactivity to the peptide encoded by said *M. tuberculosis* DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

11. A method of treating a mycobacterial infection, or for reducing the severity or intensity of a mycobacterial infection, or for preventing mycobacterial disease progression, comprising administering to a patient an isolated DNA sequence, wherein said isolated DNA sequence is:

(i) a fragment of an *M. tuberculosis* DNA sequence selected from the group consisting of SEQ ID NOs: 40 and 90; wherein said fragment has at least 15 nucleotides; or (ii) a derivative of (i);

wherein the peptide encoded by said fragment or derivative has a common antigenic cross-reactivity to the peptide encoded by said *M. tuberculosis* DNA sequence;

wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

12. An isolated DNA sequence, wherein said DNA sequence is:

(i) a fragment of a DNA sequence variant, wherein:

(a) said DNA sequence variant has at least 98% nucleotide sequence identity with isolated *M. tuberculosis* DNA sequence SEQ ID NO: 40 or SEQ ID NO: 90, wherein the length of said fragment is at least 50% of the length of SEQ ID NOs: 40 or 90 respectively; or (ii) a derivative of (i);

wherein the peptide encoded by said fragment, variant or derivative has a common antigenic cross-reactivity to the peptide encoded by said isolated M. tuberculosis DNA sequence; and wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

13. A therapeutic agent for combating mycobacterial infections, comprising an isolated DNA sequence, wherein said DNA sequence is:

(i) a fragment of a DNA sequence variant, wherein:

(a) said DNA sequence variant has at least 98% nucleotide sequence identity with isolated *M. tuberculosis*

DNA sequence SEQ ID NO: 40 or SEQ ID NO: 90, wherein the length of said fragment is at least 50% of the length of SEQ ID NOs: 40 or 90 respectively; or (ii) a derivative of (i);

wherein the peptide encoded by said fragment, variant or derivative has a common antigenic cross-reactivity to the peptide encoded by said isolated M. tuberculosis DNA sequence; and wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

14. A medicament for treating a mycobacterial infection, or for reducing the severity or intensity of a mycobacterial infection, or for preventing mycobacterial disease progression, comprising an isolated DNA sequence, wherein said DNA sequence is:

(i) (a) said DNA sequence variant has at least 98% nucleotide sequence identity with isolated *M. tuberculosis* DNA sequence SEQ ID NO: 40 or SEQ ID NO: 90, wherein the length of said fragment is at least 50% of the length of SEQ ID NOs: 40 or 90 respectively; or (ii) a derivative of (i);

wherein the peptide encoded by said fragment, variant or derivative has a common antigenic cross-reactivity to the peptide encoded by said isolated M. tuberculosis DNA sequence; and wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

15. A method of treating a mycobacterial infection, or for reducing the severity or intensity of a mycobacterial infection, or for preventing mycobacterial disease progression, comprising administering to a patient an isolated DNA sequence, wherein said DNA sequence is:

(i) a fragment of a DNA sequence variant, wherein:

(a) said DNA sequence variant has at least 98% nucleotide sequence identity with isolated *M. tuberculosis* DNA sequence SEQ ID NO: 40 or SEQ ID NO: 90, wherein the length of said fragment is at least 50% of the length of SEQ ID NOs: 40 or 90 respectively; or (ii) a derivative of (i);

wherein the peptide encoded by said fragment, variant or derivative has a common antigenic cross-reactivity to the peptide encoded by said isolated M. tuberculosis DNA sequence; and wherein said *M. tuberculosis* DNA sequence is the coding sequence of an *M. tuberculosis* gene, the expression of which is induced or up-regulated during culture of *M. tuberculosis* under continuous culture conditions defined by a dissolved oxygen tension of up to 10% air saturation measured at 37° C. when compared with a dissolved oxygen tension of at least 40% air saturation measured at 37° C.

16. A method of identifying a mycobacterial gene the expression of which is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C., said method comprising:

culturing a first mycobacterium under continuous culture conditions defined by a dissolved oxygen tension of up to 10% air saturation measured at 37° C.;

culturing a second mycobacterium under continuous culture conditions defined by a dissolved oxygen tension of at least 40% air saturation measured at 37° C., wherein the second mycobacterium is of the same species as the first mycobacterium;

obtaining first and second mRNA populations from said first and second mycobacteria, respectively;

preparing first and second cDNA populations from said first and second mRNA populations, respectively, during which cDNA preparation a detectable label is introduced into the cDNA molecules of the first and second cDNA populations;

isolating corresponding first and second cDNA molecules from the first and second cDNA populations, respectively;

comparing amounts of label or corresponding signal emitted from the label present in the isolated first and second cDNA molecules;

identifying a greater amount of label or signal provided by the isolated first cDNA molecule than that provided by the isolated second cDNA molecule; and identifying the first cDNA and the corresponding mycobacterial gene which is induced or up-regulated during culture of a mycobacterium under continuous culture conditions defined by a dissolved oxygen tension of up to 10% air saturation measured at 37° C.

17. An attenuated *M. tuberculosis* mycobacterium in which a gene has been modified thereby attenuating the virulence of the mycobacterium;

wherein the gene is a gene the expression of which is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C.; and wherein the *M. tuberculosis* gene has a wild-type coding sequence selected from the group consisting of SEQ ID NOs: 40 and 90.

18. An attenuated microbial carrier, comprising an M. tuberculosis gene having a DNA sequence selected from the group consisting of SEQ ID NOs: 40 and 90; or a variant thereof having at least 70% nucleotide sequence identity therewith, or a fragment thereof having at least 15 nucleotides, or a derivative thereof, wherein the peptide encoded by said variant, fragment or derivative has a common antigenic cross-reactivity to the peptide encoded by said *M. tuberculosis* gene;

wherein the expression of said *M. tuberculosis* gene is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C.

19. A DNA plasmid comprising a promoter, a polyadenylation signal, and a DNA sequence selected from the group consisting of SEQ ID NOs: 40 and 90, or a variant thereof having at least 70% nucleotide sequence identity therewith, or a fragment thereof having at least 15 nucleotides, or a derivative thereof, wherein the peptide encoded by said variant, fragment or derivative has a common antigenic cross-reactivity to the peptide encoded by said DNA sequence;

wherein said DNA sequence is the coding sequence of an M. tuberculosis gene, the expression of which is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C.; and wherein the promoter and polyadenylation signal are operably linked to the DNA sequence.

20. An isolated RNA sequence that is encoded by a DNA sequence selected from the group consisting of SEQ ID NOs: 40 and 90, or a variant thereof having at least 70% nucleotide sequence identity therewith, or a fragment thereof having at least 15 nucleotides, or a derivative thereof, wherein the peptide encoded by said variant, fragment or derivative has a common antigenic cross-reactivity to the peptide encoded by said DNA sequence;

wherein the DNA sequence is the coding sequence of an M. tuberculosis gene which is induced or up-regulated during culture of a mycobacterium under continuous culture conditions defined by a dissolved oxygen tension of up to 10% air saturation measured at 37° C. when compared with a dissolved oxygen tension of at least 40% air saturation measured at 37° C.

21. An attenuated microbial carrier according to claim 18, wherein the attenuated microbial carrier is attenuated salmonella, attenuated vaccinia virus, attenuated fowlpox virus or attenuated *M. bovis*.

22. A DNA plasmid according to claim 19, wherein the promoter is selected from the group consisting of CMV and SV40 promoters.

23. A DNA plasmid according to claim 19, wherein the polyadenylation signal is selected from the group consisting of SV40 and bovine growth hormone polyadenylation signals.

24. A DNA plasmid according to claim 19, wherein the promoter is a CMV promoter and the polyadenylation signal is a bovine growth hormone polyadenylation signal.

* * * * *

UNITED STATES PATENT AND TRADEMARK OFFICE

CERTIFICATE OF CORRECTION

PATENT NO. : 8,017,753 B2
APPLICATION NO. : 12/140939
DATED : September 13, 2011
INVENTOR(S) : Brian William James It is certified that error appears in the above-identified patent and that said Letters Patent is hereby corrected as shown below:

Page 2

Col. 1, line 4, please delete "abailability" and insert --availability--.
Col. 1, line 55, please delete "2000" and insert --2001--.

Signed and Sealed this
Eleventh Day of September, 2012

David J. Kappos
*Director of the United States Patent and Trademark Office*

SEQUENCE LISTING

```
<160> NUMBER OF SEQ ID NOS: 138

<210> SEQ ID NO 1
<211> LENGTH: 106
<212> TYPE: PRT
<213> ORGANISM: Mycobacterium tuberculosis

<400> SEQUENCE: 1

Met Trp Arg Tyr Pro Leu Ser Thr Arg Leu Ala Leu Pro Asn Thr Pro
1               5                   10                  15

Gly Val Ala Ser Phe Ala Met Thr Ser Ser Pro Ser Thr Val Ser Thr
            20                  25                  30

Thr Leu Leu Ser Ile Leu Arg Asp Asp Leu Asn Ile Asp Leu Thr Arg
        35                  40                  45

Val Thr Pro Asp Ala Arg Leu Val Asp Asp Val Gly Leu Asp Ser Val
    50                  55                  60

Ala Phe Ala Val Gly Met Val Ala Ile Glu Glu Arg Leu Gly Val Ala
65                  70                  75                  80

Leu Ser Glu Glu Glu Leu Leu Thr Cys Asp Thr Val Gly Glu Leu Glu
                85                  90                  95

Ala Ala Ile Ala Ala Lys Tyr Arg Asp Glu
            100                 105


<210> SEQ ID NO 2
<211> LENGTH: 318
<212> TYPE: DNA
<213> ORGANISM: Mycobacterium tuberculosis

<400> SEQUENCE: 2

atgtggcgat atccactaag tacaaggcta gccttgccta ataccccagg tgtagcctcc      60

ttcgccatga cctcatcgcc gtccaccgtc agcactacgc tgctgagcat cctgcgcgac     120

gacctcaaca ttgacctgac tcgagtcacg cctgatgcca ggttggtcga cgatgtggga     180

ctggattcgg tggccttcgc ggtcggtatg gtggccatcg aggagcggct cggagtcgca     240

ctgtccgaag aggagctctt gacgtgcgac acggtcggag aactggaggc agcgatcgcg     300

gccaaatacc gcgatgag                                                   318


<210> SEQ ID NO 3
<211> LENGTH: 538
<212> TYPE: PRT
<213> ORGANISM: Mycobacterium tuberculosis

<400> SEQUENCE: 3

Met Thr Asn Gln Gln His Asp His Asp Phe Asp His Asp Arg Arg Ser
```

-continued

```
1               5                   10                  15

Phe Ala Ser Arg Thr Pro Val Asn Asn Asn Pro Asp Lys Val Val Tyr
            20                  25                  30

Arg Arg Gly Phe Val Thr Arg His Gln Val Thr Gly Trp Arg Phe Val
        35                  40                  45

Met Arg Arg Ile Ala Ala Gly Ile Ala Leu His Asp Thr Arg Met Leu
    50                  55                  60

Val Asp Pro Leu Arg Thr Gln Ser Arg Ala Val Leu Met Gly Val Leu
65                  70                  75                  80

Ile Val Ile Thr Gly Leu Ile Gly Ser Phe Val Phe Ser Leu Ile Arg
                85                  90                  95

Pro Asn Gly Gln Ala Gly Ser Asn Ala Val Leu Ala Asp Arg Ser Thr
            100                 105                 110

Ala Ala Leu Tyr Val Arg Val Gly Glu Gln Leu His Pro Val Leu Asn
        115                 120                 125

Leu Thr Ser Ala Arg Leu Ile Val Gly Arg Pro Val Ser Pro Thr Thr
    130                 135                 140

Val Lys Ser Thr Glu Leu Asp Gln Phe Pro Arg Gly Asn Leu Ile Gly
145                 150                 155                 160

Ile Pro Gly Ala Pro Glu Arg Met Val Gln Asn Thr Ser Thr Asp Ala
                165                 170                 175

Asn Trp Thr Val Cys Asp Gly Leu Asn Ala Pro Ser Arg Gly Gly Ala
            180                 185                 190

Asp Gly Val Gly Val Thr Val Ile Ala Gly Pro Leu Glu Asp Thr Gly
        195                 200                 205

Ala Arg Ala Ala Ala Leu Gly Pro Gly Gln Ala Val Leu Val Asp Ser
    210                 215                 220

Gly Ala Gly Thr Trp Leu Leu Trp Asp Gly Lys Arg Ser Pro Ile Asp
225                 230                 235                 240

Leu Ala Asp His Ala Val Thr Ser Gly Leu Gly Leu Gly Ala Asp Val
                245                 250                 255

Pro Ala Pro Arg Ile Ile Ala Ser Gly Leu Phe Asn Ala Ile Pro Glu
            260                 265                 270

Ala Pro Pro Leu Thr Ala Pro Ile Ile Pro Asp Ala Gly Asn Pro Ala
        275                 280                 285

Ser Phe Gly Val Pro Ala Pro Ile Gly Ala Val Val Ser Ser Tyr Ala
    290                 295                 300

Leu Lys Asp Ser Gly Lys Thr Ile Ser Asp Thr Val Gln Tyr Tyr Ala
305                 310                 315                 320

Val Leu Pro Asp Gly Leu Gln Gln Ile Ser Pro Val Leu Ala Ala Ile
                325                 330                 335

Leu Arg Asn Asn Asn Ser Tyr Gly Leu Gln Gln Pro Pro Arg Leu Gly
            340                 345                 350

Ala Asp Glu Val Ala Lys Leu Pro Val Ser Arg Val Leu Asp Thr Arg
        355                 360                 365

Arg Tyr Pro Ser Glu Pro Val Ser Leu Val Asp Val Thr Arg Asp Pro
    370                 375                 380

Val Thr Cys Ala Tyr Trp Ser Lys Pro Val Gly Ala Ala Thr Ser Ser
385                 390                 395                 400

Leu Thr Leu Leu Ala Gly Ser Ala Leu Pro Val Pro Asp Ala Val His
                405                 410                 415

Thr Val Glu Leu Val Gly Ala Gly Asn Gly Gly Val Ala Thr Arg Val
            420                 425                 430
```

```
Ala Leu Ala Ala Gly Thr Gly Tyr Phe Thr Gln Thr Val Gly Gly Gly
        435                 440                 445

Pro Asp Ala Pro Gly Ala Gly Ser Leu Phe Trp Val Ser Asp Thr Gly
    450                 455                 460

Val Arg Tyr Gly Ile Asp Asn Glu Pro Gln Gly Val Ala Gly Gly Gly
465                 470                 475                 480

Lys Ala Val Glu Ala Leu Gly Leu Asn Pro Pro Pro Val Pro Ile Pro
                485                 490                 495

Trp Ser Val Leu Ser Leu Phe Val Pro Gly Pro Thr Leu Ser Arg Ala
            500                 505                 510

Asp Ala Leu Leu Ala His Asp Thr Leu Val Pro Asp Ser Arg Pro Ala
        515                 520                 525

Arg Pro Val Ser Ala Glu Gly Gly Tyr Arg
    530                 535


<210> SEQ ID NO 4
<211> LENGTH: 1614
<212> TYPE: DNA
<213> ORGANISM: Mycobacterium tuberculosis

<400> SEQUENCE: 4

atgacgaacc agcagcacga ccacgacttc gaccacgacc gtcgctcgtt cgcctcccga     60

accccggtca acaacaaccc cgacaaggtt gtctaccgcc gcggcttcgt cacccgccat    120

caggtgacgg gctggcggtt cgtgatgcgc cgaatcgccg ccggaatcgc attgcacgac    180

acccgcatgc tggtcgaccc gttgcgcact cagtcacgcg cggtgctgat gggtgtgctg    240

attgtgatca cggggttgat cggctccttc gtattctcgt tgattcggcc caatgggcag    300

gcgggtagca acgcggtgct tgccgaccgg tccaccgcgg cgctgtatgt gcgggtgggc    360

gagcagctgc acccggtgct caacctgacc tcggcccggc tgatcgtcgg ccggccggtg    420

agcccgacga cggtgaaaag tactgagttg gaccagtttc cgcgcggaaa cctgatcggc    480

atcccgggtg cgccggagcg gatggtgcag aacacctcca ccgacgcgaa ctggacggtg    540

tgtgacggcc tcaacgcacc gtcgcggggc ggtgcggatg gcgtgggtgt gacggtgatt    600

gccggcccgc tggaggacac cggcgcacgc gcggccgcgc tcgggcccgg gcaggcggtg    660

ctggtcgaca gcggcgccgg cacctggctg ttgtgggacg gcaagcgcag cccgattgat    720

ctggccgatc atgcggtcac cagcggcctc ggcctgggcg ccgacgtgcc cgcgccgcgg    780

atcatcgcct cggggctgtt caacgcgata cccgaagcac cgccactgac ggcgccgatc    840

atcccggatg ccggcaaccc ggcgagcttc ggtgtgccgg cgccgatcgg cgcggtggtg    900

agttcctacg ccctgaaaga ctcgggcaag accatatcgg acaccgtgca gtactacgcg    960

gtgctgccgg acggtttgca gcagatttcg ccggtattgg cggcaatcct gcgcaacaac   1020

aactcctatg gtctgcagca gccgcctcgg ctgggggccg acgaggtcgc caagctgccg   1080

gtgtcgcggg tgttggacac caggcgctat cccagcgagc cggtaagtct cgtcgacgtt   1140

acccgtgacc ccgtcacctg cgcgtactgg agcaagccgg tgggtgcggc caccagctcg   1200

ttgactctgt tggcaggctc ggcgctgccg gtgccagatg cggtgcacac cgtcgagctg   1260

gtcggcgccg gcaacggtgg tgtggcaacc cgagtggcgt tagcggccgg tactggctac   1320

ttcacccaga cggtgggcgg cggcccagat gcgccgggcg ccgggtcgtt gttctgggtg   1380

tcggataccg gggtgcgtta cggtatcgac aatgagcctc agggagtggc tggaggcggc   1440

aaagcggttg aggcccttgg cctgaacccg cccccggtcc ccatcccgtg gtcggtgctg   1500

tcgctgtttg tgcccggccc gacgctgtcg cgtgccgacg cgctgctggc acacgacacc   1560
```

ttggtgcccg acagcaggcc cgctcgtccg gtatcggccg agggagggta ccgg 1614

<210> SEQ ID NO 5
<211> LENGTH: 412
<212> TYPE: PRT
<213> ORGANISM: Mycobacterium tuberculosis

<400> SEQUENCE: 5

```
Met Lys Ile Arg Thr Leu Ser Gly Ser Val Leu Glu Pro Pro Ser Ala
1               5                   10                  15

Val Arg Ala Thr Pro Gly Thr Ser Met Leu Lys Leu Glu Pro Gly Gly
            20                  25                  30

Ser Thr Ile Pro Lys Ile Pro Phe Ile Arg Pro Ser Phe Pro Gly Pro
        35                  40                  45

Ala Glu Leu Ala Glu Asp Phe Val Gln Ile Ala Gln Ala Asn Trp Tyr
    50                  55                  60

Thr Asn Phe Gly Pro Asn Glu Arg Arg Phe Ala Arg Ala Leu Arg Asp
65                  70                  75                  80

Tyr Leu Gly Pro His Leu His Val Ala Thr Leu Ala Asn Gly Thr Leu
                85                  90                  95

Ala Leu Leu Ala Ala Leu His Val Ser Phe Gly Ala Gly Thr Arg Asp
            100                 105                 110

Arg Tyr Leu Leu Met Pro Ser Phe Thr Phe Val Gly Val Ala Gln Ala
        115                 120                 125

Ala Leu Trp Thr Gly Tyr Arg Pro Trp Phe Ile Asp Ile Asp Ala Asn
    130                 135                 140

Thr Trp Gln Pro Cys Val His Ser Ala Arg Ala Val Ile Glu Arg Phe
145                 150                 155                 160

Arg Asp Arg Ile Ala Gly Ile Leu Leu Ala Asn Val Phe Gly Val Gly
                165                 170                 175

Asn Pro Gln Ile Ser Val Trp Glu Glu Leu Ala Ala Glu Trp Glu Leu
            180                 185                 190

Pro Ile Val Leu Asp Ser Ala Ala Gly Phe Gly Ser Thr Tyr Ala Asp
        195                 200                 205

Gly Glu Arg Leu Gly Gly Arg Gly Ala Cys Glu Ile Phe Ser Phe His
    210                 215                 220

Ala Thr Lys Pro Phe Ala Val Gly Glu Gly Gly Ala Leu Val Ser Arg
225                 230                 235                 240

Asp Pro Arg Leu Val Glu His Ala Tyr Lys Phe Gln Asn Phe Gly Leu
                245                 250                 255

Val Gln Thr Arg Glu Ser Ile Gln Leu Gly Met Asn Gly Lys Leu Ser
            260                 265                 270

Glu Ile Ser Ala Ala Ile Gly Leu Arg Gln Leu Val Gly Leu Asp Arg
        275                 280                 285

Arg Leu Ala Ser Arg Arg Lys Val Leu Glu Cys Tyr Arg Thr Gly Met
    290                 295                 300

Ala Asp Ala Gly Val Arg Phe Gln Asp Asn Ala Asn Val Ala Ser Leu
305                 310                 315                 320

Cys Phe Ala Ser Ala Cys Cys Thr Ser Ala Asp His Lys Ala Ala Val
                325                 330                 335

Leu Gly Ser Leu Arg Arg His Ala Ile Glu Ala Arg Asp Tyr Tyr Asn
            340                 345                 350

Pro Pro Gln His Arg His Pro Tyr Phe Val Thr Asn Ala Glu Leu Val
        355                 360                 365
```

```
Glu Ser Thr Asp Leu Ala Val Thr Ala Asp Ile Cys Ser Arg Ile Val
    370                 375                 380

Ser Leu Pro Val His Asp His Met Ala Pro Asp Asp Val Ala Arg Val
385                 390                 395                 400

Val Ala Ala Val Gln Glu Ala Glu Val Arg Gly Glu
                405                 410


<210> SEQ ID NO 6
<211> LENGTH: 1236
<212> TYPE: DNA
<213> ORGANISM: Mycobacterium tuberculosis

<400> SEQUENCE: 6

atgaagatcc gaacgttatc cggctcggtg ctggagccgc cgtccgcagt acgcgcgacc     60

ccaggcacgt ccatgttaaa actcgagccg ggtggctcga cgatccccaa gatccccttc    120

atccgcccga gctttcccgg gccagccgag ctcgccgagg acttcgtaca gatcgcccag    180

gctaactggt acacgaactt cggtccgaac gagcggcggt ttgcccgcgc cctgcgcgac    240

tatctgggac ctcatctgca cgttgctacc ctcgccaacg gcaccctggc actcctcgcg    300

gcgctccacg tcagtttcgg cgccggtacg cgggaccgct acctgctgat gccgtcgttc    360

acgttcgtcg gcgtggctca ggctgcgcta tggactgggt accgtccctg gttcatcgac    420

atcgacgcca acacatggca gccatgcgtc cactccgccc gcgccgtcat cgaacgcttc    480

cgcgaccgga tcgccggcat cctgctggcc aatgtgttcg gcgtcggcaa tccccagatc    540

agcgtctggg aggagctcgc cgccgaatgg gagctaccga ttgtgctcga ctcggcggcc    600

ggcttcggct ccacgtacgc cgacggcgag cgcctcggtg gacgcggtgc atgcgagatc    660

ttctccttcc atgcgaccaa gccgttcgcg gttggtgagg gcggcgctct ggtttctcgc    720

gatccacggc tcgtcgagca cgcatacaag ttccagaact tcggcttggt gcaaacacgc    780

gagtccatcc agctcggaat gaacggcaag ctgtcggaga tcagcgccgc tattggccta    840

cgccaactag tcgggcttga tcgccgcctg gcaagtcgcc gcaaggtcct cgagtgctat    900

cgcaccggta tggccgacgc gggtgtgcgt ttccaggaca acgccaatgt tgcgtcgctc    960

tgtttcgcga gcgcttgctg cacgtccgcc gaccacaagg ccgcggttct gggtagcctg   1020

cgtaggcacg cgatcgaggc gcgcgactac tacaacccac cgcagcaccg acatccgtac   1080

tttgtgacga atgccgagtt agtcgagtcg accgatctag ccgtcacggc ggacatttgc   1140

tcgcgaatcg tgtcgctgcc agtccacgac cacatggccc cggatgacgt tgcccgggtc   1200

gtcgccgccg tgcaggaagc ggaggtgcgc ggtgaa                              1236


<210> SEQ ID NO 7
<211> LENGTH: 524
<212> TYPE: PRT
<213> ORGANISM: Mycobacterium tuberculosis

<400> SEQUENCE: 7

Val Ser Ile Ala Asp Thr Ala Ala Lys Pro Ser Thr Pro Ser Pro Ala
1               5                   10                  15

Asn Gln Pro Pro Val Arg Thr Arg Ala Val Ile Ile Gly Thr Gly Phe
            20                  25                  30

Ser Gly Leu Gly Met Ala Ile Ala Leu Gln Lys Gln Gly Val Asp Phe
        35                  40                  45

Val Ile Leu Glu Lys Ala Asp Asp Val Gly Gly Thr Trp Arg Asp Asn
    50                  55                  60

Thr Tyr Pro Gly Cys Ala Cys Asp Ile Pro Ser His Leu Tyr Ser Phe
```

-continued

```
65                  70                  75                  80

Ser Phe Glu Pro Lys Ala Asp Trp Lys His Leu Phe Ser Tyr Trp Asp
                85                  90                  95

Glu Ile Leu Gly Tyr Leu Lys Gly Val Thr Asp Lys Tyr Gly Leu Arg
            100                 105                 110

Arg Tyr Ile Glu Phe Asn Ser Leu Val Asp Arg Gly Tyr Trp Asp Asp
        115                 120                 125

Asp Glu Cys Arg Trp His Val Phe Thr Ala Asp Gly Arg Glu Tyr Val
    130                 135                 140

Ala Gln Phe Leu Ile Ser Gly Ala Gly Ala Leu His Ile Pro Ser Phe
145                 150                 155                 160

Pro Glu Ile Ala Gly Arg Asp Glu Phe Ala Gly Pro Ala Phe His Ser
                165                 170                 175

Ala Gln Trp Asp His Ser Ile Asp Leu Thr Gly Lys Arg Val Ala Ile
            180                 185                 190

Val Gly Thr Gly Ala Ser Ala Ile Gln Ile Val Pro Glu Ile Val Gly
        195                 200                 205

Gln Val Ala Glu Leu Gln Leu Tyr Gln Arg Thr Pro Pro Trp Val Val
    210                 215                 220

Pro Arg Thr Asn Glu Glu Leu Pro Val Ser Leu Arg Arg Ala Leu Arg
225                 230                 235                 240

Thr Val Pro Gly Leu Arg Ala Leu Leu Arg Leu Gly Ile Tyr Trp Ala
                245                 250                 255

Gln Glu Ala Leu Ala Tyr Gly Met Thr Lys Arg Pro Asn Thr Leu Lys
            260                 265                 270

Ile Ile Glu Ala Tyr Ala Lys Tyr Asn Ile Arg Arg Ser Val Lys Asp
        275                 280                 285

Arg Glu Leu Arg Arg Lys Leu Thr Pro Arg Tyr Arg Ile Gly Cys Lys
    290                 295                 300

Arg Ile Leu Asn Ser Ser Thr Tyr Tyr Pro Ala Val Ala Asp Pro Lys
305                 310                 315                 320

Thr Glu Leu Ile Thr Asp Arg Ile Asp Arg Ile Thr His Asp Gly Ile
                325                 330                 335

Val Thr Ala Asp Gly Thr Gly Arg Glu Val Phe Arg Glu Ala Asp Val
            340                 345                 350

Ile Val Tyr Ala Thr Gly Phe His Val Thr Asp Ser Tyr Thr Tyr Val
        355                 360                 365

Gln Ile Lys Gly Arg His Gly Glu Asp Leu Val Asp Arg Trp Asn Arg
    370                 375                 380

Glu Gly Ile Gly Ala His Arg Gly Ile Thr Val Ala Asn Met Pro Asn
385                 390                 395                 400

Leu Phe Phe Leu Leu Gly Pro Asn Thr Gly Leu Gly His Asn Ser Val
                405                 410                 415

Val Phe Met Ile Glu Ser Gln Ile His Tyr Val Ala Asp Ala Ile Ala
            420                 425                 430

Lys Cys Asp Arg Met Gly Val Gln Ala Leu Ala Pro Thr Arg Glu Ala
        435                 440                 445

Gln Asp Arg Phe Asn Gln Glu Leu Gln Arg Arg Leu Ala Gly Ser Val
    450                 455                 460

Trp Asn Ser Gly Gly Cys Arg Ser Trp Tyr Leu Asp Glu His Gly Lys
465                 470                 475                 480

Asn Thr Val Leu Trp Cys Gly Tyr Thr Trp Gln Tyr Trp Leu Thr Thr
                485                 490                 495
```

```
Arg Ser Val Asn Pro Ala Glu Tyr Arg Phe Phe Gly Ile Gly Asn Gly
            500                 505                 510

Leu Ser Ser Asp Arg Ala Thr Val Ala Ala Ala Asn
        515                 520


<210> SEQ ID NO 8
<211> LENGTH: 1572
<212> TYPE: DNA
<213> ORGANISM: Mycobacterium tuberculosis

<400> SEQUENCE: 8

gtgagcattg ccgatacggc tgccaagccg tccacgccaa gcccggccaa ccagccgccg      60

gtacgtaccc gcgccgtcat catcggaacc ggattctccg gtttgggcat ggccatcgca     120

ctgcaaaagc aaggagtgga cttcgtcata ttggagaaag ccgacgacgt cggcggcacc     180

tggcgcgaca acacctaccc cggctgcgcg tgcgacatcc cgtcgcacct gtactccttc     240

tcgttcgagc ccaaggcgga ctggaaacac ctgttttcct actgggacga aatcttgggc     300

tacctcaaag ggtcaccga caagtacggc ctgcgccgct acatcgagtt caattcgctc     360

gtcgatcgcg gctactggga cgacgacgaa tgccgctggc acgtgttcac cgccgacggg     420

cgtgaatacg tcgcgcagtt cctgatctcc ggggccggtg cgttgcacat cccgtccttc     480

cccgagatcg caggtcgcga cgaattcgcc ggccccgctt tccattccgc ccagtgggac     540

cacagtatcg acctgaccgg caagcgggtg gcgatcgtcg ggaccggtgc cagcgcgatc     600

cagatcgtgc ccgagatcgt cggccaggtc gccgaacttc agctctatca gcgcaccccg     660

ccgtgggtgg tcccgcgcac caacgaagag ctgccggtgt cgctgcgccg ggcgttgcga     720

accgtccccg ggctacgggc actgttgcgc ctcggcatct actgggccca ggaggcgctg     780

gcctacggca tgaccaagcg gcccaacacg ttgaagatca tcgaggccta tgccaaatac     840

aatattcgtc gatcggtgaa ggatcgcgag ctgcggcgca agctgacgcc gcggtatcgc     900

atcggctgca aacggatcct gaactcctct acctattacc ccgcggtggc ggacccgaag     960

accgaactga tcaccgaccg catcgaccgg atcacgcacg acgggatcgt caccgccgac    1020

ggcactggcc gtgaggtctt ccgggaagcc gatgtgatcg tgtacgccac cggcttccac    1080

gtcaccgact cctataccta tgtgcagatc aaggggcgtc acggcgagga cctggtcgac    1140

cgctggaacc gtgagggcat cggtgcacac cgcgggatca ccgtcgccaa catgcccaac    1200

ctgttcttcc tgctggggcc gaacactggg ctgggacaca actccgtggt gttcatgatc    1260

gaatcgcaga tccattacgt ggccgatgcg atcgcgaaat gcgaccggat gggcgtgcaa    1320

gcgctggccc ccacccgcga ggcgcaagac cggttcaacc aggagctgca gcgcaggctg    1380

gctgggtcgg tgtggaacag tggcggctgc cgcagctggt atctcgacga gcacggcaag    1440

aacaccgtgc tctggtgcgg ctacacctgg caatactggc tgaccacccg ctcggtcaac    1500

cccgccgagt accggttctt cgggatcggc aacggtttgt cgagcgaccg cgcgacggtc    1560

gctgcggcga ac                                                        1572


<210> SEQ ID NO 9
<211> LENGTH: 444
<212> TYPE: PRT
<213> ORGANISM: Mycobacterium tuberculosis

<400> SEQUENCE: 9

Met Ser Asp Asn Asp Pro Val Val Ile Val Gly Leu Ala Ile Glu Ala
1               5                   10                  15

Pro Gly Gly Val Glu Thr Ala Asp Asp Tyr Trp Thr Leu Leu Ser Glu
```

-continued

```
            20                  25                  30

Gln Arg Glu Gly Leu Gly Pro Phe Pro Thr Asp Arg Gly Trp Ala Leu
        35                  40                  45

Arg Glu Leu Phe Asp Gly Ser Arg Arg Asn Gly Phe Lys Pro Ile His
    50                  55                  60

Asn Leu Gly Gly Phe Leu Ser Ser Ala Thr Thr Phe Asp Pro Glu Phe
65                  70                  75                  80

Phe Arg Ile Ser Pro Arg Glu Ala Thr Ala Met Asp Pro Gln Gln Arg
                85                  90                  95

Val Gly Leu Arg Val Ala Trp Arg Thr Leu Glu Asn Ser Gly Ile Asn
            100                 105                 110

Pro Asp Asp Leu Ala Gly His Asp Val Gly Cys Tyr Val Gly Ala Ser
        115                 120                 125

Ala Leu Glu Tyr Gly Pro Ala Leu Thr Glu Phe Ser His His Ser Gly
    130                 135                 140

His Leu Ile Thr Gly Thr Ser Leu Gly Val Ile Ser Gly Arg Ile Ala
145                 150                 155                 160

Tyr Thr Leu Asp Leu Ala Gly Pro Ala Leu Thr Val Asp Thr Ser Cys
                165                 170                 175

Ser Ser Ala Leu Ala Ala Phe His Thr Ala Val Gln Ala Ile Arg Ala
            180                 185                 190

Gly Asp Cys Asp Leu Ala Leu Ala Gly Gly Val Cys Val Met Gly Thr
        195                 200                 205

Pro Gly Tyr Phe Val Glu Phe Ser Lys Gln His Ala Leu Ser Asp Asp
    210                 215                 220

Gly His Cys Arg Pro Tyr Ser Ala His Ala Ser Gly Thr Ala Trp Ala
225                 230                 235                 240

Glu Gly Ala Ala Met Phe Leu Leu Gln Arg Arg Ser Arg Ala Thr Ala
                245                 250                 255

Asp Arg Arg Arg Val Leu Ala Glu Val Arg Ala Ser Cys Leu Asn Ser
            260                 265                 270

Asp Gly Leu Ser Asp Gly Leu Thr Ala Pro Ser Gly Asp Ala Gln Thr
        275                 280                 285

Arg Leu Leu Arg Arg Ala Ile Ala Gln Ala Ala Val Val Pro Ala Asp
    290                 295                 300

Val Gly Met Val Glu Gly His Gly Thr Ala Thr Arg Leu Gly Asp Arg
305                 310                 315                 320

Thr Glu Leu Arg Ser Leu Ala Ala Ser Tyr Gly Thr Ala Pro Ala Gly
                325                 330                 335

Arg Gly Pro Leu Leu Gly Ser Val Lys Ser Asn Ile Gly His Ala Gln
            340                 345                 350

Ala Ala Ala Gly Gly Leu Gly Leu Val Lys Val Ile Leu Ala Ala Gln
        355                 360                 365

His Ala Ala Ile Pro Pro Thr Leu His Val Asp Glu Pro Ser Arg Glu
    370                 375                 380

Ile Asp Trp Glu Lys Gln Gly Leu Arg Leu Ala Asp Lys Leu Thr Pro
385                 390                 395                 400

Trp Arg Ala Val Asp Gly Trp Arg Thr Ala Ala Val Ser Ala Phe Gly
                405                 410                 415

Met Ser Gly Thr Asn Ser His Val Ile Val Ser Met Pro Asp Thr Val
            420                 425                 430

Ser Ala Pro Glu Arg Gly Pro Glu Cys Gly Glu Val
        435                 440
```

-continued

<210> SEQ ID NO 10
<211> LENGTH: 1332
<212> TYPE: DNA
<213> ORGANISM: Mycobacterium tuberculosis

<400> SEQUENCE: 10

```
atgtccgata acgacccggt cgtcatcgtc gggctggcca tcgaggcacc cggtggtgtc      60
gaaaccgccg acgactactg gacactgctc tccgaacagc gcgagggact cggaccgttc     120
cccaccgatc gaggttgggc acttcgcgag ctgttcgacg ggtcgcgtcg aaacggattc     180
aaaccgatcc acaaccttgg cggattcctt tccagcgcaa ctacattcga tcctgagttc     240
ttccgcatct caccgcgcga ggcgacggcg atggacccgc agcagcgggt ggggctgcga     300
gtagcatggc gcaccctgga gaacagcggg atcaatcccg atgacctggc cggtcacgat     360
gtgggctgtt atgtcggtgc ctcggcgctc gaatacggtc ccgctttgac cgaattctcc     420
caccacagtg gccatctgat caccgggacg tcgctgggtg tcatctccgg gcgcatcgcc     480
tacacccttg acctggccgg gccggcgctg accgtcgata cctcgtgttc gtcggcgctg     540
gcggcctttc acaccgcggt tcaagctatc cgggccggcg actgcgacct ggcactcgcc     600
ggcggcgtgt gcgtgatggg tacgcccggc tatttcgtcg agttctccaa gcagcacgcg     660
ctatccgacg acggccactg ccggccctac agcgcgcacg ccagcggaac cgcctgggca     720
gagggcgccg ccatgttcct cctgcagcgc cggtcgcggg caaccgctga ccggcgtcgt     780
gtcctcgccg aggtgcgtgc cagttgcctg aactccgatg gacttagcga cgggctgacc     840
gcgcccagcg gcgacgcgca aacgcgactg ctccggcgcg ccatcgcgca ggcagcagtt     900
gtgcccgccg atgtcgggat ggtcgaaggg cacggcaccg cgacccggct cggcgatcgc     960
accgaattgc ggtcactggc agccagctac ggcaccgccc cggccggacg cgggccgctg    1020
ttgggatcgg tcaagtcaaa catcgggcat gctcaggcgg cggcgggcgg gctgggcctt    1080
gtgaaggtca ttctggccgc ccagcacgcc gcgatcccgc cgacactgca cgtcgacgag    1140
cccagccgcg aaatcgattg ggagaaacag ggtctgcggc tggccgacaa actcacgccg    1200
tggcgggccg ttgacggatg gcgcaccgcg gcggtgtccg cgttcgggat gagcggtacc    1260
aatagccacg tgatcgtttc gatgccggac accgtttccg cgcccgagcg tggccccgag    1320
tgtggggagg tg                                                        1332
```

<210> SEQ ID NO 11
<211> LENGTH: 1004
<212> TYPE: PRT
<213> ORGANISM: Mycobacterium tuberculosis

<400> SEQUENCE: 11

```
Met Ala Pro Lys Gln Leu Pro Asp Gly Arg Val Ala Val Leu Leu Ser
1               5                   10                  15

Ala His Ala Glu Glu Leu Ile Gly Pro Asp Ala Arg Ala Ile Ala Asp
            20                  25                  30

Tyr Leu Glu Arg Phe Pro Ala Thr Thr Val Thr Glu Val Ala Arg Gln
        35                  40                  45

Leu Arg Lys Thr Arg Arg Val Arg Arg His Arg Ala Val Leu Arg Ala
    50                  55                  60

Ala Asp Arg Leu Glu Leu Ala Glu Gly Leu Arg Ala Leu Ala Ala Gly
65                  70                  75                  80

Arg Glu His Pro Leu Ile Ala Arg Ser Ser Leu Gly Ser Ala Pro Arg
                85                  90                  95
```

-continued

```
Gln Ala Phe Val Phe Pro Gly Gln Gly Gly His Trp Pro Gly Met Gly
            100                 105                 110

Ala Val Ala Tyr Arg Glu Leu Pro Thr Tyr Arg Thr Ala Thr Asp Thr
        115                 120                 125

Cys Ala Ala Ala Phe Ala Ala Ala Gly Val Asp Ser Pro Leu Pro Tyr
    130                 135                 140

Leu Ile Ala Pro Pro Gly Thr Asp Glu Arg Gln Ala Phe Cys Glu Ile
145                 150                 155                 160

Glu Ile Glu Gly Ala Gln Phe Val His Ala Val Ala Leu Ala Glu Val
                165                 170                 175

Trp Arg Ser Cys Gly Val Leu Pro Asp Leu Thr Val Gly His Ser Leu
            180                 185                 190

Gly Glu Val Ala Ala Ala Tyr Leu Ala Gly Ser Ile Thr Leu Ser Asp
        195                 200                 205

Ala Val Ala Val Val Ala Ala Arg Ala Asn Val Val Gly Arg Leu Pro
    210                 215                 220

Gly Arg Tyr Ala Val Ala Ala Leu Gly Ile Gly Glu Gln Asp Ala Ser
225                 230                 235                 240

Ala Leu Ile Ala Thr Thr Gly Gly Trp Leu Glu Leu Ser Val Val Asn
                245                 250                 255

Ala Ser Ser Thr Val Ala Val Ser Gly Glu Arg Gln Ala Val Ala Ala
            260                 265                 270

Ile Val Asp Thr Val Arg Ser Ser Gly His Phe Ala Arg Gly Ile Thr
        275                 280                 285

Val Gly Phe Pro Val His Thr Ser Val Leu Glu Ser Leu Arg Asp Glu
    290                 295                 300

Leu Cys Glu Gln Leu Pro Asp Ser Glu Phe Met Glu Ala Pro Val Gln
305                 310                 315                 320

Phe Ile Gly Gly Thr Thr Gly Asp Val Val Ala Pro Gly Thr Thr Phe
                325                 330                 335

Gly Asp Tyr Trp Tyr Ala Asn Leu Arg His Thr Val Arg Phe Asp Arg
            340                 345                 350

Ala Val Glu Ser Ala Ile Arg Cys Gly Ala Arg Ala Phe Ile Glu Ile
        355                 360                 365

Ser Ala His Pro Ala Leu Leu Phe Ala Ile Gly Gln Asn Cys Glu Gly
    370                 375                 380

Ala Ala Asn Leu Pro Asp Gly Pro Ala Val Leu Val Gly Ser Ala Arg
385                 390                 395                 400

Arg Gly Glu Arg Phe Val Asp Ala Leu Ser Ala Asn Ile Val Ser Ala
                405                 410                 415

Ala Val Ala Asp Pro Gly Tyr Pro Trp Gly Asp Leu Gly Gly Asp Pro
            420                 425                 430

Leu Asp Gly Asp Val Asp Leu Ser Gly Phe Pro Asn Ala Pro Met Arg
        435                 440                 445

Ala Val Pro Met Trp Ala His Pro Glu Pro Leu Pro Pro Val Ser Gly
    450                 455                 460

Leu Thr Ile Ala Val Glu Arg Trp Glu Arg Met Val Pro Ser Thr Pro
465                 470                 475                 480

Val Ala Gly Arg His Arg His Leu Ala Val Leu Asp Leu Gly Ala His
                485                 490                 495

Arg Ala Leu Ala Gln Thr Leu Cys Ala Ala Ile Asp Ser His Pro Asp
            500                 505                 510

Thr Glu Leu Ser Ala Ala Arg Asp Ala Glu Leu Ile Leu Val Ile Ala
        515                 520                 525
```

Pro Asp Phe Glu His Thr Asp Ala Val Arg Ala Ala Gly Ala Leu Ala
530 535 540

Asp Leu Val Gly Ala Gly Leu Leu Asp Tyr Pro Met His Ile Gly Ala
545 550 555 560

Arg Cys Gln Ser Val Cys Leu Val Thr Val Gly Ala Glu Gln Val Asp
565 570 575

Ala Ala Asp Ala Val Pro Ser Ala Gly Gln Ala Ala Leu Ala Ala Met
580 585 590

His Arg Ser Ile Gly Phe Glu His Pro Glu Gln Thr Phe Ser His Leu
595 600 605

Asp Leu Pro Ser Trp Asp Leu Asp Pro Val Leu Gly Val Ser Val Ile
610 615 620

Thr Ala Val Leu Arg Gly Phe Gly Glu Thr Ala Leu Arg Gly Ser Val
625 630 635 640

Asn Gly Tyr Thr Leu Phe Glu Arg Thr Leu Ala Asp Ala Pro Ala Val
645 650 655

Pro Asn Trp Ser Leu Asp Ser Gly Val Leu Asp Asp Val Val Val Thr
660 665 670

Gly Gly Ala Gly Ala Ile Gly Met His Tyr Ala Arg Tyr Leu Ala Glu
675 680 685

His Gly Ala Arg Arg Ile Val Leu Leu Ser Arg Arg Ala Ala Asp Gln
690 695 700

Ala Thr Val Ala Met Leu Arg Lys Gln His Gly Thr Val Ile Val Ser
705 710 715 720

Pro Pro Cys Asp Ile Thr Asp Pro Thr Gln Leu Ser Ala Ile Ala Ala
725 730 735

Glu Tyr Gly Gly Val Gly Ala Ser Leu Ile Val His Ala Ala Gly Ser
740 745 750

Val Ile Ser Gly Thr Ala Pro Gly Val Thr Ser Ala Ala Val Val Asp
755 760 765

Asn Phe Ala Ala Lys Val Leu Gly Leu Ala Gln Met Ile Glu Leu Trp
770 775 780

Pro Leu Arg Pro Asp Val Arg Thr Leu Leu Cys Ser Ser Val Met Gly
785 790 795 800

Val Trp Gly Gly His Gly Val Val Ala Tyr Ser Ala Ala Asn Arg Leu
805 810 815

Leu Asp Val Met Ala Ala Gln Leu Arg Ala Gln Gly Arg His Cys Val
820 825 830

Ala Val Lys Trp Gly Leu Trp Gln Ala Pro Lys Ala Gly Glu Pro Ala
835 840 845

Arg Gly Ile Ala Asp Ala Val Thr Ile Ala Arg Val Glu Arg Ser Gly
850 855 860

Leu Arg Gln Met Ala Pro Gln Gln Ala Ile Glu Ala Ser Leu His Glu
865 870 875 880

Phe Thr Val Asp Pro Leu Val Phe Ala Ala Asp Ala Ala Arg Leu Gln
885 890 895

Met Leu Leu Asp Ser Arg Gln Phe Glu Arg Tyr Glu Gly Pro Thr Asp
900 905 910

Pro Asn Leu Thr Ile Val Asp Ala Val Arg Thr Gln Leu Ala Ala Val
915 920 925

Leu Gly Ile Pro Gln Ala Gly Glu Val Asn Leu Gln Glu Ser Leu Phe
930 935 940

Asp Leu Gly Val Asp Ser Met Leu Ala Leu Asp Leu Arg Asn Arg Leu

-continued

```
945                 950                 955                 960

Lys Arg Ser Ile Gly Ala Thr Val Ser Leu Ala Thr Leu Met Gly Asp
                965                 970                 975

Ile Thr Gly Asp Gly Leu Val Ala Lys Leu Glu Asp Ala Asp Glu Arg
            980                 985                 990

Ser His Thr Ala Gln Lys Val Asp  Ile Ser Arg Asp
        995                 1000
```

<210> SEQ ID NO 12
<211> LENGTH: 3012
<212> TYPE: DNA
<213> ORGANISM: Mycobacterium tuberculosis

<400> SEQUENCE: 12

```
atggccccca aacagctgcc cgatgggcgg gttgcggttt tgctcagcgc ccatgccgag     60

gaactgatcg ggccggacgc tcgggccatc gccgactacc tcgagcgctt tccggctacg    120

accgtgaccg aagtggctcg gcagctgcgc aagacccgac gggtccgtcg gcatcgggcg    180

gtgcttcggg ccgccgaccg gctggaactc gccgagggct tgcgcgcgct ggccgccgga    240

cgcgagcatc cgctcatcgc gcggtcgtcg ttgggctcgg ccccgcgcca ggcgttcgtc    300

tttcccggcc agggtggtca ttggccgggc atgggcgccg tcgcctaccg cgagctgccg    360

acctatcgga ccgcgaccga cacgtgcgcc gccgcatttg cggccgctgg tgtcgactcg    420

ccgctgccat acctgatcgc cccgcccgga accgatgagc ggcaagcgtt ctgcgagatc    480

gagatcgaag gcgcgcagtt cgtccatgcc gttgcgctgg cggaggtatg gcgttcctgc    540

ggtgtgctgc ccgatctaac agtcggtcat agcctcggcg aagtagcggc ggcctatctc    600

gcaggaagta tcaccttgtc ggatgctgtg gccgtggtgg cggcccgcgc caacgtggtg    660

ggccgcttgc ctggtcgcta tgcggtggcg gcgctgggca tcggtgaaca ggacgcgagc    720

gcgctgatcg cgaccaccgg cggctggctg gaactgtctg tggtcaatgc ctcctcgacc    780

gtcgccgtgt ccggtgagcg ccaagcggta gcggccatcg ttgacacagt ccggtccagc    840

ggtcacttcg cccgcgggat caccgtgggc ttcccggtgc ataccagcgt gctcgaatcg    900

ctccgcgatg aattatgcga gcagctgcct gactccgaat ttatggaagc gccagtgcaa    960

ttcatcggcg gaaccaccgg cgacgtggtg gcgccaggca ccactttcgg cgactactgg   1020

tacgcaaacc tgcgccatac ggtgcgtttc gaccgcgctg tcgaatcggc aatccgctgt   1080

ggagcacggg cgttcatcga gatatcggcc catcccgcgc tgttgtttgc gatcggtcag   1140

aactgtgagg gcgccgccaa cctgccggac ggtcccgctg tgctggtcgg gtcggcacgt   1200

cgtggcgagc ggtttgttga tgcgttgtcg gcgaatattg ttagcgcggc ggtcgctgac   1260

cctggctacc cgtggggtga cctgggcggt gacccactcg acggcgacgt cgatctgtcc   1320

gggttcccga acgcgccgat gcgtgcggtg ccgatgtggg cgcaccccga accgctgccg   1380

ccggtgtccg gactgaccat tgcggttgag cggtgggaac ggatggtgcc gtcgacaccg   1440

gtcgctgggc ggcaccgtca cctcgcagtg ctcgatctcg gtgctcaccg cgcgctggct   1500

caaacactgt gcgcagcaat tgattcgcac cccgataccg agctgagtgc tgcgcgggac   1560

gccgagttga tcctggtgat cgcgcccgac ttcgaacaca ccgacgccgt ccgggccgcc   1620

ggtgcactcg ccgacctcgt cggggccggt ttgctggact atccgatgca tatcggtgcc   1680

cgttgccaat cggtatgtct ggtcaccgtc ggcgccgagc aggtcgacgc agcggacgcg   1740

gtgccgtcgg ccggccaggc cgcgctggcc gcgatgcatc gaagcatcgg attcgagcat   1800

cccgaacaga ctttcagcca cctggacttg ccgtcgtggg acttggaccc ggtcctcggc   1860
```

-continued

```
gtctcggtca taacggcggt actgcggggc ttcggtgaga ccgcgctacg cggctcggta   1920

aacgggtaca cgctgttcga gcgaaccctc gccgatgccc cggccgtccc gaactggtcg   1980

ttggactccg gcgtgctcga cgatgtcgtc gtcaccggtg gcgcgggtgc catcgggatg   2040

cactacgcgc ggtatctcgc cgagcatggc gcacggcgca tcgtgctgct cagccggcgc   2100

gccgcggatc aggcgacggt ggccatgctc agaaagcaac atggcaccgt gatcgtgtcg   2160

ccgccgtgcg atatcaccga tcccacccag ttgtcagcga ttgcagccga atacggtggc   2220

gtcggcgcct cgttgatcgt gcacgcggca ggcagcgtga tctctggtac cgcaccgggg   2280

gtgacgtcgg ccgccgtcgt tgacaacttc gcggccaagg tgctcggcct ggcccagatg   2340

atcgagctgt ggccgctgcg cccggatgtg cgaaccctgc tgtgttcctc ggtgatgggg   2400

gtgtggggtg gacacggggt ggtcgcgtac tcggcggcca accggctgct cgacgtgatg   2460

gccgcccagc tgcgcgccca gggcaggcac tgcgtggcgg tgaaatgggg cctatggcag   2520

gcccccaagg ccggcgaacc agctcgggga atcgcggatg cggttacgat cgcccgcgtc   2580

gagcggtctg gactccgcca gatggcgccc cagcaggcga tcgaggcgag cctgcacgaa   2640

ttcactgtcg acccgctagt gttcgccgcc gacgcggccc ggttgcagat gttgttggac   2700

agcaggcaat tcgaacggta cgagggtcca accgacccca acctgacgat cgtggacgcg   2760

gtgcgcaccc aattggcggc cgtgctcggg atcccgcagg ccggcgaggt gaacctgcag   2820

gaatcgctgt tcgatctcgg tgtcgattcc atgctggcac tggacttgcg taaccgactc   2880

aaacgatcaa tcggcgcgac ggtgtcgctg gccacgctca tgggcgacat caccggtgat   2940

ggacttgtcg cgaaactcga agatgccgac gagcgctcac acaccgcaca gaaagtggac   3000

atttcgcgtg ac                                                       3012
```

```
<210> SEQ ID NO 13
<211> LENGTH: 1461
<212> TYPE: PRT
<213> ORGANISM: Mycobacterium tuberculosis

<400> SEQUENCE: 13

Met Gly Pro Val Ala Val Thr Arg Ala Asp Ala Arg Gly Ala Ile Asp
1               5                   10                  15

Asp Val Met Ala Leu Ser Pro Leu Gln Gln Gly Leu Phe Ser Arg Ala
            20                  25                  30

Thr Leu Val Ala Ala Glu Ser Gly Ser Glu Ala Ala Glu Ala Asp Pro
        35                  40                  45

Tyr Val Ile Ala Met Ala Ala Asp Ala Ala Gly Pro Leu Asp Ile Ala
    50                  55                  60

Leu Leu Arg Asp Cys Ala Ala Ala Met Leu Thr Arg His Pro Asn Leu
65                  70                  75                  80

Arg Ala Ser Phe Leu His Gly Asn Leu Ser Arg Pro Val Gln Val Ile
                85                  90                  95

Pro Ser Ser Ala Glu Val Leu Trp Arg His Val Arg Ala His Pro Ser
            100                 105                 110

Glu Val Gly Ala Leu Ala Ala Glu Glu Arg Arg Arg Arg Phe Asp Val
        115                 120                 125

Gly Arg Gly Pro Leu Ile Arg Phe Leu Leu Ile Glu Leu Pro Asp Glu
    130                 135                 140

Cys Trp His Leu Val Ile Val Ala His His Ile Val Ile Asp Gly Trp
145                 150                 155                 160

Ser Leu Pro Leu Phe Val Ser Glu Leu Leu Ala Leu Tyr Arg Ala Gly
```

-continued

```
                165                 170                 175

Gly His Val Ala Ala Leu Pro Ala Ala Pro Arg Pro Tyr Arg Asp Tyr
            180                 185                 190

Ile Gly Trp Leu Ala Gly Arg Asp Gln Thr Ala Ser Arg Ala Met Trp
        195                 200                 205

Ala Asp His Leu Asn Gly Leu Asp Gly Pro Thr Leu Leu Ser Pro Ala
    210                 215                 220

Leu Ala Asp Thr Pro Val Gln Pro Gly Ile Pro Gly Arg Thr Glu Val
225                 230                 235                 240

Arg Leu Asp Arg Glu Ala Thr Ala Glu Leu Ala Asp Ala Ala Arg Thr
                245                 250                 255

Arg Gly Val Thr Ile Ser Thr Leu Val Gln Met Ala Trp Ala Thr Thr
            260                 265                 270

Leu Ser Ala Phe Thr Gly Arg Gly Asp Val Thr Phe Gly Val Thr Val
        275                 280                 285

Ser Gly Arg Pro Ser Glu Leu Ser Gly Val Glu Thr Met Ile Gly Leu
    290                 295                 300

Phe Ile Asn Thr Val Pro Leu Arg Val Arg Leu Asp Ala Arg Ala Thr
305                 310                 315                 320

Val Gly Gly Gln Cys Ala Val Leu Gln Arg Gln Phe Ala Met Leu Arg
                325                 330                 335

Asp His Ser Tyr Leu Gly Phe Asn Glu Phe Arg Ala Ile Ala Gly Ile
            340                 345                 350

Gly Glu Met Phe Asp Thr Leu Leu Val Tyr Glu Asn Phe Pro Pro Gly
        355                 360                 365

Glu Val Val Gly Thr Ala Glu Phe Val Ala Asn Gly Val Thr Phe Arg
    370                 375                 380

Pro Val Ala Leu Glu Ser Leu Ser His Phe Pro Val Thr Val Ala Ala
385                 390                 395                 400

His Arg Ser Thr Gly Glu Leu Thr Leu Leu Val Glu Val Leu Asp Gly
                405                 410                 415

Ala Leu Gly Thr Met Ala Pro Glu Ser Leu Gly Arg Arg Val Leu Ala
            420                 425                 430

Val Leu Gln Arg Leu Val Ser Arg Trp Asp Arg Pro Leu Arg Asp Val
        435                 440                 445

Asp Ile Leu Leu Asp Gly Glu His Asp Pro Thr Ala Pro Gly Leu Pro
    450                 455                 460

Asp Val Thr Thr Ser Ala Pro Ala Val His Thr Arg Phe Ala Glu Ile
465                 470                 475                 480

Ala Ala Ala Gln Pro Asp Ser Val Ala Val Ser Trp Ala Asp Gly Gln
                485                 490                 495

Leu Thr Tyr Arg Glu Leu Asp Ala Leu Ala Asp Arg Leu Ala Thr Gly
            500                 505                 510

Leu Arg Arg Ala Asp Val Ser Arg Glu Thr Pro Val Ala Val Ala Leu
        515                 520                 525

Ser Arg Gly Pro Arg Tyr Val Ala Ala Met Leu Ala Val Leu Lys Ala
    530                 535                 540

Gly Gly Met Ile Val Pro Leu Asp Pro Ala Met Pro Gly Glu Arg Val
545                 550                 555                 560

Ala Glu Ile Leu Arg Gln Thr Ser Ala Pro Val Val Ile Asp Glu Gly
                565                 570                 575

Val Phe Ala Ala Ser Val Gly Ala Asp Ile Leu Glu Glu Asp Arg Ala
            580                 585                 590
```

-continued

```
Ile Thr Val Pro Val Asp Gln Ala Ala Tyr Val Ile Phe Thr Ser Gly
        595                 600                 605

Thr Thr Gly Thr Pro Lys Gly Val Ile Gly Thr His Arg Ala Leu Ser
    610                 615                 620

Ala Tyr Ala Asp Asp His Ile Glu Arg Val Leu Arg Pro Ala Ala Gln
625                 630                 635                 640

Arg Leu Gly Arg Pro Leu Arg Ile Ala His Ala Trp Ser Phe Thr Phe
                645                 650                 655

Asp Ala Ala Trp Gln Pro Leu Val Ala Leu Leu Asp Gly His Ala Val
            660                 665                 670

His Ile Val Asp Asp His Arg Gln Arg Asp Ala Gly Ala Leu Val Glu
        675                 680                 685

Ala Ile Asp Arg Phe Gly Leu Asp Met Ile Asp Thr Thr Pro Ser Met
    690                 695                 700

Phe Ala Gln Leu His Asn Ala Gly Leu Leu Asp Arg Ala Pro Leu Ala
705                 710                 715                 720

Val Leu Ala Leu Gly Gly Glu Ala Leu Gly Ala Ala Thr Trp Arg Met
                725                 730                 735

Ile Gln Gln Asn Cys Ala Arg Thr Ala Met Thr Ala Phe Asn Cys Tyr
            740                 745                 750

Gly Pro Thr Glu Thr Thr Val Glu Ala Val Val Ala Ala Val Ala Glu
        755                 760                 765

His Ala Arg Pro Val Ile Gly Arg Pro Thr Cys Thr Thr Arg Ala Tyr
    770                 775                 780

Val Met Asp Ser Trp Leu Arg Pro Val Pro Asp Gly Val Ala Gly Glu
785                 790                 795                 800

Leu Tyr Leu Ala Gly Ala Gln Leu Thr Arg Gly Tyr Leu Gly Arg Pro
                805                 810                 815

Ala Glu Thr Ala Ala Arg Phe Val Ala Glu Pro Asn Gly Arg Gly Ser
            820                 825                 830

Arg Met Tyr Arg Thr Gly Asp Val Val Arg Arg Leu Pro Asp Gly Gly
        835                 840                 845

Leu Glu Phe Leu Gly Arg Ser Asp Asp Gln Val Lys Ile Arg Gly Phe
    850                 855                 860

Arg Val Glu Pro Gly Glu Ile Ala Ala Val Leu Asn Gly His His Ala
865                 870                 875                 880

Val His Gly Cys His Val Thr Ala Arg Gly His Ala Ser Gly Pro Arg
                885                 890                 895

Leu Thr Ala Tyr Val Ala Gly Gly Pro Gln Pro Pro Pro Val Ala Glu
            900                 905                 910

Leu Arg Ala Met Leu Leu Glu Arg Leu Pro Arg Tyr Leu Val Pro His
        915                 920                 925

His Ile Val Val Leu Asp Glu Leu Pro Leu Thr Pro His Gly Lys Ile
    930                 935                 940

Asp Glu Asn Ala Leu Ala Ala Ile Asn Val Thr Glu Gly Pro Ala Thr
945                 950                 955                 960

Pro Pro Gln Thr Pro Thr Glu Leu Val Leu Ala Glu Ala Phe Ala Asp
                965                 970                 975

Val Met Glu Thr Ser Asn Val Asp Val Thr Ala Gly Phe Leu Gln Met
            980                 985                 990

Gly Leu Asp Ser Ile Val Ala Leu  Ser Val Val Gln Ala  Ala Arg Arg
        995                 1000                 1005

Arg Gly  Ile Ala Leu Arg Ala  Arg Leu Met Val Glu  Cys Asp Thr
    1010                 1015                 1020
```

-continued

Ile Arg Glu Leu Ala Ala Ala Ile Asp Ser Asp Ala Ala Trp Gln
1025 1030 1035

Ala Pro Ala Asn Asp Ala Gly Glu Pro Ile Pro Val Leu Pro Asn
1040 1045 1050

Thr His Trp Leu Tyr Glu Tyr Gly Asp Pro Arg Arg Leu Ala Gln
1055 1060 1065

Thr Glu Val Ile Arg Leu Pro Asp Arg Ile Thr Arg Glu Arg Leu
1070 1075 1080

Asp Ala Val Leu Ala Ala Val Val Asp Gly His Glu Val Leu Arg
1085 1090 1095

Cys Arg Phe Asp Arg Asp Ala Met Ala Leu Val Ala Gln Pro Lys
1100 1105 1110

Thr Asp Ile Leu Ser Glu Val Trp Val Ser Gly Glu Leu Val Thr
1115 1120 1125

Ala Val Ala Glu Gln Thr Leu Gly Ala Leu Ala Ser Leu Asp Pro
1130 1135 1140

Gln Ala Gly Arg Leu Leu Ser Ala Val Trp Leu Arg Glu Pro Asp
1145 1150 1155

Gly Pro Gly Val Leu Val Leu Thr Ala His Val Leu Ala Met Asp
1160 1165 1170

Pro Ala Ser Trp Arg Ile Val Leu Gly Glu Leu Asp Ala Gly Leu
1175 1180 1185

His Ala Leu Ala Ala Gly Arg Ala Pro Ser Pro Ala Arg Glu Asn
1190 1195 1200

Thr Ser Tyr Arg Gln Trp Ser Arg Leu Leu Ala Gln Arg Ala Lys
1205 1210 1215

Ala Leu Asp Ser Val Asp Phe Trp Val Ala Glu Leu Glu Gly Ala
1220 1225 1230

Asp Pro Pro Leu Gly Ala Arg Arg Val Ala Pro Gln Thr Asp Arg
1235 1240 1245

Val Gly Glu Leu Ala Ile Thr Met Ser Ile Ser Asp Ala Asp Leu
1250 1255 1260

Thr Ala Arg Leu Leu Ser Thr Gly Arg Ser Met Thr Asp Leu Leu
1265 1270 1275

Ala Thr Ala Ala Ala Arg Met Val Thr Ala Trp Arg Arg Gln Arg
1280 1285 1290

Gly Gln Gln Thr Pro Ala Pro Leu Leu Ala Leu Glu Thr His Gly
1295 1300 1305

Arg Ala Asp Val His Val Asp Lys Thr Ala Asp Thr Ser Asp Thr
1310 1315 1320

Val Gly Leu Leu Ser Ala Ile Tyr Pro Leu Arg Ile His Cys Asp
1325 1330 1335

Gly Ala Thr Asp Phe Ala Arg Ile Pro Gly Ser Gly Ile Asp Tyr
1340 1345 1350

Gly Leu Leu Arg Tyr Leu Arg Ala Asp Thr Ala Glu Arg Leu Arg
1355 1360 1365

Ala His Arg Glu Pro Gln Leu Leu Leu Asn Tyr Leu Gly Ser Leu
1370 1375 1380

His Val Gly Val Gly Asp Leu Ala Val Asp Arg Ala Leu Leu Ala
1385 1390 1395

Asp Val Gly Gln Leu Pro Glu Pro Glu Gln Pro Val Arg His Glu
1400 1405 1410

Leu Thr Val Leu Ala Ala Leu Leu Gly Pro Ala Asp Ala Pro Val

-continued

```
    1415                1420                1425

Leu Ala  Thr Arg Trp Arg Thr  Leu Pro Asp Ile Leu  Ser Ala Asp
    1430                1435                1440

Asp Val  Ala Thr Leu Gln Ser  Leu Trp Gln Gly Ala  Leu Ala Glu
    1445                1450                1455

Ile Thr  Ala
    1460
```

<210> SEQ ID NO 14
<211> LENGTH: 4383
<212> TYPE: DNA
<213> ORGANISM: Mycobacterium tuberculosis

<400> SEQUENCE: 14

```
atgggaccag tggccgtgac gcgagccgac gcgcggggcg ccatcgacga tgtgatggcg     60
ctcagcccat tgcaacaggg actgttttct agggcgacac tggtcgccgc ggagtccggc    120
tctgaggccg cagaggccga cccgtatgtg atcgcgatgg cggccgacgc ggccggcccg    180
ctcgacatcg ccttgcttcg cgactgcgct gccgcgatgc tgacccggca ccccaacctg    240
cgggcgagct tcctacacgg gaacctgagc cggcccgtgc aggtaatacc atccagtgcc    300
gaggtgcttt ggcgtcacgt gcgcgcccac cccagtgagg tcggggcgct ggcagccgaa    360
gagcgccggc gccgcttcga cgtcggccgc ggaccactca tccggttcct gctcatcgaa    420
ctaccggacg aatgttggca tctggtcatc gtcgcgcacc acatcgtcat cgacggatgg    480
tcgttgccgc tgttcgtctc cgagctgctc gccttgtatc gggctggtgg tcacgtcgcc    540
gcgttgccgg cagcgccgcg gccgtatcgc gactacatcg gctggctggc cggccgcgat    600
cagacggcta gccgcgcaat gtgggcggac cacctcaatg gcctggacgg cccgactctg    660
ttatcgccgg cactcgccga cactcctgtg cagccgggta ttccgggacg caccgaagtg    720
cgccttgacc gtgaagccac cgcggagctg gccgatgccg cccgcacccg tggcgtcacg    780
atcagcacac ttgttcaaat ggcttgggct accacgcttt cagcattcac cggtcgtggc    840
gatgtgacgt tcggtgtgac ggtgtccggc aggcccagcg aactgtccgg cgtggaaacg    900
atgatcggcc tgttcatcaa tacggtgcca ctgcgggtcc gcctggacgc ccgcgctacc    960
gtcggcgggc aatgcgctgt cctacaacgt caattcgcca tgttgcgcga ccacagctat   1020
ctcggtttca acgagtttcg tgccatcgcc ggtatcggtg agatgttcga caccctactg   1080
gtgtatgaga acttcccgcc cggcgaggtg gtgggcaccg cggagttcgt cgcaaacggg   1140
gtgacgttcc gtccggtggc gctagagagt ttgtcgcact ttccggtgac cgtcgccgcg   1200
caccgcagca ccggtgagct cacgctgcta gtggaggtgc tcgacggtgc gctgggcacg   1260
atggcgcccg aaagcctcgg caggcgggtg ctggctgtgt tacagcgctt ggtcagccgg   1320
tgggatcggc cgctgcgcga cgtcgacatt ctgctggacg gcgagcacga tccgaccgca   1380
cccggcctgc cggatgtgac gacgtcggca cccgcggtgc atacccggtt cgccgaaatc   1440
gctgcggcac agcctgactc ggtggcggtc agttgggcgg atggtcagct gacgtaccgg   1500
gagctggatg cattggccga ccggctggcc actgggctgc gccgcgcgga cgtgagtcgc   1560
gagaccccgg tggccgtcgc gctgtcccgt ggtccgcgct acgtggccgc catgctggcg   1620
gtcctcaagg cgggtggcat gatcgtgccg ctggacccgg cgatgcccgg tgagcgtgtc   1680
gccgagatct tgcgccagac atcggctccg gtggtcatcg atgagggcgt gttcgccgct   1740
tcggttggcg ctgacatact cgaggaggac cgtgccatca cggtgccggt ggaccaggcg   1800
gcctacgtga ttttcacctc cggcaccacc ggtaccccga aaggtgtcat cggcacccat   1860
```

-continued cgggcgctgt cggcctacgc cgacgaccac atcgagcgcg tgttgcggcc ggcggcccag 1920
cggctcgggc gcccgctgcg aatcgcgcat gcctggtcgt tcaccttcga cgcggcgtgg 1980
cagccgttgg tcgcactgct tgacggccac gcggtgcaca ttgtcgacga ccatcgtcag 2040
cgggacgcag gggcgctggt cgaagcgatc gaccgattcg gtctggacat gattgacacc 2100
acgccgtcga tgttcgccca gctgcacaac gctggactgc tcgaccgggc gccgttggcg 2160
gtgcttgcgc tcggcggcga agccttgggc gccgcgacgt ggcggatgat ccagcagaac 2220
tgcgcgcgca cggccatgac ggccttcaac tgctacgggc ctaccgagac cacggtcgaa 2280
gccgtggtcg ccgccgttgc tgagcatgcg cgaccggtca tcggacgtcc gacctgcacc 2340
acccgcgcct acgtcatgga ctcctggctg cggccggtgc ccgatggcgt cgccggcgag 2400
ctgtatctgg cgggcgccca gttgacccgc ggttacctcg gccgcccggc cgagactgcg 2460
gcgcgctttg tcgctgagcc aaacgggcgc ggtagccgaa tgtaccgcac cggagatgtg 2520
gtgcgccgcc tgcccgacgg tggactggag ttcctcgggc gcagcgatga ccaggtgaag 2580
atccgcggtt tccgcgtcga gccgggtgag attgccgcgg tgctcaacgg ccaccatgcg 2640
gtgcacggtt gccatgtgac ggcccgcggc catgccagtg gcccccggct gacggcgtat 2700
gtggcaggcg gaccacaacc gccaccggtg gccgaattgc gggcgatgct gctagagcgg 2760
ttgccgcgtt atctagtccc gcaccatatc gtcgtcctcg acgagttacc gctgactcca 2820
cacggcaaga tcgacgaaaa cgctttggcg gcaatcaatg tcaccgaagg accggcaact 2880
ccgccgcaga caccgaccga gctggtgctg gccgaggcgt tcgccgatgt catggaaacc 2940
tcgaacgtcg atgtcaccgc gggctttttg cagatgggtc tagacagcat cgtggcgctg 3000
tcggtggtgc aggccgcgcg ccgtcgtggg attgcgttgc gggccaggct gatggtggag 3060
tgcgacacca tccgtgaact cgcggcggcc attgactccg atgccgcatg gcaggcaccg 3120
gccaacgatg ccggcgagcc gatcccggtg ctacccaaca ctcattggct ctacgagtac 3180
ggcgacccgc gccggctggc acaaaccgag gtcatcaggt tgcccgaccg gatcacccgc 3240
gaacgcctgg atgccgtgtt ggccgcggtc gtcgacggac acgaggtgtt gcggtgccgg 3300
ttcgaccggg atgcgatggc ccttgtcgca caaccgaaaa cggacattct cagcgaggtt 3360
tgggtcagcg gtgaactggt caccgcggtg gccgagcaga ctcttggcgc gctggcgagt 3420
ctcgaccccc aggccggccg actgctctcg gcggtgtggc tgcgcgaacc cgacgggccc 3480
ggtgttctgg tgctgaccgc ccatgtgctg gcgatggacc cagcctcctg gcggattgtg 3540
ctgggtgaac tcgacgccgg cctgcacgcg ctggcggccg ggcgcgcgcc cagcccagcg 3600
cgcgagaaca ccagctaccg gcagtggtcg cggctgctgg cgcagcgggc taaggcgctg 3660
gatagcgttg atttctgggt cgccgaactc gagggcgccg atccgccgtt gggtgcccgc 3720
agggtggcgc cgcagaccga ccgggttggt gagctagcga tcaccatgtc gatctccgac 3780
gccgatctga ccgcgcggct gctttcgacg ggacggtcga tgaccgatct gctggctacc 3840
gccgctgcgc ggatggtgac cgcctggcgc cggcaacgcg gtcaacaaac accagcaccg 3900
ctgttggcgt tggagacgca tggccgcgcg gacgtccacg tcgataagac tgccgacacc 3960
agcgacacgg tcgggctgct cagcgcgatc tatccgctgc gcatccactg cgacggcgcg 4020
accgacttcg cgcggatacc cggcagcggc atcgattacg gcctgctgcg gtacctgcgc 4080
gccgataccg cggagcgact acgcgcccac cgcgaacccc agctgctgct gaactatctg 4140
ggtagcctgc acgtcggggt gggagatctg gcggtcgacc gcgcactact ggctgatgtg 4200
gggcaactgc ctgaacccga acagccggtg cgccacgaac tgacggtgct ggcggcgctc 4260

```
ctcgggcccg ccgacgctcc cgtgctagcc acgcggtggc gcacgctgcc cgacatcctg   4320

tccgccgacg acgtcgccac gctgcaatca ctgtggcagg gcgcgctggc ggagataaca   4380

gca                                                                 4383


<210> SEQ ID NO 15
<211> LENGTH: 118
<212> TYPE: PRT
<213> ORGANISM: Mycobacterium tuberculosis

<400> SEQUENCE: 15

Met Leu Thr Cys Glu Met Arg Glu Ser Ala Leu Ala Arg Leu Gly Arg
1               5                   10                  15

Ala Leu Ala Asp Pro Thr Arg Cys Arg Ile Leu Val Ala Leu Leu Asp
            20                  25                  30

Gly Val Cys Tyr Pro Gly Gln Leu Ala Ala His Leu Gly Leu Thr Arg
        35                  40                  45

Ser Asn Val Ser Asn His Leu Ser Cys Leu Arg Gly Cys Gly Leu Val
    50                  55                  60

Val Ala Thr Tyr Glu Gly Arg Gln Val Arg Tyr Ala Leu Ala Asp Ser
65                  70                  75                  80

His Leu Ala Arg Ala Leu Gly Glu Leu Val Gln Val Val Leu Ala Val
                85                  90                  95

Asp Thr Asp Gln Pro Cys Val Ala Glu Arg Ala Ala Ser Gly Glu Ala
            100                 105                 110

Val Glu Met Thr Gly Ser
        115


<210> SEQ ID NO 16
<211> LENGTH: 354
<212> TYPE: DNA
<213> ORGANISM: Mycobacterium tuberculosis

<400> SEQUENCE: 16

atgctgacgt gtgagatgcg ggaatcggcc ctggctcgac tcggccgggc tctggctgat     60

ccgacgcggt gccggattct ggtggcgttg ctggatggcg tttgctatcc cggccagcta    120

gctgcgcacc tcgggttgac ccgatcgaat gtgtccaacc atctgtcgtg tttgcggggc    180

tgcgggctgg tagtcgcaac ctatgagggc cggcaggttc ggtatgcgct ggccgacagt    240

cacctggcgc gagccttggg cgagttggtc caggtcgttc tcgcggtgga taccgaccaa    300

ccctgtgtcg ccgagcgcgc cgcgtccggg gaggcggtcg agatgacagg tagc          354


<210> SEQ ID NO 17
<211> LENGTH: 159
<212> TYPE: PRT
<213> ORGANISM: Mycobacterium tuberculosis

<400> SEQUENCE: 17

Met Asn Asn Leu Ala Leu Trp Ser Arg Pro Val Trp Asp Val Glu Pro
1               5                   10                  15

Trp Asp Arg Trp Leu Arg Asp Phe Phe Gly Pro Ala Ala Thr Thr Asp
            20                  25                  30

Trp Tyr Arg Pro Val Ala Gly Asp Phe Thr Pro Ala Ala Glu Ile Val
        35                  40                  45

Lys Asp Gly Asp Asp Ala Val Val Arg Leu Glu Leu Pro Gly Ile Asp
    50                  55                  60

Val Asp Lys Asp Val Asn Val Glu Leu Asp Pro Gly Gln Pro Val Ser
```

-continued

```
65                  70                  75                  80

Arg Leu Val Ile Arg Gly Glu His Arg Asp Glu His Thr Gln Asp Ala
                85                  90                  95

Gly Asp Lys Asp Gly Arg Thr Leu Arg Glu Ile Arg Tyr Gly Ser Phe
            100                 105                 110

Arg Arg Ser Phe Arg Leu Pro Ala His Val Thr Ser Glu Ala Ile Ala
        115                 120                 125

Ala Ser Tyr Asp Ala Gly Val Leu Thr Val Arg Val Ala Gly Ala Tyr
    130                 135                 140

Lys Ala Pro Ala Glu Thr Gln Ala Gln Arg Ile Ala Ile Thr Lys
145                 150                 155


<210> SEQ ID NO 18
<211> LENGTH: 477
<212> TYPE: DNA
<213> ORGANISM: Mycobacterium tuberculosis

<400> SEQUENCE: 18

atgaacaatc tcgcattgtg gtcgcgtccg gtgtgggacg ttgagccctg ggaccgctgg      60

ctacgtgact tcttcggccc tgccgcgacg acggactggt accgcccggt cgccggagac     120

ttcacgccgg ccgccgagat cgtcaaggat ggcgacgacg cggtggtccg tttggaactg     180

cccggcattg acgtcgacaa ggacgtcaac gtcgagcttg accctggcca gccggtgagc     240

cgcctggtga tccgcggcga acaccgcgac gagcacacgc aagacgccgg agacaaagac     300

ggccgcaccc tgcgtgagat ccgctacgga tcattccgcc gctcgttccg gctgcccgcg     360

cacgtcacca gcgaggccat cgcggcttcc tatgacgccg gtgtgctgac cgtccgggtt     420

gccggcgcct acaaggcccc agccgaaact caggcgcagc gcatcgccat cacgaag        477


<210> SEQ ID NO 19
<211> LENGTH: 235
<212> TYPE: PRT
<213> ORGANISM: Mycobacterium tuberculosis

<400> SEQUENCE: 19

Met Thr Ser Leu Ala Glu Arg Thr Val Leu Val Thr Gly Ala Asn Arg
1               5                   10                  15

Gly Met Gly Arg Glu Tyr Val Ala Gln Leu Leu Gly Arg Lys Val Ala
            20                  25                  30

Lys Val Tyr Ala Ala Thr Arg Asn Pro Leu Ala Ile Asp Val Ser Asp
        35                  40                  45

Pro Arg Val Ile Pro Leu Gln Leu Asp Val Thr Asp Ala Val Ser Val
    50                  55                  60

Ala Glu Ala Ala Asp Leu Ala Thr Asp Val Gly Ile Leu Ile Asn Asn
65                  70                  75                  80

Ala Gly Ile Ser Arg Ala Ser Ser Val Leu Asp Lys Asp Thr Ser Ala
                85                  90                  95

Leu Arg Gly Glu Leu Glu Thr Asn Leu Phe Gly Pro Leu Ala Leu Ala
            100                 105                 110

Ser Ala Phe Ala Asp Arg Ile Ala Glu Arg Ser Gly Ala Ile Val Asn
        115                 120                 125

Val Ser Ser Val Leu Ala Trp Leu Pro Leu Gly Met Ser Tyr Gly Val
    130                 135                 140

Ser Lys Ala Ala Met Trp Ser Ala Thr Glu Ser Met Arg Ile Glu Leu
145                 150                 155                 160

Ala Pro Arg Gly Val Gln Val Val Gly Val Tyr Val Gly Leu Val Asp
```

-continued

```
            165                 170                 175

Thr Asp Met Gly Arg Phe Ala Asp Ala Pro Lys Ser Asp Pro Ala Asp
            180                 185                 190

Val Val Arg Gln Val Leu Asp Gly Ile Glu Ala Gly Lys Glu Asp Val
        195                 200                 205

Leu Ala Asp Glu Met Ser Arg Gln Val Arg Ala Ser Leu Asn Val Pro
    210                 215                 220

Ala Arg Glu Arg Ile Ala Arg Leu Met Gly Asn
225                 230                 235


<210> SEQ ID NO 20
<211> LENGTH: 705
<212> TYPE: DNA
<213> ORGANISM: Mycobacterium tuberculosis

<400> SEQUENCE: 20

atgacttcac tagccgagcg gaccgtgctc gtcaccggcg ccaaccgcgg catgggccgc      60

gaatacgtcg ctcagcttct cggtcgcaaa gtggcaaagg tctatgccgc tacccgcaac     120

ccgctggcaa tcgacgttag cgatccgcgc gtgattccgc tccaactcga cgtcaccgac     180

gcggtgtcgg tcgccgaggc agccgactta gcaaccgatg tcggcattct gatcaacaat     240

gccggcatct cccgggcgtc ctcggtgctc gacaaggaca catccgcgct tcgcggcgag     300

ctggagacga acctgttcgg accgctcgcg ctggcctccg cgttcgccga ccgcatcgcc     360

gagagatccg gtgccatcgt caacgtttcc tcggtactcg cctggcttcc ccttggcatg     420

agctatggag tgtccaaggc ggcgatgtgg agcgcgacgg agtcgatgcg tatcgagctg     480

gcgccgcgcg gtgtgcaggt ggtgggcgtc tacgtggggc tggtcgacac cgacatgggt     540

cgattcgccg acgcgccgaa gtccgatcct gccgatgtgg tccgccaggt gctcgacgga     600

atagaggctg gcaaggagga cgtgctggcc gacgagatga gccgtcaggt gcgcgcgtcg     660

ctgaatgtcc ctgcgcggga acgtatcgcg cggttgatgg gtaac                     705


<210> SEQ ID NO 21
<211> LENGTH: 386
<212> TYPE: PRT
<213> ORGANISM: Mycobacterium tuberculosis

<400> SEQUENCE: 21

Met Thr Ala Gly Ser Asp Leu Asp Asp Phe Arg Gly Leu Leu Ala Lys
1               5                   10                  15

Ala Phe Asp Glu Arg Val Val Ala Trp Thr Ala Glu Ala Glu Ala Gln
            20                  25                  30

Glu Arg Phe Pro Arg Gln Leu Ile Glu His Leu Gly Val Cys Gly Val
        35                  40                  45

Phe Asp Ala Lys Trp Ala Thr Asp Ala Arg Pro Asp Val Gly Lys Leu
    50                  55                  60

Val Glu Leu Ala Phe Ala Leu Gly Gln Leu Ala Ser Ala Gly Ile Gly
65                  70                  75                  80

Val Gly Val Ser Leu His Asp Ser Ala Ile Ala Ile Leu Arg Arg Phe
                85                  90                  95

Gly Lys Ser Asp Tyr Leu Arg Asp Ile Cys Asp Gln Ala Ile Arg Gly
            100                 105                 110

Ala Ala Val Leu Cys Ile Gly Ala Ser Glu Glu Ser Gly Gly Ser Asp
        115                 120                 125

Leu Gln Ile Val Glu Thr Glu Ile Arg Ser Arg Asp Gly Gly Phe Glu
    130                 135                 140
```

```
Val Arg Gly Val Lys Lys Phe Val Ser Leu Ser Pro Ile Ala Asp His
145                 150                 155                 160

Ile Met Val Val Ala Arg Ser Val Asp His Asp Pro Thr Ser Arg His
                165                 170                 175

Gly Asn Val Ala Val Val Ala Val Pro Ala Ala Gln Val Ser Val Gln
            180                 185                 190

Thr Pro Tyr Arg Lys Val Gly Ala Gly Pro Leu Asp Thr Ala Ala Val
        195                 200                 205

Cys Ile Asp Thr Trp Val Pro Ala Asp Ala Leu Val Ala Arg Ala Gly
    210                 215                 220

Thr Gly Leu Ala Ala Ile Ser Trp Gly Leu Ala His Glu Arg Met Ser
225                 230                 235                 240

Ile Ala Gly Gln Ile Ala Ala Ser Cys Gln Arg Ala Ile Gly Ile Thr
                245                 250                 255

Leu Ala Arg Met Met Ser Arg Arg Gln Phe Gly Gln Thr Leu Phe Glu
            260                 265                 270

His Gln Ala Leu Arg Leu Arg Met Ala Asp Leu Gln Ala Arg Val Asp
        275                 280                 285

Leu Leu Arg Tyr Ala Leu His Gly Ile Ala Glu Gln Gly Arg Leu Glu
    290                 295                 300

Leu Arg Thr Ala Ala Ala Val Lys Val Thr Ala Ala Arg Leu Gly Glu
305                 310                 315                 320

Glu Val Ile Ser Glu Cys Met His Ile Phe Gly Gly Ala Gly Tyr Leu
                325                 330                 335

Val Asp Glu Thr Thr Leu Gly Lys Trp Trp Arg Asp Met Lys Leu Ala
            340                 345                 350

Arg Val Gly Gly Gly Thr Asp Glu Val Leu Trp Glu Leu Val Ala Ala
        355                 360                 365

Gly Met Thr Pro Asp His Asp Gly Tyr Ala Ala Val Val Gly Ala Ser
    370                 375                 380

Lys Ala
385
```

<210> SEQ ID NO 22
<211> LENGTH: 1158
<212> TYPE: DNA
<213> ORGANISM: Mycobacterium tuberculosis

<400> SEQUENCE: 22

```
atgacggccg gctccgacct cgacgacttc cgcggtttgc tcgccaaagc gttcgacgag      60

cgggtggtgg catggaccgc agaagcggaa gcgcaggaac gttttccgcg ccagttgatc     120

gaacacctgg gtgtctgcgg cgtattcgat gcgaagtggg cgaccgacgc ccgtcccgac     180

gtcggtaaac tcgtcgaact cgctttcgcg ttgggccagc tggcctctgc cggcatcggt     240

gtgggtgtca gcttgcatga ctcggcgatc gcgattttgc gccggtttgg taagtcggac     300

tacttgcggg atatctgcga tcaggcgatc cgtggcgccg cggtgctgtg catcggagcc     360

tcggaggagt ccggcggatc cgacctgcag atcgtcgaaa ccgagatacg gtcccgtgac     420

ggtggtttcg aggtccgcgg cgtcaagaaa ttcgtgtcgc tgtctccgat cgccgaccac     480

atcatggtgg tggcccgcag cgtcgaccac gatccgacca gtaggcacgg caatgtcgcg     540

gtcgtggccg tgccggccgc acaagtcagc gtgcagaccc cctaccgcaa ggtcggtgcg     600

ggaccgctgg ataccgccgc ggtctgcatc gacacctggg taccggccga tgcactggtt     660

gcgcgggccg gcacggggct ggcagccatc agttggggac tggctcatga gcggatgtcg     720
```

```
atcgccgggc agatcgcagc gtcgtgtcaa cgggcgatcg gaatcaccct ggcccgcatg    780

atgagtcgac gtcagttcgg tcagacgctg ttcgaacacc aggcgctgcg gctgcgtatg    840

gcggacctgc aggcgcgtgt cgatctgctg cggtacgcgc tgcacggcat cgctgaacag    900

gggagactgg aactgcgcac ggcggcagcg gtcaaagtca ccgccgcccg gctcggtgag    960

gaagtcatct ccgaatgcat gcacatcttc ggtggggcgg gttatcttgt cgacgaaacg   1020

acgcttggca aatggtggcg ggacatgaag ctcgcccggg tcggcggcgg caccgacgag   1080

gtgctgtggg aattggtggc tgccggcatg acgcccgatc acgacggtta cgcagccgtg   1140

gtcggagctt ccaaagcg                                                 1158
```

<210> SEQ ID NO 23
<211> LENGTH: 306
<212> TYPE: PRT
<213> ORGANISM: Mycobacterium tuberculosis

<400> SEQUENCE: 23

```
Met Val Leu Arg Pro Ile Thr Gly Ala Ile Pro Pro Asp Gly Pro Trp
1               5                   10                  15

Gly Ile Trp Ala Ser Arg Arg Ile Ile Ala Gly Leu Met Gly Thr Phe
            20                  25                  30

Gly Pro Ser Leu Ala Gly Thr Arg Val Glu Gln Val Asn Ser Val Leu
        35                  40                  45

Pro Asp Gly Arg Arg Val Val Gly Glu Trp Val Tyr Gly Pro His Asn
    50                  55                  60

Asn Ala Ile Asn Ala Gly Pro Gly Gly Gly Ala Ile Tyr Tyr Val His
65                  70                  75                  80

Gly Ser Gly Tyr Thr Met Cys Ser Pro Arg Thr His Arg Arg Leu Thr
                85                  90                  95

Ser Trp Leu Ser Ser Leu Thr Gly Leu Pro Val Phe Ser Val Asp Tyr
            100                 105                 110

Arg Leu Ala Pro Arg Tyr Arg Phe Pro Thr Ala Ala Thr Asp Val Arg
        115                 120                 125

Ala Ala Trp Asp Trp Leu Ala His Val Cys Gly Leu Ala Ala Glu His
    130                 135                 140

Met Val Ile Ala Ala Asp Ser Ala Gly Gly His Leu Thr Val Asp Met
145                 150                 155                 160

Leu Leu Gln Pro Glu Val Ala Ala Arg Pro Pro Ala Ala Val Val Leu
                165                 170                 175

Phe Ser Pro Leu Ile Asp Leu Thr Phe Arg Leu Gly Ala Ser Arg Glu
            180                 185                 190

Leu Gln Arg Pro Asp Pro Val Val Arg Ala Asp Arg Ala Ala Arg Ser
        195                 200                 205

Val Ala Leu Tyr Tyr Thr Gly Val Asp Pro Ala His His Arg Leu Ala
    210                 215                 220

Leu Asp Val Ala Gly Gly Pro Pro Leu Pro Pro Thr Leu Ile Gln Val
225                 230                 235                 240

Gly Gly Ala Glu Ile Leu Glu Ala Asp Ala Arg Gln Leu Asp Ala Asp
                245                 250                 255

Ile Arg Ala Ala Gly Gly Ile Cys Glu Leu Gln Val Trp Pro Asp Gln
            260                 265                 270

Met His Val Phe Gln Ala Leu Pro Arg Met Thr Pro Glu Ala Ala Lys
        275                 280                 285

Ala Met Thr Tyr Val Ala Gln Phe Ile Arg Ser Thr Thr Ala Arg Gly
```

290 295 300

Asp Leu
305

<210> SEQ ID NO 24
<211> LENGTH: 918
<212> TYPE: DNA
<213> ORGANISM: Mycobacterium tuberculosis

<400> SEQUENCE: 24
atggtgttgc ggcccatcac cggggcgatt ccgccagacg ggccgtgggg gatatgggcc 60
tcgcgccgga tcatcgccgg actcatgggc acgttcgggc cctcgctcgc gggcacccga 120
gtggaacaag tcaactccgt tctgccggac ggacgccggg tcgtcggcga atgggtgtat 180
ggaccgcaca acaacgcgat caatgccgga cccggtggcg gcgccatcta ttacgtacac 240
ggcagcggtt acacgatgtg ttcgccccga acccaccggc ggctgacatc ctggctgtcg 300
tcattgaccg ggctaccggt attcagtgtc gattaccgac tggcgccgcg ctaccgtttc 360
ccgaccgcgg ccaccgacgt gcgggcagcc tgggattggt tagcgcacgt atgcggctta 420
gccgcggagc acatggtgat cgccgcggat tccgcgggtg gccatctgac cgtcgacatg 480
ctgctgcaac ccgaggtcgc cgcccgacct ccggcggcgg tggtgttgtt ttcgccgctg 540
atcgacctca ccttccggct gggcgccagt cgtgagctgc agcgccccga tcctgtcgtg 600
cgcgctgacc gtgcggcccg gtcggttgcg ctgtactaca ccggagtcga tcccgcccac 660
caccggctgg cgctcgatgt tgccggcggg ccaccgctgc caccgacgct gatccaggtg 720
ggtggagccg agatactcga ggccgatgcg agacaactcg atgccgacat ccgcgctgcc 780
ggcggcatat gcgagttgca agtgtggcct gatcagatgc atgtgttcca ggccctgccg 840
cggatgacgc ccgaagcggc caaagccatg acctatgttg cccagttcat ccgcagtaca 900
acagcacgtg gagacctc 918

<210> SEQ ID NO 25
<211> LENGTH: 485
<212> TYPE: PRT
<213> ORGANISM: Mycobacterium tuberculosis

<400> SEQUENCE: 25

Met Asn Val Val Asp Ile Ser Arg Trp Gln Phe Gly Ile Thr Thr Val
1 5 10 15

Tyr His Phe Ile Phe Val Pro Leu Thr Ile Gly Leu Ala Pro Leu Ile
20 25 30

Ala Val Met Gln Thr Leu Trp Val Val Thr Asp Asn Pro Ala Trp Tyr
35 40 45

Arg Leu Thr Lys Phe Phe Gly Lys Leu Phe Leu Ile Asn Phe Ala Ile
50 55 60

Gly Val Ala Thr Gly Ile Val Gln Glu Phe Gln Phe Gly Met Asn Trp
65 70 75 80

Ser Glu Tyr Ser Arg Phe Val Gly Asp Val Phe Gly Ala Pro Leu Ala
85 90 95

Met Glu Gly Leu Ala Ala Phe Phe Phe Glu Ser Thr Phe Ile Gly Leu
100 105 110

Trp Ile Phe Gly Trp Asn Arg Leu Pro Arg Leu Val His Leu Ala Cys
115 120 125

Ile Trp Ile Val Ala Ile Ala Val Asn Val Ser Ala Phe Phe Ile Ile
130 135 140

```
Ala Ala Asn Ser Phe Met Gln His Pro Val Gly Ala His Tyr Asn Pro
145                 150                 155                 160

Thr Thr Gly Arg Ala Glu Leu Ser Ser Ile Val Val Leu Leu Thr Asn
                165                 170                 175

Asn Thr Ala Gln Ala Ala Phe Thr His Thr Val Ser Gly Ala Leu Leu
            180                 185                 190

Thr Ala Gly Thr Phe Val Ala Ala Val Ser Ala Trp Trp Leu Val Arg
        195                 200                 205

Ser Ser Thr Thr His Ala Asp Ser Asp Thr Gln Ala Met Tyr Arg Pro
    210                 215                 220

Ala Thr Ile Leu Gly Cys Trp Val Ala Leu Ala Ala Thr Ala Gly Leu
225                 230                 235                 240

Leu Phe Thr Gly Asp His Gln Gly Lys Leu Met Phe Gln Gln Gln Pro
                245                 250                 255

Met Lys Met Ala Ser Ala Glu Ser Leu Cys Asp Thr Gln Thr Asp Pro
            260                 265                 270

Asn Phe Ser Val Leu Thr Val Gly Arg Gln Asn Asn Cys Asp Ser Leu
        275                 280                 285

Thr Arg Val Ile Glu Val Pro Tyr Val Leu Pro Phe Leu Ala Glu Gly
    290                 295                 300

Arg Ile Ser Gly Val Thr Leu Gln Gly Ile Arg Asp Leu Gln Gln Glu
305                 310                 315                 320

Tyr Gln Gln Arg Phe Gly Pro Asn Asp Tyr Arg Pro Asn Leu Phe Val
                325                 330                 335

Thr Tyr Trp Ser Phe Arg Met Met Ile Gly Leu Met Ala Ile Pro Val
            340                 345                 350

Leu Phe Ala Leu Ile Ala Leu Trp Leu Thr Arg Gly Gly Gln Ile Pro
        355                 360                 365

Asn Gln Arg Trp Phe Ser Trp Leu Ala Leu Leu Thr Met Pro Ala Pro
    370                 375                 380

Phe Leu Ala Asn Ser Ala Gly Trp Val Phe Thr Glu Met Gly Arg Gln
385                 390                 395                 400

Pro Trp Val Val Val Pro Asn Pro Thr Gly Asp Gln Leu Val Arg Leu
                405                 410                 415

Thr Val Lys Ala Gly Val Ser Asp His Ser Ala Thr Val Val Ala Thr
            420                 425                 430

Ser Leu Leu Met Phe Thr Leu Val Tyr Ala Val Leu Ala Val Ile Trp
        435                 440                 445

Cys Trp Leu Leu Lys Arg Tyr Ile Val Glu Gly Pro Leu Glu His Asp
    450                 455                 460

Ala Glu Pro Ala Ala His Gly Ala Pro Arg Asp Asp Glu Val Ala Pro
465                 470                 475                 480

Leu Ser Phe Ala Tyr
                485


<210> SEQ ID NO 26
<211> LENGTH: 1455
<212> TYPE: DNA
<213> ORGANISM: Mycobacterium tuberculosis

<400> SEQUENCE: 26

atgaatgtcg tcgacatttc gcggtggcag ttcggtatca ccaccgtcta tcacttcatt      60

ttcgtaccgc tgaccatcgg cctggccccg ctgatcgcgg tcatgcaaac gctgtgggtc     120

gtcaccgata accccgcctg gtatcgcctc accaaattct tcggcaaatt gttcctgatc     180
```

```
aactttgcca tcggcgtggc gaccggaatc gtgcaggaat ttcagttcgg catgaactgg    240

agcgagtact cccgattcgt cggcgatgtc ttcggcgccc cgctggccat ggagggcctg    300

gcggccttct tcttcgaatc caccttcatc gggttgtgga tcttcggctg gaacaggctg    360

ccccggctgg tgcatctggc ctgcatctgg atcgtcgcaa tcgcggtcaa cgtgtccgcg    420

ttcttcatca tcgcggcaaa ctccttcatg cagcatccgg tcggcgcgca ctacaacccg    480

accaccgggc gtgccgagtt gagcagcatc gtcgtgctgc tgaccaacaa caccgcacag    540

gcggcgttta cccacactgt cagcggtgcg ctgctgaccg ccgggacctt cgtcgccgcg    600

gtgagcgcct ggtggctggt ccgttcgagc accacgcacg ccgactcaga tacccaagcc    660

atgtatcgtc ccgcgaccat cctggggtgt tgggttgcgt tggccgccac ggccgggttg    720

ttgttcaccg gcgaccacca aggcaagctg atgttccagc agcagccgat gaagatggcg    780

tcggccgaat cgttgtgcga tacccagaca gatccaaact tctctgtcct gacggtcggc    840

cggcaaaaca actgcgacag cctcacccgt gtcatcgaag tgccctatgt gttgccgttc    900

ctcgccgagg gccggatcag cggtgtgacg ttgcagggta tccgcgatct gcagcaggaa    960

taccagcagc gcttcggacc aaacgactac cggcccaacc tcttcgtcac ctactggtca   1020

tttcgcatga tgatcgggtt gatggcgatc ccggtgctgt tcgcactgat tgcgctctgg   1080

ctcacccgtg gcggccagat ccccaatcaa cgctggttct cctggctggc gctgctaacc   1140

atgcccgccc cgttcctggc caacagcgcc ggatgggtgt tcaccgagat ggggcgccag   1200

ccctgggtcg tcgtccctaa cccgaccggt gatcagctgg ttcgactcac cgtcaaagca   1260

ggcgtctcgg atcactccgc caccgtggtc gccacgtctt tgctgatgtt caccttggtc   1320

tacgcggtac ttgcggtcat ctggtgctgg ctgctcaagc gttacatcgt cgaaggcccc   1380

ctggaacacg acgcggaacc ggctgcgcac ggggcacccc gcgacgacga ggtagcacca   1440

ttgtcgtttg cttac                                                    1455
```

```
<210> SEQ ID NO 27
<211> LENGTH: 301
<212> TYPE: PRT
<213> ORGANISM: Mycobacterium tuberculosis

<400> SEQUENCE: 27

Met Pro Arg Ala His Asp Asp Asn Trp Asp Leu Ala Ser Ser Val Gly
1               5                   10                  15

Ala Thr Ala Thr Met Val Ala Ala Gly Arg Ala Leu Ala Thr Lys Asp
            20                  25                  30

Pro Arg Gly Leu Ile Asn Asp Pro Phe Ala Glu Pro Leu Val Arg Ala
        35                  40                  45

Val Gly Leu Asp Phe Phe Thr Lys Leu Ile Asp Gly Glu Leu Asp Ile
    50                  55                  60

Ala Thr Thr Gly Asn Leu Ser Pro Gly Arg Ala Gln Ala Met Ile Asp
65                  70                  75                  80

Gly Ile Ala Val Arg Thr Lys Tyr Phe Asp Asp Tyr Phe Arg Thr Ala
                85                  90                  95

Thr Asp Gly Gly Val Arg Gln Val Val Ile Leu Ala Ala Gly Leu Asp
            100                 105                 110

Ala Arg Ala Tyr Arg Leu Pro Trp Pro Ala Gly Thr Val Val Tyr Glu
        115                 120                 125

Ile Asp Gln Pro Gln Val Ile Asp Phe Lys Thr Thr Thr Leu Ala Gly
    130                 135                 140

Ile Gly Ala Lys Pro Thr Ala Ile Arg Arg Thr Val Tyr Ile Asp Leu
```

-continued

```
145                 150                 155                 160

Arg Ala Asp Trp Pro Ala Ala Leu Gln Ala Ala Gly Leu Asp Ser Thr
                165                 170                 175

Ala Pro Thr Ala Trp Leu Ala Glu Gly Met Leu Ile Tyr Leu Pro Pro
            180                 185                 190

Asp Pro Arg Thr Gly Cys Ser Thr Thr Ala Pro Asn Ser Val Leu Arg
        195                 200                 205

Ala Ala Arg Ser Leu Pro Asn Leu Ser Arg Ala Leu Trp Ile Ser Thr
    210                 215                 220

Gln Ala Gly Tyr Glu Lys Trp Arg Ile Arg Phe Ala Ser Thr Ala Trp
225                 230                 235                 240

Thr Ser Thr Trp Arg Arg Trp Cys Ile Pro Ala Asn Ala Ala Thr Ser
                245                 250                 255

Ser Thr Thr Cys Ala Pro Arg Ala Gly Thr Leu Arg Ala Gln Cys Gly
            260                 265                 270

Pro Thr Tyr Ser Gly Ala Met Val Cys Pro Phe Pro Pro His Thr Thr
        275                 280                 285

Thr Ile Arg Ser Ala Lys Ser Ser Ser Ser Ala Val Val
    290                 295                 300
```

<210> SEQ ID NO 28
<211> LENGTH: 903
<212> TYPE: DNA
<213> ORGANISM: Mycobacterium tuberculosis

<400> SEQUENCE: 28

```
atgccgcgcg ctcacgacga caactgggat ctagcctcca gcgtcggggc taccgcgacc     60

atggttgctg ccggacgcgc gttggcgacc aaggatccac gaggtttgat caacgacccg    120

ttcgccgaac cgctggtgcg cgcggtcggg ctggatttct tcaccaagtt gatcgacggc    180

gagctcgata tcgcgacgac cgggaacctt tcgccggggc gggcacaggc gatgatcgac    240

gggatagcgg tgcgcaccaa gtacttcgac gactacttcc gcactgccac ggacggcgga    300

gtgcgacaag tggtgatcct ggcagccggg ttggacgcgc gcgcctatcg gttgccgtgg    360

ccggccggca ccgtggtcta cgagatcgac caaccacagg tgatcgactt caagacaacc    420

accttggccg gcatcggcgc caagcccacc gccattcggc gcacggtgta catcgacttg    480

cgcgcggact ggccggcggc actgcaagct gccggcctgg actcgacggc accgacagca    540

tggttggccg aaggcatgct gatctacctg ccgccggatc ccaggaccgg ttgttcgaca    600

acagcaccga actcagtgtt gcgggcagca cgatcgctac cgaacttgtc ccgggcattg    660

tggatttcga cgcaggccgg gtacgagaaa tggcggattc gtttcgcaag cacggcgtgg    720

acatcgacat ggcgtcgctg gtgtattccg gcgaacgcag ccacgtcgtc gactacctgc    780

gcgccaaggg ctgggacgtt gagggcacag tgcggaccga cctattcagg cgcaatggtt    840

tgcccgttcc cgccccacac gacgacgatc cgctcggcga aatcatcttc atcagcggtc    900

gtt                                                                  903
```

<210> SEQ ID NO 29
<211> LENGTH: 188
<212> TYPE: PRT
<213> ORGANISM: Mycobacterium tuberculosis

<400> SEQUENCE: 29

```
Met Ala Gly Leu Phe Thr Pro Pro Ala Ser Gly Ala Ala Thr Leu Gln
1               5                   10                  15
```

```
Arg Ala Ala Arg Asp Ala Ala Pro Asp Ala Arg Trp Leu Leu Ala Val
            20                  25                  30

Ser Asp Arg Asn Gly Ile Val Ser Thr Ser Ala Thr Thr Cys Asn Tyr
        35                  40                  45

Pro Pro Ala Ala Lys Asp Ser Ala Gln Asp Gly Phe Arg His Ala Leu
    50                  55                  60

Ala Ala Ala Ile Ala Ala Asp Ile Asp Glu Ala Leu Arg His Gly Tyr
65                  70                  75                  80

Gly Asp Leu Leu Glu Leu Ala Tyr Pro Leu Met Ser Trp Pro Arg Arg
                85                  90                  95

Gly Val Phe Gly Gly Pro Thr Pro Ala Pro Arg Gly Leu Ala Thr Arg
            100                 105                 110

Gln Cys Pro Pro Arg Thr Val His Val Asp Arg Val Arg Pro Asn Gly
        115                 120                 125

Ala Glu Arg Ala Leu Arg Ala Arg Phe Arg Pro Ile Leu Arg Pro Gln
    130                 135                 140

Phe Thr Leu Gly Asp Gly Ala Asn Gly Leu Pro Leu Ala Ala Cys Thr
145                 150                 155                 160

Lys Thr Gly Ala Tyr Val Pro His Leu Pro Tyr Ser Pro Ile Ala Val
                165                 170                 175

Asp Pro Gln Pro Ser Ala Gly Gln Gln Gly Pro Ser
            180                 185
```

<210> SEQ ID NO 30
<211> LENGTH: 564
<212> TYPE: DNA
<213> ORGANISM: Mycobacterium tuberculosis

<400> SEQUENCE: 30

```
atggcgggtc tcttcacgcc cccggcttcc ggtgccgcga cacttcagcg tgctgcgcga      60

gatgctgccc cggacgcgcg ctggctactc gcggtctccg accgcaacgg gatcgtcagc     120

acttcggcga cgacgtgcaa ctacccgccc gctgcgaaag actctgcgca agacgggttt     180

aggcacgcac tggccgctgc catcgctgcg gacatcgatg aagcactccg tcacggctac     240

ggagatctgc ttgagcttgc gtacccgctc atgagctggc cgcgccgggg cgtttttggc     300

gggccgaccc cggccccacg tgggctcgct acgcgacagt gcccgccccg gacagttcac     360

gttgaccggg tgaggccaaa cggcgccgag cgtgcactga gggcgagatt ccggccgatt     420

ctccgccctc agttcacgct gggcgacggc gctaacgggc tgcccttggc cgcgtgcacc     480

aagacgggtg catacgtgcc gcacttgcca tactcaccca tcgcggtgga cccccaaccc     540

agtgccggtc aacaagggcc ttcc                                            564
```

<210> SEQ ID NO 31
<211> LENGTH: 241
<212> TYPE: PRT
<213> ORGANISM: Mycobacterium tuberculosis

<400> SEQUENCE: 31

```
Met Ser Thr Val Leu Thr Tyr Ile Arg Ala Val Asp Ile Tyr Glu His
1               5                   10                  15

Met Thr Glu Ser Leu Asp Leu Glu Phe Glu Ser Ala Tyr Arg Gly Glu
            20                  25                  30

Ser Val Ala Phe Gly Glu Gly Val Arg Pro Pro Trp Ser Ile Gly Glu
        35                  40                  45

Pro Gln Pro Glu Leu Ala Ala Leu Ile Val Gln Gly Lys Phe Arg Gly
    50                  55                  60
```

```
Asp Val Leu Asp Val Gly Cys Gly Glu Ala Ala Ile Ser Leu Ala Leu
65                  70                  75                  80

Ala Glu Arg Gly His Thr Thr Val Gly Leu Asp Leu Ser Pro Ala Ala
                85                  90                  95

Val Glu Leu Ala Arg His Glu Ala Ala Lys Arg Gly Leu Ala Asn Ala
            100                 105                 110

Ser Phe Glu Val Ala Asp Ala Ser Ser Phe Thr Gly Tyr Asp Gly Arg
        115                 120                 125

Phe Asp Thr Ile Val Asp Ser Thr Leu Phe His Ser Met Pro Val Glu
    130                 135                 140

Ser Arg Glu Gly Tyr Leu Gln Ser Ile Val Arg Ala Ala Ala Pro Gly
145                 150                 155                 160

Ala Ser Tyr Phe Val Leu Val Phe Asp Arg Ala Ala Ile Pro Glu Gly
                165                 170                 175

Pro Ile Asn Ala Val Thr Glu Asp Glu Leu Arg Ala Ala Val Ser Lys
            180                 185                 190

Tyr Trp Ile Ile Asp Glu Ile Lys Pro Ala Arg Leu Tyr Ala Arg Phe
        195                 200                 205

Pro Ala Gly Phe Ala Gly Met Pro Ala Leu Leu Asp Ile Arg Glu Glu
    210                 215                 220

Pro Asn Gly Leu Gln Ser Ile Gly Gly Trp Leu Leu Ser Ala His Leu
225                 230                 235                 240

Gly


<210> SEQ ID NO 32
<211> LENGTH: 723
<212> TYPE: DNA
<213> ORGANISM: Mycobacterium tuberculosis

<400> SEQUENCE: 32

atgtcaactg tgttgacata tatcagggcc gttgatatat atgaacacat gactgaatcg      60

ctggatcttg agttcgaatc cgcctaccgc ggtgaatccg tcgccttcgg ggagggagtc     120

cgaccgccat ggagcatcgg cgaaccccag cccgagctgg ccgccctgat cgtgcagggc     180

aagttccgcg gcgacgtcct cgacgtgggc tgcggggagg ccgcgatttc gctggcactg     240

gccgaacggg gacacaccac ggtcggactg gacctctccc ccgccgccgt agaactggct     300

cggcatgaag cagcgaagcg cggcctggcc aatgccagct tcgaggtggc cgacgccagt     360

tcgtttaccg gctatgacgg caggttcgac accatcgtcg acagcacgct gttccactcc     420

atgccggtcg agtcccggga gggctatctg caatcgatcg tgcgtgcggc ggcaccgggc     480

gcctcctact tcgtgttggt attcgaccgg gcggcgatac ccgaggggcc gatcaatgcg     540

gtcaccgagg acgagctgcg cgcggcggtg tccaagtact ggatcatcga tgagatcaag     600

cccgcgcggc tgtacgcgag gttcccggcc ggcttcgccg gcatgcccgc actcctggac     660

atccgcgaag agcccaacgg gctgcagtcg atcggtggct ggctgctctc ggcccacctg     720

ggc                                                                   723


<210> SEQ ID NO 33
<211> LENGTH: 175
<212> TYPE: PRT
<213> ORGANISM: Mycobacterium tuberculosis

<400> SEQUENCE: 33

Val Ser Arg Leu Leu Leu Ser Tyr Ala Val Val Glu Leu Ala Val Val
1               5                   10                  15
```

```
Phe Ala Leu Ala Ala Thr Ile Gly Phe Gly Trp Thr Leu Leu Val Leu
            20                  25                  30

Leu Ala Thr Phe Val Leu Gly Phe Gly Leu Leu Ala Pro Leu Gly Gly
        35                  40                  45

Trp Gln Leu Gly Arg Arg Leu Leu Trp Leu Arg Ser Gly Leu Ala Glu
    50                  55                  60

Pro Arg Ser Ala Leu Ser Asp Gly Ala Leu Val Thr Val Ala Ser Val
65                  70                  75                  80

Leu Val Leu Val Pro Gly Leu Val Thr Thr Thr Met Gly Leu Leu Leu
                85                  90                  95

Leu Val Pro Pro Ile Arg Ala Leu Ala Arg Pro Gly Leu Thr Ala Ile
            100                 105                 110

Ala Val Arg Gly Phe Leu Arg Asn Val Pro Leu Thr Ala Asp Ala Ala
        115                 120                 125

Ala Asn Met Ala Gly Ala Phe Gly Glu Ser Gly Thr Asp Pro Asp Phe
    130                 135                 140

Ile Asp Gly Glu Val Ile Asp Val Ile Asp Val Glu Pro Leu Thr Leu
145                 150                 155                 160

Gln Pro Pro Arg Val Ala Ala Glu Pro Pro Ser Pro Gly Ser Asn
                165                 170                 175
```

<210> SEQ ID NO 34
<211> LENGTH: 525
<212> TYPE: DNA
<213> ORGANISM: Mycobacterium tuberculosis

<400> SEQUENCE: 34

```
gtgtcgcggc tgctgctcag ctacgccgtc gtcgagctcg cggtggtttt cgcgctggcg      60

gcgacgatcg ggtttggctg gactttgctg gtgttgctgg cgacgttcgt cctcgggttc     120

ggtctgctgg cgccgctcgg tggctggcag ctcggccgac ggctcctgtg gttgcgatcc     180

ggcttggcgg aaccacgaag cgcactgagt gacggcgcgc tggtcaccgt tgcctcggtc     240

ttggtgcttg ttcctggtct ggtcaccacg acgatggggc tgttgctgct ggtgccgccg     300

atccgggcgc tcgctcgacc cgggctgacc gcgatcgccg tgcgcggttt cctgcggaac     360

gtgccactga cggccgatgc ggcggccaac atggccgggg ccttcggcga gagcggcacc     420

gacccggact ttattgatgg cgaggtcatc gacgtcatag atgtcgagcc gttgaccctt     480

cagccccctc gggtagccgc agaacctcca tcgccggggt cgaat                     525
```

<210> SEQ ID NO 35
<211> LENGTH: 130
<212> TYPE: PRT
<213> ORGANISM: Mycobacterium tuberculosis

<400> SEQUENCE: 35

```
Val Val Trp Met Arg Ser Ala Ile Val Ala Val Ala Leu Gly Val Thr
1               5                   10                  15

Val Ala Ala Val Ala Ala Ala Cys Trp Leu Pro Gln Leu His Arg His
            20                  25                  30

Val Ala His Pro Asn His Pro Leu Thr Thr Ser Val Gly Ser Glu Phe
        35                  40                  45

Val Ile Asn Thr Asp His Gly His Leu Val Asp Asn Ser Met Pro Pro
    50                  55                  60

Cys Pro Glu Arg Leu Ala Thr Ala Val Leu Pro Arg Ser Ala Thr Pro
65                  70                  75                  80
```

```
Val Leu Leu Pro Asp Val Val Ala Ala Ala Pro Gly Met Thr Ala Ala
                85                  90                  95

Leu Thr Asp Pro Val Ala Pro Ala Ala Arg Gly Pro Pro Ala Ala Gln
            100                 105                 110

Gly Ser Val Arg Thr Gly Gln Asp Leu Leu Thr Arg Phe Cys Leu Ala
        115                 120                 125

Arg Arg
    130
```

```
<210> SEQ ID NO 36
<211> LENGTH: 390
<212> TYPE: DNA
<213> ORGANISM: Mycobacterium tuberculosis

<400> SEQUENCE: 36

gtggtgtgga tgcgatcggc gattgtcgcg gtcgcgctgg gggtgacggt agccgccgtc      60

gccgctgcat gctggctccc ccagctccac cgtcatgtgg ctcacccaaa ccacccgttg     120

acgacgtccg taggtagcga attcgtcatc aacaccgacc acgggcacct ggtggacaac     180

tcgatgccac cgtgcccgga acggctcgcg acggcggtgc tgccgcgctc cgccactccg     240

gtgttactac cagacgtcgt ggcggctgcg cccggcatga cagccgcgct taccgacccc     300

gtcgcgccgg ccgcgcgcgg tccgccggcg gcgcagggat ccgttcgcac cggtcaagac     360

ctgttgaccc ggttctgcct ggctcgtcgc                                      390
```

```
<210> SEQ ID NO 37
<211> LENGTH: 314
<212> TYPE: PRT
<213> ORGANISM: Mycobacterium tuberculosis

<400> SEQUENCE: 37

Val Pro Arg Thr Asp Asn Asp Ser Trp Ala Ile Thr Glu Ser Val Gly
1               5                   10                  15

Ala Thr Ala Leu Gly Val Ala Ala Ala Arg Ala Ala Glu Thr Glu Ser
            20                  25                  30

Asp Asn Pro Leu Ile Asn Asp Pro Phe Ala Arg Ile Phe Val Asp Ala
        35                  40                  45

Ala Gly Asp Gly Ile Trp Ser Met Tyr Thr Asn Arg Thr Leu Leu Ala
    50                  55                  60

Gly Ala Thr Asp Leu Asp Pro Asp Leu Arg Ala Pro Ile Gln Gln Met
65                  70                  75                  80

Ile Asp Phe Met Ala Ala Arg Thr Ala Phe Phe Asp Glu Tyr Phe Leu
                85                  90                  95

Ala Thr Ala Asp Ala Gly Val Arg Gln Val Val Ile Leu Ala Ser Gly
            100                 105                 110

Leu Asp Ser Arg Ala Trp Arg Leu Pro Trp Pro Asp Gly Thr Val Val
        115                 120                 125

Tyr Glu Leu Asp Gln Pro Lys Val Leu Glu Phe Lys Ser Ala Thr Leu
    130                 135                 140

Arg Gln His Gly Ala Gln Pro Ala Ser Gln Leu Val Asn Val Pro Ile
145                 150                 155                 160

Asp Leu Arg Gln Asp Trp Pro Lys Ala Leu Gln Lys Ala Gly Phe Asp
                165                 170                 175

Pro Ser Lys Pro Cys Ala Trp Leu Ala Glu Gly Leu Val Arg Tyr Leu
            180                 185                 190

Pro Ala Arg Ala Gln Asp Leu Leu Phe Glu Arg Ile Asp Ala Leu Ser
        195                 200                 205
```

Arg Pro Gly Ser Trp Leu Ala Ser Asn Val Pro Gly Ala Gly Phe Leu
    210                 215                 220

Asp Pro Glu Arg Met Arg Arg Gln Arg Ala Asp Met Arg Arg Met Arg
225                 230                 235                 240

Ala Ala Ala Ala Lys Leu Val Glu Thr Glu Ile Ser Asp Val Asp Asp
                245                 250                 255

Leu Trp Tyr Ala Glu Gln Arg Thr Ala Val Ala Glu Trp Leu Arg Glu
            260                 265                 270

Arg Gly Trp Asp Val Ser Thr Ala Thr Leu Pro Glu Leu Leu Ala Arg
        275                 280                 285

Tyr Gly Arg Ser Ile Pro His Ser Gly Glu Asp Ser Ile Pro Pro Asn
    290                 295                 300

Leu Phe Val Ser Ala Gln Arg Ala Thr Ser
305                 310

<210> SEQ ID NO 38
<211> LENGTH: 942
<212> TYPE: DNA
<213> ORGANISM: Mycobacterium tuberculosis

<400> SEQUENCE: 38
gtgccgcgga ccgacaacga ttcctgggcc attaccgaga gcgtgggcgc caccgcactg 60
ggtgtggcgg cggcgcgtgc ggccgagacc gagagcgaca acccattgat caacgatccg 120
ttcgcgcgga tctttgtgga cgcggccggc gacgggatat ggagcatgta cacgaatcgc 180
acgttgctgg ccggtgcgac cgacctcgac ccggacctgc gggcgccgat acagcagatg 240
atcgatttca tggccgcccg gaccgcgttt ttcgacgagt atttcctggc taccgccgac 300
gctggggtga ggcaagtagt gatcctcgcc tcgggcctgg actcgcgtgc ctggcggctg 360
ccctggccgg acggcaccgt ggtgtacgag ctggaccagc ccaaggtgct ggaattcaaa 420
tcagccacgt tgcgccagca tggcgcgcag ccggcttcgc agctggtgaa cgttcccata 480
gaccttcgtc aggactggcc aaaggcactg cagaaagccg gatttgaccc atcgaagccg 540
tgtgcgtggt tagccgaagg gttggtgcgg tacctgccgg cgcgggctca ggatctgttg 600
ttcgagcgta tcgatgcgct cagcaggccg ggcagttggt tggcgtccaa cgtccccggc 660
gccggttttc tcgaccctga gcgaatgcga cgccagcgtg cggacatgcg gcggatgcgg 720
gccgcggcag ccaagctggt cgaaactgag atatcagatg tcgatgacct ctggtatgca 780
gagcagcgca ccgcggtcgc cgagtggctg cgtgaacgtg gctgggacgt gtcgacggca 840
acgttgcccg agctgctggc tcggtatggc cgcagcatcc ctcacagtgg cgaagactca 900
atcccgccaa accttttcgt atccgcgcag cgggccacga gc 942

<210> SEQ ID NO 39
<211> LENGTH: 504
<212> TYPE: PRT
<213> ORGANISM: Mycobacterium tuberculosis

<400> SEQUENCE: 39

Val Ser Phe Val Val Thr Val Pro Glu Ala Val Ala Ala Ala Ala Gly
1               5                   10                  15

Asp Leu Ala Ala Ile Gly Ser Thr Leu Arg Glu Ala Thr Ala Ala Ala
            20                  25                  30

Ala Gly Pro Thr Thr Gly Leu Ala Ala Ala Ala Ala Asp Asp Val Ser
        35                  40                  45

Ile Ala Val Ser Gln Leu Phe Gly Arg Tyr Gly Gln Glu Phe Gln Thr

```
    50                  55                  60

Val Ser Asn Gln Leu Ala Ala Phe His Thr Glu Phe Val Arg Thr Leu
65                  70                  75                  80

Asn Arg Gly Ala Ala Ala Tyr Leu Asn Thr Glu Ser Ala Asn Gly Gly
                85                  90                  95

Gln Leu Phe Gly Gln Ile Glu Ala Gly Gln Arg Ala Val Ser Ala Ala
            100                 105                 110

Ala Ala Ala Ala Pro Gly Gly Ala Tyr Gly Gln Leu Val Ala Asn Thr
        115                 120                 125

Ala Thr Asn Leu Glu Ser Leu Tyr Gly Ala Trp Ser Ala Asn Pro Phe
    130                 135                 140

Pro Phe Leu Arg Gln Ile Ile Ala Asn Gln Gln Val Tyr Trp Gln Gln
145                 150                 155                 160

Ile Ala Ala Ala Leu Ala Asn Ala Val Gln Asn Phe Pro Ala Leu Val
                165                 170                 175

Ala Asn Leu Pro Ala Ala Ile Asp Ala Ala Val Gln Gln Phe Leu Ala
            180                 185                 190

Phe Asn Ala Ala Tyr Tyr Ile Gln Gln Ile Ile Ser Ser Gln Ile Gly
        195                 200                 205

Phe Ala Gln Leu Phe Ala Thr Thr Val Gly Gln Gly Val Thr Ser Val
    210                 215                 220

Ile Ala Gly Trp Pro Asn Leu Ala Ala Glu Leu Gln Leu Ala Phe Gln
225                 230                 235                 240

Gln Leu Leu Val Gly Asp Tyr Asn Ala Ala Val Ala Asn Leu Gly Lys
                245                 250                 255

Ala Met Thr Asn Leu Leu Val Thr Gly Phe Asp Thr Ser Asp Val Thr
            260                 265                 270

Ile Gly Thr Met Gly Thr Thr Ile Ser Val Thr Ala Lys Pro Lys Leu
        275                 280                 285

Leu Gly Pro Leu Gly Asp Leu Phe Thr Ile Met Thr Ile Pro Ala Gln
    290                 295                 300

Glu Ala Gln Tyr Phe Thr Asn Leu Met Pro Pro Ser Ile Leu Arg Asp
305                 310                 315                 320

Met Ser Gln Asn Phe Thr Asn Val Leu Thr Thr Leu Ser Asn Pro Asn
                325                 330                 335

Ile Gln Ala Val Ala Ser Phe Asp Ile Ala Thr Thr Ala Gly Thr Leu
            340                 345                 350

Ser Thr Phe Phe Gly Val Pro Leu Val Leu Thr Tyr Ala Thr Leu Gly
        355                 360                 365

Ala Pro Phe Ala Ser Leu Asn Ala Ile Ala Thr Ser Ala Glu Thr Ile
    370                 375                 380

Glu Gln Ala Leu Leu Ala Gly Asn Tyr Leu Gly Ala Val Gly Ala Leu
385                 390                 395                 400

Ile Asp Ala Pro Ala His Ala Leu Asp Gly Phe Leu Asn Ser Ala Thr
                405                 410                 415

Val Leu Asp Thr Pro Ile Leu Val Pro Thr Gly Leu Pro Ser Pro Leu
            420                 425                 430

Pro Pro Thr Val Gly Ile Thr Leu His Leu Pro Phe Asp Gly Ile Leu
        435                 440                 445

Val Pro Pro His Pro Val Thr Ala Thr Ile Ser Phe Pro Gly Ala Pro
    450                 455                 460

Val Pro Ile Pro Gly Phe Pro Thr Thr Val Thr Val Phe Gly Thr Pro
465                 470                 475                 480
```

Phe Met Gly Met Ala Pro Leu Leu Ile Asn Tyr Ile Pro Gln Gln Leu
485 490 495

Ala Leu Ala Ile Lys Pro Ala Ala
500

<210> SEQ ID NO 40
<211> LENGTH: 1512
<212> TYPE: DNA
<213> ORGANISM: Mycobacterium tuberculosis

<400> SEQUENCE: 40

```
gtgtcgttcg tggtcacagt gccggaggcc gtggcggctg cggcggggga tttggcggcc     60
atcggctcga cgcttcggga agcgaccgct gcggcggcgg gccccacgac cgggctggcg    120
gccgcggccg ccgacgacgt gtcgatcgct gtctcgcagc tgttcggcag gtacggccag    180
gaatttcaaa ccgtgagcaa ccaactggcc gcgtttcata ccgagttcgt acgcacgttg    240
aaccgcggcg cggcggcgta tctcaacacc gaaagcgcta acggcgggca gctgttcggt    300
cagatcgagg cgggacagcg cgccgtttcc gcggccgcgg ccgccgctcc gggcggcgca    360
tacggccaac tcgttgccaa cacggccacc aacctggaat ccctctacgg cgcatggtcg    420
gccaacccgt tcccattcct ccgccagatc atcgccaacc agcaggttta ctggcagcag    480
atcgccgcgg cgctcgccaa cgccgtccag aacttccccg ccctggtggc gaatttgcca    540
gcggccatcg acgcggccgt ccagcaattc ctggccttca acgcggcgta ctacatccaa    600
cagattatta gctcgcagat cggcttcgcc cagctattcg ccacgacggt cggtcagggg    660
gtcaccagcg tcattgccgg gtggcccaac cttgcggcgg agcttcagct agcgtttcaa    720
cagcttctgg tgggtgacta caacgccgcg gtggcgaacc tgggtaaggc catgacaaac    780
cttctggtca ccgggttcga caccagcgac gtgacgatcg gcacaatggg caccaccatt    840
agtgtcaccg cgaaacccaa gctgctgggc ccgctgggag atctgttcac catcatgacc    900
atcccggcac aagaggcgca gtacttcacc aacctgatgc ccccctccat cctgcgagac    960
atgtcgcaga acttcaccaa cgtgctcacg acgctctcca acccgaacat ccaggcggtc   1020
gcttcgttcg atatcgcaac caccgccggg actttgagca ccttcttcgg ggtgccattg   1080
gtgctcactt acgccacatt gggtgcgccg ttcgcgtcac tgaacgcgat tgcgacgagc   1140
gcggaaacca tcgagcaggc cctgttggcc ggcaactacc taggggcggt gggtgcgctt   1200
atcgacgccc cggcccacgc gttagacggc ttcctcaaca gcgcaaccgt gttggatacg   1260
ccgatcctgg tgcccacggg gctcccgtcc cctctgcccc cgacggtcgg gatcacgctg   1320
cacttgcctt tcgacgggat tctcgtgccg ccgcatcccg tcaccgcgac gatcagcttc   1380
ccgggtgctc cggttcctat tcccggtttc ccaaccaccg taaccgtttt cggcacaccc   1440
ttcatgggaa tggctccgct gctgatcaac tacattcccc aacagctcgc cctggcaatc   1500
aaaccggcgg ct                                                       1512
```

<210> SEQ ID NO 41
<211> LENGTH: 368
<212> TYPE: PRT
<213> ORGANISM: Mycobacterium tuberculosis

<400> SEQUENCE: 41

Met Thr Ser Gly Ser Leu Gln Phe Thr Val Leu Arg Ala Val Asn Pro
1 5 10 15

Ala Thr Asp Ala Gln Arg Glu Ser Met Leu Arg Glu Pro Gly Phe Gly
20 25 30

```
Lys Tyr His Thr Asp His Met Val Ser Ile Asp Tyr Ala Glu Gly Arg
        35                  40                  45

Gly Trp His Asn Ala Arg Val Ile Pro Tyr Gly Pro Ile Glu Leu Asp
    50                  55                  60

Pro Ser Ala Ile Val Leu His Tyr Ala Gln Glu Val Phe Glu Gly Leu
65                  70                  75                  80

Lys Ala Tyr Arg Trp Ala Asp Gly Ser Ile Val Ser Phe Arg Ala Asp
                85                  90                  95

Ala Asn Ala Ala Arg Leu Arg Ser Ser Ala Arg Arg Leu Ala Ile Pro
            100                 105                 110

Glu Leu Pro Asp Ala Val Phe Ile Glu Ser Leu Arg Gln Leu Ile Ala
        115                 120                 125

Val Asp Lys Ala Trp Val Pro Gly Ala Gly Gly Glu Glu Ala Leu Tyr
    130                 135                 140

Leu Arg Pro Phe Ile Phe Ala Thr Glu Pro Gly Leu Gly Val Arg Pro
145                 150                 155                 160

Ala Thr Gln Tyr Arg Tyr Leu Leu Ile Ala Ser Pro Ala Gly Ala Tyr
                165                 170                 175

Phe Lys Gly Gly Ile Ala Pro Val Ser Val Trp Val Ser Thr Glu Tyr
            180                 185                 190

Val Arg Ala Cys Pro Gly Gly Thr Gly Ala Ala Lys Phe Gly Gly Asn
        195                 200                 205

Tyr Ala Ala Ser Leu Leu Ala Gln Ala Glu Ala Ala Glu Asn Gly Cys
    210                 215                 220

Asp Gln Val Val Trp Leu Asp Ala Val Glu Arg Arg Tyr Ile Glu Glu
225                 230                 235                 240

Met Gly Gly Met Asn Ile Phe Phe Val Leu Gly Ser Gly Gly Ser Ala
                245                 250                 255

Arg Leu Val Thr Pro Glu Leu Ser Gly Ser Leu Leu Pro Gly Ile Thr
            260                 265                 270

Arg Asp Ser Leu Leu Gln Leu Ala Ile Asp Ala Gly Phe Ala Val Glu
        275                 280                 285

Glu Arg Arg Ile Asp Ile Asp Glu Trp Gln Lys Lys Ala Ala Ala Gly
    290                 295                 300

Glu Ile Thr Glu Val Phe Ala Cys Gly Thr Ala Ala Val Ile Thr Pro
305                 310                 315                 320

Val Ala Arg Val Arg His Gly Ala Ser Glu Phe Arg Ile Ala Asp Gly
                325                 330                 335

Gln Pro Gly Glu Val Thr Met Ala Leu Arg Asp Thr Leu Thr Gly Ile
            340                 345                 350

Gln Arg Gly Thr Phe Ala Asp Thr His Gly Trp Met Ala Arg Leu Gly
        355                 360                 365
```

<210> SEQ ID NO 42
<211> LENGTH: 1104
<212> TYPE: DNA
<213> ORGANISM: Mycobacterium tuberculosis

<400> SEQUENCE: 42

```
atgaccagcg gctcccttca attcacggtg ttacgtgcgg tcaatccggc caccgacgcg     60

cagcgtgaat cgatgctgcg ggagccgggt ttcggcaaat accacaccga ccatatggtg    120

tcgatcgact atgccgaggg ccgtggttgg cacaacgcgc gggtaatccc ttatggcccg    180

atcgagctgg atccctcggc gatcgtgctg cactatgcgc aggaggtgtt cgaagggctc    240

aaagcctacc gctgggccga cgggtccatc gtgtcgtttc gcgccgacgc caacgccgcc    300
```

```
aggttgcgtt cgtcggcgcg gcggttggcg attcccgaac tgcccgacgc ggtgttcatc    360

gaatccctgc gccagctaat cgctgtcgac aaagcttggg tgcccggtgc cggcggtgag    420

gaggcgctgt atctgcggcc gttcatcttc gccaccgagc cgggactggg cgtgcggcct    480

gccacccaat accgttacct gttgatcgcc tcgccggccg gtgcgtactt caagggcggc    540

atcgcccctg tcagcgtctg ggtttcgacg gagtatgtac gggcctgtcc gggcggcacc    600

ggtgcggcca agttcggcgg caactacgcc gcctcgttgc tggcgcaggc cgaagccgcc    660

gagaacggat gcgaccaggt ggtgtggctg gacgctgtgg aacgccgcta tatcgaagag    720

atgggtggca tgaacatctt cttcgtgctc ggcagcggcg gatcggcgcg gctggtcacc    780

ccggagctgt ccggttccct gctgcccggg atcacacggg attcgttgtt gcagttggct    840

attgatgccg gattcgcggt cgaggaacgc aggattgata tcgacgagtg gcagaagaaa    900

gccgccgccg gcgagatcac cgaggtgttt gcgtgcggca ccgccgctgt catcaccccg    960

gtcgcgcggg tgcggcacgg tgccagcgag ttcagaatcg ccgacggtca gccgggtgag   1020

gtgaccatgg cactacgcga tacgctgacc ggcatccagc ggggcacctt cgcggacacc   1080

cacggctgga tggcgcggct gggg                                          1104
```

```
<210> SEQ ID NO 43
<211> LENGTH: 249
<212> TYPE: PRT
<213> ORGANISM: Mycobacterium tuberculosis

<400> SEQUENCE: 43

Val Thr Ala Asp Trp Val Val Thr Phe Thr Phe Asp Ala Asp Pro Ser
1               5                   10                  15

Met Glu Thr Met Asp Ala Trp Glu Thr Gln Leu Glu Gly Phe Asp Ala
            20                  25                  30

Leu Val Ser Arg Val Pro Gly His Gly Ile Asp Val Thr Val Tyr Ala
        35                  40                  45

Pro Gly Asp Trp Ser Val Phe Asp Ala Leu Ala Lys Met Ala Gly Glu
    50                  55                  60

Val Met Pro Val Val Gln Ala Lys Ser Pro Ile Ala Val Gln Ile Ile
65                  70                  75                  80

Ser Glu Pro Glu His Arg Leu Arg Ala Glu Ala Phe Thr Thr Pro Glu
                85                  90                  95

Leu Met Ser Ala Ala Glu Ile Ala Asp Glu Leu Gly Val Ser Arg Gln
            100                 105                 110

Arg Val His Gln Leu Arg Ser Thr Ala Gly Phe Pro Ala Pro Leu Ala
        115                 120                 125

Asp Leu Arg Gly Gly Ala Val Trp Asp Ala Ala Ala Val Arg Arg Phe
    130                 135                 140

Ala Glu Thr Trp Glu Arg Lys Pro Gly Arg Pro His Thr Gly Thr Ala
145                 150                 155                 160

Lys Phe Ala Tyr Ser Trp Ala Val Gly Pro Ala Val Gly Arg Ser Gly
                165                 170                 175

Lys Ala Pro Asn Val Arg Trp Arg Val Glu Asn Pro Asp Lys Ile Arg
            180                 185                 190

Phe Val Leu Arg Asn Ile Gly Asp Asp Ile Ala Glu Asp Val Glu Ile
        195                 200                 205

Asp Leu Ser Arg Ile Asp Ala Ile Thr Arg Asn Val Pro Lys Lys Thr
    210                 215                 220

Val Ile Arg Pro Gly Glu Gly Leu Asn Met Val Leu Ile Ala Ala Trp
```

225 230 235 240

Gly His Pro Leu Pro Asn Gln Leu Tyr
245

<210> SEQ ID NO 44
<211> LENGTH: 747
<212> TYPE: DNA
<213> ORGANISM: Mycobacterium tuberculosis

<400> SEQUENCE: 44
gtgacagccg actgggtcgt caccttcacg tttgatgctg acccttcgat ggagaccatg 60
gacgcctggg agacgcagct cgagggcttc gacgcactgg tatctcgggt cccaggacac 120
ggcattgacg tcacggtcta tgcgcccggc gattggagtg tgttcgacgc gctcgccaag 180
atggctggcg aggttatgcc ggtagttcaa gccaagagtc ccattgctgt gcagatcatt 240
agcgagccag agcatcgtct gcgcgctgag gcgttcacaa cgcccgagtt gatgtctgcg 300
gctgagatcg cggatgagtt gggggtttcg cgtcagaggg tgcaccaatt gaggtcgaca 360
gcagggtttc ccgctccgtt ggcagatttg cgtggaggcg cggtgtggga tgcggcagcg 420
gtgcgcaggt ttgcggagac ctgggagcga aagcccggtc ggccgcatac cgggactgcc 480
aagttcgcgt actcgtgggc ggtgggaccg gcggtcggca ggtccggtaa ggcacctaac 540
gtccggtggc gtgtcgagaa cccagacaaa atccgctttg tgttgcgcaa catcggcgac 600
gatatcgcag aagatgtcga gattgacctc tcgcgaatcg atgcgatcac tcgaaatgtc 660
ccgaagaaga cggtgattcg ccccggagag gggctcaaca tggtcttgat agcggcttgg 720
ggccatcccc ttccaaatca gctatac 747

<210> SEQ ID NO 45
<211> LENGTH: 129
<212> TYPE: PRT
<213> ORGANISM: Mycobacterium tuberculosis

<400> SEQUENCE: 45

Met Arg Leu Ile Leu Asn Val Ile Trp Leu Val Phe Gly Gly Leu Trp
1 5 10 15

Leu Ala Leu Gly Tyr Leu Leu Ala Ser Leu Val Cys Phe Leu Leu Ile
20 25 30

Ile Thr Ile Pro Phe Gly Phe Ala Ala Leu Arg Ile Ala Ser Tyr Ala
35 40 45

Leu Trp Pro Phe Gly Arg Thr Ile Val Glu Lys Pro Thr Ala Gly Thr
50 55 60

Gly Ala Leu Ile Gly Asn Val Ile Trp Val Leu Leu Phe Gly Ile Trp
65 70 75 80

Leu Ala Leu Gly His Leu Val Ser Ala Ala Ala Met Ala Val Thr Ile
85 90 95

Ile Gly Ile Pro Leu Ala Leu Ala Asn Leu Lys Leu Ile Pro Val Ser
100 105 110

Leu Val Pro Leu Gly Lys Asp Ile Val Gly Val Asn Ser Gln Val Pro
115 120 125

Thr

<210> SEQ ID NO 46
<211> LENGTH: 387
<212> TYPE: DNA
<213> ORGANISM: Mycobacterium tuberculosis

<400> SEQUENCE: 46

```
atgcgactaa tcctgaacgt tatctggttg gtgttcggtg gcctctggct ggccctcggg     60

tacctgctgg cgtcgcttgt ctgcttcctg ctcatcatca ccattccgtt tggcttcgcg    120

gcgctgcgca tcgcgtcgta cgcgttgtgg ccgttcggcc ggacgatcgt cgaaaagcca    180

accgccggga ccggggcctt gatcggcaac gtcatctggg tgctgctgtt cgggatctgg    240

ctggccctcg ggcatttggt gagtgccgcg gcaatggcag tcacgatcat cggcattccg    300

ctagcactgg ccaacttgaa actgatcccg gtgtcgctgg tgccgctggg caaggacatc    360

gtcggggtca actcacaggt gcccaca                                         387
```

<210> SEQ ID NO 47
<211> LENGTH: 346
<212> TYPE: PRT
<213> ORGANISM: Mycobacterium tuberculosis

<400> SEQUENCE: 47

```
Met Asp Phe Thr Ile Phe Pro Pro Glu Phe Asn Ser Leu Asn Ile Gln
1               5                   10                  15

Gly Ser Ala Arg Pro Phe Leu Val Ala Ala Asn Ala Trp Lys Asn Leu
            20                  25                  30

Ser Asn Glu Leu Ser Tyr Ala Ala Ser Arg Phe Glu Ser Glu Ile Asn
        35                  40                  45

Gly Leu Ile Thr Ser Trp Arg Gly Pro Ser Ser Thr Ile Met Ala Ala
    50                  55                  60

Ala Val Ala Pro Phe Arg Ala Trp Ile Val Thr Thr Ala Ser Leu Ala
65                  70                  75                  80

Glu Leu Val Ala Asp His Ile Ser Val Val Ala Gly Ala Tyr Glu Ala
                85                  90                  95

Ala His Ala Ala His Val Pro Leu Pro Val Ile Glu Thr Asn Arg Leu
            100                 105                 110

Thr Arg Leu Ala Leu Ala Thr Thr Asn Ile Phe Gly Ile His Thr Pro
        115                 120                 125

Ala Ile Phe Ala Leu Asp Ala Leu Tyr Ala Gln Tyr Trp Ser Gln Asp
    130                 135                 140

Gly Glu Ala Met Asn Leu Tyr Ala Thr Met Ala Ala Ala Ala Ala Arg
145                 150                 155                 160

Leu Thr Pro Phe Ser Pro Pro Ala Pro Ile Ala Asn Pro Gly Ala Leu
                165                 170                 175

Ala Arg Leu Tyr Glu Leu Ile Gly Ser Val Ser Glu Thr Val Gly Ser
            180                 185                 190

Phe Ala Ala Pro Ala Thr Lys Asn Leu Pro Ser Lys Leu Trp Thr Leu
        195                 200                 205

Leu Thr Lys Gly Thr Tyr Pro Leu Thr Ala Ala Arg Ile Ser Ser Ile
    210                 215                 220

Pro Val Glu Tyr Val Leu Ala Phe Val Glu Gly Ser Asn Met Gly Gln
225                 230                 235                 240

Met Met Gly Asn Leu Ala Met Arg Ser Leu Thr Pro Thr Leu Lys Gly
                245                 250                 255

Pro Leu Glu Leu Leu Pro Asn Ala Val Arg Pro Ala Val Ser Ala Thr
            260                 265                 270

Leu Gly Asn Ala Asp Thr Ile Gly Gly Leu Ser Val Pro Pro Ser Trp
        275                 280                 285

Val Ala Asp Lys Ser Ile Thr Pro Leu Ala Lys Ala Val Pro Thr Ser
    290                 295                 300
```

```
Ala Pro Gly Gly Pro Ser Gly Thr Ser Trp Ala Gln Leu Gly Leu Ala
305                 310                 315                 320

Ser Leu Ala Gly Gly Ala Val Gly Ala Val Ala Ala Arg Thr Arg Ser
                325                 330                 335

Gly Val Ile Leu Arg Ser Pro Ala Ala Gly
            340                 345


<210> SEQ ID NO 48
<211> LENGTH: 1038
<212> TYPE: DNA
<213> ORGANISM: Mycobacterium tuberculosis

<400> SEQUENCE: 48

atggatttca caatttttcc gccggagttc aactccctca acatccaagg tagcgctcgt      60

ccgtttctag tagccgcgaa cgcctggaag aatctgtcca acgagctgag ctacgcggcc     120

agtcggttcg agagtgagat caacgggctg atcacatcgt ggcgggggcc atcgtcgacg     180

atcatggcag ctgcggtcgc cccatttcgg gcctggattg tcacgaccgc ttccctggct     240

gaactcgtcg ccgaccacat cagcgtcgtg gcaggcgcct atgaagcggc gcacgcagca     300

cacgtgccgc tgccggtgat cgagaccaac cgactgacgc gcctcgctct cgccacgacc     360

aacattttcg ggattcacac ccccgcgatc tttgccctcg atgcactgta tgcccagtac     420

tggtcccaag atggcgaggc gatgaacctc tacgccacaa tggcggcggc cgccgcacgg     480

ctgacaccgt tctcgccccc ggcgccgatc gccaacccgg gcgcgctggc cagactttat     540

gaactgatcg gttcggtgtc cgagacggtg ggtcattcg ccgcgccggc gaccaagaat     600

ctgccttcga agctgtggac gctgttgacg aagggcacct acccgctcac agccgcgcga     660

atctcgtcga tacccgtgga atacgtgttg gcctttgtcg agggcagcaa catgggccag     720

atgatgggca acctcgccat gcggagcctg acacccacgc tcaagggccc gctggagttg     780

ctacccaacg cggtcaggcc cgcggtgtcg gcaacattgg gaaatgcgga tacgatcggg     840

gggttgtcgg tgccccccag ctgggttgcg gacaaatcga ttacgccgtt ggccaaagcc     900

gtcccgacct ccgcgccggg cggtccgtcg ggaacctcgt gggcccagct gggattggca     960

agcctggccg ggggcgctgt gggcgccgtc gcggcaagaa cccgttccgg agtgatactg    1020

cggtcacccg ccgccggc                                                  1038


<210> SEQ ID NO 49
<211> LENGTH: 876
<212> TYPE: PRT
<213> ORGANISM: Mycobacterium tuberculosis

<400> SEQUENCE: 49

Met Leu Pro Lys Ser Trp Asp Pro Ala Ala Met Glu Ser Ala Ile Tyr
1               5                   10                  15

Gln Lys Trp Leu Asp Ala Gly Tyr Phe Thr Ala Asp Pro Thr Ser Thr
            20                  25                  30

Lys Pro Ala Tyr Ser Ile Val Leu Pro Pro Pro Asn Val Thr Gly Ser
        35                  40                  45

Leu His Met Gly His Ala Leu Glu His Thr Met Met Asp Ala Leu Thr
    50                  55                  60

Arg Arg Lys Arg Met Gln Gly Tyr Glu Val Leu Trp Gln Pro Gly Thr
65                  70                  75                  80

Asp His Ala Gly Ile Ala Thr Gln Ser Val Val Glu Gln Gln Leu Ala
                85                  90                  95

Val Asp Gly Lys Thr Lys Glu Asp Leu Gly Arg Glu Leu Phe Val Asp
```

-continued

```
            100                 105                 110

Lys Val Trp Asp Trp Lys Arg Glu Ser Gly Gly Ala Ile Gly Gly Gln
        115                 120                 125

Met Arg Arg Leu Gly Asp Gly Val Asp Trp Ser Arg Asp Arg Phe Thr
    130                 135                 140

Met Asp Glu Gly Leu Ser Arg Ala Val Arg Thr Ile Phe Lys Arg Leu
145                 150                 155                 160

Tyr Asp Ala Gly Leu Ile Tyr Arg Ala Glu Arg Leu Val Asn Trp Ser
                165                 170                 175

Pro Val Leu Gln Thr Ala Ile Ser Asp Leu Glu Val Asn Tyr Arg Asp
            180                 185                 190

Val Glu Gly Glu Leu Val Ser Phe Arg Tyr Gly Ser Leu Asp Asp Ser
        195                 200                 205

Gln Pro His Ile Val Val Ala Thr Thr Arg Val Glu Thr Met Leu Gly
    210                 215                 220

Asp Thr Ala Ile Ala Val His Pro Asp Asp Glu Arg Tyr Arg His Leu
225                 230                 235                 240

Val Gly Thr Ser Leu Ala His Pro Phe Val Asp Arg Glu Leu Ala Ile
                245                 250                 255

Val Ala Asp Glu His Val Asp Pro Glu Phe Gly Thr Gly Ala Val Lys
            260                 265                 270

Val Thr Pro Ala His Asp Pro Asn Asp Phe Glu Ile Gly Val Arg His
        275                 280                 285

Gln Leu Pro Met Pro Ser Ile Leu Asp Thr Lys Gly Arg Ile Val Asp
    290                 295                 300

Thr Gly Thr Arg Phe Asp Gly Met Asp Arg Phe Glu Ala Arg Val Ala
305                 310                 315                 320

Val Arg Gln Ala Leu Ala Ala Gln Gly Arg Val Val Glu Glu Lys Arg
                325                 330                 335

Pro Tyr Leu His Ser Val Gly His Ser Glu Arg Ser Gly Glu Pro Ile
            340                 345                 350

Glu Pro Arg Leu Ser Leu Gln Trp Trp Val Arg Val Glu Ser Leu Ala
        355                 360                 365

Lys Ala Ala Gly Asp Ala Val Arg Asn Gly Asp Thr Val Ile His Pro
    370                 375                 380

Ala Ser Met Glu Pro Arg Trp Phe Ser Trp Val Asp Asp Met His Asp
385                 390                 395                 400

Trp Cys Ile Ser Arg Gln Leu Trp Trp Gly His Arg Ile Pro Ile Trp
                405                 410                 415

Tyr Gly Pro Asp Gly Glu Gln Val Cys Val Gly Pro Asp Glu Thr Pro
            420                 425                 430

Pro Gln Gly Trp Glu Gln Asp Pro Asp Val Leu Asp Thr Trp Phe Ser
        435                 440                 445

Ser Ala Leu Trp Pro Phe Ser Thr Leu Gly Trp Pro Asp Lys Thr Ala
    450                 455                 460

Glu Leu Glu Lys Phe Tyr Pro Thr Ser Val Leu Val Thr Gly Tyr Asp
465                 470                 475                 480

Ile Leu Phe Phe Trp Val Ala Arg Met Met Met Phe Gly Thr Phe Val
                485                 490                 495

Gly Asp Asp Ala Ala Ile Thr Leu Asp Gly Arg Arg Gly Pro Gln Val
            500                 505                 510

Pro Phe Thr Asp Val Phe Leu His Gly Leu Ile Arg Asp Glu Ser Gly
        515                 520                 525
```

```
Arg Lys Met Ser Lys Ser Lys Gly Asn Val Ile Asp Pro Leu Asp Trp
    530                 535                 540

Val Glu Met Phe Gly Ala Asp Ala Leu Arg Phe Thr Leu Ala Arg Gly
545                 550                 555                 560

Ala Ser Pro Gly Gly Asp Leu Ala Val Ser Glu Asp Ala Val Arg Ala
                565                 570                 575

Ser Arg Asn Phe Gly Thr Lys Leu Phe Asn Ala Thr Arg Tyr Ala Leu
            580                 585                 590

Leu Asn Gly Ala Ala Pro Ala Pro Leu Pro Ser Pro Asn Glu Leu Thr
        595                 600                 605

Asp Ala Asp Arg Trp Ile Leu Gly Arg Leu Glu Glu Val Arg Ala Glu
    610                 615                 620

Val Asp Ser Ala Phe Asp Gly Tyr Glu Phe Ser Arg Ala Cys Glu Ser
625                 630                 635                 640

Leu Tyr His Phe Ala Trp Asp Glu Phe Cys Asp Trp Tyr Leu Glu Leu
                645                 650                 655

Ala Lys Thr Gln Leu Ala Gln Gly Leu Thr His Thr Thr Ala Val Leu
            660                 665                 670

Ala Ala Gly Leu Asp Thr Leu Leu Arg Leu Leu His Pro Val Ile Pro
        675                 680                 685

Phe Leu Thr Glu Ala Leu Trp Leu Ala Leu Thr Gly Arg Glu Ser Leu
    690                 695                 700

Val Ser Ala Asp Trp Pro Glu Pro Ser Gly Ile Ser Val Asp Leu Val
705                 710                 715                 720

Ala Ala Gln Arg Ile Asn Asp Met Gln Lys Leu Val Thr Glu Val Arg
                725                 730                 735

Arg Phe Arg Ser Asp Gln Gly Leu Ala Asp Arg Gln Lys Val Pro Ala
            740                 745                 750

Arg Met His Gly Val Arg Asp Ser Asp Leu Ser Asn Gln Val Ala Ala
        755                 760                 765

Val Thr Ser Leu Ala Trp Leu Thr Glu Pro Gly Pro Asp Phe Glu Pro
    770                 775                 780

Ser Val Ser Leu Glu Val Arg Leu Gly Pro Glu Met Asn Arg Thr Val
785                 790                 795                 800

Val Val Glu Leu Asp Thr Ser Gly Thr Ile Asp Val Ala Ala Glu Arg
                805                 810                 815

Arg Arg Leu Glu Lys Glu Leu Ala Gly Ala Gln Lys Glu Leu Ala Ser
            820                 825                 830

Thr Ala Ala Lys Leu Ala Asn Ala Asp Phe Leu Ala Lys Ala Pro Asp
        835                 840                 845

Ala Val Ile Ala Lys Ile Arg Asp Arg Gln Arg Val Ala Gln Gln Glu
    850                 855                 860

Thr Glu Arg Ile Thr Thr Arg Leu Ala Ala Leu Gln
865                 870                 875
```

<210> SEQ ID NO 50
<211> LENGTH: 2628
<212> TYPE: DNA
<213> ORGANISM: Mycobacterium tuberculosis

<400> SEQUENCE: 50

```
atgctgccca agtcgtggga tccggccgcg atggagagcg ccatctatca gaagtggctg      60

gacgctggct acttcaccgc ggacccgacc agcaccaagc cggcctattc gatcgtgctg     120

ccgccgccga acgtgaccgg cagcctgcac atgggccacg cgctggaaca caccatgatg     180
```

-continued

```
gacgccttga cgcggcgcaa gcggatgcag ggctatgagg tgctctggca gccgggcacc    240
gaccatgccg ggatcgccac ccagagcgtg gtcgagcagc agctggcggt cgacggcaag    300
actaaagaag acctcggccg cgagctgttc gtggacaagg tgtgggattg gaagcgagag    360
tctggcggtg ccatcggcgg ccagatgcgc cgactcggtg acggggtgga ctggagccgc    420
gaccggttca ccatggacga aggtctgtcg cgggcggtgc gcacgatctt caagcggctt    480
tatgacgccg ggctgatcta tcgggccgag cggctggtca actggtcgcc ggtgctgcag    540
accgcgatct ccgacctcga ggtcaactac cgcgacgtcg aaggcgagct ggtgtcgttt    600
aggtacggct cgcttgacga ctcgcaaccc cacatcgtgg tcgccaccac ccgggtcgag    660
acgatgctgg gcgataccgc gatcgccgtc catcccgatg acgagcgcta ccgtcacctg    720
gtcggcacca gcctggcgca cccattcgtc gaccgggagc tggccattgt cgccgacgag    780
cacgtggacc ctgaattcgg caccggcgcg gtcaaagtca cacccgccca cgaccccaac    840
gacttcgaaa tcggggtgcg ccaccagctg ccgatgccct cgatcctgga caccaagggc    900
cggatcgtcg acaccggaac gcgattcgac ggcatggacc gcttcgaggc acgggtcgcg    960
gtgcgccaag cgctcgcggc ccagggccgc gtggtcgaag aaaagcgacc ctacctgcac   1020
agcgtcggac actccgaacg cagcggcgag ccgatcgagc cgcggctatc cctgcagtgg   1080
tgggtccggg tggaatcgct ggccaaagcg gccggggatg cggtgcgcaa cggggacacc   1140
gtgattcacc cggccagcat ggaaccccgc tggttctcct gggtcgacga catgcacgac   1200
tggtgcatct cgcgacagct ctggtggggg catcggatcc cgatctggta cggacccgac   1260
ggcgaacagg tgtgcgtcgg cccggacgaa acacccccgc agggctggga acaggatcct   1320
gacgtgctgg atacctggtt ttcgtcggcg ctgtggccgt tttccacgct gggttggccg   1380
gacaagacgg cggagctgga aaagttctat ccgacaagcg ttctggttac cggctatgac   1440
atcttgttct tttgggtggc cagaatgatg atgttcggca ccttcgtcgg cgacgacgcc   1500
gccatcaccc tcgacggccg ccggggcccg caggtgccgt tcaccgacgt gtttctgcat   1560
gggctgatcc gcgacgagtc tggccgcaag atgagcaagt ccaagggcaa cgtcatcgac   1620
ccgctggatt gggtggaaat gttcggggcc gatgcgctgc ggttcacgct ggcccgcggg   1680
gccagtcccg gtggtgactt ggcggtgagc gaggatgccg tgcgggcgtc gcgcaatttc   1740
gggaccaagc tgttcaacgc cactcggtac gcactgctca atggcgccgc gccagcaccc   1800
ctgccatcgc cgaacgagct gaccgacgcc gaccgctgga ttctcggaag gttggaagag   1860
gttcgggccg aagttgattc ggccttcgac ggatacgagt tcagccgcgc ttgtgagtcc   1920
ctgtatcact tcgcctggga cgaattctgc gactggtacc tcgaactggc caaaacgcag   1980
cttgcccagg gactcacaca caccaccgcc gtgctggccg ccgggctgga cacgctgctg   2040
cgcctgctgc acccggtgat tcccttcctc accgaggcgc tatggctggc gctgaccggc   2100
agggaatcgc tggtcagcgc cgactggccg gagccttccg ggattagcgt ggaccttgtt   2160
gccgcgcaac ggattaacga tatgcagaag ttggtgaccg aagtgcggcg gttccgcagc   2220
gatcaaggtc tggccgaccg gcagaaggtt ccggcccgaa tgcacggtgt gcgggactcg   2280
gatctgagca accaggtggc cgccgtgacc tcgctggcgt ggctcaccga gccgggcccg   2340
gattttgagc cgtcggtctc gttggaggtt cggctcggcc ccgagatgaa ccgcaccgtc   2400
gtcgtcgagc tcgacacctc gggcaccatc gacgtggccg ccgagcgtcg ccgcctggaa   2460
aaggagttgg ccggcgccca aaaggagctg gcgtcgaccg ccgccaagtt ggccaacgcg   2520
gactttctgg ccaaagcgcc cgacgccgtc attgccaaga tccgggaccg ccagcgcgtg   2580
```

gcgcagcagg aaaccgagcg catcaccacc cggttggctg cgctgcaa 2628

<210> SEQ ID NO 51
<211> LENGTH: 431
<212> TYPE: PRT
<213> ORGANISM: Mycobacterium tuberculosis

<400> SEQUENCE: 51

```
Met Asn Pro Thr Leu Ala Val Leu Gly Ala Gly Ala Lys Ala Val Ala
1               5                   10                  15

Val Ala Ala Lys Ala Ser Val Leu Arg Asp Met Gly Val Asp Val Pro
            20                  25                  30

Asp Val Ile Ala Val Glu Arg Ile Gly Val Gly Ala Asn Trp Gln Ala
        35                  40                  45

Ser Gly Gly Trp Thr Asp Gly Ala His Arg Leu Gly Thr Ser Pro Glu
    50                  55                  60

Lys Asp Val Gly Phe Pro Tyr Arg Ser Ala Leu Val Pro Arg Arg Asn
65                  70                  75                  80

Ala Glu Leu Asp Glu Arg Met Thr Arg Tyr Ser Trp Gln Ser Tyr Leu
                85                  90                  95

Ile Ala Thr Ala Ser Phe Ala Glu Trp Ile Asp Arg Gly Arg Pro Ala
            100                 105                 110

Pro Thr His Arg Arg Trp Ser Gln Tyr Leu Ala Trp Val Ala Asp His
        115                 120                 125

Ile Gly Leu Lys Val Ile His Gly Glu Val Glu Arg Leu Ala Val Thr
    130                 135                 140

Gly Asp Arg Trp Ala Leu Cys Thr His Glu Thr Thr Val Gln Ala Asp
145                 150                 155                 160

Ala Leu Met Ile Thr Gly Pro Gly Gln Ala Glu Lys Ser Leu Leu Pro
                165                 170                 175

Gly Asn Pro Arg Val Leu Ser Ile Ala Gln Phe Trp Asp Arg Ala Ala
            180                 185                 190

Gly His Asp Arg Ile Asn Ala Glu Arg Val Ala Val Ile Gly Gly Gly
        195                 200                 205

Glu Thr Ala Ala Ser Met Leu Asn Glu Leu Phe Arg His Arg Val Ser
    210                 215                 220

Thr Ile Thr Val Ile Ser Pro Gln Val Thr Leu Phe Thr Arg Gly Glu
225                 230                 235                 240

Gly Phe Phe Glu Asn Ser Leu Phe Ser Asp Pro Thr Asp Trp Ala Ala
                245                 250                 255

Leu Thr Phe Asp Glu Arg Arg Asp Ala Leu Ala Arg Thr Asp Arg Gly
            260                 265                 270

Val Phe Ser Ala Thr Val Gln Glu Ala Leu Leu Ala Asp Asp Arg Ile
        275                 280                 285

His His Leu Arg Gly Arg Val Ala His Ala Val Gly Arg Gln Gly Gln
    290                 295                 300

Ile Arg Leu Thr Leu Ser Thr Asn Arg Gly Ser Glu Asn Phe Glu Thr
305                 310                 315                 320

Val His Gly Phe Asp Leu Val Ile Asp Gly Ser Gly Ala Asp Pro Leu
                325                 330                 335

Trp Phe Thr Ser Leu Phe Ser Gln His Thr Leu Asp Leu Leu Glu Leu
            340                 345                 350

Gly Leu Gly Gly Pro Leu Thr Ala Asp Arg Leu Gln Glu Ala Ile Gly
        355                 360                 365

Tyr Asp Leu Ala Val Thr Asp Val Thr Pro Lys Leu Phe Leu Pro Thr
```

```
    370                 375                 380

Leu Ser Gly Leu Thr Gln Gly Pro Gly Phe Pro Asn Leu Ser Cys Leu
385                 390                 395                 400

Gly Leu Leu Ser Asp Arg Val Leu Gly Ala Gly Ile Phe Thr Pro Thr
                405                 410                 415

Lys His Asn Asp Thr Arg Arg Ser Gly Glu His Gln Ser Phe Arg
            420                 425                 430


<210> SEQ ID NO 52
<211> LENGTH: 1293
<212> TYPE: DNA
<213> ORGANISM: Mycobacterium tuberculosis

<400> SEQUENCE: 52

atgaatccga cgctcgcggt cctgggcgct ggagccaagg cggtggcggt cgcggccaag      60

gcatccgtgc tgcgtgacat gggggtcgac gtgcccgacg tgatcgccgt cgaacgcatc     120

ggggtcgggg ccaactggca ggccagcggt ggctggaccg acggagccca ccggctgggc     180

accagcccag aaaaggatgt cggttttccc taccggtcgg cgctggtgcc acggcgcaac     240

gcagaattgg acgagcggat gacccgctac agctggcagt cgtatctgat cgccaccgcg     300

tcgttcgcgg aatggatcga ccggggccgc ccggcgccca cccatcgcag gtggagtcag     360

tacctagcct gggtggccga tcacattggc ctcaaggtga tccacggcga ggtcgaacgg     420

ctcgccgtca ccggtgaccg ctgggcgttg tgcacccacg agaccaccgt gcaggccgac     480

gcgttgatga tcaccgggcc cggccaggct gaaaagtcgc tactgcccgg aaacccgcgc     540

gtgctctcaa tcgcacagtt ctgggaccgt gccgccggcc acgaccggat caacgccgag     600

cgggtcgcgg tgatcggtgg cggagagacg gccgcatcga tgctcaacga gctgttccgg     660

catcgggtct caaccatcac cgtcatctcc ccgcaggtaa ccctgttcac ccgcggcgag     720

ggattcttcg agaactcact gttttccgat ccgaccgact gggcggcctt gacgttcgac     780

gaacggcgcg acgcgctggc ccgcaccgac cgaggagtgt tctcggcgac cgtgcaggaa     840

gcgctgctgg ccgatgaccg catccatcat ctgcgtggcc gggtcgccca cgcggtgggc     900

cgtcaggggc agatccggtt gacgctgagc accaaccggg gcagcgagaa cttcgagacc     960

gtgcacggat tcgatctcgt catcgacggc tcgggcgccg atccgctgtg gttcacctca    1020

ctgttcagtc agcacaccct cgacctgctc gagctgggac tgggtggacc gctgaccgcc    1080

gaccgcctgc aggaagcgat cggctacgac ttggcagtca ccgacgtcac gcccaagctg    1140

ttcctgccca ccctgtccgg actcacccag gggcccgggt tccccaacct gagctgcctc    1200

ggcttgttgt cggaccgggt gctcggcgcc ggcatcttta cgccgaccaa acacaacgac    1260

acaaggagaa gcggtgagca ccaatccttt cga                                 1293


<210> SEQ ID NO 53
<211> LENGTH: 71
<212> TYPE: PRT
<213> ORGANISM: Mycobacterium tuberculosis

<400> SEQUENCE: 53

Val Ser Thr Asn Pro Phe Asp Asp Asp Asn Gly Ala Phe Phe Val Leu
1               5                   10                  15

Val Asn Asp Glu Asp Gln His Ser Leu Trp Pro Val Phe Ala Asp Ile
            20                  25                  30

Pro Ala Gly Trp Arg Val Val His Gly Glu Ala Ser Arg Ala Ala Cys
        35                  40                  45
```

-continued

```
Leu Asp Tyr Val Glu Lys Asn Trp Thr Asp Leu Arg Pro Lys Ser Leu
    50                  55                  60

Arg Asp Ala Met Val Glu Asp
65                  70


<210> SEQ ID NO 54
<211> LENGTH: 213
<212> TYPE: DNA
<213> ORGANISM: Mycobacterium tuberculosis

<400> SEQUENCE: 54

gtgagcacca atcctttcga tgacgacaac ggcgcattct tcgtgctggt caacgacgaa      60

gaccagcaca gcctgtggcc ggtgttcgcc gatatcccgg ccggctggcg cgtggtgcac     120

ggcgaagcca gccgtgccgc ctgcctggac tacgtggaaa agaactggac cgatctgcgg     180

ccgaagagcc tgcgtgacgc catggtcgag gac                                  213


<210> SEQ ID NO 55
<211> LENGTH: 201
<212> TYPE: PRT
<213> ORGANISM: Mycobacterium tuberculosis

<400> SEQUENCE: 55

Val Thr Ala Val Ala Ala Gly Ala Leu Val Val Glu Thr Asp Ser Phe
1               5                   10                  15

Arg Leu Arg Leu Leu Asp Gly Leu Val Ala Ser Ile Gly Glu Arg Gly
            20                  25                  30

Tyr Arg Ala Thr Thr Val Ser Asp Ile Val Arg His Ala Arg Thr Ser
        35                  40                  45

Lys Arg Thr Phe Tyr Asp Arg Phe Thr Ser Lys Glu Gln Cys Phe Leu
    50                  55                  60

Glu Leu Leu Leu Ala Asp Asn Glu Thr Leu Gly Asn Ser Ile Arg Ala
65                  70                  75                  80

Ala Val Asp Pro Asn Ala Asp Trp His Asp Gln Ile Arg Gln Ala Val
                85                  90                  95

Glu Ala Tyr Val Thr His Ile Glu Ser Arg Pro Ala Val Thr Leu Ser
            100                 105                 110

Trp Ile Arg Glu Phe Pro Ser Leu Gly Ala Ala Ala Tyr Pro Val Gln
        115                 120                 125

Arg Arg Gly Met Glu Gln Leu Thr Ser Leu Leu Ile Glu Leu Ser Ala
    130                 135                 140

Ser Pro Gly Phe Arg Arg Ala Asn Leu Pro Pro Leu Asn Val Pro Leu
145                 150                 155                 160

Ala Val Ile Leu Leu Gly Gly Leu Arg Glu Leu Thr Ala Leu Thr Val
                165                 170                 175

Glu Asp Gly Gln Pro Ile Arg Asn Ile Val Glu Pro Ala Val Asp Ala
            180                 185                 190

Ser Ile Ala Leu Leu Gly Pro Arg Ser
        195                 200


<210> SEQ ID NO 56
<211> LENGTH: 603
<212> TYPE: DNA
<213> ORGANISM: Mycobacterium tuberculosis

<400> SEQUENCE: 56

gtgacagcag tcgccgccgg cgcgttggtc gtcgagaccg actcgtttcg gctacggttg      60

ctcgacggcc tggtcgcctc gatcggtgag cggggttatc gcgccaccac cgtctccgac     120
```

-continued atcgtccggc acgcccgcac atccaagcgc acgttctacg accggttcac cagcaaggaa 180
cagtgctttt tggaactcct gctagcggac aacgagacgt tgggcaacag catccgggcg 240
gccgtcgatc caaacgccga ctggcacgac cagattcgtc aggcggtcga ggcctacgtc 300
acccatatcg aatccaggcc ggcggtgacg ttgagttgga tccgtgaatt cccgtcgctc 360
ggtgccgccg cttaccccgt ccagcgccgc ggcatggagc agctaaccag cctgctgatc 420
gagctcagcg ccagccctgg gttccggcgg gctaacctac cgccactgaa tgtgccactg 480
gccgtaatct tgctgggcgg tttgcgtgaa ctgaccgcgc tgaccgtcga ggacggccag 540
ccgatccgga acatcgtcga gccggcggtg gatgcgtcaa tcgcgctgct cggtccccgc 600
agc 603

<210> SEQ ID NO 57
<211> LENGTH: 534
<212> TYPE: PRT
<213> ORGANISM: Mycobacterium tuberculosis

<400> SEQUENCE: 57

Val Ser Gln Ile Pro Val Lys Leu Leu Val Asn Gly Arg Val Tyr Ser
1 5 10 15

Pro Thr His Pro Glu Ala Thr Ala Met Ala Val Arg Gly Asp Val Val
20 25 30

Ala Trp Leu Gly Ser Asp Asp Val Gly Arg Asp Gln Phe Pro Asp Ala
35 40 45

Asp Val Gln Asp Leu Asp Gly Arg Phe Val Ala Pro Gly Phe Val Asp
50 55 60

Ser His Ile His Leu Thr Ala Thr Gly Leu Met Leu Ser Gly Leu Asp
65 70 75 80

Leu Arg Pro Ala Thr Ser Arg Ala Gln Cys Leu Arg Met Val Ala Asp
85 90 95

Tyr Ala Ala Asp His Pro Gly Gln Pro Leu Trp Gly His Gly Trp Asp
100 105 110

Glu Ser Ala Trp Pro Glu Asn Ala Ala Pro Ser Thr Ala Asp Leu Asp
115 120 125

Ala Val Leu Gly Asp Cys Pro Ala Tyr Leu Ala Arg Ile Asp Ser His
130 135 140

Ser Ala Leu Val Ser Ser Gly Leu Arg Arg Leu Val Pro Glu Leu Ala
145 150 155 160

Ala Ala Thr Gly Tyr Thr Ala Gln Arg Pro Leu Thr Gly Asp Ala His
165 170 175

His Leu Ala Arg Ala Ala Ala Arg Tyr Leu Leu Thr Asp Val Gln Leu
180 185 190

Ala Asp Ala Arg Ala Val Ala Leu Gln Ala Ile Ala Ala Ala Gly Val
195 200 205

Val Ala Val His Glu Cys Ala Gly Pro Glu Ile Gly Gly Leu Asp Asp
210 215 220

Trp Leu Arg Leu Arg Ala Leu Glu His Gly Val Glu Val Ile Gly Tyr
225 230 235 240

Trp Gly Glu Ala Val Ala Thr Pro Ala Gln Ala Arg Asp Leu Val Thr
245 250 255

Glu Thr Gly Ala Arg Gly Leu Ala Gly Asp Leu Phe Val Asp Gly Ala
260 265 270

Leu Gly Ser Arg Thr Ala Trp Leu His Glu Pro Tyr Ala Asp Ala Pro
275 280 285

```
Asp Cys Ile Gly Thr Cys His Leu Asp Val Asp Gly Ile Glu Ala His
    290                 295                 300

Val Arg Ala Cys Thr Lys Ala Glu Val Thr Ala Gly Phe His Val Ile
305                 310                 315                 320

Gly Asp Ala Ala Val Ser Ala Ala Val Ala Ala Phe Glu Arg Val Val
                325                 330                 335

Ala Asp Leu Gly Val Val Ala Val Ala Arg Cys Gly His Arg Leu Glu
            340                 345                 350

His Val Glu Met Val Thr Ala Asp Gln Ala Ala Lys Leu Gly Ala Trp
        355                 360                 365

Gly Val Ile Ala Ser Val Gln Pro Asn Phe Asp Glu Leu Trp Gly Gly
    370                 375                 380

Gly Asp Gly Met Tyr Ala Arg Arg Leu Gly Ala Gln Arg Gly Ser Glu
385                 390                 395                 400

Leu Asn Pro Leu Ala Leu Leu Ala Ser Gln Gly Val Pro Leu Ala Leu
                405                 410                 415

Gly Ser Asp Ala Pro Val Thr Gly Phe Asp Pro Trp Ala Ser Val Arg
            420                 425                 430

Ala Ala Val Asn His Arg Thr Pro Gly Ser Gly Val Ser Ala Arg Ala
        435                 440                 445

Ala Phe Ala Ala Ala Thr Arg Gly Gly Trp Arg Ala Gly Gly Val Arg
    450                 455                 460

Asp Gly Arg Ile Gly Thr Leu Val Pro Gly Ala Pro Ala Ser Tyr Ala
465                 470                 475                 480

Ile Trp Asp Ala Gly Asp Phe Asp Val Asp Ala Pro Arg Asp Ala Val
                485                 490                 495

Gln Arg Trp Ser Thr Asp Pro Arg Ser Arg Val Pro Ala Leu Pro Arg
            500                 505                 510

Leu Gly Pro Thr Asp Ala Leu Pro Arg Cys Arg Gln Thr Val His Arg
        515                 520                 525

Gly Ala Val Ile Tyr Gly
    530
```

<210> SEQ ID NO 58
<211> LENGTH: 1602
<212> TYPE: DNA
<213> ORGANISM: Mycobacterium tuberculosis

<400> SEQUENCE: 58

```
gtgagccaga ttcccgtcaa actcctggtc aacggccggg tgtacagccc cacccacccc     60

gaagccaccg cgatggcggt gcgcggcgat gtcgtcgcct ggttgggcag cgacgacgtc    120

ggccgcgacc agttcccaga cgctgacgtg caggatctcg acggccgatt cgtggcgccg    180

gggttcgtgg acagccacat ccacctgacc gcgaccggtc tgatgctcag cgggctggac    240

ttgcggcccg cgacctcacg cgcgcagtgc ctacggatgg tcgccgacta tgcggccgac    300

catccgggtc agccgctgtg ggtcacggt tgggatgagt cggcctggcc ggagaatgct    360

gcgcccagca ccgccgacct agacgcggtt ctcggtgact gtcccgccta cctggccagg    420

atcgactcgc actccgcgtt ggtctcctcc ggactgcggc ggctggtccc cgagctggcg    480

gcggcaaccg gttacacggc ccagcggccg ctgaccggtg atgcccacca cctagcccgg    540

gccgccgcac gctacctctt gaccgacgtc cagcttgccg acgcccgggc cgtggcgctg    600

caggccatag ccgcggccgg cgtcgtcgcc gtgcacgaat gcgccggtcc ggaaatcggc    660

gggctcgacg actggttgcg gctgcgtgca ctcgagcacg gagtcgaggt gatcgggtac    720
```

-continued tggggtgagg ccgtggccac gccggcccag gcccgtgacc tggtgaccga gaccggggct 780
cgagggctgg ccggtgattt gttcgtcgac ggggcgctcg ggtcgcgcac cgcctggctg 840
cacgagccct acgcggacgc ccccgactgc atcggcacct gccaccttga cgtagacggc 900
atcgaagcgc acgtacgagc atgcaccaag gccgaagtga ccgccggctt ccacgtcatc 960
ggcgacgctg cggtgtcggc cgcagtcgcc gccttcgaac gggtggtggc agatctcggc 1020
gtggttgccg tcgcccgctg cggccaccgc ctcgagcatg tggagatggt caccgcggac 1080
caggccgcga agctgggcgc ttggggggtc atcgccagtg tgcagcccaa cttcgatgag 1140
ctgtggggcg gtggcgacgg catgtacgct cgccgcctgg gcgcccagcg aggcagcgaa 1200
ctcaacccgc tggcgctgtt agcatcccaa ggcgtgcccc tcgcgcttgg ctccgacgcg 1260
cccgtcacgg gctttgatcc ctgggccagc gtgcgcgcgg cggtcaatca ccgcacgccg 1320
ggcagcgggg tatcggcgcg ggcggcgttt gctgccgcga cccgcggcgg ctggcgggcc 1380
ggtggtgttc gagacggccg gatcggcacc ctggtgccgg gcgcgcccgc gtcctacgcg 1440
atatgggacg ccggggactt tgacgtcgac gcaccgcgcg acgcagtcca gcgctggtct 1500
accgacccgc gctcccgggt acccgcattg ccgcggctgg gcccgaccga cgccttgccg 1560
cgttgccgcc aaaccgtgca tcgaggtgcg gtcatctatg gc 1602

<210> SEQ ID NO 59
<211> LENGTH: 151
<212> TYPE: PRT
<213> ORGANISM: Mycobacterium tuberculosis

<400> SEQUENCE: 59

Met Leu Lys Gly Phe Lys Glu Phe Leu Ala Arg Gly Asn Ile Val Asp
1 5 10 15

Leu Ala Val Ala Val Val Ile Gly Thr Ala Phe Thr Ala Leu Val Thr
20 25 30

Lys Phe Thr Asp Ser Ile Ile Thr Pro Leu Ile Asn Arg Ile Gly Val
35 40 45

Asn Ala Gln Ser Asp Val Gly Ile Leu Arg Ile Gly Ile Gly Gly Gly
50 55 60

Gln Thr Ile Asp Leu Asn Val Leu Leu Ser Ala Ala Ile Asn Phe Phe
65 70 75 80

Leu Ile Ala Phe Ala Val Tyr Phe Leu Val Val Leu Pro Tyr Asn Thr
85 90 95

Leu Arg Lys Lys Gly Glu Val Glu Gln Pro Gly Asp Thr Gln Val Val
100 105 110

Leu Leu Thr Glu Ile Arg Asp Leu Leu Ala Gln Thr Asn Gly Asp Ser
115 120 125

Pro Gly Arg His Gly Gly Arg Gly Thr Pro Ser Pro Thr Asp Gly Pro
130 135 140

Arg Ala Ser Thr Glu Ser Gln
145 150

<210> SEQ ID NO 60
<211> LENGTH: 453
<212> TYPE: DNA
<213> ORGANISM: Mycobacterium tuberculosis

<400> SEQUENCE: 60
atgctcaaag gattcaagga gtttctcgcg cggggtaata tcgtcgacct ggctgtcgcg 60
gtggtaatcg gcacagcgtt cacggcgttg gtcaccaagt tcaccgacag catcattacg 120

```
ccgctgatca accggatcgg cgtcaacgca cagtccgacg tcggcatctt gcggatcggt    180

atcggcggtg gtcagaccat tgacttgaac gtcttgttgt cggcagcgat caactttttc    240

ctgatcgcgt tcgcggtgta cttcctagtc gtgctgccct acaacacact acgcaagaag    300

ggggaggtcg agcagccggg cgacacccaa gtcgtgctgc tcaccgaaat ccgcgatctg    360

ctcgcgcaaa cgaacgggga ctcgccgggg aggcacggcg gccgtgggac accatcgcca    420

accgacgggc ctcgcgcgag cacagaatcg caa                                 453
```

<210> SEQ ID NO 61
<211> LENGTH: 759
<212> TYPE: PRT
<213> ORGANISM: Mycobacterium tuberculosis

<400> SEQUENCE: 61

```
Met Gly Ser Ala Ser Glu Gln Arg Val Thr Leu Thr Asn Ala Asp Lys
1               5                   10                  15

Val Leu Tyr Pro Ala Thr Gly Thr Thr Lys Ser Asp Ile Phe Asp Tyr
            20                  25                  30

Tyr Ala Gly Val Ala Glu Val Met Leu Gly His Ile Ala Gly Arg Pro
        35                  40                  45

Ala Thr Arg Lys Arg Trp Pro Asn Gly Val Asp Gln Pro Ala Phe Phe
    50                  55                  60

Glu Lys Gln Leu Ala Leu Ser Ala Pro Pro Trp Leu Ser Arg Ala Thr
65                  70                  75                  80

Val Ala His Arg Ser Gly Thr Thr Thr Tyr Pro Ile Ile Asp Ser Ala
                85                  90                  95

Thr Gly Leu Ala Trp Ile Ala Gln Gln Ala Ala Leu Glu Val His Val
            100                 105                 110

Pro Gln Trp Arg Phe Val Ala Glu Pro Gly Ser Gly Glu Leu Asn Pro
        115                 120                 125

Gly Pro Ala Thr Arg Leu Val Phe Asp Leu Asp Pro Gly Glu Gly Val
    130                 135                 140

Met Met Ala Gln Leu Ala Glu Val Ala Arg Ala Val Arg Asp Leu Leu
145                 150                 155                 160

Ala Asp Ile Gly Leu Val Thr Phe Pro Val Thr Ser Gly Ser Lys Gly
                165                 170                 175

Leu His Leu Tyr Thr Pro Leu Asp Glu Pro Val Ser Ser Arg Gly Ala
            180                 185                 190

Thr Val Leu Ala Lys Arg Val Ala Gln Arg Leu Glu Gln Ala Met Pro
        195                 200                 205

Ala Leu Val Thr Ser Thr Met Thr Lys Ser Leu Arg Ala Gly Lys Val
    210                 215                 220

Phe Val Asp Trp Ser Gln Asn Ser Gly Ser Lys Thr Thr Ile Ala Pro
225                 230                 235                 240

Tyr Ser Leu Arg Gly Arg Thr His Pro Thr Val Ala Ala Pro Arg Thr
                245                 250                 255

Trp Ala Glu Leu Asp Asp Pro Ala Leu Arg Gln Leu Ser Tyr Asp Glu
            260                 265                 270

Val Leu Thr Arg Ile Ala Arg Asp Gly Asp Leu Leu Glu Arg Leu Asp
        275                 280                 285

Ala Asp Ala Pro Val Ala Asp Arg Leu Thr Arg Tyr Arg Arg Met Arg
    290                 295                 300

Asp Ala Ser Lys Thr Pro Glu Pro Ile Pro Thr Ala Lys Pro Val Thr
305                 310                 315                 320
```

```
Gly Asp Gly Asn Thr Phe Val Ile Gln Glu His His Ala Arg Arg Pro
                325                 330                 335

His Tyr Asp Phe Arg Leu Glu Cys Asp Gly Val Leu Val Ser Trp Ala
            340                 345                 350

Val Pro Lys Asn Leu Pro Asp Asn Thr Ser Val Asn His Leu Ala Ile
        355                 360                 365

His Thr Glu Asp His Pro Leu Glu Tyr Ala Thr Phe Glu Gly Ala Ile
    370                 375                 380

Pro Ser Gly Glu Tyr Gly Ala Gly Lys Val Ile Ile Trp Asp Ser Gly
385                 390                 395                 400

Thr Tyr Asp Thr Glu Lys Phe His Asp Asp Pro His Thr Gly Glu Val
                405                 410                 415

Ile Val Asn Leu His Gly Gly Arg Ile Ser Gly Arg Tyr Ala Leu Ile
            420                 425                 430

Arg Thr Asn Gly Asp Arg Trp Leu Ala His Arg Leu Lys Asn Gln Lys
        435                 440                 445

Asp Gln Lys Val Phe Glu Phe Asp Asn Leu Ala Pro Met Leu Ala Thr
    450                 455                 460

His Gly Thr Val Ala Gly Leu Lys Ala Ser Gln Trp Ala Phe Glu Gly
465                 470                 475                 480

Lys Trp Asp Gly Tyr Arg Leu Leu Val Glu Ala Asp His Gly Ala Val
                485                 490                 495

Arg Leu Arg Ser Arg Ser Gly Arg Asp Val Thr Ala Glu Tyr Pro Gln
            500                 505                 510

Leu Arg Ala Leu Ala Glu Asp Leu Ala Asp His His Val Val Leu Asp
        515                 520                 525

Gly Glu Ala Val Val Leu Asp Ser Ser Gly Val Pro Ser Phe Ser Gln
    530                 535                 540

Met Gln Asn Arg Gly Arg Asp Thr Arg Val Glu Phe Trp Ala Phe Asp
545                 550                 555                 560

Leu Leu Tyr Leu Asp Gly Arg Ala Leu Leu Gly Thr Arg Tyr Gln Asp
                565                 570                 575

Arg Arg Lys Leu Leu Glu Thr Leu Ala Asn Ala Thr Ser Leu Thr Val
            580                 585                 590

Pro Glu Leu Leu Pro Gly Asp Gly Ala Gln Ala Phe Ala Cys Ser Arg
        595                 600                 605

Lys His Gly Trp Glu Gly Val Ile Ala Lys Arg Arg Asp Ser Arg Tyr
    610                 615                 620

Gln Pro Gly Arg Arg Cys Ala Ser Trp Val Lys Asp Lys His Trp Asn
625                 630                 635                 640

Thr Gln Glu Val Val Ile Gly Gly Trp Arg Ala Gly Glu Gly Gly Arg
                645                 650                 655

Ser Ser Gly Val Gly Ser Leu Leu Met Gly Ile Pro Gly Pro Gly Gly
            660                 665                 670

Leu Gln Phe Ala Gly Arg Val Gly Thr Gly Leu Ser Glu Arg Glu Leu
        675                 680                 685

Ala Asn Leu Lys Glu Met Leu Ala Pro Leu His Thr Asp Glu Ser Pro
    690                 695                 700

Phe Asp Val Pro Leu Pro Ala Arg Asp Ala Lys Gly Ile Thr Tyr Val
705                 710                 715                 720

Lys Pro Ala Leu Val Ala Glu Val Arg Tyr Ser Glu Trp Thr Pro Glu
                725                 730                 735

Gly Arg Leu Arg Gln Ser Ser Trp Arg Gly Leu Arg Pro Asp Lys Lys
```

-continued 740 745 750

Pro Ser Glu Val Val Arg Glu
755

<210> SEQ ID NO 62
<211> LENGTH: 2277
<212> TYPE: DNA
<213> ORGANISM: Mycobacterium tuberculosis

<400> SEQUENCE: 62
atgggttcgg cgtcggagca acgggtgacg ctgaccaacg ccgacaaggt gctctatccc 60
gccaccggga ccacaaagtc cgatatcttc gactactacg ccggtgttgc cgaagtcatg 120
ctcggccaca tcgcgggacg gccggcgacg cgcaagcgct ggcctaacgg cgtcgaccaa 180
cccgcgttct tcgaaaagca gttggcgttg tcggcgccgc cttggctgtc acgtgcaacg 240
gtggcgcacc ggtccgggac gacgacctat ccgatcatcg atagcgcaac cgggctggcc 300
tggatcgccc aacaggcggc gctggaggtg cacgtgccgc agtggcggtt tgtcgccgag 360
cccggatcag gtgagttaaa tccgggcccg gcaacgcgtt tggtgttcga cctggacccg 420
ggcgaaggcg tgatgatggc ccagctggcc gaggtggcgc gcgcggttcg tgatcttctc 480
gccgatatcg ggttggtcac cttcccggtc accagcggca gcaagggatt gcatctgtac 540
acaccgctgg atgagccggt gagcagcagg ggagccacgg tgttggccaa gcgcgtcgcg 600
cagcgattgg agcaggcgat gcccgcgttg gtcacctcga ccatgaccaa aagcctgcgg 660
gccgggaagg tgtttgtgga ctggagccag aacagcggct cgaagaccac catcgcgccg 720
tactcactac gtggccggac gcatccgacc gtcgcggcgc cacgcacctg ggcggagctc 780
gacgaccccg cactgcgtca gctctcctac gacgaggtgc tgacccggat tgcccgcgac 840
ggcgatctgc tcgagcggct ggatgccgac gctccggtag cggaccggtt gacccgatac 900
cgccgcatgc gcgacgcatc gaaaactccc gagccgattc ccacggcgaa acccgttacc 960
ggagacggca atacgttcgt catccaggag catcacgcgc gtcggccgca ctacgatttc 1020
cggctggaat gcgacggcgt gctggtctcg tgggcggtac cgaaaaacct gcccgacaac 1080
acatcggtta accatctagc gatacacacc gaggaccacc cgctggaata cgccacgttc 1140
gagggcgcga ttcccagcgg ggagtacggc gccggcaagg tgatcatctg ggactccggc 1200
acttacgaca ccgagaagtt ccacgatgac ccgcacacgg gggaggtcat cgtgaatctg 1260
cacggcggcc ggatctctgg gcgttatgcg ctgattcgga ccaacggcga tcggtggctg 1320
gcgcaccgcc taaagaatca gaaagaccag aaggtgttcg agttcgacaa tctggcccca 1380
atgcttgcca cgcacggcac ggtggccggt ctaaaggcca gccagtgggc gttcgaaggc 1440
aagtgggacg gctaccggtt gctggttgag gctgaccacg gcgccgtgcg gctgcggtcc 1500
cgcagcgggc gcgatgtcac cgccgagtat ccgcaattgc gggcattggc ggaggatctc 1560
gccgatcacc acgtggtgct ggacggcgag gccgtcgtac ttgactcctc tggtgtgccc 1620
agcttcagcc agatgcagaa tcggggccgc gacacccgtg tcgagttctg ggcgttcgac 1680
ctgctctacc tcgacggccg cgcgctgcta ggcacccgct accaagaccg gcgtaagctg 1740
ctcgaaaccc tagctaacgc aaccagtctc accgttcccg agctgctgcc cggtgacggc 1800
gcccaagcgt ttgcgtgctc gcgcaagcac ggctgggagg gcgtgatcgc caagaggcgt 1860
gactcgcgct atcagccggg ccggcgctgc gcgtcgtggg tcaaggacaa gcactggaac 1920
acccaggaag tcgtcattgg tggctggcgc gccggggaag gcgggcgcag cagtggcgtc 1980
gggtcgctgc tcatgggcat ccccggtcca ggtgggctgc agttcgccgg gcgggtcggt 2040

```
accggcctca gcgaacgcga actggccaac ctcaaggaga tgctggcgcc gctgcatacc   2100

gacgagtccc ccttcgacgt accactgccc gcgcgtgacg ccaagggcat cacatatgtc   2160

aagccggcgc tggttgcaga ggtgcgctac agcgagtgga ctccggaggg ccggctgcgt   2220

caatcaagct ggcgtgggct gcggccggac aagaaaccca gtgaggtggt gcgcgaa      2277
```

<210> SEQ ID NO 63
<211> LENGTH: 170
<212> TYPE: PRT
<213> ORGANISM: Mycobacterium tuberculosis

<400> SEQUENCE: 63

```
Val Val Pro Ala Gln His Arg Pro Pro Asp Arg Pro Gly Asp Pro Ala
1               5                   10                  15

His Asp Pro Gly Arg Gly Arg Arg Leu Gly Ile Asp Val Gly Ala Ala
            20                  25                  30

Arg Ile Gly Val Ala Cys Ser Asp Pro Asp Ala Ile Leu Ala Thr Pro
        35                  40                  45

Val Glu Thr Val Arg Arg Asp Arg Ser Gly Lys His Leu Arg Arg Leu
    50                  55                  60

Ala Ala Leu Ala Ala Glu Leu Glu Ala Val Glu Val Ile Val Gly Leu
65                  70                  75                  80

Pro Arg Thr Leu Ala Asp Arg Ile Gly Arg Ser Ala Gln Asp Ala Ile
                85                  90                  95

Glu Leu Ala Glu Ala Leu Ala Arg Arg Val Ser Pro Thr Pro Val Arg
            100                 105                 110

Leu Ala Asp Glu Arg Leu Thr Thr Val Ser Ala Gln Arg Ser Leu Arg
        115                 120                 125

Gln Ala Gly Val Arg Ala Ser Glu Gln Arg Ala Val Ile Asp Gln Ala
    130                 135                 140

Ala Ala Val Ala Ile Leu Gln Ser Trp Leu Asp Glu Arg Leu Ala Ala
145                 150                 155                 160

Met Ala Gly Thr Gln Glu Gly Ser Asp Ala
                165                 170
```

<210> SEQ ID NO 64
<211> LENGTH: 510
<212> TYPE: DNA
<213> ORGANISM: Mycobacterium tuberculosis

<400> SEQUENCE: 64

```
gtggtcccag cacagcaccg cccgcccgac cggcccggcg atccagcgca cgaccctgga     60

cggggacgac gcctcggtat cgacgtgggc gccgcgcgta tcggcgtggc ttgcagcgac    120

ccggacgcga tcttggccac cccggtggaa acggtgcgcc gcgatcgttc cggcaagcac    180

ctgcgcaggc tggctgcgct ggccgccgag ttggaggcgg tcgaggtgat cgtcgggctc    240

ccgcgcacgc tggccgaccg catcggccgc tcggcccaag acgcaatcga actggccgag    300

gcgctggcac gccgtgtttc tcctacgccg gtgcggctgg ccgacgagcg gctcaccacg    360

gtcagtgctc aacgatcttt gcggcaggcg gggtgcgggc cctccgagca gcgtgcggtg    420

atcgaccaag cggccgcagt ggcaatactg cagagctggc tggatgaacg tctcgcggcg    480

atggccggga ctcaagaagg ctccgatgcc                                     510
```

<210> SEQ ID NO 65
<211> LENGTH: 120
<212> TYPE: PRT

<213> ORGANISM: Mycobacterium tuberculosis

<400> SEQUENCE: 65

```
Met Thr Ala Pro Glu Thr Pro Ala Ala Gln His Ala Glu Pro Ala Ile
1               5                   10                  15

Ala Val Glu Arg Ile Arg Thr Ala Leu Leu Gly Tyr Arg Ile Met Ala
            20                  25                  30

Trp Thr Thr Gly Leu Trp Leu Ile Ala Leu Cys Tyr Glu Ile Val Val
        35                  40                  45

Arg Tyr Val Val Lys Val Asp Asn Pro Pro Thr Trp Ile Gly Val Val
    50                  55                  60

His Gly Trp Val Tyr Phe Thr Tyr Leu Leu Leu Thr Leu Asn Leu Ala
65                  70                  75                  80

Val Lys Val Arg Trp Pro Leu Gly Lys Thr Ala Gly Val Leu Leu Ala
                85                  90                  95

Gly Thr Ile Pro Leu Leu Gly Ile Val Val Glu His Phe Gln Thr Lys
            100                 105                 110

Glu Ile Lys Ala Arg Phe Gly Leu
        115                 120
```

<210> SEQ ID NO 66
<211> LENGTH: 360
<212> TYPE: DNA
<213> ORGANISM: Mycobacterium tuberculosis

<400> SEQUENCE: 66

```
atgaccgcac ccgaaacgcc cgcggcgcag cacgccgagc ctgccatcgc cgtcgagagg      60

attcgcaccg ctttgctcgg ctaccggatc atggcgtgga cgacgggcct ctggctcatc     120

gcactgtgct acgagatcgt ggtccgctac gtcgtcaagg ttgacaatcc gccgacgtgg     180

atcggtgtgg tgcacggctg ggtgtacttc acgtatctgc ttctgacgtt gaacctggcg     240

gtcaaggtcc gctggccgct cggcaaaaca gccggtgttc tgctcgccgg cacaattccg     300

ctgctcggca tcgtcgtcga gcacttccag accaaagaga tcaaggcccg cttcgggctt     360
```

<210> SEQ ID NO 67
<211> LENGTH: 122
<212> TYPE: PRT
<213> ORGANISM: Mycobacterium tuberculosis

<400> SEQUENCE: 67

```
Leu Leu Ala Thr Phe Trp Gly Trp Arg Ala Gln Gln Leu Pro Asp Gly
1               5                   10                  15

Thr Val Ile Trp Thr Leu Pro Gly Asp Gln Thr Tyr Val Thr Thr Pro
            20                  25                  30

Gly Ser Ala Leu Leu Phe Pro Ala Leu Cys Thr Pro Thr Gly Asp Pro
        35                  40                  45

Pro Arg Pro Asp Pro Ala Arg Ala Asp Arg Arg Gly Gln Arg Thr Ala
    50                  55                  60

Met Met Pro Arg Arg Ala Ser Thr Arg Ala Gln Asn Arg Ala His Tyr
65                  70                  75                  80

Ile Ala Ala Glu Arg His Arg Asn His Gln Ala Arg Arg Ile Ala His
                85                  90                  95

Val Val Thr Gln Thr Ala Thr Thr Ala Pro Glu Thr Asn Gly Pro Pro
            100                 105                 110

Pro Asp Pro Asp Asp Asp Pro Pro Pro Phe
        115                 120
```

<210> SEQ ID NO 68
<211> LENGTH: 366
<212> TYPE: DNA
<213> ORGANISM: Mycobacterium tuberculosis

<400> SEQUENCE: 68

```
ttgctggcca ccttctgggg ctggcgcgcc cagcaactgc ccgacggcac cgtgatttgg      60

acgctgccgg gtgaccagac ctatgtcacc accccgggca gcgcgctgct gttcccggcg     120

ctgtgcaccc ccaccggtga cccacctcga cccgacccgg cccgcgccga ccgccgcggg     180

cagcgcaccg cgatgatgcc gcgccgggcc agcacccgag cgcaaaaccg cgcccactac     240

atcgccgccg aacgccaccg caaccaccaa gcccgccgga ttgcccacgt ggtcacccaa     300

accgccacaa ccgcccccga gactaacggc ccaccacccg atcccgacga cgacccgccg     360

cccttc                                                                366
```

<210> SEQ ID NO 69
<211> LENGTH: 208
<212> TYPE: PRT
<213> ORGANISM: Mycobacterium tuberculosis

<400> SEQUENCE: 69

```
Val Ser Val Gly Glu Gly Pro Asp Thr Lys Pro Thr Ala Arg Gly Gln
1               5                   10                  15

Pro Ala Ala Val Gly Arg Val Val Val Leu Ser Gly Pro Ser Ala Val
            20                  25                  30

Gly Lys Ser Thr Val Val Arg Cys Leu Arg Glu Arg Ile Pro Asn Leu
        35                  40                  45

His Phe Ser Val Ser Ala Thr Thr Arg Ala Pro Arg Pro Gly Glu Val
    50                  55                  60

Asp Gly Val Asp Tyr His Phe Ile Asp Pro Thr Arg Phe Gln Gln Leu
65                  70                  75                  80

Ile Asp Gln Gly Glu Leu Leu Glu Trp Ala Glu Ile His Gly Gly Leu
                85                  90                  95

His Arg Ser Gly Thr Leu Ala Gln Pro Val Arg Ala Ala Ala Ala Thr
            100                 105                 110

Gly Val Pro Val Leu Ile Glu Val Asp Leu Ala Gly Ala Arg Ala Ile
        115                 120                 125

Lys Lys Thr Met Pro Glu Ala Val Thr Val Phe Leu Ala Pro Pro Ser
    130                 135                 140

Trp Gln Asp Leu Gln Ala Arg Leu Ile Gly Arg Gly Thr Glu Thr Ala
145                 150                 155                 160

Asp Val Ile Gln Arg Arg Leu Asp Thr Ala Arg Ile Glu Leu Ala Ala
                165                 170                 175

Gln Gly Asp Phe Asp Lys Val Val Val Asn Arg Arg Leu Glu Ser Ala
            180                 185                 190

Cys Ala Glu Leu Val Ser Leu Leu Val Gly Thr Ala Pro Gly Ser Pro
        195                 200                 205
```

<210> SEQ ID NO 70
<211> LENGTH: 624
<212> TYPE: DNA
<213> ORGANISM: Mycobacterium tuberculosis

<400> SEQUENCE: 70

```
gtgagcgtcg gcgagggacc ggacaccaag cccaccgcgc gtggccaacc ggcggcagtg      60

ggacgtgtgg tggtgctgtc cggtccttcc gcggtcggca aatccacggt ggttcggtgt     120
```

ctgcgcgagc ggatcccgaa tctgcatttc agtgtctcgg ccacgacgcg ggcgccacgc 180
ccgggcgagg tcgacggtgt cgactaccac ttcatcgacc ccacccgctt tcagcagctc 240
atcgaccagg gtgagttgct ggaatgggca gaaatccacg gcggcctgca ccggtcgggc 300
actttggccc agccggtgcg ggcggccgcg gcgactggtg tgccggtgct tatcgaggtt 360
gacctggccg gggccagggc gatcaagaag acgatgcccg aggctgtcac cgtgtttctg 420
gcgccaccta gctggcagga tcttcaggcc agactgattg gccgcggcac cgaaacagct 480
gacgttatcc aacgccgcct ggacaccgcg cggatcgaat tggcagcgca gggcgacttt 540
gacaaggtcg tggtgaacag gcgattagag tctgcgtgtg cggaattggt atccttgctg 600
gtgggaacgg caccgggctc cccg 624

<210> SEQ ID NO 71
<211> LENGTH: 122
<212> TYPE: PRT
<213> ORGANISM: Mycobacterium tuberculosis

<400> SEQUENCE: 71

Met Thr Lys Lys Pro Arg Asn Pro Ala Asp Tyr Val Ile Gly Asp Asp
1 5 10 15

Val Glu Val Ser Asp Val Asp Leu Lys Gln Glu Glu Val Tyr Val Asp
20 25 30

Gly Glu Arg Leu Thr Asp Glu Arg Val Glu Gln Met Ala Ser Glu Ser
35 40 45

Leu Arg Leu Ala Arg Glu Arg Glu Ala Asn Leu Ile Pro Gly Gly Lys
50 55 60

Ser Leu Ser Gly Gly Ser Ala His Ser Pro Ala Val Gln Val Val Val
65 70 75 80

Ser Lys Ala Thr His Ala Lys Leu Lys Glu Leu Ala Arg Ser Arg Lys
85 90 95

Met Ser Val Ser Lys Leu Leu Arg Pro Val Leu Asp Glu Phe Val Gln
100 105 110

Arg Glu Thr Gly Arg Ile Leu Pro Arg Arg
115 120

<210> SEQ ID NO 72
<211> LENGTH: 366
<212> TYPE: DNA
<213> ORGANISM: Mycobacterium tuberculosis

<400> SEQUENCE: 72
atgacgaaga agccacgtaa ccccgccgac tacgtgatcg gcgacgatgt cgaggtgtct 60
gacgtcgatc tcaagcaaga ggaggtctat gtcgatggcg agcggctaac ggacgagcgc 120
gtcgagcaga tggcttcaga gtcgctgcgg ctggcgcgcg aacgagaagc caacctgatt 180
cctggcggca agtctctgtc cggcggctct gcgcactcgc cggctgtgca ggtggtcgtt 240
tcgaaggcta cccacgccaa gctcaaggag ctggcgcgca gccggaagat gagcgtatct 300
aagctgctgc gtcccgtgct cgacgagttc gtacagcgag aaacgggtcg gattctccca 360
cggcgt 366

<210> SEQ ID NO 73
<211> LENGTH: 333
<212> TYPE: PRT
<213> ORGANISM: Mycobacterium tuberculosis

<400> SEQUENCE: 73

-continued

```
Met Phe Tyr Asp Asp Asp Ala Asp Leu Ser Ile Ile Gln Gly Arg Lys
1               5                   10                  15

Val Gly Val Ile Gly Tyr Gly Ser Gln Gly His Ala His Ser Leu Ser
            20                  25                  30

Leu Arg Asp Ser Gly Val Gln Val Arg Val Gly Leu Lys Gln Gly Ser
        35                  40                  45

Arg Ser Arg Pro Lys Val Glu Glu Gln Gly Leu Asp Val Asp Thr Pro
    50                  55                  60

Ala Glu Val Ala Lys Trp Ala Asp Val Val Met Val Leu Ala Pro Asp
65                  70                  75                  80

Thr Ala Gln Ala Glu Ile Phe Ala Gly Asp Ile Glu Pro Asn Leu Lys
                85                  90                  95

Pro Gly Asp Ala Leu Phe Phe Gly His Gly Leu Asn Val His Phe Gly
            100                 105                 110

Leu Ile Lys Pro Pro Ala Asp Val Ala Val Ala Met Val Ala Pro Lys
        115                 120                 125

Gly Pro Gly His Leu Val Arg Arg Gln Phe Val Asp Gly Lys Gly Val
    130                 135                 140

Pro Cys Leu Val Ala Val Glu Gln Asp Pro Arg Gly Asp Gly Leu Ala
145                 150                 155                 160

Leu Ala Leu Ser Tyr Ala Lys Ala Ile Gly Gly Thr Arg Ala Gly Val
                165                 170                 175

Ile Lys Thr Thr Phe Lys Asp Glu Thr Glu Thr Asp Leu Phe Gly Glu
            180                 185                 190

Gln Thr Val Leu Cys Gly Gly Thr Glu Glu Leu Val Lys Ala Gly Phe
        195                 200                 205

Glu Val Met Val Glu Ala Gly Tyr Pro Ala Glu Leu Ala Tyr Phe Glu
    210                 215                 220

Val Leu His Glu Leu Lys Leu Ile Val Asp Leu Met Tyr Glu Gly Gly
225                 230                 235                 240

Leu Ala Arg Met Tyr Tyr Ser Val Ser Asp Thr Ala Glu Phe Gly Gly
                245                 250                 255

Tyr Leu Ser Gly Pro Arg Val Ile Asp Ala Gly Thr Lys Glu Arg Met
            260                 265                 270

Arg Asp Ile Leu Arg Glu Ile Gln Asp Gly Ser Phe Val His Lys Leu
        275                 280                 285

Val Ala Asp Val Glu Gly Gly Asn Lys Gln Leu Glu Glu Leu Arg Arg
    290                 295                 300

Gln Asn Ala Glu His Pro Ile Glu Val Val Gly Lys Lys Leu Arg Asp
305                 310                 315                 320

Leu Met Ser Trp Val Asp Arg Pro Ile Thr Glu Thr Ala
                325                 330
```

<210> SEQ ID NO 74
<211> LENGTH: 999
<212> TYPE: DNA
<213> ORGANISM: Mycobacterium tuberculosis

<400> SEQUENCE: 74

```
atgttctacg acgacgacgc agacctgtcg atcattcagg gccgcaaggt tggtgtgatc      60

ggctacggca gccaggggca cgcgcactcg ctaagcctgc gcgactcggg tgtgcaggtg     120

cgcgtcgggc tgaagcaggg ttcgcggtcg cggcccaagg tagaagagca gggcctggac     180

gtcgacactc ccgccgaggt cgccaaatgg gccgatgtgg tcatggtgtt ggcccccgac     240
```

-continued

```
accgcccagg ccgagatctt cgcaggagac atcgaaccca acctcaagcc cggtgacgcg    300

ctgttcttcg gtcacggact caacgttcac ttcggcttga tcaagccgcc cgccgacgtc    360

gccgtcgcga tggtcgcccc gaagggaccg ggtcatttgg tgcgccgcca gttcgtcgac    420

ggcaagggtg tgccgtgttt ggttgcggta gagcaggatc cgcgaggcga cggcttggcg    480

ctggcgctgt cgtatgccaa agcgatcggc ggcacccggg ccggcgtcat caagacgacg    540

ttcaaagacg agaccgaaac cgacctgttc ggtgagcaaa cggtgttgtg cggcggcacc    600

gaggaattgg tcaaggccgg gttcgaggtc atggtcgaag ccggctaccc cgcggaattg    660

gcctacttcg aggtgctgca cgagctgaag ctgatcgtcg acttgatgta cgagggtggc    720

ctggcgcgga tgtactactc ggtgtcggac accgcggaat tcggcggcta cctctcaggc    780

ccgcgcgtca tcgatgccgg caccaaggag cggatgcgcg acatcctgcg ggagatccag    840

gacggtagct ttgtccacaa gctggtcgcc gacgtcgagg gcggcaacaa acagctcgaa    900

gagttgcgcc ggcaaaacgc cgagcacccc atcgaggtcg tcggcaagaa actccgcgac    960

ctgatgagct gggtggaccg cccgatcacc gagacggcc                           999


<210> SEQ ID NO 75
<211> LENGTH: 258
<212> TYPE: PRT
<213> ORGANISM: Mycobacterium tuberculosis

<400> SEQUENCE: 75

Met Pro Pro Leu Thr Ser Leu Ala Pro Thr Thr Ala Glu Arg Ile Arg
1               5                   10                  15

Ser Ala Cys Ala Arg Ala Gly Gly Ala Leu Leu Val Val Glu Arg Glu
            20                  25                  30

Asp Pro Val Pro Val Pro Ile His His Leu Leu Tyr Asp Gly Ser Phe
        35                  40                  45

Ala Val Ala Val Pro Val Asp Arg Gly Glu Val Ser Gly Ser Gln Ala
    50                  55                  60

Leu Leu Glu Leu Thr Asp Tyr Ala Pro Leu Pro Val Arg Glu Pro Val
65                  70                  75                  80

Arg Ser Leu Val Trp Ile Arg Gly Cys Leu His Gln Ile Pro Pro Ala
                85                  90                  95

Glu Leu Val Glu Thr Leu Asp Leu Ile Ala Thr Asp Asn Pro Asn Pro
            100                 105                 110

Ala Leu Leu Gln Val Glu Thr Pro Arg Pro Gly Pro Ala Asp Ala Ala
        115                 120                 125

Glu Thr Arg Tyr Thr Met Gln Arg Leu Glu Ile Glu Ser Val Val Val
    130                 135                 140

Thr Asp Ala Thr Gly Ala Glu Pro Val Thr Val Ala Asp Leu Leu Ala
145                 150                 155                 160

Ala Arg Pro Asp Pro Phe Cys Glu Ile Glu Ser Thr Leu Leu Trp His
                165                 170                 175

Leu Ala Thr Ala His Asp Asp Val Val Ala Arg Leu Val Ser Arg Leu
            180                 185                 190

Pro Ala Pro Leu Arg Arg Gly Gln Ile Arg Pro Leu Gly Leu Asp Arg
        195                 200                 205

Tyr Gly Val Arg Phe Arg Ile Glu Ala Arg Asp Gly Asp Arg Asp Ile
    210                 215                 220

Arg Leu Pro Phe His Lys Pro Val Asp Asp Met Thr Gly Leu Ser Gln
225                 230                 235                 240

Ala Ile Arg Val Leu Met Gly Cys Pro Phe Arg Asn Gly Leu Arg Ala
```

-continued 245 250 255

Arg Arg

<210> SEQ ID NO 76
<211> LENGTH: 774
<212> TYPE: DNA
<213> ORGANISM: Mycobacterium tuberculosis

<400> SEQUENCE: 76
atgccgccgc tcaccagtct cgcgccgact actgccgagc gaattcgcag cgcctgcgcg 60
cgggccgggg gcgccttgct ggtggttgag cgggaggatc cggtccccgt gcccatacac 120
catttgttgt acgacgggtc cttcgccgtg gcggttccgg tcgatcgtgg cgaggtgtcc 180
ggttcgcaag cgctgctgga gttgactgac tatgcgccgc tgccggtgcg tgaacccgtc 240
cgttcgctgg tgtggatccg cggctgcctc caccagatcc cgcccgcaga gctggttgag 300
accctggacc tgatcgccac cgataatccg aatccggccc tgctacaagt cgagaccccg 360
aggcccgggc cggccgatgc ggcggagacc cggtatacca tgcagcggct ggagatcgaa 420
tccgtagtgg tgaccgacgc caccggcgcc gaacccgtta ccgtggcgga cctgctcgcg 480
gcccgacccg atccgttttg tgaaatcgaa tcaaccttgc tctggcacct agccaccgcc 540
catgacgatg tggtcgcgcg gctggtatcc aggctgccgg caccgctacg acgcggacag 600
atccgccccc tcggtctcga tcggtacggc gtccggtttc gcattgaagc tcgcgacgga 660
gaccgcgaca tccgactgcc gttccataag ccggtggacg acatgaccgg gctaagccag 720
gccatccggg tgctcatggg ttgcccgttc cgcaacgggc tgcgcgcccg cagg 774

<210> SEQ ID NO 77
<211> LENGTH: 384
<212> TYPE: PRT
<213> ORGANISM: Mycobacterium tuberculosis

<400> SEQUENCE: 77

Met Arg Ala Lys Arg Glu Ala Pro Lys Ser Arg Ser Ser Asp Arg Arg
1 5 10 15

Arg Arg Ala Asp Ser Pro Ala Ala Ala Thr Arg Arg Thr Thr Thr Asn
20 25 30

Ser Ala Pro Ser Arg Arg Ile Arg Ser Arg Ala Gly Lys Thr Ser Ala
35 40 45

Pro Gly Arg Gln Ala Arg Val Ser Arg Pro Gly Pro Gln Thr Ser Pro
50 55 60

Met Leu Ser Pro Phe Asp Arg Pro Ala Pro Ala Lys Asn Thr Ser Gln
65 70 75 80

Ala Lys Ala Arg Ala Lys Ala Arg Lys Ala Lys Ala Pro Lys Leu Val
85 90 95

Arg Pro Thr Pro Met Glu Arg Leu Ala Ala Arg Leu Thr Ser Ile Asp
100 105 110

Leu Arg Pro Arg Thr Leu Ala Asn Lys Val Pro Phe Val Val Leu Val
115 120 125

Ile Gly Ser Leu Gly Val Gly Leu Gly Leu Thr Leu Trp Leu Ser Thr
130 135 140

Asp Ala Ala Glu Arg Ser Tyr Gln Leu Ser Asn Ala Arg Glu Arg Thr
145 150 155 160

Arg Met Leu Gln Gln His Lys Glu Ala Leu Glu Arg Asp Val Arg Glu
165 170 175

Ala Ala Ser Ala Pro Ala Leu Ala Glu Ala Ala Arg Arg Gln Gly Met

```
            180                 185                 190

Ile Pro Thr Arg Asp Thr Ala His Leu Val Gln Asp Pro Asp Gly Asn
        195                 200                 205

Trp Val Val Val Gly Thr Pro Lys Pro Ala Asp Gly Val Pro Pro Pro
    210                 215                 220

Pro Leu Asn Thr Lys Leu Pro Glu Asp Pro Pro Pro Pro Pro Lys Pro
225                 230                 235                 240

Ala Ala Val Pro Leu Glu Val Pro Val Arg Val Thr Pro Gly Pro Asp
                245                 250                 255

Asp Pro Ala Pro Pro Ala Arg Ser Gly Pro Glu Val Leu Val Arg Thr
            260                 265                 270

Pro Asp Gly Thr Ala Thr Leu Gly Gly Ala Thr His Leu Pro Thr Gln
        275                 280                 285

Ala Gly Pro Gln Leu Pro Gly Pro Val Pro Ile Pro Gly Ala Pro Gly
    290                 295                 300

Pro Met Pro Ala Pro Pro Leu Gly Ala Val Pro Ser Pro Ala Pro Ala
305                 310                 315                 320

Glu Asn Pro Val Pro Leu Gln Val Gly Ala Ala Pro Pro Ala Gly Leu
                325                 330                 335

Pro Gly Pro Ala Pro Val Ala Ala Thr Pro Gly Leu Ser Gly Gly Ser
            340                 345                 350

Gln Pro Met Val Ala Pro Pro Ala Pro Val Pro Ala Asn Gly Glu Gln
        355                 360                 365

Phe Gly Pro Val Thr Ala Pro Val Pro Thr Ala Pro Gly Ala Pro Arg
    370                 375                 380
```

<210> SEQ ID NO 78
<211> LENGTH: 1152
<212> TYPE: DNA
<213> ORGANISM: Mycobacterium tuberculosis

<400> SEQUENCE: 78

```
atgagggcca agcgtgaggc accgaaaagc cgcagcagcg atcgtcgcag gagagccgac      60

agtcctgccg cggcgacgag gcgaacgact acgaactcgg cgccgtcgcg ccgcatccgg     120

agccgtgccg gcaagacctc ggcacccggc cggcaggccc gggtgtcgcg ccctggaccg     180

caaaccagcc cgatgctcag cccgttcgac cggccggccc ccgcaaagaa caccagccag     240

gccaaggcgc gggccaaggc ccgaaaagcc aaggcgccca agctggtccg tcctacgccg     300

atggagcgtc tcgccgcccg gctcacgtcg atcgacctgc ggccgcgcac gttggcaaac     360

aaggttccgt ttgtggtgct ggttatcggt tcgctcggcg tcggactagg cctcacactg     420

tggttgtcca ccgatgccgc cgagaggtcc taccagctga gcaacgcccg ggagcggacc     480

cggatgctgc agcagcacaa ggaagcgctg gaacgcgacg tacgcgaggc tgcgtcggcg     540

ccggcgctgg ccgaggcggc tcgtcgccag ggcatgatcc cgacgaggga taccgcccac     600

ctggttcagg atccggacgg caattgggtg gtggtcggta cacccaagcc ggctgacgga     660

gttccaccgc cgccgctgaa cacgaagttg cccgaagatc cgccgccgcc cccgaaaccc     720

gcggcggtgc cctcgaggt gccggtccgg gtgacaccag gccccgatga tcccgctccg      780

cccgcccggt ctggcccgga ggtgctggtg cgtaccccag acggcacagc gacgctgggc     840

ggcgcaaccc acctgcccac ccaggccggc ccgcagctgc ccggtccggt gccgatacct     900

ggggcgccgg gtccgatgcc ggctcctccg ctcggcgcag tgccatcccc ggcaccagcg     960

gaaaatccgg tgccgctcca ggtgggtgcg gcgcccccgg ccgggctccc tggaccagca    1020
```

-continued

```
ccggtggctg cgacgcccgg gctgtcgggt gggtcgcaac ccatggtggc accacccgct   1080

ccagtgccgg ccaacggcga acagttcggt cccgtcacgg cgccggtgcc aacggcgccg   1140

ggggctccca gg                                                       1152


<210> SEQ ID NO 79
<211> LENGTH: 346
<212> TYPE: PRT
<213> ORGANISM: Mycobacterium tuberculosis

<400> SEQUENCE: 79

Met Asn Gly Leu Gly Asp Val Leu Ala Val Ala Arg Lys Ala Arg Gly
1               5                   10                  15

Leu Thr Gln Ile Glu Leu Ala Glu Leu Val Gly Leu Thr Gln Pro Ala
            20                  25                  30

Ile Asn Arg Tyr Glu Ser Gly Asp Arg Asp Pro Asp Gln His Ile Val
        35                  40                  45

Ala Lys Leu Ala Glu Ile Leu Gly Val Thr Asp Asp Leu Leu Ile His
    50                  55                  60

Gly Asn Arg Phe Arg Gly Ala Leu Ala Val Asp Ala His Met Arg Arg
65                  70                  75                  80

His Lys Thr Thr Lys Ala Ser Ala Trp Arg Gln Leu Glu Ala Arg Leu
                85                  90                  95

Asn Leu Leu Arg Val His Ala Ser Phe Leu Phe Glu Glu Val Ala Ile
            100                 105                 110

Asn Ser Glu Gln His Val Pro Ala Phe Asp Pro Glu Phe Thr Ala Ala
        115                 120                 125

Glu Asp Ala Ala Arg Leu Val Arg Ala Gln Trp Arg Met Pro Met Gly
    130                 135                 140

Pro Val Val Asn Leu Thr Arg Trp Met Glu Ala Ala Gly Cys Leu Val
145                 150                 155                 160

Phe Glu Glu Asp Phe Ala Thr Gln Arg Ile Asp Gly Leu Ser Gln Trp
                165                 170                 175

Val Asp Asp Tyr Pro Val Met Leu Ile Asn Ala Asn Ala Ala Pro Asp
            180                 185                 190

Arg Lys Arg Leu Thr Leu Ala His Glu Leu Gly His Leu Val Leu His
        195                 200                 205

Ser Thr Asn Pro Thr Glu Asn Met Glu Thr Glu Ala Thr Ala Phe Ala
    210                 215                 220

Ala Glu Phe Leu Met Pro Glu Ser Glu Ile Arg Pro Glu Leu Arg Arg
225                 230                 235                 240

Leu Asp Leu Gly Lys Leu Leu Glu Leu Lys Arg Glu Trp Gly Val Ser
                245                 250                 255

Met Gln Ala Leu Leu Ala Arg Ala Tyr Arg Met Gly Leu Val Ser Ala
            260                 265                 270

Glu Ala Arg Thr Lys Leu Tyr Lys Ala Met Asn Ala Arg Gly Trp Lys
        275                 280                 285

Thr Lys Glu Pro Gly Ile Glu Ser Ile Val Arg Glu Lys Pro Ser Leu
    290                 295                 300

Pro Ala His Ile Gly Met Thr Leu Arg Ser Arg Gly Phe Thr Asp Gln
305                 310                 315                 320

Gln Ala Ala Ala Ile Ala Gly Tyr Ala Asn Pro Ala Asp Asn Pro Phe
                325                 330                 335

Arg Pro Glu Gly Gly Arg Leu His Ala Ile
            340                 345
```

-continued

<210> SEQ ID NO 80
<211> LENGTH: 1038
<212> TYPE: DNA
<213> ORGANISM: Mycobacterium tuberculosis

<400> SEQUENCE: 80
atgaacggcc tgggagacgt gctcgcggtc gcccggaagg ctcgtggact cacccagatc 60
gaattggccg agctggtggg actcacccag ccggcgatca accggtacga atcaggcgac 120
cgtgaccccg accaacacat cgtggccaag ctggccgaaa tcctcggtgt gaccgacgat 180
ctgctcatac acgggaacag gtttcgaggt gcgctcgcag tcgatgcgca tatgcgccgc 240
cacaagacca cgaaggcgtc ggcctggcgt cagctggagg cccggttgaa cctgttgcgc 300
gtgcacgcgt cattcctctt cgaggaagtg gctatcaata gcgagcaaca tgtgcccgcg 360
ttcgacccgg agttcaccgc cgccgaggac gccgcccggt tagtccgtgc ccagtggcgc 420
atgccgatgg gcccggtcgt caacctgacc cggtggatgg aggccgcggg ctgcctggtg 480
ttcgaagagg acttcgccac ccagcgcatc gacgggttgt cgcagtgggt cgacgactac 540
cccgtcatgc tgatcaacgc caacgcagca cccgaccgaa aacgcttgac ccttgcccac 600
gaactcggcc acctcgtgct gcattccacc aaccccacgg agaacatgga gaccgaagcc 660
accgccttcg ccgccgagtt tctcatgccc gagagcgaga ttcggcccga gctgcgtcgg 720
ctcgatctcg gcaagttgct cgaactgaaa cgggaatggg gcgtctcgat gcaagccctc 780
ctggcgcggg catatcgcat gggcctggta tcggccgagg ctcgcaccaa gctctacaag 840
gcgatgaacg cgcgcggctg gaaaaccaaa gagccaggca tcgagtccat cgtgcgagaa 900
aaaccgagcc tacccgccca catcggcatg acactccgaa gccgcggatt caccgaccag 960
caagccgccg ccatcgccgg atacgccaat cctgcggaca atccattccg ccccgaaggt 1020
ggccgcctcc atgcgatt 1038

<210> SEQ ID NO 81
<211> LENGTH: 139
<212> TYPE: PRT
<213> ORGANISM: Mycobacterium tuberculosis

<400> SEQUENCE: 81

Met Ile Val Asp Thr Ser Ala Val Val Ala Leu Val Gln Gly Glu Arg
1 5 10 15

Pro His Ala Thr Leu Val Ala Ala Ala Leu Ala Gly Ala His Ser Pro
20 25 30

Val Met Ser Ala Pro Thr Val Ala Glu Cys Leu Ile Val Leu Thr Ala
35 40 45

Arg His Gly Pro Val Ala Arg Thr Ile Phe Glu Arg Leu Arg Ser Glu
50 55 60

Ile Gly Leu Ser Val Ser Ser Phe Thr Ala Glu His Ala Ala Ala Thr
65 70 75 80

Gln Arg Ala Phe Leu Arg Tyr Gly Lys Gly Arg His Arg Ala Ala Leu
85 90 95

Asn Phe Gly Asp Cys Met Thr Tyr Ala Thr Ala Gln Leu Gly His Gln
100 105 110

Pro Leu Leu Ala Val Gly Asn Asp Phe Pro Gln Thr Asp Leu Glu Phe
115 120 125

Arg Gly Val Val Gly Tyr Trp Pro Gly Val Ala
130 135

<210> SEQ ID NO 82
<211> LENGTH: 417
<212> TYPE: DNA
<213> ORGANISM: Mycobacterium tuberculosis

<400> SEQUENCE: 82

```
atgatcgtgg acacaagcgc cgtggtggcc ctggttcaag gcgagcggcc gcacgccacc     60

ctggtcgcgg ccgccctggc cggcgcccat agccccgtca tgtctgcacc caccgtcgcc    120

gaatgcctga ttgtcttgac cgcccgtcac ggccccgttg cgcgcacgat cttcgaacga    180

cttcgcagcg aaatcggctt gagcgtgtca tctttcaccg ccgagcatgc cgctgccacg    240

caacgagcct ttctgcgata cggcaagggg cgccaccgcg cggctctcaa cttcggagac    300

tgtatgacgt acgcgaccgc ccagctgggc caccaaccac tgctggccgt cggcaacgac    360

ttcccgcaaa ccgaccttga gttccgcggc gtcgtcggct actggccagg cgtcgcg       417
```

<210> SEQ ID NO 83
<211> LENGTH: 376
<212> TYPE: PRT
<213> ORGANISM: Mycobacterium tuberculosis

<400> SEQUENCE: 83

```
Leu Ile Cys Phe Asp Asp Val Ser Lys Val Tyr Ala His Gly Ala Thr
1               5                   10                  15

Ala Val Asp Arg Leu Thr Leu Glu Val Pro Asn Gly Met Leu Thr Val
            20                  25                  30

Phe Val Gly Pro Ser Gly Cys Gly Lys Thr Thr Ala Leu Arg Met Ile
        35                  40                  45

Asn Arg Met Val Asp Pro Thr Ser Gly Thr Ile Thr Val Asp Gly Thr
    50                  55                  60

Asp Val Ser Thr Val Asn Ala Val Lys Leu Arg Leu Gly Ile Gly Tyr
65                  70                  75                  80

Val Ile Gln Asn Ala Gly Leu Met Pro His Gln Arg Val Ile Asp Asn
                85                  90                  95

Val Ala Thr Val Pro Val Leu Lys Gly Gln Pro Arg Arg Ala Ala Arg
            100                 105                 110

Lys Ala Gly Tyr Glu Val Leu Glu Arg Val Gly Leu Asp Pro Lys Val
        115                 120                 125

Ala Thr Arg Tyr Pro Ala Gln Leu Ser Gly Gly Glu Gln Gln Arg Val
    130                 135                 140

Gly Val Ala Arg Ala Leu Ala Ala Asp Pro Pro Ile Leu Leu Met Asp
145                 150                 155                 160

Glu Pro Phe Ser Ala Val Asp Pro Val Val Arg His Glu Leu Gln Asn
                165                 170                 175

Glu Ile Leu Arg Leu Gln Ala Glu Leu His Lys Thr Ile Val Phe Val
            180                 185                 190

Thr His Asp Ile Asp Glu Ala Leu Lys Leu Ala Asp Leu Val Ala Val
        195                 200                 205

Phe Ala Pro Gly Gly Ala Leu Ala Gln Tyr Asp Glu Thr Ala Arg Leu
    210                 215                 220

Leu Ser Ser Pro Ala Asn Asp Phe Val Ser Lys Phe Ile Gly Leu Gly
225                 230                 235                 240

Arg Gly Tyr Arg Trp Leu Gln Leu Phe Asp Ala Ala Gly Leu Pro Val
                245                 250                 255

Arg Asp Ile Glu Gln Val Ser Val Asn Gly Leu Ser Asp Ala Arg Asp
            260                 265                 270
```

-continued

```
Arg Gln Val Arg Asp Gly Trp Val Leu Val Val Asp Gly Ala Gly Ala
        275                 280                 285

Pro Leu Gly Trp Ile Asp Ala Asp Gly Arg Arg Arg His Arg Gly Gly
    290                 295                 300

Ala Ala Leu Ser Asp Ala Met Thr Val Gly Gly Ser Val Phe Arg Pro
305                 310                 315                 320

Asn Gly Asn Leu Ser Gln Ala Leu Asp Ala Ala Leu Ser Ser Pro Ser
                325                 330                 335

Gly Val Gly Val Ala Val Asp Gly Gly Gly Lys Val Ile Gly Gly Ile
            340                 345                 350

Leu Ala Ala Asp Val Leu Ala Glu Phe Gln Lys Gly Lys Lys Ala Gly
        355                 360                 365

Gly Gly Ala Lys Pro Cys Thr Thr
    370                 375
```

<210> SEQ ID NO 84
<211> LENGTH: 1128
<212> TYPE: DNA
<213> ORGANISM: Mycobacterium tuberculosis

<400> SEQUENCE: 84

```
ttgatctgct ttgacgatgt cagcaaggtg tacgcacacg gtgccaccgc cgtagaccgg      60

ctgacgctgg aagtccctaa cggcatgctg accgtcttcg tcggcccctc cggctgcggc     120

aagacgacgg cgctgcgaat gatcaaccga atggtggatc cgacctcggg caccatcact     180

gtcgacggta ccgacgtgtc gacggtcaat gcggtgaagc tgcgcctggg aattggctat     240

gtcatccaga acgcggggct gatgcctcat caacgggtca tcgacaacgt cgcaacggtg     300

ccggtgctga agggtcagcc gcgccgggca gcccgcaaag ccggttatga ggtgcttgag     360

cgtgtcgggc tggaccccaa ggtcgccacc cgctacccgg cccagctctc gggcggcgaa     420

cagcaacggg tcggcgtggc acgggcactc gcggccgatc cgccgatctt gttgatggac     480

gagccgttct cggccgtcga cccggtggtt cgccacgagc tacagaacga aatacttcgt     540

ctgcaagccg agttgcacaa gaccattgtc ttcgtgacgc acgacatcga cgaggcgttg     600

aagctcgccg atctggtggc ggtgttcgcc ccgggcggcg cgcttgcgca gtacgacgaa     660

actgcccggc tgttatccag tccggcgaat gacttcgtgt cgaagttcat cggtctcggt     720

cgcggctatc ggtggctgca gctgttcgac gcggccggac tacctgtgcg cgacatcgag     780

caagtctcgg tgaacggcct ttccgatgcc cgggacaggc aagttcgtga cggctgggtg     840

ctggtggtcg acggtgcggg tgcgccgttg ggctggatcg acgccgatgg ccggcggcgt     900

caccgcggcg gcgcggcatt gtcggatgcc atgaccgtcg gcggttcggt gttccgcccg     960

aacggtaacc tcagccaggc gctggacgcc gccttgtcct cgccgtcggg ggtcggtgtc    1020

gccgttgacg gcggtggcaa ggtcatcggc gggatactgg ccgccgacgt gctggccgag    1080

ttccaaaaag gcaagaaggc cggcggcgga gctaagccat gcactacc                 1128
```

<210> SEQ ID NO 85
<211> LENGTH: 145
<212> TYPE: PRT
<213> ORGANISM: Mycobacterium tuberculosis

<400> SEQUENCE: 85

```
Val Ser Glu Thr Phe Asp Val Asp Val Leu Val His Ala Thr His Arg
1               5                   10                  15

Ala Ser Pro Phe His Asp Lys Ala Lys Thr Leu Val Glu Arg Phe Leu
            20                  25                  30
```

```
Ala Gly Pro Gly Leu Val Tyr Leu Leu Trp Pro Val Ala Leu Gly Tyr
        35                  40                  45

Leu Arg Val Val Thr His Pro Thr Leu Leu Gly Ala Pro Leu Ala Pro
    50                  55                  60

Glu Val Ala Val Glu Asn Ile Glu Gln Phe Thr Ser Arg Pro His Val
65                  70                  75                  80

Arg Gln Val Gly Glu Ala Asn Gly Phe Trp Pro Val Tyr Arg Arg Val
                85                  90                  95

Ala Asp Pro Val Lys Pro Arg Gly Asn Leu Val Pro Asp Ala His Leu
            100                 105                 110

Val Ala Leu Met Arg His His Gly Ile Ala Thr Ile Trp Ser His Asp
        115                 120                 125

Arg Asp Phe Arg Lys Phe Glu Gly Ile Arg Ile Arg Asp Pro Phe Ser
    130                 135                 140

Gly
145


<210> SEQ ID NO 86
<211> LENGTH: 435
<212> TYPE: DNA
<213> ORGANISM: Mycobacterium tuberculosis

<400> SEQUENCE: 86

gtgagcgaaa cctttgacgt cgatgttctg gtccatgcga cgcaccgagc cagcccgttt      60

cacgataagg cgaagacgct cgttgagcga ttcctggctg ggccagggct ggtatatcta     120

ttgtggcccg tcgcgctggg ttatctacgg gttgtcaccc atccgacgtt gttgggtgcg     180

ccgctggcgc ctgaggtcgc cgtcgaaaac atcgagcaat tcacctcacg accgcacgtg     240

cggcaggtcg gcgaggccaa cggattctgg cccgtctatc ggcgagtagc cgacccggtc     300

aagccgcgag gcaatctggt tcccgacgcc cacctcgtcg cgctcatgcg ccatcacggc     360

atcgccacga tctggagtca cgaccgcgac ttccgcaagt tcgagggcat tagaattcgc     420

gaccccttct ccggc                                                       435


<210> SEQ ID NO 87
<211> LENGTH: 185
<212> TYPE: PRT
<213> ORGANISM: Mycobacterium tuberculosis

<400> SEQUENCE: 87

Met Ser Arg Gln Trp His Trp Leu Ala Ala Thr Leu Leu Leu Ile Thr
1               5                   10                  15

Thr Ala Ala Cys Ser Arg Pro Gly Thr Glu Glu Pro Asp Cys Pro Thr
            20                  25                  30

Lys Ile Thr Leu Pro Pro Gly Ala Thr Pro Thr Thr Thr Leu Asp Pro
        35                  40                  45

Arg Cys Ile Val Arg Ala Thr Thr Thr Gly Thr Ala Asp Gly Asp Ala
    50                  55                  60

Ala Ser Arg Trp Thr Gly Thr Val Arg Ile Ala Gly Phe Tyr Ala Ser
65                  70                  75                  80

Ile Cys Asn Ala Val Trp Asp Gly Asn Val Ser Leu Ala Gly Lys Asp
                85                  90                  95

Glu Leu Thr Gly Lys Ala Thr Leu Ile Leu Val Glu Thr Ser Cys Pro
            100                 105                 110

Gly Lys Val Val Ala Gly Glu Leu Val Leu Lys Gly Asn Val Gly Ser
        115                 120                 125
```

Asp Ser Leu Ala Ile Thr Trp Ala His Pro Glu Leu Pro Gln Arg Ala
130 135 140

Phe Asp Leu Gly Ala Gly Gln Gly Thr Ile Arg Arg Ser Gly Asp Arg
145 150 155 160

Ala Glu Gly Thr Phe Asn Ser Asp Met Gly Gly Gly Thr Glu Phe Phe
165 170 175

Leu Thr Trp Ser Leu Thr Met Arg Asn
180 185

<210> SEQ ID NO 88
<211> LENGTH: 555
<212> TYPE: DNA
<213> ORGANISM: Mycobacterium tuberculosis

<400> SEQUENCE: 88
atgagtcgac agtggcactg gctggcagcg acgctgctcc tgatcaccac cgccgcgtgc 60
agtcgtccgg gcaccgagga accggattgc ccgacgaaaa taaccttgcc gcccggtgct 120
acgcccacca cgaccctcga cccgagatgc atagtgcgcg cgaccaccac cggcacagcc 180
gacggcgatg cggcgtcgcg ctggaccgga accgtgcgga tcgccgggtt ctatgcctcg 240
atctgcaacg cggtatggga cgggaacgtc agccttgcgg gaaaggacga gctgaccggc 300
aaggctacgc ttatcctcgt cgaaaccagt tgcccgggca aggttgtcgc cggcgaactc 360
gtgctgaagg ggaacgtcgg ttcggacagc ctcgcgatca cctgggcgca ccccgaactc 420
ccgcagcggg cgttcgacct cggcgccgga cagggcacga tccgccgatc gggcgaccgt 480
gccgagggaa cgttcaactc ggatatgggt gggggcaccg agttcttctt gacgtggtcg 540
ctgacgatgc gtaac 555

<210> SEQ ID NO 89
<211> LENGTH: 219
<212> TYPE: PRT
<213> ORGANISM: Mycobacterium tuberculosis

<400> SEQUENCE: 89

Met Ala Val His Gly Phe Leu Leu Glu Arg Val Ser Val Val Arg Asp
1 5 10 15

Glu Ala Thr Val Leu Arg Gln Val Ser Ala His Phe Pro Ala Gly Arg
20 25 30

Cys Ser Ala Val Arg Gly Ala Ser Gly Ser Gly Lys Thr Thr Leu Leu
35 40 45

Arg Leu Leu Asn Arg Leu Ile Asp Pro Thr Ser Gly Lys Val Trp Leu
50 55 60

Asp Gly Val Pro Leu Thr Asp Leu Asp Val Leu Val Leu Arg Arg Arg
65 70 75 80

Val Gly Leu Val Ala Gln Ala Pro Val Val Leu Thr Asp Ala Val Leu
85 90 95

Asn Glu Val Arg Val Gly Arg Pro Asp Leu Pro Glu Gly Arg Val Thr
100 105 110

Glu Leu Leu Ala Arg Leu Cys Leu Gly Gln Ser Ala Arg Glu Ala Phe
115 120 125

Leu Pro His Gln Arg Ser Ala Leu Arg Thr Ala Leu Ile Pro Ala Ile
130 135 140

Asp Ser Thr Lys Val Val Gly Leu Ile Ser Leu Pro Gly Ala Met Ser
145 150 155 160

Gly Leu Ile Leu Ala Gly Val Asp Pro Leu Thr Ala Ile Arg Tyr Gln

-continued 165 170 175

Ile Val Val Met Tyr Leu Leu Leu Ala Ala Thr Ala Val Ala Ala Leu
180 185 190

Thr Cys Ala Arg Leu Ala Glu Arg Ala Leu Phe Asp Arg Ala His Arg
195 200 205

Leu Val Ser Leu Pro Ala Ala Thr Arg Arg Ala
210 215

<210> SEQ ID NO 90
<211> LENGTH: 657
<212> TYPE: DNA
<213> ORGANISM: Mycobacterium tuberculosis

<400> SEQUENCE: 90
atggcggtgc atggtttcct gctcgaacgg gtcagcgtgg tgcgcgacga ggcgacggtg 60
ctgcggcagg tcagcgcgca ttttcccgct ggccgctgca gtgcggtgcg gggcgccagt 120
ggatcgggaa agaccacgct gctgcggttg ctgaaccggc tcatcgatcc gacgtccgga 180
aaagtctggc ttgacggtgt gccgctcacc gatctggatg tgctcgtgtt acgtcggcgg 240
gtcggcctgg ttgcgcaggc tcccgtggtg cttaccgatg cggtgctcaa tgaggttcgc 300
gtcggacgcc cggacctgcc agaaggtcga gtgaccgagc tgctggcgcg gctgtgtctc 360
ggccagtccg cacgcgaagc gttcttgccg caccaacgat ccgccttgcg cactgcgctg 420
atacccgcga tcgactccac gaaagtcgtt gggctgatta gccttccggg tgcgatgtcc 480
ggacttatcc tggccggggt cgacccgctg accgcgatcc gctaccaaat cgtggtgatg 540
tacctgctgc tcgccgccac cgcggtggca gcgctgacct gtgcacgcct ggctgaacgt 600
gccttattcg accgcgcgca ccggctcgtt tcgctgcccg cggcgactcg tcgggca 657

<210> SEQ ID NO 91
<211> LENGTH: 358
<212> TYPE: PRT
<213> ORGANISM: Mycobacterium tuberculosis

<400> SEQUENCE: 91

Val Arg Ala Arg Phe Gly Asp Arg Ala Pro Trp Leu Val Glu Thr Thr
1 5 10 15

Leu Leu Arg Arg Arg Ala Ala Gly Lys Leu Gly Glu Leu Cys Pro Asn
20 25 30

Val Gly Val Ser Gln Trp Leu Phe Thr Asp Glu Ala Leu Gln Gln Ala
35 40 45

Thr Ala Ala Pro Val Ala Arg His Arg Ala Arg Arg Leu Ala Gly Arg
50 55 60

Val Val His Asp Ala Thr Cys Ser Ile Gly Thr Glu Leu Ala Ala Leu
65 70 75 80

Arg Glu Leu Ala Val Arg Ala Val Gly Ser Asp Ile Asp Pro Val Arg
85 90 95

Leu Ala Met Ala Arg His Asn Leu Ala Ala Leu Gly Met Glu Ala Asp
100 105 110

Leu Cys Arg Ala Asp Val Leu His Pro Val Thr Arg Asp Ala Val Val
115 120 125

Val Ile Asp Pro Ala Arg Arg Ser Asn Gly Arg Arg Arg Phe His Leu
130 135 140

Ala Asp Tyr Gln Pro Gly Leu Gly Pro Leu Leu Asp Arg Tyr Arg Gly
145 150 155 160

Arg Asp Val Val Val Lys Cys Ala Pro Gly Ile Asp Phe Glu Glu Val

-continued

```
                165                 170                 175

Gly Arg Leu Gly Phe Glu Gly Glu Ile Glu Val Ile Ser Tyr Arg Gly
            180                 185                 190

Gly Val Arg Glu Ala Cys Leu Trp Ser Ala Gly Leu Ala Gly Ser Gly
        195                 200                 205

Ile Arg Arg Arg Ala Ser Ile Leu Asp Ser Gly Glu Gln Ile Gly Asp
    210                 215                 220

Asp Glu Pro Asp Asp Cys Gly Val Arg Pro Ala Gly Lys Trp Ile Val
225                 230                 235                 240

Asp Pro Asp Gly Ala Val Val Arg Ala Gly Leu Val Arg Asn Tyr Gly
                245                 250                 255

Ala Arg His Gly Leu Trp Gln Leu Asp Pro Gln Ile Ala Tyr Leu Ser
            260                 265                 270

Gly Asp Arg Leu Pro Pro Ala Leu Arg Gly Phe Glu Val Leu Glu Gln
        275                 280                 285

Leu Ala Phe Asp Glu Arg Arg Leu Arg Gln Val Leu Ser Ala Leu Asp
    290                 295                 300

Cys Gly Ala Ala Glu Ile Leu Val Arg Gly Val Ala Ile Asp Pro Asp
305                 310                 315                 320

Ala Leu Arg Arg Arg Leu Arg Leu Arg Gly Ser Arg Pro Leu Ala Val
                325                 330                 335

Val Ile Thr Arg Ile Gly Ala Gly Ser Leu Ser His Val Thr Ala Tyr
            340                 345                 350

Val Cys Arg Pro Ser Arg
        355


<210> SEQ ID NO 92
<211> LENGTH: 1074
<212> TYPE: DNA
<213> ORGANISM: Mycobacterium tuberculosis

<400> SEQUENCE: 92

gtgcgcgccc ggtttggcga tcgggcgccg tggctggtgg agaccacgct gctgcgccgc     60

cgcgccgccg gcaaactggg cgagctgtgt ccgaacgttg gggtgtcgca atggctattc    120

accgatgagg cgctgcagca ggctaccgca gcacccgtgg cccggcaccg ggccaggcga    180

ctggccggtc gggtagtgca cgacgcgacc tgctccatcg gcaccgagct ggccgcgctg    240

cgcgagctag ctgtccgggc ggtcggcagc gatatcgacc cggtgcggct ggccatggcg    300

cgccacaacc tggccgccct gggaatggaa gctgacctgt gccgcgccga tgtgctgcat    360

ccggtgaccc gcgacgcggt cgtcgtcatc gacccggcgc gtcgcagcaa cgggcggcga    420

cgcttccacc tcgccgacta ccagcccggc ctgggccccc tactggaccg ctaccgcggc    480

cgtgatgtgg tcgtcaagtg cgctcccgga atagatttcg aggaggtggg ccggctcggt    540

ttcgagggcg agatcgaggt gatctcatac cgcggtgggg ttcgagaagc atgtctttgg    600

tcggccgggt tggccggatc gggtatccgc cgtcgagcca gcatcctcga ttccggtgaa    660

caaatcggtg acgacgagcc cgacgactgc ggtgtgcggc ccgccgggaa atggatcgtc    720

gaccccgacg gcgccgtcgt ccgtgccggc ctggtacgca actacggcgc ccggcatggg    780

ctgtggcagc tcgatcccca aatcgcttac ctgtccggtg accggctgcc gcctgcgttg    840

cgcgggttcg aggtgctcga gcagctggcc ttcgacgagc gtcggctgcg tcaggtgctg    900

tcagcgctgg attgcggggc agccgaaatc ctggtgcgcg gcgttgcgat cgatcccgac    960

gctctgcggc gacggctccg gctgcggggc agcagaccgc tggcggtggt catcacccgc   1020
```

attggtgccg ggtccttgag ccatgtgacc gcctatgtgt gtcggccgtc ccgg 1074

<210> SEQ ID NO 93
<211> LENGTH: 471
<212> TYPE: PRT
<213> ORGANISM: Mycobacterium tuberculosis

<400> SEQUENCE: 93

Val Thr Glu Thr Ala Ser Glu Thr Gly Ser Trp Arg Glu Leu Leu Ser
1 5 10 15

Arg Tyr Leu Gly Thr Ser Ile Val Leu Ala Gly Gly Val Ala Leu Tyr
20 25 30

Ala Thr Asn Glu Phe Leu Thr Ile Ser Leu Leu Pro Ser Thr Ile Ala
35 40 45

Asp Ile Gly Gly Ser Arg Leu Tyr Ala Trp Val Thr Thr Leu Tyr Leu
50 55 60

Val Gly Ser Val Val Ala Ala Thr Thr Val Asn Thr Met Leu Leu Arg
65 70 75 80

Val Gly Ala Arg Ser Ser Tyr Leu Met Gly Leu Ala Val Phe Gly Leu
85 90 95

Ala Ser Leu Val Cys Ala Ala Ala Pro Ser Met Gln Ile Leu Val Ala
100 105 110

Gly Arg Thr Leu Gln Gly Ile Ala Gly Gly Leu Leu Ala Gly Leu Gly
115 120 125

Tyr Ala Leu Ile Asn Ser Thr Leu Pro Lys Ser Leu Trp Thr Arg Gly
130 135 140

Ser Ala Leu Val Ser Ala Met Trp Gly Val Ala Thr Leu Ile Gly Pro
145 150 155 160

Ala Thr Gly Gly Leu Phe Ala Gln Leu Gly Leu Trp Arg Trp Ala Phe
165 170 175

Gly Val Met Thr Leu Leu Thr Ala Leu Met Ala Met Leu Val Pro Val
180 185 190

Ala Leu Gly Ala Gly Gly Val Gly Pro Gly Gly Glu Thr Pro Val Gly
195 200 205

Ser Thr His Lys Val Pro Val Trp Ser Leu Leu Leu Met Gly Ala Ala
210 215 220

Ala Leu Ala Ile Ser Val Ala Ala Leu Pro Asn Tyr Leu Val Gln Thr
225 230 235 240

Ala Gly Leu Leu Ala Ala Ala Ala Leu Leu Val Ala Val Phe Val Val
245 250 255

Val Asp Trp Arg Ile His Ala Ala Val Leu Pro Pro Ser Val Phe Gly
260 265 270

Ser Gly Pro Leu Lys Trp Ile Tyr Leu Thr Met Ser Val Gln Met Ile
275 280 285

Ala Ala Met Val Asp Thr Tyr Val Pro Leu Phe Gly Gln Arg Leu Gly
290 295 300

His Leu Thr Pro Val Ala Ala Gly Phe Leu Gly Ala Ala Leu Ala Val
305 310 315 320

Gly Trp Thr Val Gly Glu Val Ala Ser Ala Ser Leu Asn Ser Ala Arg
325 330 335

Val Ile Gly His Val Val Ala Ala Ala Pro Leu Val Met Ala Ser Gly
340 345 350

Leu Ala Leu Gly Ala Val Thr Gln Arg Ala Asp Ala Pro Val Gly Ile
355 360 365

Ile Ala Leu Trp Ala Leu Ala Leu Leu Ile Ile Gly Thr Gly Ile Gly

```
    370                 375                 380

Ile Ala Trp Pro His Leu Thr Val Arg Ala Met Asp Ser Val Ala Asp
385                 390                 395                 400

Pro Ala Glu Ser Ser Ala Ala Ala Ala Ala Ile Asn Val Val Gln Leu
                405                 410                 415

Ile Ser Gly Ala Phe Gly Ala Gly Leu Ala Gly Val Val Val Asn Thr
            420                 425                 430

Ala Lys Gly Gly Glu Val Ala Ala Ala Arg Gly Leu Tyr Met Ala Phe
        435                 440                 445

Thr Val Leu Ala Ala Ala Gly Val Ile Ala Ser Tyr Gln Ala Thr His
    450                 455                 460

Arg Asp Arg Arg Leu Pro Arg
465                 470


<210> SEQ ID NO 94
<211> LENGTH: 1413
<212> TYPE: DNA
<213> ORGANISM: Mycobacterium tuberculosis

<400> SEQUENCE: 94

gtgaccgaaa cagcgagcga gaccggcagc tggcgtgagc tactgagcag gtatctgggc      60

acctccatag tgctggccgg tggcgtcgcg ctttacgcca ccaacgagtt tctgacaatc     120

agcctgctgc cgagcacaat cgccgacatc gggggtagcc ggctgtacgc ctgggtgaca     180

accctgtatc tggtcgggtc ggtggtggcg gcgaccaccg tcaatacgat gttgctgcgc     240

gtcggggcgc gctcgtcgta tctgatgggg ttggccgtct tcggtctggc cagcctggta     300

tgtgcggcgg cgccgagcat gcagattctg gtggccgggc gtaccttgca aggaatagcc     360

ggtgggctgc tggccggcct aggctacgcg ctgatcaact cgaccttgcc caagtcgctg     420

tggacccgtg gctcagcact ggtgtcggcg atgtgggggg tcgcgacgct gatcggaccg     480

gcgaccggag gccttttcgc gcagctcggg ctgtggcgat gggcgttcgg cgtgatgacg     540

ttgctgaccg cgttgatggc catgttggtg ccggtcgcgc tcggtgccgg gggggtcggc     600

ccgggcggcg agacgccggt gggcagcaca cacaaggtgc cggtgtggtc gctattgctg     660

atgggggccg ccgcactggc gatcagcgtc gccgcgcttc cgaactacct cgtccagacg     720

gccgggctgc tagccgccgc cgcgctgctg gttgcggtgt ttgtggtagt cgactggcgg     780

atacacgcag cggtgttgcc gcccagcgta tttggctccg gaccgttgaa atggatttac     840

ctgaccatgt cggtgcagat gattgcggca atggtcgata cctacgtgcc gctgttcggt     900

cagcgactgg gacacctgac cccggtggca gccgggttct tgggtgccgc gctggcggtg     960

ggctggacgg tcggtgaggt cgccagcgcc tcgttgaaca gtgcacgagt tatcggccat    1020

gtcgtggcag ccgcaccgct ggtgatggcg tcggggttgg cgctaggcgc cgtcacccag    1080

cgcgccgatg cgccggtggg gatcatcgcg ctgtgggcgc tggcgctgct gatcatcggg    1140

accggcatcg ggatcgcctg gccgcatcta acggtgcgcg ctatggattc tgtcgccgac    1200

ccggccgaga gcagcgcggc ggccgcggcg atcaatgtcg tacagctgat ctccggtgct    1260

ttcggcgccg ggctggccgg tgtggtggtc aacactgcca agggcggcga agtggcggcg    1320

gctcgtgggc tatacatggc atttacggtg ctggccgccg ctggtgtcat cgcctcctac    1380

caggccacgc accgcgaccg gcgcttaccg cgt                                 1413


<210> SEQ ID NO 95
<211> LENGTH: 325
<212> TYPE: PRT
```

<213> ORGANISM: Mycobacterium tuberculosis

<400> SEQUENCE: 95

```
Met Thr Ser Ala Pro Ala Thr Met Arg Trp Gly Asn Leu Pro Leu Ala
1               5                   10                  15

Gly Glu Ser Gly Thr Met Thr Leu Arg Gln Ala Ile Asp Leu Ala Ala
            20                  25                  30

Ala Leu Leu Ala Glu Ala Gly Val Asp Ser Ala Arg Cys Asp Ala Glu
        35                  40                  45

Gln Leu Ala Ala His Leu Ala Gly Thr Asp Arg Gly Arg Leu Pro Leu
    50                  55                  60

Phe Glu Pro Pro Gly Asp Glu Phe Phe Gly Arg Tyr Arg Asp Ile Val
65                  70                  75                  80

Thr Ala Arg Ala Arg Arg Val Pro Leu Gln His Leu Ile Gly Thr Val
                85                  90                  95

Ser Phe Gly Pro Val Val Leu His Val Gly Pro Gly Val Phe Val Pro
            100                 105                 110

Arg Pro Glu Thr Glu Ala Ile Leu Ala Trp Ala Thr Ala Gln Ser Leu
        115                 120                 125

Pro Ala Arg Pro Leu Ile Val Asp Ala Cys Thr Gly Ser Gly Ala Leu
    130                 135                 140

Ala Val Ala Leu Ala Gln His Arg Ala Asn Leu Gly Leu Lys Ala Arg
145                 150                 155                 160

Ile Ile Gly Ile Asp Asp Ser Asp Cys Ala Leu Asp Tyr Ala Arg Arg
                165                 170                 175

Asn Ala Ala Gly Thr Pro Val Glu Leu Val Arg Ala Asp Val Thr Thr
            180                 185                 190

Pro Arg Leu Leu Pro Glu Leu Asp Gly Gln Val Asp Leu Met Val Ser
        195                 200                 205

Asn Pro Pro Tyr Ile Pro Asp Ala Ala Val Leu Glu Pro Glu Val Ala
    210                 215                 220

Gln His Asp Pro His His Ala Leu Phe Gly Gly Pro Asp Gly Met Thr
225                 230                 235                 240

Val Ile Ser Ala Val Val Gly Leu Ala Gly Arg Trp Leu Arg Pro Gly
                245                 250                 255

Gly Leu Phe Ala Val Glu His Asp Asp Thr Thr Ser Ser Ser Thr Val
            260                 265                 270

Asp Leu Val Ser Ser Thr Lys Leu Phe Val Asp Val Gln Ala Arg Lys
        275                 280                 285

Asp Leu Ala Gly Arg Pro Arg Phe Val Thr Ala Met Arg Trp Gly His
    290                 295                 300

Leu Pro Leu Ala Gly Glu Asn Gly Ala Ile Asp Pro Arg Gln Arg Arg
305                 310                 315                 320

Cys Arg Ala Lys Arg
                325
```

<210> SEQ ID NO 96
<211> LENGTH: 975
<212> TYPE: DNA
<213> ORGANISM: Mycobacterium tuberculosis

<400> SEQUENCE: 96

```
atgacctccg cgccggcgac gatgcggtgg gggaacctcc cgcttgcggg ggagagcggc      60

acaatgaccc tgcgtcaggc gatcgacttg gctgctgcgc tattggccga agcgggggtc     120

gactcggcgc gttgcgacgc tgagcagttg gccgctcacc tagcgggcac agaccgcggt     180
```

```
aggctacccc tgttcgagcc gcccggcgac gagttcttcg ggcgctatcg cgacatcgtc    240

accgctcgtg cgcggcgggt gccgttgcag catctcatcg ggactgtgtc gtttgggccc    300

gtggtgctgc atgtcggccc gggtgtgttt gtaccgcgtc cggagaccga agccattttg    360

gcctgggcca ccgcgcagtc gctgccggcg cggccgctga ttgtcgacgc atgcacggga    420

tctggcgcgt tggcggtcgc attggcccag caccgggcca accttggact aaaggcccgc    480

atcatcggca ttgacgactc cgactgcgcc cttgactatg cccgccgcaa tgcggcgggt    540

accccggtag agttggtgcg tgccgacgtc accacgcccc gcctgctccc cgaactcgac    600

ggacaagtcg acctgatggt ttccaacccg ccctacatcc ctgatgctgc tgttttggaa    660

cctgaagtag cgcaacatga cccgcatcac gcgttgttcg gcggtcccga cgggatgacg    720

gtgatatccg cggtcgtcgg gcttgctggg cgctggctgc gtcccggtgg cctgttcgcc    780

gtcgaacacg acgacaccac gtcgtcgtca actgtcgatt tggtcagcag cacaaaactt    840

ttcgtggacg tacaagcccg gaaagatctg gccggacggc cgaggtttgt gacggcgatg    900

aggtgggggc acctcccgct tgcaggggag aacggcgcca ttgacccgcg ccagcgacga    960

tgcagagcga agcga                                                      975
```

<210> SEQ ID NO 97
<211> LENGTH: 163
<212> TYPE: PRT
<213> ORGANISM: Mycobacterium tuberculosis

<400> SEQUENCE: 97

```
Met Ser Pro Ser Pro Ala Ala Ala Asn Arg Ser Glu Val Gly Gly Pro
1               5                   10                  15

Leu Pro Gly Leu Gly Ala Asp Leu Leu Ala Val Val Ala Arg Leu Asn
            20                  25                  30

Arg Leu Ala Thr Gln Arg Ile Gln Met Pro Leu Pro Ala Ala Gln Ala
        35                  40                  45

Arg Leu Leu Ala Thr Ile Glu Ala Gln Gly Glu Ala Arg Ile Gly Asp
    50                  55                  60

Leu Ala Ala Val Asp His Cys Ser Gln Pro Thr Met Thr Thr Gln Val
65                  70                  75                  80

Arg Arg Leu Glu Asp Ala Gly Leu Val Thr Arg Thr Ala Asp Pro Gly
                85                  90                  95

Asp Ala Arg Ala Val Arg Ile Arg Ile Thr Pro Glu Gly Ile Arg Thr
            100                 105                 110

Leu Thr Ala Val Arg Ala Asp Arg Ala Ala Ala Ile Glu Pro Gln Leu
        115                 120                 125

Ala Leu Leu Pro Pro Ala Asp Arg Arg Val Leu Ala Asp Ala Val Asp
    130                 135                 140

Val Leu Arg Arg Leu Leu Asp His Ala Ala Thr Thr Pro Gly Arg Ala
145                 150                 155                 160

Thr Arg Gln
```

<210> SEQ ID NO 98
<211> LENGTH: 489
<212> TYPE: DNA
<213> ORGANISM: Mycobacterium tuberculosis

<400> SEQUENCE: 98

```
atgagtccct cccccgccgc cgccaaccgc agcgaggtcg gcgggccact accgggcctg     60

ggagcggatc tgttggcagt ggtcgcgcgg ctcaaccgcc tagccacgca gcgcatccag    120
```

```
atgccactgc ccgcggctca agccagactg ctggccacca tcgaagccca gggggaagcc    180

cggatcggcg acttggccgc cgtcgatcac tgctcgcaac caacgatgac cacgcaggta    240

cgacgactcg aggacgctgg actggttacc cgaaccgccg acccgggaga cgcccgggcg    300

gtccgcatcc gcatcacgcc ggaaggcatc cgcacgttga ccgcggtgcg ggcagaccgc    360

gcggctgcga tcgagcctca gctggccctg ctcccaccgg cggaccgccg ggtgttggcg    420

gatgcggtag acgtgttgcg ccggctgctc gaccatgccg ccaccacgcc gggccgggcg    480

acgcggcaa                                                            489
```

<210> SEQ ID NO 99
<211> LENGTH: 257
<212> TYPE: PRT
<213> ORGANISM: Mycobacterium tuberculosis

<400> SEQUENCE: 99

```
Met Glu Leu Leu Gly Gly Pro Arg Val Gly Asn Thr Glu Ser Gln Leu
1               5                   10                  15

Cys Val Ala Asp Gly Asp Asp Leu Pro Thr Tyr Cys Ser Ala Asn Ser
            20                  25                  30

Glu Asp Leu Asn Ile Thr Thr Ile Thr Thr Leu Ser Pro Thr Ser Met
        35                  40                  45

Ser His Pro Gln Gln Val Arg Asp Asp Gln Trp Val Glu Pro Ser Asp
    50                  55                  60

Gln Leu Gln Gly Thr Ala Val Phe Asp Ala Thr Gly Asp Lys Ala Thr
65                  70                  75                  80

Met Pro Ser Trp Asp Glu Leu Val Arg Gln His Ala Asp Arg Val Tyr
                85                  90                  95

Arg Leu Ala Tyr Arg Leu Ser Gly Asn Gln His Asp Ala Glu Asp Leu
            100                 105                 110

Thr Gln Glu Thr Phe Ile Arg Val Phe Arg Ser Val Gln Asn Tyr Gln
        115                 120                 125

Pro Gly Thr Phe Glu Gly Trp Leu His Arg Ile Thr Thr Asn Leu Phe
    130                 135                 140

Leu Asp Met Val Arg Arg Arg Ala Arg Ile Arg Met Glu Ala Leu Pro
145                 150                 155                 160

Glu Asp Tyr Asp Arg Val Pro Ala Asp Glu Pro Asn Pro Glu Gln Ile
                165                 170                 175

Tyr His Asp Ala Arg Leu Gly Pro Asp Leu Gln Ala Ala Leu Ala Ser
            180                 185                 190

Leu Pro Pro Glu Phe Arg Ala Ala Val Val Leu Cys Asp Ile Glu Gly
        195                 200                 205

Leu Ser Tyr Glu Glu Ile Gly Ala Thr Leu Gly Val Lys Leu Gly Thr
    210                 215                 220

Val Arg Ser Arg Ile His Arg Gly Arg Gln Ala Leu Arg Asp Tyr Leu
225                 230                 235                 240

Ala Ala His Pro Glu His Gly Glu Cys Ala Val His Val Asn Pro Val
                245                 250                 255

Arg
```

<210> SEQ ID NO 100
<211> LENGTH: 771
<212> TYPE: DNA
<213> ORGANISM: Mycobacterium tuberculosis

<400> SEQUENCE: 100

```
atggaactcc tcggcggacc ccgggttggg aatacggaat cgcaactttg cgttgccgac     60

ggtgacgact tgccaactta ttgcagtgca aattcggagg atctcaatat cacgaccatc    120

acgaccttga gtccgaccag catgtctcat ccccaacagg tccgcgatga ccagtgggtg    180

gagccgtctg accaattgca gggcaccgcc gtattcgacg ccaccgggga caaggccacc    240

atgccgtcct gggatgagct ggtccgtcag cacgccgatc gggtgtaccg gctggcttat    300

cggctctccg gcaaccagca cgatgccgaa gacctgaccc aggagacctt tatcagggtg    360

ttccggtcgg tccagaatta ccagccgggc accttcgaag gctggctaca ccgcatcacc    420

accaacttgt tcctggacat ggtccgccgc cgggctcgca tccggatgga ggcgttaccc    480

gaggactacg accgggtgcc cgccgatgag cccaaccccg agcagatcta ccacgacgca    540

cggctgggac ctgacctgca ggctgccttg gcctcgctgc cgccggagtt tcgtgccgcg    600

gtggtgctgt gtgacatcga gggtctgtcg tacgaggaga tcggcgccac actgggcgtg    660

aagctcggga cggtacgtag ccggatacac cgcggacgcc aggcactgcg ggactacctg    720

gcagcgcacc ccgaacatgg cgagtgcgca gttcacgtca acccagttcg c             771
```

<210> SEQ ID NO 101
<211> LENGTH: 472
<212> TYPE: PRT
<213> ORGANISM: Mycobacterium tuberculosis

<400> SEQUENCE: 101

```
Val Thr Arg Arg Gly Lys Ile Val Cys Thr Leu Gly Pro Ala Thr Gln
1               5                   10                  15

Arg Asp Asp Leu Val Arg Ala Leu Val Glu Ala Gly Met Asp Val Ala
            20                  25                  30

Arg Met Asn Phe Ser His Gly Asp Tyr Asp Asp His Lys Val Ala Tyr
        35                  40                  45

Glu Arg Val Arg Val Ala Ser Asp Ala Thr Gly Arg Ala Val Gly Val
    50                  55                  60

Leu Ala Asp Leu Gln Gly Pro Lys Ile Arg Leu Gly Arg Phe Ala Ser
65                  70                  75                  80

Gly Ala Thr His Trp Ala Glu Gly Glu Thr Val Arg Ile Thr Val Gly
                85                  90                  95

Ala Cys Glu Gly Ser His Asp Arg Val Ser Thr Thr Tyr Lys Arg Leu
            100                 105                 110

Ala Gln Asp Ala Val Ala Gly Asp Arg Val Leu Val Asp Asp Gly Lys
        115                 120                 125

Val Ala Leu Val Val Asp Ala Val Glu Gly Asp Asp Val Val Cys Thr
    130                 135                 140

Val Val Glu Gly Gly Pro Val Ser Asp Asn Lys Gly Ile Ser Leu Pro
145                 150                 155                 160

Gly Met Asn Val Thr Ala Pro Ala Leu Ser Glu Lys Asp Ile Glu Asp
                165                 170                 175

Leu Thr Phe Ala Leu Asn Leu Gly Val Asp Met Val Ala Leu Ser Phe
            180                 185                 190

Val Arg Ser Pro Ala Asp Val Glu Leu Val His Glu Val Met Asp Arg
        195                 200                 205

Ile Gly Arg Arg Val Pro Val Ile Ala Lys Leu Glu Lys Pro Glu Ala
    210                 215                 220

Ile Asp Asn Leu Glu Ala Ile Val Leu Ala Phe Asp Ala Val Met Val
225                 230                 235                 240
```

-continued

```
Ala Arg Gly Asp Leu Gly Val Glu Leu Pro Leu Glu Glu Val Pro Leu
                245                 250                 255

Val Gln Lys Arg Ala Ile Gln Met Ala Arg Glu Asn Ala Lys Pro Val
            260                 265                 270

Ile Val Ala Thr Gln Met Leu Asp Ser Met Ile Glu Asn Ser Arg Pro
        275                 280                 285

Thr Arg Ala Glu Ala Ser Asp Val Ala Asn Ala Val Leu Asp Gly Ala
    290                 295                 300

Asp Ala Leu Met Leu Ser Gly Glu Thr Ser Val Gly Lys Tyr Pro Leu
305                 310                 315                 320

Ala Ala Val Arg Thr Met Ser Arg Ile Ile Cys Ala Val Glu Glu Asn
                325                 330                 335

Ser Thr Ala Ala Pro Pro Leu Thr His Ile Pro Arg Thr Lys Arg Gly
            340                 345                 350

Val Ile Ser Tyr Ala Ala Arg Asp Ile Gly Glu Arg Leu Asp Ala Lys
        355                 360                 365

Ala Leu Val Ala Phe Thr Gln Ser Gly Asp Thr Val Arg Arg Leu Ala
    370                 375                 380

Arg Leu His Thr Pro Leu Pro Leu Leu Ala Phe Thr Ala Trp Pro Glu
385                 390                 395                 400

Val Arg Ser Gln Leu Ala Met Thr Trp Gly Thr Glu Thr Phe Ile Val
                405                 410                 415

Pro Lys Met Gln Ser Thr Asp Gly Met Ile Arg Gln Val Asp Lys Ser
            420                 425                 430

Leu Leu Glu Leu Ala Arg Tyr Lys Arg Gly Asp Leu Val Val Ile Val
        435                 440                 445

Ala Gly Ala Pro Pro Gly Thr Val Gly Ser Thr Asn Leu Ile His Val
    450                 455                 460

His Arg Ile Gly Glu Asp Asp Val
465                 470
```

<210> SEQ ID NO 102
<211> LENGTH: 1416
<212> TYPE: DNA
<213> ORGANISM: Mycobacterium tuberculosis

<400> SEQUENCE: 102

```
gtgacgagac gcgggaaaat cgtctgcact ctcgggccgg ccacccagcg ggacgacctg     60

gtcagagcgc tggtcgaggc cggaatggac gtcgcccgaa tgaacttcag ccacggcgac    120

tacgacgatc acaaggtcgc ctatgagcgg gtccgggtag cctccgacgc caccgggcgc    180

gcggtcggcg tgctcgccga cctgcagggc ccgaagatca ggttgggacg cttcgcctcc    240

ggggccaccc actgggccga aggcgaaacc gtccggatca ccgtgggcgc ctgcgagggc    300

agccacgatc gggtgtccac cacctacaag cggctagccc aggacgcggt ggccggtgac    360

cgggtgctgg tcgacgacgg caaagtcgca ttggtggtcg acgccgtcga gggcgacgac    420

gtggtctgca ccgtcgtcga aggcggcccg gtcagcgaca acaagggcat ctcgttgccc    480

ggaatgaacg tgaccgcgcc ggccctgtcg gagaaggaca tcgaggatct cacgttcgcg    540

ctgaacctcg gcgtcgacat ggtggcgctt tccttcgtcc gctccccggc cgatgtcgaa    600

ctggtccacg aggtgatgga tcggatcggg cgacgggtgc cggtgatcgc caagctggag    660

aagccggaag ccatcgacaa tctcgaagcg atcgtgctgg cgttcgacgc cgtcatggtc    720

gctcggggcg acctaggtgt tgagctgccg ctcgaagagg tcccgctggt acagaagcga    780

gccatccaga tggcccggga gaacgccaag ccggtcattg tggcgaccca gatgctcgac    840
```

```
tcgatgatcg agaactcgcg gccgacccga gctgaggcct ccgacgtcgc caacgcggtg    900

ctcgatggcg ccgacgcgct gatgctgtcc ggggaaacct cggtagggaa gtacccccctt    960

gctgcggtcc ggacaatgtc gcgcatcatc tgcgcggtcg aggagaactc cacggccgca   1020

ccgccgttga cacacattcc ccggaccaag cgtggggtca tctcgtatgc ggcccgtgac   1080

atcggcgaac gactcgacgc caaggccttg gtggccttca ctcagtccgg tgataccgtg   1140

cggcgactgg cccgcctgca taccccgctg ccgctgctgg ccttcaccgc gtggcccgag   1200

gtgcgcagcc aactggcgat gacctggggc accgagacgt tcatcgtgcc gaagatgcag   1260

tccaccgatg gcatgatccg ccaggtcgac aaatcgctgc tcgaactcgc ccgctacaag   1320

cgtggtgact tggtggtcat cgtcgcgggt gcgccgccag gcacagtggg ttcgaccaac   1380

ctgatccacg tgcaccggat cggggaagat gacgtc                             1416
```

<210> SEQ ID NO 103
<211> LENGTH: 269
<212> TYPE: PRT
<213> ORGANISM: Mycobacterium tuberculosis

<400> SEQUENCE: 103

```
Met Thr Ser Val Lys Leu Asp Leu Asp Ala Ala Asp Leu Arg Ile Ser
1               5                   10                  15

Arg Gly Ser Val Pro Ala Ser Thr Gln Leu Ala Glu Ala Leu Lys Ala
            20                  25                  30

Gln Ile Ile Gln Gln Arg Leu Pro Arg Gly Gly Arg Leu Pro Ser Glu
        35                  40                  45

Arg Glu Leu Ile Asp Arg Ser Gly Leu Ser Arg Val Thr Val Arg Ala
    50                  55                  60

Ala Val Gly Met Leu Gln Arg Gln Gly Trp Leu Val Arg Arg Gln Gly
65                  70                  75                  80

Leu Gly Thr Phe Val Ala Asp Pro Val Glu Gln Glu Leu Ser Cys Gly
                85                  90                  95

Val Arg Thr Ile Thr Glu Val Leu Leu Ser Cys Gly Val Thr Pro Gln
            100                 105                 110

Val Asp Val Leu Ser His Gln Thr Gly Pro Ala Pro Gln Arg Ile Ser
        115                 120                 125

Glu Thr Leu Gly Leu Val Glu Val Leu Cys Ile Arg Arg Arg Ile Arg
    130                 135                 140

Thr Gly Asp Gln Pro Leu Ala Leu Val Thr Ala Tyr Leu Pro Pro Gly
145                 150                 155                 160

Val Gly Pro Ala Val Glu Pro Leu Leu Ser Gly Ser Ala Asp Thr Glu
                165                 170                 175

Thr Thr Tyr Ala Met Trp Glu Arg Arg Leu Gly Val Arg Ile Ala Gln
            180                 185                 190

Ala Thr His Glu Ile His Ala Ala Gly Ala Ser Pro Asp Val Ala Asp
        195                 200                 205

Ala Leu Gly Leu Ala Val Gly Ser Pro Val Leu Val Val Asp Arg Thr
    210                 215                 220

Ser Tyr Thr Asn Asp Gly Lys Pro Leu Glu Val Val Val Phe His His
225                 230                 235                 240

Arg Pro Glu Arg Tyr Gln Phe Ser Val Thr Leu Pro Arg Thr Leu Pro
                245                 250                 255

Gly Ser Gly Ala Gly Ile Ile Glu Lys Arg Asp Phe Ala
            260                 265
```

<210> SEQ ID NO 104
<211> LENGTH: 807
<212> TYPE: DNA
<213> ORGANISM: Mycobacterium tuberculosis

<400> SEQUENCE: 104
atgacatctg tcaagctgga cctggacgct gccgatctgc ggatatcgcg tggcagcgtg 60
ccggcgagta cccagcttgc cgaggcgcta aaggcccaga tcatccagca gcggctgccg 120
cgcggcgggc gcttgcccag cgaacgagaa ttgatcgacc gttccggttt gagccgcgtg 180
accgtgcgcg cggcggtcgg catgctgcaa cgtcagggat ggctagtgcg ccggcaaggc 240
ttgggtacct tcgtcgccga tccggtggaa caggagctca gttgcggcgt gcgcaccatc 300
acagaggtgt tgttgagctg tggtgttacc ccgcaggtcg acgtgctgtc acaccagacc 360
ggaccggcgc cgcaacggat ttccgagacg ctgggtttgg ttgaggtcct ctgtattcgc 420
cggcgcatcc gcactggcga tcaacccttg gccctggtca cggcctatct tccgcccggc 480
gtgggcccag ccgtcgagcc gttgctatcg ggcagcgcgg acaccgaaac cacatatgcg 540
atgtgggagc ggcgactggg tgtacgcatt gcacaggcta cccacgaaat ccatgccgcc 600
ggggcctccc ccgacgtagc cgacgcgttg ggtctggcgg tgggttcgcc ggtactggtc 660
gtcgaccgca ccagctacac caatgacggc aagccccttg aagtggtcgt gttccaccat 720
cgccccgagc ggtaccagtt ctccgtcacg ttaccccgaa cgttgcccgg atcaggtgcc 780
ggaattatcg agaaacgaga tttcgca 807

<210> SEQ ID NO 105
<211> LENGTH: 293
<212> TYPE: PRT
<213> ORGANISM: Mycobacterium tuberculosis

<400> SEQUENCE: 105

Val Phe Ala Leu Ser Asn Asn Leu Asn Arg Val Asn Ala Cys Met Asp
1               5                   10                  15

Gly Phe Leu Ala Arg Ile Arg Ser His Val Asp Ala His Ala Pro Glu
            20                  25                  30

Leu Arg Ser Leu Phe Asp Thr Met Ala Ala Glu Ala Arg Phe Ala Arg
        35                  40                  45

Asp Trp Leu Ser Glu Asp Leu Ala Arg Leu Pro Val Gly Ala Ala Leu
    50                  55                  60

Leu Glu Val Gly Gly Gly Val Leu Leu Leu Ser Cys Gln Leu Ala Ala
65                  70                  75                  80

Glu Gly Phe Asp Ile Thr Ala Ile Glu Pro Thr Gly Glu Gly Phe Gly
                85                  90                  95

Lys Phe Arg Gln Leu Gly Asp Ile Val Leu Glu Leu Ala Ala Ala Arg
            100                 105                 110

Pro Thr Ile Ala Pro Cys Lys Ala Glu Asp Phe Ile Ser Glu Lys Arg
        115                 120                 125

Phe Asp Phe Ala Phe Ser Leu Asn Val Met Glu His Ile Asp Leu Pro
    130                 135                 140

Asp Glu Ala Val Arg Arg Val Ser Glu Val Leu Lys Pro Gly Ala Ser
145                 150                 155                 160

Tyr His Phe Leu Cys Pro Asn Tyr Val Phe Pro Tyr Glu Pro His Phe
                165                 170                 175

Asn Ile Pro Thr Phe Phe Thr Lys Glu Leu Thr Cys Arg Val Met Arg
            180                 185                 190

```
His Arg Ile Glu Gly Asn Thr Gly Met Asp Asp Pro Lys Gly Val Trp
        195                 200                 205

Arg Ser Leu Asn Trp Ile Thr Val Pro Lys Val Lys Arg Phe Ala Ala
    210                 215                 220

Lys Asp Ala Thr Leu Thr Leu Arg Phe His Arg Ala Met Leu Val Trp
225                 230                 235                 240

Met Leu Glu Arg Ala Leu Thr Asp Lys Glu Phe Ala Gly Arg Arg Ala
                245                 250                 255

Gln Trp Met Val Ala Ala Ile Arg Ser Ala Val Lys Leu Arg Val His
            260                 265                 270

His Leu Ala Gly Tyr Val Pro Ala Thr Leu Gln Pro Ile Met Asp Val
        275                 280                 285

Arg Leu Thr Lys Arg
    290
```

<210> SEQ ID NO 106
<211> LENGTH: 879
<212> TYPE: DNA
<213> ORGANISM: Mycobacterium tuberculosis

<400> SEQUENCE: 106

```
gtgtttgcgt tgagtaataa tctgaaccgt gtgaacgcat gcatggatgg attccttgcc      60

cgtatccgct cacatgttga tgcgcacgcg ccagaattgc gttcactgtt cgatacgatg     120

gcggccgagg cccgatttgc acgcgactgg ctgtccgagg acctcgcgcg gttgcctgtc     180

ggtgcagcat tgctggaagt gggcgggggg gtacttctgc tcagctgtca actggcggcg     240

gagggatttg acatcaccgc catcgagccg acgggtgaag gttttggcaa gttcagacag     300

cttggcgaca tcgtgctgga attggctgca gcacgaccca ccatcgcgcc atgcaaggcg     360

gaagacttta tttccgagaa gcggttcgac ttcgccttct cgctgaatgt gatggagcac     420

atcgaccttc cggatgaggc agtcaggcgg gtatcggaag tgctgaaacc gggggccagt     480

taccacttcc tgtgcccgaa ttacgtattc ccgtacgaac cgcatttcaa tatcccaaca     540

ttcttcacca aagagctgac atgccgggtg atgcgacatc gcatcgaggg caatacgggc     600

atggatgacc cgaagggagt ctggcgttcg ctcaactgga ttacggttcc caaggtgaaa     660

cgctttgcgg cgaaggatgc gacgctgacc ttgcgcttcc accgtgcaat gttggtatgg     720

atgctggaac gcgcgctgac ggataaggaa ttcgctggtc gccgggcaca atggatggtc     780

gctgctattc gctcggcggt gaaattgcgt gtgcatcatc tggcaggcta tgttcccgct     840

acgctgcagc ccatcatgga tgtgcggcta acgaagagg                            879
```

<210> SEQ ID NO 107
<211> LENGTH: 412
<212> TYPE: PRT
<213> ORGANISM: Mycobacterium tuberculosis

<400> SEQUENCE: 107

```
Val Thr Pro His Tyr Arg Gln Ala Ala Ala Ser Arg Leu Asp Thr His
1               5                   10                  15

Arg Thr Gln Lys Leu Arg Ser Gln Thr Asn Gly Gly Lys Asp Arg His
            20                  25                  30

Gln Leu Thr Tyr Glu Gln Phe Ala Arg Met Leu Thr Leu Met Gly Pro
        35                  40                  45

Ser Asp Leu Trp Thr Val Glu Arg Ala Ala Arg His Trp Gly Val Ser
    50                  55                  60

Ala Ser Arg Ala Arg Ala Ile Leu Ser Ser Arg His Ile His Arg Val
```

-continued 65 70 75 80

Ser Gly Tyr Pro Ala Gln Ala Ile Lys Ala Val Thr Leu Arg Gln Gly
85 90 95

Ala Arg Thr Asp Leu Lys Thr Ala Asn His Leu Val Pro Ala Ala Gln
100 105 110

Ala Phe Thr Met Ala Glu Thr Gly Ala Ala Ile Gly Glu Thr Glu Asp
115 120 125

Glu Arg Ala Arg Leu Arg Ile Phe Phe Glu Phe Leu Arg Gly Ala Asp
130 135 140

Glu Thr Gly Thr Ser Ala Leu Asp Leu Ile Val Asp Glu Pro Ala Leu
145 150 155 160

Ile Gly Glu His Arg Phe Asp Ala Leu Leu Ala Ala Ala Ala Glu Tyr
165 170 175

Ile Ser Ala Arg Trp Gly Arg Pro Gly Pro Leu Trp Ser Val Ser Ile
180 185 190

Glu Arg Phe Leu Asp Thr Ala Trp Trp Val Ser Asp Leu Pro Ser Ala
195 200 205

Arg Ala Phe Ala Ala Val Trp Thr Pro Ala Pro Phe Arg Arg Arg Gly
210 215 220

Ile Tyr Leu Asp Arg His Asp Leu Thr Ser Asp Gly Val Cys Val Met
225 230 235 240

Pro Glu Pro Val Phe Asn Arg Thr Glu Leu Gln Arg Ala Phe Thr Ala
245 250 255

Leu Ala Ala Lys Leu Glu Arg Arg Gly Val Val Gly Gln Val His Val
260 265 270

Val Gly Gly Ala Ala Met Leu Leu Ala Tyr Asn Ser Arg Val Thr Thr
275 280 285

Arg Asp Ile Asp Ala Leu Phe Ser Thr Asp Gly Pro Met Leu Glu Ala
290 295 300

Ile Arg Glu Val Ala Asp Glu Met Gly Trp Pro Arg Thr Trp Leu Asn
305 310 315 320

Asn Gln Ala Ser Gly Tyr Val Ser Arg Thr Pro Gly Glu Gly Ala Pro
325 330 335

Val Phe Asp His Pro Phe Leu His Val Val Ala Thr Pro Ala Gln His
340 345 350

Leu Leu Ala Met Lys Val Val Ala Ala Arg Gly Val Arg Asp Gly Glu
355 360 365

Asp Ile Arg Leu Leu Leu Asp Arg Leu Arg Ile Thr Ser Ala Ala Gly
370 375 380

Val Trp Glu Ile Val Ala Arg Tyr Phe Pro Ala Glu Thr Ile Thr Asp
385 390 395 400

Arg Ser Arg Leu Leu Val Glu Asp Leu Leu Asn Gln
405 410

<210> SEQ ID NO 108
<211> LENGTH: 1236
<212> TYPE: DNA
<213> ORGANISM: Mycobacterium tuberculosis

<400> SEQUENCE: 108
gtgaccccac actatcgcca agccgcggcg tcgcggctcg atacccaccg cacgcaaaag 60
ctccgttccc agaccaacgg agggaaggac cggcaccagt tgacatacga gcagttcgct 120
cgtatgttga cgctgatggg gccgagcgat ctgtggacgg tggaacgcgc ggcgcgccat 180
tggggcgtga gcgcgtcgcg cgctcgcgct atcctgtcga gccgccacat tcaccgggtc 240

-continued

```
agcggctacc ccgcgcaggc gatcaaggcg gtcaccctgc gccagggtgc gcgcaccgac    300

ctcaaaaccg ccaaccatct cgtgccggcc gcacaagcgt tcaccatggc cgagacgggt    360

gccgcgatcg gagagaccga agatgagcgg gcacgactgc gcattttctt cgagttcctc    420

cgcggcgccg atgagaccgg gacatccgcg ctcgatctca tcgttgacga gcccgcgctg    480

atcggtgagc accggttcga tgctttgttg gccgcggctg cggaatacat ttcggcgcgc    540

tggggccggc ctggaccctt gtggtcggtg agtatcgaac ggtttctgga cacggcctgg    600

tgggtcagcg acctcccgtc ggcacgagcg tttgccgccg tgtggacgcc ggcgccgttc    660

cggcgccgcg gcatttacct agatcgccac gacctcacga gcgatggagt gtgtgtcatg    720

cccgaaccgg tgttcaaccg aaccgagctc cagcgggcgt tcactgccct ggcggccaag    780

ctggaacgca gaggcgttgt cggtcaggtg cacgttgtcg gcggggcggc gatgctactc    840

gcctacaact cccgtgtcac cactcgcgat atcgacgcgt tgttctcaac tgacgggcct    900

atgctcgaag cgattcgtga ggtcgctgac gaaatgggtt ggccgcgaac gtggctcaac    960

aatcaggcca gcggttacgt ctcccgcaca ccaggtgaag gcgcccccgt tttcgatcac   1020

ccattcctgc atgtcgtagc cacacccgcg cagcaccttc tcgcgatgaa agtcgttgcg   1080

gcacgcggcg tgcgtgacgg cgaagacatt cgcctcctgc tcgatcggct gcgaatcacc   1140

agcgcggccg gcgtatggga gattgtcgca cgctactttc ccgccgaaac catcaccgac   1200

cggtcgaggc tcctcgtcga ggacctcctc aaccaa                             1236


<210> SEQ ID NO 109
<211> LENGTH: 328
<212> TYPE: PRT
<213> ORGANISM: Mycobacterium tuberculosis

<400> SEQUENCE: 109

Val Pro Gly Ala Arg Glu Leu Thr Leu Arg Val Glu Arg Gly Ala Leu
1               5                   10                  15

Phe Arg Arg Arg Trp Ala Ala Ser Ala Ala Ser Ser Ala Arg Ala Ala
            20                  25                  30

Ile Arg Arg Asp Pro Arg Arg Cys Ala Leu Gly Thr Arg Pro Arg Trp
        35                  40                  45

Val Ser Phe Leu Val Ile Val Leu Val Ile Met Asn Val Val Thr Ala
    50                  55                  60

His Pro Lys Tyr Pro Asn Asp Pro Leu Ala Leu Val Leu Ile Glu Leu
65                  70                  75                  80

Arg His Pro Arg Thr Glu Pro Pro Val Pro Ser Ala Ile Ser Ile Leu
                85                  90                  95

Lys Glu Glu Leu Ala Arg Trp Thr Pro Ile Leu Glu Gln Glu Glu Val
            100                 105                 110

Arg Gln Val Asn Leu Glu Thr Gly Glu His Thr Ala His Ser Gln Lys
        115                 120                 125

Lys Leu Val Ala Arg Asp Arg Arg Thr Ala Ile Thr Phe Arg Pro Asp
    130                 135                 140

Ala Met Thr Leu Glu Val Thr Asp Tyr Pro Gly Trp Glu Glu Phe Arg
145                 150                 155                 160

Ser Ile Val His Ala Met Val Thr Ala Arg Gln Asp Val Ala Pro Val
                165                 170                 175

Asp Gly Cys Ile Arg Ile Gly Leu Arg Tyr Ile Asn Glu Ile Arg Ala
            180                 185                 190

Ser Leu Ala Glu Pro Ser Gly Trp Ala Tyr Trp Val Ala Glu Ser Leu
```

```
        195                 200                 205

Leu Gly Pro Gly Thr Gln Leu Ala Asp Leu Lys Leu Thr Thr Thr Ala
    210                 215                 220

Gln Arg His Val Ile Gln Cys Glu Gly Pro Glu Pro Gly Asp Ser Leu
225                 230                 235                 240

Thr Leu Arg Tyr Ala Gly Ala Arg Gly Ala Val Ile Gln Ser Thr Pro
                245                 250                 255

Phe Leu Gln Arg Leu Lys Glu Pro Pro Ala Glu Gly Asp Phe Phe Leu
            260                 265                 270

Ile Asp Ile Asp Ser Ala Trp Ser Asp Pro Cys Lys Gly Ile Pro Ala
        275                 280                 285

Leu Asp Ala His Leu Val Asp Glu Val Ala Glu Arg Leu His Thr Pro
    290                 295                 300

Ile Gly Pro Leu Phe Glu Ser Leu Ile Thr Ser Glu Leu Arg Thr Lys
305                 310                 315                 320

Val Leu Gln Gln Pro Gly Gln Glu
                325
```

<210> SEQ ID NO 110
<211> LENGTH: 984
<212> TYPE: DNA
<213> ORGANISM: Mycobacterium tuberculosis

<400> SEQUENCE: 110

```
gtgcccggcg cgcgcgagtt gacgctgcgc gtcgagcgcg gggctctatt tcggcgtcga      60

tgggcagcat cggcagcgtc atcagctcgc gcagcaattc gtcgtgatcc gcggcgctgc     120

gcgctgggta cccggcctcg atgggtatca tttttggtta tcgttctggt tatcatgaat     180

gttgtgacgg cccatcccaa gtacccgaat gaccctcttg cgctggtatt gattgaactg     240

cgccatccgc ggaccgagcc gccggtgcca tctgctatct ccatcctgaa ggaggagctg     300

gcgcgatgga ctcccatact cgaacaggag gaggtgcggc aggtcaacct agaaacgggc     360

gaacataccg cacactcaca gaagaagctc gttgcccgtg atcgccgcac cgcgatcacg     420

tttcgacccg acgccatgac cctcgaagtc accgactacc cgggctggga ggagtttcgg     480

tccatcgttc acgcgatggt cacagcccgc caggacgtgg ccccagtcga tggctgcatc     540

cggatcggtc tgcgctacat caacgagatt cgggcatcgc tggcggagcc atccggctgg     600

gcgtactggg tggcggaaag tctcctcggg cctgggacac agcttgccga tctcaaactc     660

accaccaccg cgcaacggca cgtcattcag tgcgaaggcc cggagccagg cgactccttg     720

acactgaggt acgccggtgc gcgcggcgcg gtcatccagt caaccccgtt tctccagcgg     780

ttgaaagaac ctccggcaga aggagatttc ttcctcatcg atatcgacag cgcgtggagc     840

gacccctgca agggcatccc agcgctcgac gcccacctgg tggacgaggt cgccgaaagg     900

ctccacacac ccatcggccc actgttcgaa tcgctgataa cttccgaact ccgtacaaag     960

gtgctgcaac aacctgggca ggag                                            984
```

<210> SEQ ID NO 111
<211> LENGTH: 463
<212> TYPE: PRT
<213> ORGANISM: Mycobacterium tuberculosis

<400> SEQUENCE: 111

```
Met Ala Ile Arg Gln His Val Gly Ala Leu Phe Thr Asp Leu Tyr Glu
1               5                   10                  15

Val Thr Met Ala Gln Ala Tyr Trp Ala Glu Arg Met Ser Gly Thr Ala
```

-continued

```
            20                  25                  30

Val Phe Glu Ile Phe Phe Arg Lys Leu Pro Pro Gly Arg Ser Tyr Ile
        35                  40                  45

Met Ala Ala Gly Leu Ala Asp Val Val Glu Phe Leu Glu Ala Phe Arg
    50                  55                  60

Phe Asp Glu Gln Asp Leu Arg Tyr Leu Arg Gly Leu Gly Gln Phe Ser
65                  70                  75                  80

Asp Glu Phe Leu Arg Trp Leu Ala Gly Val Arg Phe Thr Gly Asp Val
                85                  90                  95

Trp Ala Ala Pro Glu Gly Thr Val Ile Phe Pro Asn Glu Pro Ala Val
            100                 105                 110

Gln Leu Ile Ala Pro Ile Ile Glu Ala Gln Leu Val Glu Thr Phe Val
        115                 120                 125

Leu Asn Gln Ile His Leu Gln Ser Val Leu Ala Ser Lys Ala Ala Arg
    130                 135                 140

Val Val Ala Ala Ala Arg Gly Arg Pro Val Val Asp Phe Gly Ala Arg
145                 150                 155                 160

Arg Ala His Gly Thr Asp Ala Ala Cys Lys Val Ala Arg Thr Ser Tyr
                165                 170                 175

Leu Ala Gly Ala Ala Gly Thr Ser Asn Leu Leu Ala Ala Arg Gln Tyr
            180                 185                 190

Gly Ile Pro Thr Phe Gly Thr Met Ala His Ser Phe Val Gln Ala Phe
        195                 200                 205

Asp Ser Glu Val Ala Ala Phe Glu Ala Phe Ala Arg Leu Tyr Pro Ala
    210                 215                 220

Thr Met Leu Leu Val Asp Thr Tyr Asp Thr Leu Arg Gly Val Asp His
225                 230                 235                 240

Val Ile Glu Leu Ala Lys Arg Leu Gly Asn Arg Phe Asp Val Arg Ala
                245                 250                 255

Val Arg Leu Asp Ser Gly Asp Leu Asp Glu Leu Ser Lys Ala Thr Arg
            260                 265                 270

Ala Arg Leu Asp Thr Ala Gly Leu Glu Gln Val Glu Ile Phe Ala Ser
        275                 280                 285

Ser Gly Leu Asp Glu Asn Arg Ile Ala Ala Leu Leu Ala Ala Arg Cys
    290                 295                 300

Pro Ile Asp Gly Phe Gly Val Gly Thr Gln Leu Val Val Ala Gln Asp
305                 310                 315                 320

Ala Pro Ala Leu Asp Met Ala Tyr Lys Leu Val Ala Tyr Asp Gly Ser
                325                 330                 335

Gly Arg Thr Lys Phe Ser Ser Gly Lys Val Ile Tyr Pro Gly Arg Lys
            340                 345                 350

Gln Val Phe Arg Lys Leu Glu His Gly Val Phe Cys Gly Asp Thr Leu
        355                 360                 365

Gly Glu His Gly Glu Asn Leu Pro Gly Asp Pro Leu Leu Val Pro Ile
    370                 375                 380

Met Thr Asn Gly Arg Arg Ile Arg Gln His Ala Pro Thr Leu Asp Gly
385                 390                 395                 400

Ala Arg Asp Trp Ala Arg Gln Gln Ile Asp Ala Leu Pro Pro Glu Leu
                405                 410                 415

Arg Ser Leu Glu Asp Thr Gly Tyr Ser Tyr Pro Val Ala Val Ser Asp
            420                 425                 430

Arg Ile Val Gly Glu Leu Ala Arg Leu Arg His Ala Asp Thr Ala Glu
        435                 440                 445
```

-continued

```
Ala His Pro Gly Ser Asn Val Val Gly Ala Lys Ala Lys Arg Pro
    450                 455                 460
```

<210> SEQ ID NO 112
<211> LENGTH: 1389
<212> TYPE: DNA
<213> ORGANISM: Mycobacterium tuberculosis

<400> SEQUENCE: 112

```
atggcgatcc gccaacacgt cggcgcgctg ttcaccgacc tgtacgaggt gacgatggcc      60

caggcctact gggccgaaag aatgtcgggc acagcggttt tcgagatatt cttccgcaag     120

cttccgcctg gcaggtccta catcatggcc gccgggctgg ccgatgtggt cgagttcctc     180

gaagcgtttc gattcgacga gcaggatctg cgttacctgc gtggcctggg ccagttttcc     240

gacgagttcc tgaggtggct ggccggagtg cgtttcaccg gagatgtctg ggccgcgccg     300

gaaggaaccg tgatttttcc gaacgaaccc gcggtccagc tgatcgcgcc aatcatcgag     360

gcccagcttg tcgagacgtt tgtgctgaac cagattcatc tgcaaagcgt gctcgcgagc     420

aaggccgcgc gggtggtcgc cgccgcgcgc ggacgaccgg tggtggattt cggcgcgcgg     480

cgcgctcacg gcaccgacgc ggcctgcaag gtcgcgcgca ccagttatct cgcgggcgct     540

gcgggcacgt cgaatctgct cgcggcccgc caatatggga tcccgacgtt cggcaccatg     600

gcgcacagct ttgttcaagc cttcgacagt gaggtggccg cgttcgaggc gttcgcccgg     660

ctctacccag ccaccatgct gctcgtggac acctacgaca cgctacgcgg cgtcgatcac     720

gtcatcgagt tggccaagcg gctgggcaat cgcttcgatg tgcgcgcggt ccggctggat     780

tccggcgacc tcgatgagct gtccaaggcg acccgtgcac ggctcgacac cgccggtctc     840

gagcaggtcg agatcttcgc gtcgtcgggc ctcgacgaaa accgcatcgc cgcgcttttg     900

gctgcccgct gtccgatcga cggcttcggc gtgggcaccc agctcgtcgt ggctcaagac     960

gcgcccgcgc tggacatggc ctacaagctg gtggcatacg acggcagcgg gcgcaccaag    1020

ttctccagcg gcaaggtgat ctacccggga cgcaagcagg tgttccgtaa gctcgagcac    1080

ggagtctttt gcggcgacac gctcggcgag cacggtgaaa accttcccgg ggacccgttg    1140

ctggtgccca tcatgaccaa cggccgacgc atccggcagc atgcacccac attggacggc    1200

gcgcgggact gggcccgcca gcagatcgac gcgctcccgc cggagctgcg ctcgctcgag    1260

gacaccggct actcgtatcc ggtggcggtc agcgacagga tcgtgggcga actcgcccgg    1320

ctgcggcacg ccgacacggc cgaagcccac cccgggtcca acgtcgtcgg ggcgaaggcc    1380

aaacgaccc                                                            1389
```

<210> SEQ ID NO 113
<211> LENGTH: 138
<212> TYPE: PRT
<213> ORGANISM: Mycobacterium tuberculosis

<400> SEQUENCE: 113

```
Leu Gln Pro Asp Arg Asn Leu Leu Ala Asp Leu Asp His Ile Phe Val
1               5                   10                  15

Asp Arg Ser Leu Gly Ala Val Gln Val Pro Gln Leu Leu Arg Asp Ala
            20                  25                  30

Gly Phe Arg Leu Thr Thr Met Arg Glu His Tyr Gly Glu Thr Gln Ala
        35                  40                  45

Gln Ser Val Ser Asp His Lys Trp Ile Ala Met Thr Ala Glu Cys Gly
    50                  55                  60

Trp Ile Gly Phe His Lys Asp Ala Asn Ile Arg Arg Asn Ala Val Glu
```

65 70 75 80

Arg Arg Thr Val Leu Asp Thr Gly Ala Arg Leu Phe Cys Val Pro Arg
85 90 95

Ala Asp Ile Leu Ala Glu Gln Val Ala Ala Arg Tyr Ile Ala Ser Leu
100 105 110

Ala Ala Ile Ala Arg Ala Ala Arg Phe Pro Gly Pro Phe Ile Tyr Thr
115 120 125

Val His Pro Ser Lys Ile Val Arg Val Leu
130 135

<210> SEQ ID NO 114
<211> LENGTH: 414
<212> TYPE: DNA
<213> ORGANISM: Mycobacterium tuberculosis

<400> SEQUENCE: 114
ttgcagcctg atcggaatct cctcgccgac ctcgatcaca tctttgtcga ccggagtttg 60
ggcgctgtgc aagtcccgca actccttcgg gatgccggat tccggctgac aacgatgcgg 120
gagcactacg gcgagacgca ggctcagagt gtcagcgacc acaagtggat cgcaatgacc 180
gccgagtgcg gctggattgg atttcacaag gatgccaata tccggcgcaa cgccgtcgag 240
cgacggacgg tgctcgacac gggagcccgg ctattctgtg tgccgcgggc cgacatcctg 300
gcagagcaag tcgcggcacg gtatattgcg tcccttgcgg cgattgcccg tgccgcacga 360
tttccgggac cattcatcta cacggttcac ccgagcaaga tcgttcgcgt gctc 414

<210> SEQ ID NO 115
<211> LENGTH: 288
<212> TYPE: PRT
<213> ORGANISM: Mycobacterium tuberculosis

<400> SEQUENCE: 115

Met Asn Ser Pro Arg Glu Pro Leu Val Pro Pro Pro Thr Pro Arg Pro
1 5 10 15

Ala Ala Thr Val Met Leu Val Arg Asp Pro Asp Ala Gly Ser Ala Ser
20 25 30

Gly Leu Ala Val Phe Leu Met Arg Arg His Ala Ala Met Asp Phe Ala
35 40 45

Ala Gly Val Met Val Phe Pro Gly Gly Gly Val Asp Asp Arg Asp Arg
50 55 60

Asp Ala Asp Leu Gly Arg Leu Gly Ala Trp Ala Gly Pro Pro Pro Gln
65 70 75 80

Trp Trp Ala Gln Arg Phe Gly Ile Glu Pro Asp Leu Ala Glu Ala Leu
85 90 95

Val Cys Ala Ala Ala Arg Glu Thr Phe Glu Glu Ser Gly Val Leu Phe
100 105 110

Ala Gly Pro Val Asp Gln Asp His Ser Ala Pro Asn Ser Ile Val Ser
115 120 125

Asp Ala Ser Val Tyr Gly Asp Ala Arg Arg Ala Leu Ala Asp Arg Thr
130 135 140

Leu Ser Phe Ala Asp Phe Leu Gln Arg Glu Lys Leu Val Leu Arg Ser
145 150 155 160

Asp Leu Leu Arg Pro Trp Ala Asn Trp Val Thr Pro Glu Ala Glu Leu
165 170 175

Thr Arg Arg Tyr Asp Thr Tyr Phe Phe Val Gly Ala Leu Pro Glu Gly
180 185 190

```
Gln Arg Ala Asp Gly Glu Asn Thr Glu Ser Asp Arg Ala Gly Trp Val
        195                 200                 205

Leu Pro Ala Asp Ala Ile Ala Asp Phe Ala Ala Gly Arg Asn Phe Leu
    210                 215                 220

Leu Pro Pro Thr Trp Thr Gln Leu Asp Ser Leu Ala Gly His Thr Val
225                 230                 235                 240

Ala Asp Val Leu Ala Val Glu Arg Gln Ile Val Pro Val Gln Pro Gln
                245                 250                 255

Leu Ala Arg Asn Gly Asp Asn Trp Glu Ile Glu Phe Phe Asp Ser Asp
            260                 265                 270

Arg Tyr Asn Gln Ala Arg Arg Ser Gly Gly Ser Thr Gly Trp Pro Leu
        275                 280                 285


<210> SEQ ID NO 116
<211> LENGTH: 864
<212> TYPE: DNA
<213> ORGANISM: Mycobacterium tuberculosis

<400> SEQUENCE: 116

atgaattcac ctcgcgagcc actggtaccc ccgcctacac cgaggccggc ggcgaccgtg      60

atgttggtcc gcgacccgga cgccggatca gcgtccggtc tggccgtctt cttgatgcgg     120

cggcacgctg cgatggattt cgccgccggg gtaatggtgt ttcccggcgg gggagtcgac     180

gaccgcgacc gcgacgccga cttgggccgg ctgggggcat gggccggtcc gccgccgcag     240

tggtgggcgc agcggttcgg catcgagcct gatctcgccg aagccttggt ctgcgcggcg     300

gcccgcgaga cgttcgagga gtcgggggtg ctattcgccg ggccggtcga tcaggaccat     360

tcggcaccga acagcatcgt ctcggatgcc tcggtgtacg gcgacgcgcg tcgcgcactg     420

gccgaccgga cgctgtcctt cgcggacttc ctgcagcggg aaaagctggt gctgcgatcc     480

gacctgctac ggccctgggc caactgggtc accccggagg ccgaactgac ccggcgctac     540

gacacctact tctttgtggg tgccctacct gaaggtcagc gcgccgacgg cgagaacacc     600

gaatccgacc gggctggttg ggtgttgcca gccgacgcta tcgccgactt cgccgccggc     660

cgcaacttct tgctgccgcc gacctggacg caactggact cgctggccgg tcataccgtt     720

gccgacgtgc tggccgtcga acgccaaatc gtcccggtgc agccacagct ggcccgcaac     780

ggcgacaact gggagatcga gttcttcgat tccgaccgct ataaccaggc ccggagatcg     840

ggcggatcga ccgggtggcc gctg                                            864


<210> SEQ ID NO 117
<211> LENGTH: 456
<212> TYPE: PRT
<213> ORGANISM: Mycobacterium tuberculosis

<400> SEQUENCE: 117

Met Val Ser Thr His Ala Val Val Ala Gly Glu Thr Leu Ser Ala Leu
1               5                   10                  15

Ala Leu Arg Phe Tyr Gly Asp Ala Glu Leu Tyr Arg Leu Ile Ala Ala
            20                  25                  30

Ala Ser Gly Ile Ala Asp Pro Asp Val Val Asn Val Gly Gln Arg Leu
        35                  40                  45

Ile Met Pro Asp Phe Thr Arg Tyr Thr Val Val Ala Gly Asp Thr Leu
    50                  55                  60

Ser Ala Leu Ala Leu Arg Phe Tyr Gly Asp Ala Glu Leu Asn Trp Leu
65                  70                  75                  80

Ile Ala Ala Ala Ser Gly Ile Ala Asp Pro Asp Val Val Asn Val Gly
```

-continued

```
                85                  90                  95

Gln Arg Leu Ile Met Pro Asp Phe Thr Arg Tyr Thr Val Val Ala Gly
            100                 105                 110

Asp Thr Leu Ser Ala Leu Ala Ala Arg Phe Tyr Gly Asp Ala Ser Leu
        115                 120                 125

Tyr Pro Leu Ile Ala Ala Val Asn Gly Ile Ala Asp Pro Gly Val Ile
    130                 135                 140

Asp Val Gly Gln Val Leu Val Ile Phe Ile Gly Arg Ser Asp Gly Phe
145                 150                 155                 160

Gly Leu Arg Ile Val Asp Arg Asn Glu Asn Asp Pro Arg Leu Trp Tyr
                165                 170                 175

Tyr Arg Phe Gln Thr Ser Ala Ile Gly Trp Asn Pro Gly Val Asn Val
            180                 185                 190

Leu Leu Pro Asp Asp Tyr Arg Thr Ser Gly Arg Thr Tyr Pro Val Leu
        195                 200                 205

Tyr Leu Phe His Gly Gly Gly Thr Asp Gln Asp Phe Arg Thr Phe Asp
    210                 215                 220

Phe Leu Gly Ile Arg Asp Leu Thr Ala Gly Lys Pro Ile Ile Ile Val
225                 230                 235                 240

Met Pro Asp Gly Gly His Ala Gly Trp Tyr Ser Asn Pro Val Ser Ser
                245                 250                 255

Phe Val Gly Pro Arg Asn Trp Glu Thr Phe His Ile Ala Gln Leu Leu
            260                 265                 270

Pro Trp Ile Glu Ala Asn Phe Arg Thr Tyr Ala Glu Tyr Asp Gly Arg
        275                 280                 285

Ala Val Ala Gly Phe Ser Met Gly Gly Phe Gly Ala Leu Lys Tyr Ala
    290                 295                 300

Ala Lys Tyr Tyr Gly His Phe Ala Ser Ala Ser Ser His Ser Gly Pro
305                 310                 315                 320

Ala Ser Leu Arg Arg Asp Phe Gly Leu Val Val His Trp Ala Asn Leu
                325                 330                 335

Ser Ser Ala Val Leu Asp Leu Gly Gly Gly Thr Val Tyr Gly Ala Pro
            340                 345                 350

Leu Trp Asp Gln Ala Arg Val Ser Ala Asp Asn Pro Val Glu Arg Ile
        355                 360                 365

Asp Ser Tyr Arg Asn Lys Arg Ile Phe Leu Val Ala Gly Thr Ser Pro
    370                 375                 380

Asp Pro Ala Asn Trp Phe Asp Ser Val Asn Glu Thr Gln Val Leu Ala
385                 390                 395                 400

Gly Gln Arg Glu Phe Arg Glu Arg Leu Ser Asn Ala Gly Ile Pro His
                405                 410                 415

Glu Ser His Glu Val Pro Gly Gly His Val Phe Arg Pro Asp Met Phe
            420                 425                 430

Arg Leu Asp Leu Asp Gly Ile Val Ala Arg Leu Arg Pro Ala Ser Ile
        435                 440                 445

Gly Ala Ala Ala Glu Arg Ala Asp
    450                 455
```

<210> SEQ ID NO 118
<211> LENGTH: 1368
<212> TYPE: DNA
<213> ORGANISM: Mycobacterium tuberculosis

<400> SEQUENCE: 118

```
atggtcagca cacatgcggt tgtcgcgggg gagacgctgt cggcgttggc gttgcgcttc     60
```

```
tatggcgacg cggaactgta tcggctgatc gccgccgcca gcgggatcgc cgatcccgac    120
gtcgtcaatg tggggcagcg gctgattatg cctgacttca cgcgatacac cgttgttgcc    180
ggggacacgc tgtcggcgtt ggcgttgcgc ttctatggcg acgcggaatt gaattggctg    240
atcgccgccg ccagcgggat cgccgatccc gacgtcgtca atgtggggca gcggctgatt    300
atgcctgact tcacgcgata caccgttgtt gccggggaca cgctgtcggc attggctgcg    360
cgcttctatg gcgacgcctc cctatatccg cttatcgccg ccgtcaatgg catcgccgat    420
cctggcgtca tcgacgtcgg gcaggtactg gtcatattca tcgggcgtag cgacgggttc    480
ggcctaagga tcgtggaccg caacgagaac gatccccgcc tgtggtacta ccggttccag    540
acctccgcga tcggctggaa ccccggagtc aacgtcctgc ttcccgatga ctaccgcacc    600
agcggacgca cctatcccgt cctctacctg ttccacggcg gcggcaccga ccaggatttc    660
cgcacgttcg actttctggg catccgcgac ctgaccgccg gaaagccgat catcatcgtg    720
atgcccgacg gcgggcacgc gggctggtat tccaacccgg tcagctcgtt cgtcggccca    780
cggaactggg agacattcca catcgcccag ctgctcccct ggatcgaggc gaacttccga    840
acctacgccg aatacgacgg ccgcgcggtc gccgggtttt cgatgggtgg cttcggcgcg    900
ctgaagtacg cagcaaagta ctacggccac ttcgcgtcgg cgagcagcca ctccggaccg    960
gcaagtctgc gccgcgactt cggcctggta gtgcattggg caaacctgtc ctcggcggtg   1020
ctggatctag gcggcggcac ggtttacggc gcgccgctct gggaccaagc tagggtcagc   1080
gccgacaacc cggtcgagcg tatcgacagc taccgcaaca agcggatctt cctggtcgcc   1140
ggcaccagtc cggacccggc caactggttc gacagcgtga acgagaccca ggtgctagcc   1200
gggcagaggg agttccgcga acgcctcagc aacgccggca tcccgcatga atcgcacgag   1260
gtgcctggcg gtcacgtctt ccggcccgac atgttccgtc tcgacctcga cggcatcgtc   1320
gcccggctgc gccccgcgag catcggggcg gccgcagaac gcgccgat                1368
```

<210> SEQ ID NO 119
<211> LENGTH: 224
<212> TYPE: PRT
<213> ORGANISM: Mycobacterium tuberculosis

<400> SEQUENCE: 119

```
Met Ser Gly Arg Ser Arg Leu Pro Gly Ser Ser Ser Arg Arg Asp Ala
1               5                   10                  15

Ala Arg Ile Val Ala Glu Arg Val Val Ala Thr Val Ala Gly Val Ala
            20                  25                  30

Val Ala Val Asp Glu Val Asp Ala Ala Glu Ala Arg Leu Arg Asp Gly
        35                  40                  45

Pro Arg Ala Ala Ala Leu Pro Ala Ser Gly Thr Ser Glu Gly Arg Gln
    50                  55                  60

Leu Arg Arg Trp Leu Thr Gln Leu Ile Val Thr Glu Arg Val Val Ala
65                  70                  75                  80

Ala Glu Ala Ala Ala Arg Gly Leu Thr Ala Ala Gly Ala Pro Ala Glu
                85                  90                  95

Ala Asp Leu Leu Pro Asp Ala Thr Ala Arg Leu Glu Ile Gly Ser Val
            100                 105                 110

Ala Ala Ala Val Leu Ala Asp Pro Leu Ala Arg Ala Leu Phe Ala Ala
        115                 120                 125

Val Thr Ala Arg Val Ala Val Thr Asp Asp Ala Val Ala Asp Tyr His
    130                 135                 140
```

```
Ala Arg Asn Pro Leu Arg Phe Ala Ala Pro Cys Pro Gly Gln His Gly
145                 150                 155                 160

Trp Arg Ala Pro Ala Ala Ala Ala Pro Pro Leu Asp Gln Val Arg Arg
                165                 170                 175

Ala Ile Thr Glu His Leu Leu Gly Ala Ala Arg Arg Arg Ala Phe Arg
            180                 185                 190

Val Trp Leu Asp Ala Arg Arg Asn Ala Leu Val Val Leu Ala Pro Gly
        195                 200                 205

Tyr Glu His Pro Gly Asp Pro Arg Gln Pro Asp Asn Thr Arg Arg His
    210                 215                 220
```

<210> SEQ ID NO 120
<211> LENGTH: 672
<212> TYPE: DNA
<213> ORGANISM: Mycobacterium tuberculosis

<400> SEQUENCE: 120

```
atgagcgggc gaagccgatt gcccggctcc tcctcacgcc gcgacgcggc gcgcatcgtc      60

gccgagcggg tggtcgcgac cgtcgccggt gtcgcggtag cggtcgacga ggtcgacgcg     120

gccgaagcgc ggctgcgcga cggaccgcgc gcggccgcgc tgccggcgag cggcaccagc     180

gagggacgcc aactgcggcg ctggctcacc caactgatcg tgaccgagcg ggtggtagcc     240

gccgaggccg ccgcacgtgg tctgaccgcg gcgggcgccc ccgccgaggc ggacctgctg     300

cccgacgcga cggctcggct ggagatcggc agcgtcgccg ccgcggtgct ggcggatcct     360

ttggcgcggg cgttgttcgc cgccgtcacc gcgcgggtcg cggtcaccga cgacgccgtg     420

gccgactacc atgcccgcaa cccgctgcgg ttcgccgcgc catgtcccgg ccagcacggc     480

tggcgtgccc cggcggcggc cgccccaccg ctggatcagg tgcgccgcgc gatcaccgag     540

catctgttgg gggccgcgcg ccgccgcgcc ttccgggtgt ggctggacgc gcgccggaac     600

gccctggtgg tgctggcccc cggctatgag caccccggcg acccgcgcca acccgacaac     660

acccgccggc ac                                                         672
```

<210> SEQ ID NO 121
<211> LENGTH: 307
<212> TYPE: PRT
<213> ORGANISM: Mycobacterium tuberculosis

<400> SEQUENCE: 121

```
Met Asp Arg Cys Cys Gln Arg Ala Thr Ala Phe Ala Cys Ala Leu Arg
1               5                   10                  15

Pro Thr Lys Leu Ile Asp Tyr Glu Glu Met Phe Arg Gly Ala Met Gln
            20                  25                  30

Ala Arg Ala Met Val Ala Asn Pro Asp Gln Trp Ala Asp Ser Asp Arg
        35                  40                  45

Asp Gln Val Asn Thr Arg His Tyr Leu Ser Thr Ser Met Arg Val Ala
    50                  55                  60

Leu Asp Arg Gly Glu Phe Phe Leu Val Tyr Gln Pro Ile Ile Arg Leu
65                  70                  75                  80

Ala Asp Asn Arg Ile Ile Gly Ala Glu Ala Leu Leu Arg Trp Glu His
                85                  90                  95

Pro Thr Leu Gly Thr Leu Leu Pro Gly Arg Phe Ile Asp Arg Ala Glu
            100                 105                 110

Asn Asn Gly Leu Met Val Pro Leu Thr Ala Phe Val Leu Glu Gln Ala
        115                 120                 125

Cys Arg His Val Arg Ser Trp Arg Asp His Ser Thr Asp Pro Gln Pro
```

```
    130                 135                 140

Phe Val Ser Val Asn Val Ser Ala Ser Thr Ile Cys Asp Pro Gly Phe
145                 150                 155                 160

Leu Val Leu Val Glu Gly Val Leu Gly Glu Thr Gly Leu Pro Ala His
                165                 170                 175

Ala Leu Gln Leu Glu Leu Ala Glu Asp Ala Arg Leu Ser Arg Asp Glu
            180                 185                 190

Lys Ala Val Thr Arg Leu Gln Glu Leu Ser Ala Leu Gly Val Gly Ile
        195                 200                 205

Ala Ile Asp Asp Phe Gly Ile Gly Phe Ser Ser Leu Ala Tyr Leu Pro
    210                 215                 220

Arg Leu Pro Val Asp Val Val Lys Leu Gly Gly Lys Phe Ile Glu Cys
225                 230                 235                 240

Leu Asp Gly Asp Ile Gln Ala Arg Leu Ala Asn Glu Gln Ile Thr Arg
                245                 250                 255

Ala Met Ile Asp Leu Gly Asp Lys Leu Gly Ile Thr Val Thr Ala Lys
            260                 265                 270

Leu Val Glu Thr Pro Ser Gln Ala Ala Arg Leu Arg Ala Phe Gly Cys
        275                 280                 285

Lys Ala Ala Gln Gly Trp His Phe Ala Lys Ala Leu Pro Val Asp Phe
    290                 295                 300

Phe Arg Glu
305


<210> SEQ ID NO 122
<211> LENGTH: 921
<212> TYPE: DNA
<213> ORGANISM: Mycobacterium tuberculosis

<400> SEQUENCE: 122

atggatcgtt gttgtcagcg cgctacagcg ttcgcttgcg cgctcaggcc gaccaagttg     60

atcgactacg aagagatgtt taggggcgcg atgcaagcgc gagcgatggt agccaatcct    120

gaccaatggg cggactccga ccgcgaccag gtcaacactc gccattatct gtccacttcg    180

atgcgcgtgg cactggatcg cggtgaattc ttcctcgtct accagccaat catccggctt    240

gccgacaacc gcatcatcgg cgccgaggcc ctgctgcgct gggaacaccc gacgttgggc    300

acgctactcc cgggccggtt catcgaccgt gccgagaaca acggactgat ggtgccgctc    360

acggccttcg tgctcgagca ggcctgccgc cacgtccgca gttggcgtga ccacagcacc    420

gacccgcaac cgtttgtcag cgtcaacgtc tccgccagca ccatctgcga tcccggcttc    480

ctggtgctgg tcgaaggtgt gctcggcgaa accggcctgc ccgcccatgc cctgcagctc    540

gaactggccg aggacgcgcg ccttagcaga gacgagaagg cggtgaccag gctacaagaa    600

ttgtccgctc tcggcgtcgg catcgccatc gacgacttcg gcattggatt ctccagcctc    660

gcctaccttc cccgcctccc cgtcgacgtg gtcaaactcg gggggaaagtt catcgagtgc    720

ctcgatggcg acattcaagc tcggctggcc aacgaacaga tcacccgggc aatgatcgac    780

cttggcgaca agctcggtat caccgtcact gcaaagctag tcgaaacccc cagccaagcc    840

gcccggttgc gcgccttcgg ctgtaaagcc gcacaaggct ggcactttgc caaggcactg    900

ccggtcgact ttttcagaga g                                               921


<210> SEQ ID NO 123
<211> LENGTH: 379
<212> TYPE: PRT
<213> ORGANISM: Mycobacterium tuberculosis
```

<400> SEQUENCE: 123

Met Ser Val Arg Leu Ala Asp Val Ile Asp Val Leu Asp Gln Ala Tyr
1               5                   10                  15

Pro Pro Arg Leu Ala Gln Ser Trp Asp Ser Val Gly Leu Val Cys Gly
            20                  25                  30

Asp Pro Asp Asp Val Val Asp Ser Val Thr Val Ala Val Asp Ala Thr
        35                  40                  45

Pro Ala Val Val Asp Gln Val Pro Gln Ala Gly Leu Leu Leu Val His
    50                  55                  60

His Pro Leu Leu Leu Arg Gly Val Asp Thr Val Ala Ala Asn Thr Pro
65                  70                  75                  80

Lys Gly Val Leu Val His Arg Leu Ile Arg Thr Gly Arg Ser Leu Phe
                85                  90                  95

Thr Ala His Thr Asn Ala Asp Ser Ala Ser Pro Gly Val Ser Asp Ala
            100                 105                 110

Leu Ala His Ala Val Gly Leu Thr Val Asp Ala Val Leu Asp Pro Val
        115                 120                 125

Pro Gly Ala Ala Asp Leu Asp Lys Trp Val Ile Tyr Val Pro Arg Glu
    130                 135                 140

Asn Ser Glu Ala Val Arg Ala Ala Val Phe Glu Ala Gly Ala Gly His
145                 150                 155                 160

Ile Gly Asp Tyr Ser His Cys Ser Trp Ser Val Ala Gly Thr Gly Gln
                165                 170                 175

Phe Leu Ala His Asp Gly Ala Ser Pro Ala Ile Gly Ser Val Gly Thr
            180                 185                 190

Val Glu Arg Val Ala Glu Asp Arg Val Glu Val Val Ala Pro Ala Arg
        195                 200                 205

Ala Arg Ala Glu Val Leu Ala Ala Met Arg Ala Ala His Pro Tyr Glu
    210                 215                 220

Glu Pro Ala Phe Asp Ile Phe Ala Leu Val Pro Pro Pro Val Gly Ser
225                 230                 235                 240

Gly Leu Gly Arg Ile Gly Arg Leu Pro Lys Pro Glu Pro Leu Arg Thr
                245                 250                 255

Phe Val Ala Arg Leu Glu Ala Ala Leu Pro Pro Thr Ala Thr Gly Val
            260                 265                 270

Arg Ala Ala Gly Asp Pro Asp Leu Leu Val Ser Arg Val Ala Val Cys
        275                 280                 285

Gly Gly Ala Gly Asp Ser Leu Leu Ala Thr Val Ala Ala Ala Asp Val
    290                 295                 300

Gln Ala Tyr Val Thr Ala Asp Leu Arg His His Pro Ala Asp Glu His
305                 310                 315                 320

Cys Arg Ala Ser Gln Val Ala Leu Ile Asp Val Ala His Trp Ala Ser
                325                 330                 335

Glu Phe Pro Trp Cys Gly Gln Ala Ala Glu Val Leu Arg Ser His Phe
            340                 345                 350

Gly Ala Ser Leu Pro Val Arg Val Cys Thr Ile Cys Thr Asp Pro Trp
        355                 360                 365

Asn Leu Asp His Glu Thr Gly Arg Asp Gln Ala
    370                 375

<210> SEQ ID NO 124
<211> LENGTH: 1137
<212> TYPE: DNA
<213> ORGANISM: Mycobacterium tuberculosis

<400> SEQUENCE: 124
atgagtgtgc ggctggccga tgtcatcgac gtgctggacc aggcctaccc gccgcggctt 60
gcccagtcgt gggattcggt gggtctggtg tgcggcgacc ccgacgacgt ggtggattcg 120
gtgaccgttg cggtggacgc gacgccggcg gtggtggacc aggttcccca ggccggactg 180
ctattggtgc accacccgtt gttactgcgt ggggtcgata cggtcgcggc caacacgcca 240
aagggtgtgc tggtgcaccg cctgatccgg accggtcgct cgttgtttac cgcgcacacc 300
aacgccgact cggcgtcgcc gggtgtgtcc gacgcgctgg cacacgctgt tggtctgacc 360
gtcgacgccg ttctcgaccc ggtgcccgga gcggccgatc tcgacaagtg ggtcatctat 420
gtgccgcgcg agaactcaga ggcggtgcgg gcagcggtct ttgaggccgg tgccggccat 480
atcggcgact actcgcactg cagctggagt gtcgcgggta ccgggcagtt cctggcgcac 540
gacggggcgt cgcccgccat aggcagcgtc ggtaccgtcg aacgggtggc cgaggaccgg 600
gtcgaggtcg tcgcacccgc acgagcgcgc gccgaggtgt tggcggcgat gcgcgccgcg 660
cacccttacg aggagccggc attcgacatc ttcgcgctgg taccaccgcc ggtcggcagc 720
gggttaggcc ggattggcag actgccaaaa cccgaaccgc tgcgcacctt tgttgcccgt 780
ctggaggccg cgttgccgcc gactgcgacc ggtgtgcgcg ccgccgggga tcccgacctg 840
ctggtgtcgc gggtcgcggt ctgcggcggc gccggggact cgttgcttgc caccgtggcc 900
gccgcggacg tgcaagcgta cgttacggcc gatctgcgac atcatccagc cgacgagcat 960
tgccgagctt cgcaagtggc cctgatcgac gtcgcgcatt gggcaagcga attcccgtgg 1020
tgcggccagg ccgccgaagt gttgcggtct catttcggcg cgtcgctgcc ggtgcgtgtg 1080
tgcaccatct gcaccgaccc gtggaacctc gatcacgaaa ctgggagaga tcaggca 1137

<210> SEQ ID NO 125
<211> LENGTH: 167
<212> TYPE: PRT
<213> ORGANISM: Mycobacterium tuberculosis

<400> SEQUENCE: 125

Met Thr His Arg Ser Ser Arg Leu Glu Val Gly Pro Val Ala Arg Gly
1 5 10 15

Asp Val Ala Thr Ile Glu His Ala Glu Leu Pro Pro Gly Trp Val Leu
20 25 30

Thr Thr Ser Gly Arg Ile Ser Gly Val Thr Glu Pro Gly Glu Leu Ser
35 40 45

Val His Tyr Pro Phe Pro Ile Ala Asp Leu Val Ala Leu Asp Asp Ala
50 55 60

Leu Thr Tyr Ser Ser Arg Ala Cys Gln Val Arg Phe Ala Ile Tyr Leu
65 70 75 80

Gly Asp Leu Gly Arg Asp Thr Ala Ala Arg Ala Arg Glu Ile Leu Gly
85 90 95

Lys Val Pro Thr Pro Asp Asn Ala Val Leu Leu Ala Val Ser Pro Asn
100 105 110

Gln Cys Ala Ile Glu Val Val Tyr Gly Ser Gln Val Arg Gly Arg Gly
115 120 125

Ala Glu Ser Ala Ala Pro Leu Gly Val Ala Ala Ala Ser Ser Ala Phe
130 135 140

Glu Gln Gly Glu Leu Val Asp Gly Leu Ile Ser Ala Ile Arg Val Leu
145 150 155 160

Ser Ala Gly Ile Ala Pro Gly

165

<210> SEQ ID NO 126
<211> LENGTH: 501
<212> TYPE: DNA
<213> ORGANISM: Mycobacterium tuberculosis

<400> SEQUENCE: 126
atgacgcatc ggagttcacg gttggaggtg gggccagtgg cacgtggtga cgttgcgacg 60
attgagcacg ccgagctgcc gccgggttgg gtgctgacca ccagcggacg gatctcgggg 120
gtcaccgagc ccggggaact gtccgtgcac tacccgttcc ccatcgcaga tctcgtcgcc 180
ctggacgacg cgctgaccta cagctcgcgg gcgtgtcagg tgaggttcgc catctacctc 240
ggcgacttgg gtcgtgacac cgccgcgcgg gcccgcgaga tcttgggcaa ggtgcccacg 300
ccggacaatg ctgtgctgct cgcggtctcg cccaaccagt gcgccatcga agtggtctac 360
ggctcgcaag tccgcggccg cggtgccgag tcggcggctc cgctcggggt tgccgccgct 420
tcctcagcgt tcgagcaggg tgagctggta gatgggctga tcagcgcgat ccgcgtgctc 480
agcgcgggga tcgcgccggg c 501

<210> SEQ ID NO 127
<211> LENGTH: 494
<212> TYPE: PRT
<213> ORGANISM: Mycobacterium tuberculosis

<400> SEQUENCE: 127

Met Thr Asp Ile Ile Arg Ser Asp Ala Ala Thr Leu Ala Ala Lys Ile
1 5 10 15

Ala Ile Lys Glu Val Ser Ser Ala Glu Ile Thr Arg Ala Cys Leu Asp
20 25 30

Gln Ile Glu Ala Thr Asp Glu Thr Tyr His Ala Phe Leu His Val Ala
35 40 45

Ala Asp Glu Ala Leu Ala Ala Ala Ala Ala Ile Asp Lys Gln Val Ala
50 55 60

Ala Gly Glu Pro Leu Pro Ser Ala Leu Ala Gly Val Pro Leu Ala Leu
65 70 75 80

Lys Asp Val Phe Thr Thr Ser Asp Met Pro Thr Thr Cys Gly Ser Lys
85 90 95

Ile Leu Glu Gly Trp Arg Ser Pro Tyr Asp Ala Thr Leu Thr Ala Arg
100 105 110

Leu Arg Ala Ala Gly Ile Pro Ile Leu Gly Lys Thr Asn Met Asp Glu
115 120 125

Phe Ala Met Gly Ser Ser Thr Glu Asn Ser Ala Tyr Gly Pro Thr Arg
130 135 140

Asn Pro Trp Asn Leu Asp Arg Val Pro Gly Gly Ser Gly Gly Gly Ser
145 150 155 160

Ala Ala Ala Leu Ala Ala Phe Gln Ala Pro Leu Ala Ile Gly Ser Asp
165 170 175

Thr Gly Gly Ser Ile Arg Gln Pro Ala Ala Leu Thr Ala Thr Val Gly
180 185 190

Val Lys Pro Thr Tyr Gly Thr Val Ser Arg Tyr Gly Leu Val Ala Cys
195 200 205

Ala Ser Ser Leu Asp Gln Gly Gly Pro Cys Ala Arg Thr Val Leu Asp
210 215 220

Thr Ala Leu Leu His Gln Val Ile Ala Gly His Asp Pro Arg Asp Ser
225 230 235 240

```
Thr Ser Val Asp Ala Glu Val Pro Asp Val Val Gly Ala Ala Arg Ala
                245                 250                 255

Gly Ala Val Gly Asp Leu Arg Gly Val Arg Val Gly Val Val Arg Gln
            260                 265                 270

Leu His Gly Gly Glu Gly Tyr Gln Pro Gly Val Leu Ala Ser Phe Glu
        275                 280                 285

Ala Ala Val Glu Gln Leu Thr Ala Leu Gly Ala Glu Val Ser Glu Val
    290                 295                 300

Asp Cys Pro His Phe Asp His Ala Leu Ala Ala Tyr Tyr Leu Ile Leu
305                 310                 315                 320

Pro Ser Glu Val Ser Ser Asn Leu Ala Arg Phe Asp Ala Met Arg Tyr
                325                 330                 335

Gly Leu Arg Val Gly Asp Asp Gly Thr Arg Ser Ala Glu Glu Val Met
            340                 345                 350

Ala Met Thr Arg Ala Ala Gly Phe Gly Pro Glu Val Lys Arg Arg Ile
        355                 360                 365

Met Ile Gly Thr Tyr Ala Leu Ser Ala Gly Tyr Tyr Asp Ala Tyr Tyr
    370                 375                 380

Asn Gln Ala Gln Lys Val Arg Thr Leu Ile Ala Arg Asp Leu Asp Ala
385                 390                 395                 400

Ala Tyr Arg Ser Val Asp Val Leu Val Ser Pro Thr Thr Pro Thr Thr
                405                 410                 415

Ala Phe Arg Met Gly Glu Lys Val Asp Asp Pro Leu Ala Met Tyr Leu
            420                 425                 430

Phe Asp Leu Cys Thr Leu Pro Leu Asn Leu Ala Gly His Cys Gly Met
        435                 440                 445

Ser Val Pro Ser Gly Leu Ser Pro Asp Asp Gly Leu Pro Val Gly Leu
    450                 455                 460

Gln Ile Met Ala Pro Ala Leu Ala Asp Asp Arg Leu Tyr Arg Val Gly
465                 470                 475                 480

Ala Ala Tyr Glu Ala Ala Arg Gly Pro Leu Leu Ser Ala Ile
                485                 490
```

<210> SEQ ID NO 128
<211> LENGTH: 1482
<212> TYPE: DNA
<213> ORGANISM: Mycobacterium tuberculosis

<400> SEQUENCE: 128

```
gtgacggaca tcatccgatc cgacgccgcg acgctggccg ccaagatcgc catcaaggag     60

gtgtcgtcgg ccgagatcac ccgggcctgc ctggatcaga tcgaggcgac cgacgagacg    120

taccacgcct tcctgcatgt ggcggccgat gaggcgctgg cggcggcggc cgccatcgac    180

aagcaggtgg ccgctggaga acccttgccg tcggcgctgg ccggggtgcc gctggcgctc    240

aaggacgtct tcaccaccag cgacatgccc accacctgcg ggtcaaaaat cctggaggga    300

tggcgatctc cctacgacgc cacgctgacc gcgcggttgc gcgccgcggg gatcccgatc    360

ctgggcaaga ccaacatgga cgagttcgcg atgggctcgt cgacggagaa ctccgcttac    420

ggtcccaccc gcaacccgtg gaatctcgac cgggtacccg gcggttccgg tggcggcagc    480

gcggcggcgc tggccgcgtt ccaggcgccg ctggccatcg gatccgacac cggggggtcg    540

atccgccagc cggccgcgct gaccgcgacc gtcggcgtca aacccaccta cggcacggtg    600

tcgcgctatg ggctggtggc ctgcgcgtcc tcgctggatc agggcggccc gtgtgcgcgc    660

accgtcttgg acaccgcgct gttgcatcag gtgatcgccg gccacgaccc gcgcgactcc    720
```

```
acgtcggtcg acgccgaggt gcccgacgtg gtgggcgccg ctagggccgg cgcggtcggg    780

gatctgcgtg gcgtgcgggt cggcgtggtt cgacagctgc acggcggcga gggctaccag    840

ccgggcgtgc tggcctcctt cgaggctgcc gtggagcagc taaccgcgct gggcgctgag    900

gtcagcgagg tcgactgccc gcacttcgac catgccctgg ccgcctatta cctgattctg    960

ccctcggagg tgtcgagcaa tctggcgcgc ttcgacgcga tgcgctacgg gctgcgggtc   1020

ggcgacgacg gcacccgcag cgccgaggag gtgatggcga tgacccgggc cgccggtttc   1080

gggcccgagg tcaagcggcg catcatgatc ggcacctacg cgttgtcggc cggctactac   1140

gacgcctatt acaaccaggc gcagaaggtg cgcacgctga tcgcccgcga cctcgacgcg   1200

gcgtatcggt ccgtcgacgt gctggtgtcg cccacgaccc cgaccaccgc gttccggatg   1260

ggtgagaagg tggacgatcc gctggcgatg tacttgttcg acctgtgcac gctgccgctg   1320

aacttggccg gccactgcgg catgtctgtg ccgtcggggc tctccccgga cgacgggttg   1380

ccggttggcc tacagatcat ggcgccggca ttggccgacg accggctcta ccgggtgggg   1440

gcggcttatg aggccgcccg cggcccgcta ctgagcgcca tt                      1482
```

<210> SEQ ID NO 129
<211> LENGTH: 387
<212> TYPE: PRT
<213> ORGANISM: Mycobacterium tuberculosis

<400> SEQUENCE: 129

```
Met Thr Val Gly Leu Gly Met Pro Gln Pro Pro Ala Pro Thr Leu Ala
1               5                   10                  15

Pro Arg Arg Ala Thr Arg Gln Leu Met Val Gly Asn Val Gly Val Gly
            20                  25                  30

Ser Asp His Pro Val Ser Val Gln Ser Met Cys Thr Thr Lys Thr His
        35                  40                  45

Asp Val Asn Ser Thr Leu Gln Gln Ile Ala Glu Leu Thr Ala Ala Gly
    50                  55                  60

Cys Asp Ile Val Arg Val Ala Cys Pro Arg Gln Glu Asp Ala Asp Ala
65                  70                  75                  80

Leu Ala Glu Ile Ala Arg His Ser Gln Ile Pro Val Val Ala Asp Ile
                85                  90                  95

His Phe Gln Pro Arg Tyr Ile Phe Ala Ala Ile Asp Ala Gly Cys Ala
            100                 105                 110

Ala Val Arg Val Asn Pro Gly Asn Ile Lys Glu Phe Asp Gly Arg Val
        115                 120                 125

Gly Glu Val Ala Lys Ala Ala Gly Ala Ala Gly Ile Pro Ile Arg Ile
    130                 135                 140

Gly Val Asn Ala Gly Ser Leu Asp Lys Arg Phe Met Glu Lys Tyr Gly
145                 150                 155                 160

Lys Ala Thr Pro Glu Ala Leu Val Glu Ser Ala Leu Trp Glu Ala Ser
                165                 170                 175

Leu Phe Glu Glu His Gly Phe Gly Asp Ile Lys Ile Ser Val Lys His
            180                 185                 190

Asn Asp Pro Val Val Met Val Ala Ala Tyr Glu Leu Leu Ala Ala Arg
        195                 200                 205

Cys Asp Tyr Pro Leu His Leu Gly Val Thr Glu Ala Gly Pro Ala Phe
    210                 215                 220

Gln Gly Thr Ile Lys Ser Ala Val Ala Phe Gly Ala Leu Leu Ser Arg
225                 230                 235                 240
```

```
Gly Ile Gly Asp Thr Ile Arg Val Ser Leu Ser Ala Pro Pro Val Glu
                245                 250                 255

Glu Val Lys Val Gly Asn Gln Val Leu Glu Ser Leu Asn Leu Arg Pro
            260                 265                 270

Arg Ser Leu Glu Ile Val Ser Cys Pro Ser Cys Gly Arg Ala Gln Val
        275                 280                 285

Asp Val Tyr Thr Leu Ala Asn Glu Val Thr Ala Gly Leu Asp Gly Leu
    290                 295                 300

Asp Val Pro Leu Arg Val Ala Val Met Gly Cys Val Val Asn Gly Pro
305                 310                 315                 320

Gly Glu Ala Arg Glu Ala Asp Leu Gly Val Ala Ser Gly Asn Gly Lys
                325                 330                 335

Gly Gln Ile Phe Val Arg Gly Glu Val Ile Lys Thr Val Pro Glu Ala
            340                 345                 350

Gln Ile Val Glu Thr Leu Ile Glu Glu Ala Met Arg Leu Ala Ala Glu
        355                 360                 365

Met Gly Glu Gln Asp Pro Gly Ala Thr Pro Ser Gly Ser Pro Ile Val
    370                 375                 380

Thr Val Ser
385


<210> SEQ ID NO 130
<211> LENGTH: 1161
<212> TYPE: DNA
<213> ORGANISM: Mycobacterium tuberculosis

<400> SEQUENCE: 130

gtgactgtag gcttgggcat gccgcagccc ccggcaccca cgctcgctcc ccggcgcgcc     60

acccgtcagc tgatggtcgg caacgtcggc gtgggcagtg accatccggt ctcggtgcaa    120

tcgatgtgca ccaccaaaac ccacgacgtc aactcgacat tgcaacaaat cgccgagctg    180

accgcggccg gatgcgacat cgtgcgggtg gcctgcccgc gccaggagga cgccgacgcg    240

ctggccgaga tcgcccggca cagccagatc ccggtagtcg cggacataca tttccagccg    300

cgctacatat tcgccgccat cgacgctgga tgtgccgcgg tgcgggtcaa cccgggcaac    360

atcaaggagt ttgacggccg ggtgggtgag gtcgccaagg cggcgggtgc ggccgggatc    420

ccgatccgaa tcggtgtcaa cgccggttcg ctggacaaac ggttcatgga gaagtatggc    480

aaagccacgc ccgaggcgct ggttgagtcg gcgctgtggg aggcttcgct tttcgaggag    540

catggcttcg gtgacatcaa gatcagcgtc aagcacaacg acccggtggt gatggtcgcc    600

gcctacgagc tgcttgctgc acggtgcgac tacccactgc acctcggtgt caccgaggcc    660

ggccctgctt tccagggcac catcaagtcc gcggttgcct tcggcgcgtt gctgtcgcgg    720

ggcataggcg acaccatccg ggtgtcgttg tcggccccgc cggtcgagga agtcaaggtg    780

ggcaatcagg ttctcgagtc gttgaacctg cggccgcgtt cgctcgagat cgtgtcttgc    840

ccgtcgtgcg gtcgcgcgca agtcgacgtc tacaccctgg ccaacgaggt aaccgccggc    900

ctggatggtc tcgatgtgcc gttgcgggtg gccgtgatgg ggtgtgtcgt caatggtccg    960

ggtgaagcac gtgaggccga cctgggcgtg gcgtccggca acggcaaagg tcagatcttt   1020

gtacggggcg aagtgatcaa gaccgtgccc gaagcacaga tcgtcgagac gctgatcgag   1080

gaggcgatgc ggctggccgc cgaaatgggc gagcaagatc cgggcgcgac accgagcggt   1140

tcgcctattg tgaccgtaag c                                              1161


<210> SEQ ID NO 131
```

<211> LENGTH: 132
<212> TYPE: PRT
<213> ORGANISM: Mycobacterium tuberculosis

<400> SEQUENCE: 131

Met Thr Met Thr Asp Pro Ile Ala Asp Phe Leu Thr Arg Leu Arg Asn
1 5 10 15

Ala Asn Ser Ala Tyr His Asp Glu Val Ser Leu Pro His Ser Lys Leu
20 25 30

Lys Ala Asn Ile Ala Gln Ile Leu Lys Asn Glu Gly Tyr Ile Ser Asp
35 40 45

Phe Arg Thr Glu Asp Ala Arg Val Gly Lys Ser Leu Val Ile Gln Leu
50 55 60

Lys Tyr Gly Pro Ser Arg Glu Arg Ser Ile Ala Gly Leu Arg Arg Val
65 70 75 80

Ser Lys Pro Gly Leu Arg Val Tyr Ala Lys Ser Thr Asn Leu Pro Arg
85 90 95

Val Leu Gly Gly Leu Gly Val Ala Ile Ile Ser Thr Ser Ser Gly Leu
100 105 110

Leu Thr Asp Arg Gln Ala Ala Arg Gln Gly Val Gly Gly Glu Val Leu
115 120 125

Ala Tyr Val Trp
130

<210> SEQ ID NO 132
<211> LENGTH: 396
<212> TYPE: DNA
<213> ORGANISM: Mycobacterium tuberculosis

<400> SEQUENCE: 132
atgacgatga cggacccgat cgcagacttt ttgacccgtc tgcgtaacgc caactcggcg 60
tatcacgacg aggtcagctt gccgcactcc aagctcaagg ccaacatcgc gcagattctc 120
aagaacgagg ggtacatcag cgacttccga accgaggacg ctcgggtcgg taaatcgctg 180
gttatccagc tcaagtacgg ccctagccgg gagcgcagca tcgccgggtt gcggcgggtg 240
tccaagcccg gcctgcgggt gtacgcgaaa tccaccaatc tgccgcgggt gctcggcggc 300
ctgggcgtgg cgatcatctc gacctcctcg ggcctgctga ctgaccggca ggcagctaga 360
cagggcgtgg gcggcgaagt cctcgcatat gtctgg 396

<210> SEQ ID NO 133
<211> LENGTH: 388
<212> TYPE: PRT
<213> ORGANISM: Mycobacterium tuberculosis

<400> SEQUENCE: 133

Met Ala Gly Ser Ala Thr Val Glu Lys Arg Leu Asp Phe Gly Leu Leu
1 5 10 15

Gly Pro Leu Gln Met Thr Ile Asp Gly Thr Pro Val Pro Ser Gly Thr
20 25 30

Pro Lys Gln Arg Ala Val Leu Ala Met Leu Val Ile Asn Arg Asn Arg
35 40 45

Pro Val Gly Val Asp Ala Leu Ile Thr Ala Leu Trp Glu Glu Trp Pro
50 55 60

Pro Ser Gly Ala Arg Ala Ser Ile His Ser Tyr Val Ser Asn Leu Arg
65 70 75 80

Lys Leu Leu Gly Gly Ala Gly Ile Asp Pro Arg Val Val Leu Ala Ala
85 90 95

Ala Pro Pro Gly Tyr Arg Leu Ser Ile Pro Asp Asn Thr Cys Asp Leu
100 105 110

Gly Arg Phe Val Ala Glu Lys Thr Ala Gly Val His Ala Ala Ala Ala
115 120 125

Gly Arg Phe Glu Gln Ala Ser Arg His Leu Ser Ala Ala Leu Arg Glu
130 135 140

Trp Arg Gly Pro Val Leu Asp Asp Leu Arg Asp Phe Gln Phe Val Glu
145 150 155 160

Pro Phe Ala Thr Ala Leu Val Glu Asp Lys Val Leu Ala His Thr Ala
165 170 175

Lys Ala Glu Ala Glu Ile Ala Cys Gly Arg Ala Ser Ala Val Ile Ala
180 185 190

Glu Leu Glu Ala Leu Thr Phe Glu His Pro Tyr Arg Glu Pro Leu Trp
195 200 205

Thr Gln Leu Ile Thr Ala Tyr Tyr Leu Ser Asp Arg Gln Ser Asp Ala
210 215 220

Leu Gly Ala Tyr Arg Arg Val Lys Thr Thr Leu Ala Asp Asp Leu Gly
225 230 235 240

Ile Asp Pro Gly Pro Thr Leu Arg Ala Leu Asn Glu Arg Ile Leu Arg
245 250 255

Gln Gln Pro Leu Asp Ala Lys Lys Ser Ala Lys Thr Thr Ala Ala Gly
260 265 270

Thr Val Thr Val Leu Asp Gln Arg Thr Met Ala Ser Gly Gln Gln Ala
275 280 285

Val Ala Tyr Leu His Asp Ile Ala Ser Gly Arg Gly Tyr Pro Leu Gln
290 295 300

Ala Ala Ala Thr Arg Ile Gly Arg Leu His Asp Asn Asp Ile Val Leu
305 310 315 320

Asp Ser Ala Asn Val Ser Arg His His Ala Val Ile Val Asp Thr Gly
325 330 335

Thr Asn Tyr Val Ile Asn Asp Leu Arg Ser Ser Asn Gly Val His Val
340 345 350

Gln His Glu Arg Ile Arg Ser Ala Val Thr Leu Asn Asp Gly Asp His
355 360 365

Ile Arg Ile Cys Asp His Glu Phe Thr Phe Gln Ile Ser Ala Gly Thr
370 375 380

His Gly Gly Thr
385

<210> SEQ ID NO 134
<211> LENGTH: 1164
<212> TYPE: DNA
<213> ORGANISM: Mycobacterium tuberculosis

<400> SEQUENCE: 134
atggctggta gcgcgacagt ggagaagcgg ctcgacttcg gcctgcttgg accattgcag 60
atgactatcg acggcacccc ggtgccatcg ggcaccccca agcaacgggc tgtgctagcc 120
atgttggtca tcaaccgcaa caggcccgta ggagtcgacg ccctaatcac cgccctctgg 180
gaggagtggc caccctcggg cgcacgcgcg agtatccact cctacgtgtc taatctgcgt 240
aagctcctcg gtggcgccgg gatcgaccca cgggtggtgt tggccgcagc gccgccgggt 300
tatcggctca gcatccccga caacacttgc gatctggggc ggtttgttgc cgaaaaaacc 360
gcgggcgtgc acgcggccgc cgccggccgg ttcgaacaag ccagccgcca cctgtcggcc 420

```
gcattgagag aatggcgtgg gccggtgctc gatgacctgc gcgacttcca gttcgtcgaa    480

ccctttgcca cggcgctggt agaagacaag gttcttgccc ataccgccaa ggcggaggcc    540

gaaatcgcgt gtgggcgggc cagcgcagtg atcgccgagc tcgaggctct gacattcgaa    600

cacccctacc gggagccgct gtggacacag ctgatcaccg cctactacct ctccgaccgg    660

caatccgatg cgctgggcgc ctatcgccgg gtgaagacaa cactggccga cgacctcggc    720

atcgaccccg gtccgacgtt gcgcgctctc aacgagcgga ttctgcgtca gcaaccgctg    780

gatgccaaga agtccgccaa aaccaccgct gccggcaccg tcacggtgct cgatcagcgc    840

accatggcgt cgggccagca ggcggtggcc tacctgcacg acatcgcctc gggtcgcggc    900

tacccactgc aagccgcggc gacccggatc gggcgtctgc atgacaacga catcgtccta    960

gacagcgcca acgtcagccg ccaccacgcc gtcatcgtcg acacgggcac caactacgtc   1020

atcaacgacc tccgatcgtc caacggcgtg catgtgcagc acgagcgaat ccgctccgcg   1080

gtcacgctga acgacggcga ccacattcgc atctgtgacc atgaattcac gttccagatc   1140

agcgcgggga cgcatggcgg cacg                                           1164
```

<210> SEQ ID NO 135
<211> LENGTH: 441
<212> TYPE: PRT
<213> ORGANISM: Mycobacterium tuberculosis

<400> SEQUENCE: 135

```
Met Pro Gly Asp Glu Lys Pro Val Gly Val Ala Val Leu Gly Leu Gly
1               5                   10                  15

Asn Val Gly Ser Glu Val Val Arg Ile Ile Glu Asn Ser Ala Glu Asp
            20                  25                  30

Leu Ala Ala Arg Val Gly Ala Pro Leu Val Leu Arg Gly Ile Gly Val
        35                  40                  45

Arg Arg Val Thr Thr Asp Arg Gly Val Pro Ile Glu Leu Leu Thr Asp
    50                  55                  60

Asp Ile Glu Glu Leu Val Ala Arg Glu Asp Val Asp Ile Val Val Glu
65                  70                  75                  80

Val Met Gly Pro Val Glu Pro Ser Arg Lys Ala Ile Leu Gly Ala Leu
                85                  90                  95

Glu Arg Gly Lys Ser Val Val Thr Ala Asn Lys Ala Leu Leu Ala Thr
            100                 105                 110

Ser Thr Gly Glu Leu Ala Gln Ala Ala Glu Ser Ala His Val Asp Leu
        115                 120                 125

Tyr Phe Glu Ala Ala Val Ala Gly Ala Ile Pro Val Ile Arg Pro Leu
    130                 135                 140

Thr Gln Ser Leu Ala Gly Asp Thr Val Leu Arg Val Ala Gly Ile Val
145                 150                 155                 160

Asn Gly Thr Thr Asn Tyr Ile Leu Ser Ala Met Asp Ser Thr Gly Ala
                165                 170                 175

Asp Tyr Ala Ser Ala Leu Ala Asp Ala Ser Ala Leu Gly Tyr Ala Glu
            180                 185                 190

Ala Asp Pro Thr Ala Asp Val Glu Gly Tyr Asp Ala Ala Ala Lys Ala
        195                 200                 205

Ala Ile Leu Ala Ser Ile Ala Phe His Thr Arg Val Thr Ala Asp Asp
    210                 215                 220

Val Tyr Arg Glu Gly Ile Thr Lys Val Thr Pro Ala Asp Phe Gly Ser
225                 230                 235                 240

Ala His Ala Leu Gly Cys Thr Ile Lys Leu Leu Ser Ile Cys Glu Arg
```

-continued

```
                245                 250                 255

Ile Thr Thr Asp Glu Gly Ser Gln Arg Val Ser Ala Arg Val Tyr Pro
            260                 265                 270

Ala Leu Val Pro Leu Ser His Pro Leu Ala Ala Val Asn Gly Ala Phe
        275                 280                 285

Asn Ala Val Val Val Glu Ala Glu Ala Ala Gly Arg Leu Met Phe Tyr
    290                 295                 300

Gly Gln Gly Ala Gly Gly Ala Pro Thr Ala Ser Ala Val Thr Gly Asp
305                 310                 315                 320

Leu Val Met Ala Ala Arg Asn Arg Val Leu Gly Ser Arg Gly Pro Arg
                325                 330                 335

Glu Ser Lys Tyr Ala Gln Leu Pro Val Ala Pro Met Gly Phe Ile Glu
            340                 345                 350

Thr Arg Tyr Tyr Val Ser Met Asn Val Ala Asp Lys Pro Gly Val Leu
        355                 360                 365

Ser Ala Val Ala Ala Glu Phe Ala Lys Arg Glu Val Ser Ile Ala Glu
    370                 375                 380

Val Arg Gln Glu Gly Val Val Asp Glu Gly Gly Arg Arg Val Gly Ala
385                 390                 395                 400

Arg Ile Val Val Val Thr His Leu Ala Thr Asp Ala Ala Leu Ser Glu
                405                 410                 415

Thr Val Asp Ala Leu Asp Asp Leu Asp Val Val Gln Gly Val Ser Ser
            420                 425                 430

Val Ile Arg Leu Glu Gly Thr Gly Leu
        435                 440
```

<210> SEQ ID NO 136
<211> LENGTH: 1323
<212> TYPE: DNA
<213> ORGANISM: Mycobacterium tuberculosis

<400> SEQUENCE: 136

```
gtgcccggtg acgaaaagcc ggtcggcgta gcggtactcg gtttgggcaa cgtcggcagc      60

gaggttgtcc gcatcatcga gaacagcgcc gaggatctcg cggctcgtgt cggtgcccca     120

ttggtcctgc ggggcatcgg cgtgcgccgc gtgacgaccg atcgcggcgt gccgatcgaa     180

ttgttgaccg acgacattga agagctcgtg gcccgcgagg atgtcgatat cgtggtggaa     240

gtgatggggc cggtggaacc gtcgcgcaag gcgatcctgg gcgcccttga gcgcggcaag     300

tccgtcgtta cggcgaacaa ggctttactc gccacctcca ccggcgaatt ggcacaggcc     360

gccgaaagcg cccatgttga tctgtatttc gaggcggccg tggcgggcgc cattccggtc     420

atccgtccgc tcacccagtc gctggccggc gacacggtgc tgcgagtggc cgggatcgtc     480

aacggcacca ccaactacat cctctcggcg atggacagca ccggcgctga ctatgccagc     540

gccctggccg acgcaagtgc gctgggctat gcggaggctg atcccaccgc agacgtcgaa     600

ggctacgacg ccgcggccaa ggcagcgatc ctggcatcca ttgccttcca cacccgggtg     660

accgcagacg acgtgtatcg cgaaggcatc accaaggtca ctccggccga cttcggatcc     720

gcgcacgcgc tgggttgcac catcaaactg ctgtcgatct gtgagcgcat aaccaccgac     780

gaaggttcgc agcgggtatc ggcccgcgtc tatccggccc tggtacctct gtcgcatccg     840

cttgccgcgg tcaacggcgc gttcaatgcc gtggtggtcg aggccgaggc cgcgggccgg     900

ctgatgttct acggccaggg cgcgggcggc gcgccgaccg cctctgcggt gaccggtgac     960

ctagtgatgg ccgcccgcaa ccgggtactc ggcagccgcg gcccccgtga gtctaaatac    1020
```

gctcaacttc cggtggcacc aatgggtttc attgaaacgc gctattacgt cagcatgaac 1080
gtcgccgaca agccgggcgt cttgtccgcg gtggcggcgg aattcgccaa acgcgaggtg 1140
agcatcgccg aggtgcgcca ggagggcgtt gtggacgaag gtggtcgacg ggtgggagcc 1200
cgaatcgtgg tggtcacgca cctcgccact gacgccgcac tctcggaaac cgttgatgca 1260
ctggacgact tggatgtcgt gcagggtgtg tccagcgtga tacgactgga aggaaccggc 1320
tta 1323

<210> SEQ ID NO 137
<211> LENGTH: 216
<212> TYPE: PRT
<213> ORGANISM: Mycobacterium tuberculosis

<400> SEQUENCE: 137

Met Ser Asn Pro Gln Pro Glu Lys Val Arg Val Val Val Gly Asp Asp
1               5                   10                  15

His Pro Leu Phe Arg Glu Gly Val Val Arg Ala Leu Ser Leu Ser Gly
            20                  25                  30

Ser Val Asn Val Val Gly Glu Ala Asp Asp Gly Ala Ala Ala Leu Glu
        35                  40                  45

Leu Ile Lys Ala His Leu Pro Asp Val Ala Leu Leu Asp Tyr Arg Met
    50                  55                  60

Pro Gly Met Asp Gly Ala Gln Val Ala Ala Ala Val Arg Ser Tyr Glu
65                  70                  75                  80

Leu Pro Thr Arg Val Leu Leu Ile Ser Ala His Asp Glu Pro Ala Ile
                85                  90                  95

Val Tyr Gln Ala Leu Gln Gln Gly Ala Ala Gly Phe Leu Leu Lys Asp
            100                 105                 110

Ser Thr Arg Thr Glu Ile Val Lys Ala Val Leu Asp Cys Ala Lys Gly
        115                 120                 125

Arg Asp Val Val Ala Pro Ser Leu Val Gly Gly Leu Ala Gly Glu Ile
    130                 135                 140

Arg Gln Arg Ala Ala Pro Val Ala Pro Val Leu Ser Ala Arg Glu Arg
145                 150                 155                 160

Glu Val Leu Asn Arg Ile Ala Cys Gly Gln Ser Ile Pro Ala Ile Ala
                165                 170                 175

Ala Glu Leu Tyr Val Ala Pro Ser Thr Val Lys Thr His Val Gln Arg
            180                 185                 190

Leu Tyr Glu Lys Leu Gly Val Ser Asp Arg Ala Ala Ala Val Ala Glu
        195                 200                 205

Ala Met Arg Gln Arg Leu Leu Asp
    210                 215

<210> SEQ ID NO 138
<211> LENGTH: 648
<212> TYPE: DNA
<213> ORGANISM: Mycobacterium tuberculosis

<400> SEQUENCE: 138
atgagcaatc cgcagccgga gaaagtgcgc gtggtggtcg gcgacgacca cccgttattt 60
cgcgagggcg ttgtgcgagc gctttcgttg agtggctcgg tgaacgtggt cggcgaggcc 120
gacgacggcg ccgcggccct ggagttgatc aaggcccatt tgcccgacgt cgcattgctg 180
gactaccgca tgcccggcat ggacggcgcg caggttgcgg cggcggtgcg cagctacgag 240
ttgccaaccc gggtgctgct tatttccgcg cacgacgagc cggcgatcgt ctaccaggca 300

-continued

```
ctccaacagg gcgccgccgg attcctgctc aaggattcga ctcgcaccga gatcgtcaag    360

gcggtgctcg attgcgcgaa gggccgcgac gtggtggcgc cctcgctggt cgggggcctc    420

gccggggaga ttcgccagcg cgcggcaccc gtggccccgg tgctcagcgc gcgcgagcgc    480

gaggtgctca atcgcattgc gtgcggtcaa agcatccccg cgatcgcagc cgagctatat    540

gtggcgccgt cgacggtaaa gacccacgtg caacggttgt acgagaagct cggcgtcagc    600

gaccgagctg ccgcggtcgc cgaggcgatg cggcagaggc tgctcgac                 648
```